United States Patent
Schiemann et al.

(10) Patent No.: US 8,530,650 B2
(45) Date of Patent: Sep. 10, 2013

(54) 2, 5-DIAMINO-SUBSTITUTED PYRIDO [4, 3-D] PYRIMIDINES AS AUTOTAXIN INHIBITORS AGAINST CANCER

(75) Inventors: Kai Schiemann, Seeheim-Jugenheim (DE); Melanie Schultz, Darmstadt (DE); Wolfgang Staehle, Ingelheim (DE); Ingo Kober, Gross-Gerau (DE); Dirk Wienke, Darmstadt (DE); Mireille Krier, Darmstadt (DE)

(73) Assignee: MERCK PATENT GmbH, Darmstadt (DE)

( * ) Notice: Subject to any disclaimer, the term of this patent is extended or adjusted under 35 U.S.C. 154(b) by 16 days.

(21) Appl. No.: 13/132,181

(22) PCT Filed: Nov. 3, 2009

(86) PCT No.: PCT/EP2009/007876
§ 371 (c)(1),
(2), (4) Date: Jun. 1, 2011

(87) PCT Pub. No.: WO2010/063352
PCT Pub. Date: Jun. 10, 2010

(65) Prior Publication Data
US 2011/0237583 A1    Sep. 29, 2011

(30) Foreign Application Priority Data
Dec. 1, 2008 (EP) .................................... 08020824

(51) Int. Cl.
*C07D 487/04* (2006.01)
*A61K 31/5025* (2006.01)

(52) U.S. Cl.
USPC ..................... 544/236; 514/252.04

(58) Field of Classification Search
USPC ..................... 544/236; 514/252.04
See application file for complete search history.

(56) References Cited

U.S. PATENT DOCUMENTS 5,654,307 A * 8/1997 Bridges et al. ........... 514/264.11

OTHER PUBLICATIONS

Wermuth, The Practice of Medicinal Chemsitry, 2d ed. (2003), 768 pages. Chapters 9-10 provided.*
Kubinyi (3D QSAR in Drug Design: Ligand-Protein Interactions and Molecular Similarity, vol. 2-3, Springer, 1998, 800 pages). pp. 243-244.*
Parrill et al. (Bioorganic & Medicinal Chemistry, vol. 16, Issue 4, pp. 1784-1795).*
"1-{2-[(4-chlorobenzyl)amino]pyrido[4,3-d]pyrimidin 5 yl}-4-piperidinecarboxylic acid," Aurora Screening Library, Publication Date: Aug. 20, 2009, XP-007911538.
"3-Piperidinecarboxylic acid, 1-[2-[[(4-methoxyphenyl)methyl]amino]pyrido[4,3-d]pyrimidin-5-yl]-,"
Akos Screening Library, Publication Date: Jul. 27, 2009, XP-007911539.
Fry, D. W. et al., "Biochemical and Antiproliferative properties of 4-[Ar(alk)ylamino]pyridopyrimidines, a New Chemical Class of Potent and Specific Epidermal Growth Factor Receptor Tyrosine Kinase Inhibitors," Biochemical Pharmacology, 1997, vol. 54 pp. 877-887.

* cited by examiner

*Primary Examiner* — Robert Havlin
(74) *Attorney, Agent, or Firm* — Millen, White, Zelano & Branigan, P.C.

(57) ABSTRACT

The present invention relates to pyridopyrimidine derivatives according to formula (I) as autotaxin inhibitors and the use of such compounds for the treatment and/or prophylaxis of physiological and/or pathophysiological conditions, which are caused, mediated and/or propagated by increased lysophosphatic acid levels and/or the activation of autotaxin, in particular of different cancers.

17 Claims, No Drawings

2,5-DIAMINO-SUBSTITUTED PYRIDO [4,3-D] PYRIMIDINES AS AUTOTAXIN INHIBITORS AGAINST CANCER

TECHNICAL FIELD

The present invention relates to pyridopyrimidine derivatives as autotaxin inhibitors and the use of such compounds for the treatment and/or prophylaxis of physiological and/or pathophysiological conditions, which are caused, mediated and/or propagated by increased lysophosphatic acid levels and/or the activation of autotaxin, in particular of different cancers.

PRIOR ART

Autotaxin (ATX) is the enzyme apparently responsible for increased lysophosphatidic acid (LPA) levels in ascites and plasma of ovarian cancer patients (Xu et al., Clinical Cancer Research 1995, 1: 1223; Xu et al., Biochem. J. 1995, 309: 933), because it transforms lysophatidylcholine (LPC) to LPA (Tokumura et al., J. Biol. Chem. 2002, 277: 39436; Umezu-Gozo et al., J. Biol. Chem. 2002, 158: 227).

LPA is an intracellular lipid mediator, which influences a multiplicity of biologic and biochemical processes such as smooth muscle contraction, thrombocyte aggregation and apoptosis (Tigyi et al., Prog. Lipid Res. 2003, 42: 498; Mills et al., Nat. Rev. Cancer 2003, 3: 582; Lynch et al. Prost. Lipid Med. 2001, 64: 33). Furthermore, LPA is found in increased concentrations in plasma and ascites fluid of ovarian cancer patients of early and late phase.

LPA has been shown to promote tumor cell proliferation, survival, migration and invasion into neighboring tissues, which can result in the formation of metastases (Xu et al., Clinical Cancer Research 1995, 1: 1223; Xu et al., Biochem. J. 1995, 309: 933). These biological and pathobiological processes are switched on through the activation of G-protein coupled receptors by LPA (Contos et al., Mol. Pharm. 2000, 58: 1188).

Increased levels of LPA, altered receptor expression and altered responses to LPA may contribute to the initiation, progression or outcome of ovarian cancer. Furthermore, LPA is potentially also involved in prostate, breast, melanoma, head and neck, bowel and thyroid cancers.

For all these reasons in the course of treating tumor patients it is desirable to lower the LPA level. This can be achieved through the inhibition of enzymes which are involved in LPA biosynthesis, such as ATX (Sano et al., J. Biol. Chem. 2002, 277: 21197; Aoki et al., J. Biol. Chem. 2003, 277: 48737).

ATX belongs to the family of nucleotide pyrophosphates and phosphodiesterases (Goding et al., Immunol. Rev. 1998, 161: 11). It represents an important starting point for anti-tumor therapy (Mills et al. Nat. Rev. Cancer 2003, 3: 582; Goto et al. J. Cell. Biochem. 2004, 92: 1115), since it is increasingly expressed in tumors and effects tumor cell proliferation and invasion into neighboring tissues both of which can lead to the formation of metastases (Nam et al. 2000, Oncogene, Vol. 19 Seite 241). In addition, in the course of angiogenesis ATX together with other anti-angiogenetic factors brings about blood vessel formation (Nam et al. Cancer Res. 2001, 61: 6938). Angiogenesis is an important process during tumor growth as it secures supply of the tumor with nutrients. Therefore, the inhibition of angiogenesis is an important starting point of cancer and tumor therapy, by means of which the tumor is to be starved (Folkman, Nature Reviews Drug Discovery 2007, 6: 273-286).

Mutagenesis studies suggest an essential function of the PDE domain of ATX for LPA generation. Though this particular PDE domain shares little homology with other known PDEs, it is considered to be druggable by NCEs.

No severe adverse effects are expected for the inhibition of ATX as LPA involved in wound healing in this context is produced by another pathway.

Since ATX is a relatively novel target, the amount of pre-clinical data on protein production, in vitro and in vivo assays is rather limited. No target-dependent cell model has been described but LPA itself is an excellent biomarker to follow ATX inhibition in vitro and in vivo. Neither structural information nor reference compounds are available.

Compounds that are capable of inhibiting ATX are described in Peng et al. (Bioorganic & Medicinal Chemistry Letters 2007, 17: 1634-1640). The there described compounds represent lipid analogues, which structurally share no similarities with the compounds of the present invention.

Further prior art documents are as follows:

WO 2003/097615 is directed to treatment of fibroproliferative diseases, such as diabetic neuropathy, involving identifying a non-peptide small molecule, selectively binding to a transforming growth factor beta kinase receptor and administering the molecule to subjects. The patent application does neither disclose pyridopyrimidines nor does it mention the inhibition of autotaxin.

US 2003/0139431 relates to the use of quinazoline- and quinolino-guanidine derivatives for treating urge incontinence, pain, memory disorders, endocrine disorders, psychotic behaviour, diabetes, hypertension and gastrointestinal disorders. The patent application does neither disclose pyridopyrimidines nor does it mention the inhibition of autotaxin.

WO 2005/003100 deals with the use of quinazoline derivatives for the treatment of tubulin inhibitor mediated diseases, such as cancer, autoimmune diseases, autoimmune lymphoproliferative syndrome, inflammation and viral infections. The patent application does neither disclose pyridopyrimidines nor does it mention the inhibition of autotaxin.

WO 2006/062972 discloses heterocyclic compounds that function as selective inhibitors of serine protease enzymes of the coagulation cascade and can be used for the treatment of arterial cardiovascular thromboembolic disorders, thromboembolic disorders, unstable angina and acute coronary syndrome. The patent application does neither disclose pyridopyrimidines nor does it mention the inhibition of autotaxin.

WO 2006/072828 is directed to heteroaromatic quinoline compounds that serve as PDE inhibitors, in particular PDE10 inhibitors. These compounds can be used for the treatment of central nervous system disorders, such as psychotic disorders, anxiety disorders, movement disorders, mood disorders and neurodegenerative disorders. The patent application does neither disclose pyridopyrimidines nor does it mention the inhibition of autotaxin.

WO 2006/074147 describes 4-arylamino-quinazoline as caspase-3 cascade activators that can be used for the treatment of cancer, autoimmune diseases, autoimmune lymphoproliferative syndrome, synovial cell hyperplasia, inflammation and viral infections. The patent application does neither disclose pyridopyrimidines nor does it mention the inhibition of autotaxin.

WO 2006/108107 deals with diarylamine derivatives that are steroid hormone nuclear receptor modulators and can be used for the treatment of hypokalemia, hypertension, congestive heart failure, renal failure, atherosclerosis and obesity. The patent application does neither disclose pyridopyrimidines nor does it mention the inhibition of autotaxin.

WO 2007/030582 relates to alkyl amine compounds as potassium channel 1 function inhibitors that are useful for the treatment of arrhythmia, atrial fibrillation, atrial flutter, supraventricular arrhythmias, gastrointestinal disorders, esophagitis and asthma. The patent application does neither disclose pyridopyrimidines nor does it mention the inhibition of autotaxin.

WO 2007/076034 describes fused bicyclic arene compounds that function as hepatitis C virus replication inhibitors and can be used for the treatment hepatitis C or other viral infections. The patent application does neither disclose pyridopyrimidines nor does it mention the inhibition of autotaxin.

WO 2007/110868 discloses novel heterocyclic compounds that exhibit a dopamine receptor, preferably D4 receptor, antagonistic activity and/or a PDE5 inhibitory activity. These compounds can be used for the treatment of descreased libido, orgasm disorder and erectile dysfunction. The patent application does neither disclose pyridopyrimidines nor does it mention the inhibition of autotaxin.

The citation of any reference in this application is not an admission that the reference is relevant prior art to this application.

DESCRIPTION OF THE INVENTION

The present invention has the object to provide novel autotaxin inhibitors.

The object of the present invention has surprisingly been solved in one aspect by providing pyridopyrimidine derivatives according to formula (I)

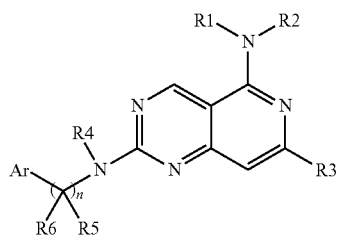

wherein:
Ar is independently aryl or heteroaryl, which may optionally be substituted with one or more identical or different substituents Z;
R1, R2 are independently from each other selected from the group consisting of:
(i) "hydrogen, alkyl, $(C_9\text{-}C_{30})$alkyl, cycloalkyl, cycloalkylalkyl, heterocyclyl, heterocyclylalkyl, aryl, arylalkyl, heteroaryl, heteroarylalkyl, halogen, —F, —Cl, —Br, —I, —CN, —CF$_3$, —N$_3$, —NH$_2$, —NHX1, —NX2X3, —NO$_2$, —OH, —OCF$_3$, —SH, —O—SO$_3$H, —OP(O)(OH)$_2$, —CHO, —COOH, —C(O)NH$_2$, —SO$_3$H, —P(O)(OH)$_2$, —C(O)—X4, —C(O)O—X5, —C(O)NH—X6, —C(O)NX7X8, —O—X9, —O(—X10-O)$_a$—H(a=1, 2, 3, 4, 5), —O(—X11-O)$_b$—X12 (b=1, 2, 3, 4, 5), —OC(O)—X13, —OC(O)—O—X14, —OC(O)—NHX15, —O—C(O)—NX16X17, —OP(O)(OX18)(OX19), —OSi(X20)(X21)(X22), —OS(O$_2$)—X23, —NHC(O)—NH$_2$, —NHC(O)—X24, —NX25C(O)—X26, —NH—C(O)—O—X27, —NH—C(O)—NH—X28, —NH—C(O)—NX29X30, —NX31—C(O)—O—X32, —NX33-C(O)—NH—X34, —NX35-C(O)—NX36X37, —NHS(O$_2$)—X38, —NX39S(O$_2$)—X40, —S—X41, —S(O)—X42, —S(O$_2$)—X43, —S(O$_2$)NH—X44, —S(O$_2$)NX45X46, —S(O$_2$)O—X47, —P(O)(OX48)(OX49), —Si(X50)(X51)(X52), —C(NH)—NH$_2$, —C(NX53)-NH$_2$, —C(NH)—NHX54, —C(NH)—NX55X56, —C(NX57)-NHX58, —C(NX59)-NX60X61, —NH—C(O)—NH—O—X62, —NH—C(O)—NX63-O—X64, —NX65-C(O)—NX66-O—X67, —N(—C(O)—NH—O—X68)$_2$, —N(—C(O)—NX69-O—X70)$_2$, —N(—C(O)—NH—O—X71)(—C(O)—NX72-O—X73), —C(S)—X74, —C(S)—O—X75, —C(S)—NH—X76, —C(S)—NX77X78, —C(O)—NH—O—X79, —C(O)—NX80—O—X81, —C(S)—NH—O—X82, —C(S)—NX83-O—X84, —C(O)—NH—NH—X85, —C(O)—NH—NX86X87, —C(O)—NX88-NX89X90, —C(S)—NH—NH—X91, —C(S)—NH—NX92X93, —C(S)—NX94-NX95X96, —C(O)—C(O)—O—X97, —C(O)—C(O)—NH$_2$, —C(O)—C(O)—NHX98, —C(O)—C(O)—NX99X100, —C(S)—C(O)—O—X101, —C(O)—C(S)—O—X102, —C(S)—C(S)—O—X103, —C(S)—C(O)—NH$_2$, —C(S)—C(O)—NHX104, —C(S)—C(O)—NX105X106, —C(S)—C(S)—NH$_2$, —C(S)—C(S)—NHX107, —C(S)—C(S)—NX108X109, —C(O)—C(S)—NH$_2$, —C(O)—C(S)—NHX110, —C(O)—C(S)—NX111X112";

wherein X1, X2, X3, X4, X5, X6, X7, X8, X9, X10, X11, X12, X13, X14, X15, X16, X17, X18, X19, X20, X21, X22, X23, X24, X25, X26, X27, X28, X29, X30, X31, X32, X33, X34, X35, X36, X37, X38, X39, X40, X41, X42, X43, X44, X45, X46, X47, X48, X49, X50, X51, X52, X53, X54, X55, X56, X57, X58, X59, X60, X61, X62, X63, X64, X65, X66, X67, X68, X69, X70, X71, X72, X73, X74, X75, X76, X77, X78, X79, X80, X81, X82, X83, X84, X85, X86, X87, X88, X89, X90, X91, X92, X93, X94, X95, X96, X97, X98, X99, X100, X101, X102, X103, X104, X105, X106, X107, X108, X109, X110, X111, X112 are independently from each other selected from the group consisting of: "alkyl, $(C_9\text{-}C_{30})$alkyl, cycloalkyl, cycloalkylalkyl, heterocyclyl, heterocyclylalkyl, aryl, arylalkyl, heteroaryl, heteroarylalkyl" and wherein alternatively X7, X8 and/or X16, X17 and/or X29, X30 and/or X36, X37 and/or X45, X46 and/or X55, X56 and/or X60, X61 and/or X77, X78 and/or X86, X87 and/or X89, X90 and/or X92, X93 and/or X95, X96 and/or X99, X100 and/or X105, X106 and/or X108, X109 and/or X111, X112 respectively together can also form "heterocyclyl";
wherein optionally above substituents of substituents group (i) can in turn independently from each other be substituted with one or more identical or different substituents Z;
or R1, R2 can together with the nitrogen atom to which they are attached to form "heterocyclyl", which is optionally substituted with one or more identical or different substituents Z;
with the proviso that if R1, R2 together with the nitrogen atom which they are attached to form "heterocyclyl", which is optionally substituted with one or more identical or different substituents Z, "heterocyclyl" is not selected from the group consisting of: "4-piperidine-1-yl-carboxylic acid (4-carboxy-piperidine-1-yl), 3-piperidine-1-yl-carboxylic acid (3-carboxy-piperidine-1-yl), 4-piperidine-1-yl-carboxylic acid ethyl ester (4-ethylcarboxyate-piperidine-1-yl), 3-piperidine-1-yl-carboxylic acid ethyl ester (3-ethylcarboxate-piperidine-1-yl)";

R3 is independently selected from the group consisting of:
(i) "hydrogen, alkyl, $(C_9-C_{30})$alkyl, cycloalkyl, cycloalkylalkyl, heterocyclyl, heterocyclylalkyl, aryl, arylalkyl, heteroaryl, heteroarylalkyl, halogen, —F, —Cl, —Br, —I, —CN, —CF$_3$, —NH$_2$, —NHX113, —NX114X115, —NO$_2$, —OH, —OCF$_3$, —SH, —CHO, —COOH, —C(O)NH$_2$, —SO$_3$H, —C(O)NH—X116, —C(O)NX117X118, —C(O)O—X119, —X120-OH, —X121-NHX122, —X123-NX124X125";
wherein X113, X114, X115, X116, X117, X118, X119, X120, X121, X122, X123, X124, X125 are independently from each other selected from the group consisting of: "alkyl, $(C_3-C_{30})$alkyl, cycloalkyl, cycloalkylalkyl, heterocyclyl, heterocyclylalkyl, aryl, arylalkyl, heteroaryl, heteroarylalkyl";
wherein optionally above substituents of substituents group (i) can in turn independently from each other be substituted with one or more identical or different substituents Z;

R4 is independently selected from the group consisting of:
(i) "hydrogen, alkyl, $(C_9-C_{30})$alkyl, cycloalkyl, cycloalkylalkyl, heterocyclyl, heterocyclylalkyl, aryl, arylalkyl, heteroaryl, heteroarylalkyl, —X126—NHX127, —X128-NX129X130";
wherein X126, X127, X128, X129, X130 are independently from each other selected from the group consisting of: "alkyl, $(C_3-C_{30})$alkyl, cycloalkyl, cycloalkylalkyl, heterocyclyl, heterocyclylalkyl, aryl, arylalkyl, heteroaryl, heteroarylalkyl";
wherein optionally above substituents of substituents group (i) can in turn independently from each other be substituted with one or more identical or different substituents Z;

R5, R6 are each independently from each other selected from the group consisting of:
(i) "hydrogen, alkyl, $(C_9-C_{30})$alkyl, cycloalkyl, cycloalkylalkyl, heterocyclyl, heterocyclylalkyl, aryl, arylalkyl, heteroaryl, heteroarylalkyl;
wherein optionally above substituents of substituents group (i) can in turn independently from each other be substituted with one or more identical or different substituents Z;

Z is independently selected from the group consisting of:
(i) "hydrogen, alkyl, $(C_9-C_{30})$alkyl, cycloalkyl, cycloalkylalkyl, heterocyclyl, heterocyclylalkyl, aryl, arylalkyl, heteroaryl, heteroarylalkyl, halogen, —F, —Cl, —Br, —I, —CN, —CF$_3$, —N$_3$, —NH$_2$, —NHX131, —NX132X133, —NO$_2$, —OH, —OCF$_3$, —SH, —O—SO$_3$H, —OP(O)(OH)$_2$, —CHO, —COOH, —C(O)NH$_2$, —SO$_3$H, —P(O)(OH)$_2$, —C(O)—X134, —C(O)O—X135, —C(O)NH—X136, —C(O)NX137X138, —O—X139, —O(—X140-O)$_a$—H (a=1, 2, 3, 4, 5), —O(—X141-O)$_b$—X142 (b=1, 2, 3, 4, 5), —OC(O)—X143, —OC(O)—O—X144, —OC(O)—NHX145, —O—C(O)—NX146X147, —OP(O)(OX148)(OX149), —OSi(X150)(X151)(X152), —OS(O$_2$)—X153, —NHC(O)—NH$_2$, —NHC(O)—X154, —NX155C(O)—X156, —NH—C(O)—O—X157, —NH—C(O)—NH—X158, —NH—C(O)—NX159X160, —NX161-C(O)—O—X162, —NX163-C(O)—NH—X164, —NX165-C(O)—NX166X167, —NHS(O$_2$)—X168, —NX169S(O$_2$)—X170, —S—X171,
—S(O)—X172, —S(O$_2$)—X173, —S(O$_2$)NH—X174, —S(O$_2$)NX175X176, —S(O$_2$)O—X177, —P(O)(OX178)(OX179), —Si(X180)(X181)(X182), —C(NH)—NH$_2$, —C(NX183)-NH$_2$, —C(NH)—NHX184, —C(NH)—NX185X186, —C(NX187)-NHX188, —C(NX189)—NX190X191, —NH—C(O)—NH—O—X192, —NH—C(O)—NX193-O—X194, —NX195-C(O)—NX196-O—X197, —N(—C(O)—NH—O—X198)$_2$, —N(—C(O)—NX199-O—X200)$_2$, —N(—C(O)—NH—O—X201)(—C(O)—NX202-O—X203), —C(S)—X204, —C(S)—O—X205, —C(S)—NH—X206, —C(S)—NX207X208, —C(O)—NH—O—X209, —C(O)—NX210-O—X211, —C(S)—NH—O—X212, —C(S)—NX213-O—X214, —C(O)—NH—NH—X215, —C(O)—NH—NX216X217, —C(O)—NX218-NX219X220, —C(S)—NH—NH—X221, —C(S)—NH—NX222X223, —C(S)—NX224-NX225X226, —C(O)—C(O)—O—X227, —C(O)—C(O)—NH$_2$, —C(O)—C(O)—NHX228, —C(O)—C(O)—NX229X230, —C(S)—C(O)—O—X231, —C(O)—C(S)—O—X232, —C(S)—C(S)—O—X233, —C(S)—C(O)—NH$_2$, —C(S)—C(O)—NHX234, —C(S)—C(O)—NX235X236, —C(S)—C(S)—NH$_2$, —C(S)—C(S)—NHX237, —C(S)—C(S)—NX238X239, —C(O)—C(S)—NH$_2$, —C(O)—C(S)—NHX240, —C(O)—C(S)—NX241X242";
wherein X131, X132, X133, X134, X135, X136, X137, X138, X139, X140, X141, X142, X143, X144, X145, X146, X147, X148, X149, X150, X151, X152, X153, X154, X155, X156, X157, X158, X159, X160, X161, X162, X163, X164, X165, X166, X167, X168, X169, X170, X171, X172, X173, X174, X175, X176, X177, X178, X179, X180, X181, X182, X183, X184, X185, X186, X187, X188, X189, X190, X191, X192, X193, X194, X195, X196, X197, X198, X199, X200, X201, X202, X203, X204, X205, X206, X207, X208, X209, X210, X211, X212, X213, X214, X215, X216, X217, X218, X219, X220, X221, X222, X223, X224, X225, X226, X227, X228, X229, X230, X231, X232, X233, X234, X235, X236, X237, X238, X239, X240, X241, X242 are independently from each other selected from the group consisting of: "alkyl, $(C_9-C_{30})$alkyl, cycloalkyl, cycloalkylalkyl, heterocyclyl, heterocyclylalkyl, aryl, arylalkyl, heteroaryl, heteroarylalkyl" and wherein alternatively X137, X138 and/or X146, X147 and/or X159, X160 and/or X166, X167 and/or X175, X176 and/or X185, X186 and/or X190, X191 and/or X207, X208 and/or X216, X217 and/or X219, X220 and/or X222, X223 and/or X225, X226 and/or X229, X230 and/or X235, X236 and/or X238, X239 and/or X241, X242 respectively together can also form "heterocyclyl";

n is 0, 1, 2;
and the physiologically acceptable salts, derivatives, prodrugs, solvates and stereoisomers thereof, including mixtures thereof in all ratios.

In a preferred embodiment, pyridopyrimidine derivatives according to formula (I) are provided, wherein:
R1, R2 are independently from each other selected from the group consisting of:
(i) "hydrogen, alkyl, aryl, arylalkyl, heteroarylalkyl, heterocyclyl, heterocyclylalkyl",
wherein optionally above substituents of substituents group (i) can in turn independently from each other be substituted with one or more identical or different substituents Z selected from the group consisting of: "—F, —Cl, —CN, —O—X243, —C(O)—X244, —C(O)O—X245", wherein X243, X244, X245 are independently from each other selected from the group consisting of: "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl";

or wherein R1, R2 can together with the nitrogen atom which they are attached to form "heterocyclyl", which is optionally substituted with one or more identical or different substituents Z selected from the group consisting of: "—COOH, —C(O)$NH_2$, heteroaryl, alkyl-COOH, alkyl-NX246X247, aryl-halogen, heterocyclylalkyl-X248, —C(O)—X249, —C(O)-alkyl-$NH_2$, —C(O)-alkyl-CN, —C(O)-alkyl-C(O)—X250, —C(O)-alkyl-C(O)—NX251X252, —C(O)-alkyl-O-alkyl-O—X253, —C(O)-alkyl-O—C(O)—X254, —C(O)-alkyl-C(O)O—X255, —C(O)-alkyl-NX256X257, —C(O)-heteroarylalkyl, —C(O)-heteroarylalkyl-X258, —C(O)-heterocyclyl-X259, —C(O)-heterocyclyl-X260-OH, —C(O)-heterocyclylalkyl(—$NH_2$)(=O), —C(O)O—X261, —C(O)O-alkyl-O—X262, —C(O)O-heterocyclylalkyl-X263, —C(O)NX264X265, —C(O)NH—X266, —C(O)NH-alkyl-OH, —C(O)NH-alkyl-O—X267, —C(O)NH-alkyl-C(O)O—X268, —C(O)NH-alkyl-NX269X270, —C(O)NH-arylalkyl(-halogen)(-halogen), —C(O)NH-heteroaryl-X271, —C(O)N(X272-O—X273)(X274-O—X275), —S($O_2$)—X276, —S($O_2$)-alkyl-S($O_2$)—X277, —S($O_2$)-heteroaryl-halogen";

wherein X246, X247, X248, X249, X250, X251, X252, X253, X254, X255, X256, X257, X258, X259, X260, X261, X262, X263, X264, X265, X266, X267, X268, X269, X270, X271, X272, X273, X274, X275, X276, X277 are independently from each other selected from the group consisting of: "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and wherein alternatively X246, X247 and/or X251, X252 and/or X256, X257 and/or X264, X265 and/or X269, X270 respectively together can also form "heterocyclyl";

with the proviso that if R1, R2 together with the nitrogen atom which they are attached to form "heterocyclyl", which is optionally substituted with one or more identical or different substituents Z, "heterocyclyl" is not selected from the group consisting of: "4-piperidine-1-yl-carboxylic acid (4-carboxy-piperidine-1-yl), 3-piperidine-1-yl-carboxylic acid (3-carboxy-piperidine-1-yl), 4-piperidine-1-yl-carboxylic acid ethyl ester (4-ethylcarboxyate-piperidine-1-yl), 3-piperidine-1-yl-carboxylic acid ethyl ester (3-ethylcarboxyate-piperidine-1-yl)";

and the physiologically acceptable salts, derivatives, prodrugs, solvates and stereoisomers thereof, including mixtures thereof in all ratios.

In a further preferred embodiment, pyridopyrimidine derivatives according to formula (I) and above embodiments are provided, wherein:

R1, R2 are independently from each other selected from the group consisting of:
(i) "hydrogen, propyl, isobutyl, phenyl, benzyl, benzo[1,3]dioxolyl, pyridinylmethyl, piperidinylethyl, piperidinylpropyl, pyrrolidinylpropyl, 2,3-dihydro-benzo[1,4]dioxinyl", wherein optionally above substituents of substituents group (i) can in turn independently from each other be substituted with one or more identical or different substituents Z selected from the group consisting of: "—F, —Cl, —CN, methyl, methoxy, ethoxy, methylcarbonyl, methylcarboxyate-yl (carboxoic acid methyl ester), isopropoxy";

or wherein R1, R2 can together with the nitrogen atom which they are attached to form "heterocyclyl" selected from the group consisting of: "pyrrolidinyl, piperidinyl, piperazinyl", which are optionally substituted with one or more identical or different substituents Z selected from the group consisting of: "hydrogen, —COOH, fluorophenyl, thiazolyl, pyridinyl, pyrimidinyl, methyl-piperidinyl-methyl, N,N-dimethyl-oxobutyramide, amino-butanone-yl, carboxy-methyl, pyridinyl-ethyl-amino-yl, pyridinyl-propyl-amino-yl, methyl-carbonyl, cyano-methyl-carbonyl, butanoyl-carbonyl, methoxy-ethoxy-methyl-carbonyl, dimethyl-amino-methyl-carbonyl, diethyl-amino-ethyl-carbonyl, furanyl-carbonyl, morpholinyl-carbonyl, pyridinyl-methyl-carbonyl, pyridinyl-ethyl-carbonyl, methyl-pyrazolyl-ethyl-carbonyl, imidazolyl-ethyl-carbonyl, pyrrolidinyl-carbonyl, methyl-piperazinyl-carbonyl, ethyl-piperazinyl-carbonyl, propyl-piperazinyl-carbonyl, pyridinyl-piperazinyl-carbonyl, amino-pyrrolidone-methyl-carbonyl, benzoimidazolyl-ethyl-carbonyl, hydroxyl-ethyl-piperazinyl-carbonyl, pyrrolidinyl-methyl-pyrrolidinyl-carbonyl, pyridinyl-acetamide-yl, methyl-carboxylic acid amide-yl, carboxylic acid methylamide-yl, carboxylic acid dimethylamide-yl, carboxylic acid diethylamide-yl, carboxylic acid hydroxy-ethylamide-yl, carboxylic acid propylamide-yl, carboxylic acid isopropylamide-yl, carboxylic acid cyclopropylamide-yl, carboxylic acid allylamide-yl, carboxylic acid (furanyl-methyl)-amide-yl, carboxylic acid pyridinyl-amide-yl, carboxylic acid (pyridinylmethyl)-amide-yl, carboxylic acid (dimethylaminoethyl)-amide-yl, carboxylic acid (diethylaminoethyl)-amide-yl, carboxylic acid (diethylaminopropyl)-amide-yl, carboxylic acid (methoxy-ethyl)-amide-yl, carboxylic acid (methoxy-propyl)-amide-yl, carboxylic acid (ethoxy-propyl)-amide-yl, carboxylic acid (methyl-isoxazolyl)-amide-yl, carboxylic acid bis(methoxy-ethyl)amide-yl, carboxylic acid (chloro)(fluoro)benzylamide-yl, carboxylic acid ethyl ester, carboxylic acid methoxy-propyl-ester, carboxylic acid ethoxy-propyl-ester, carboxylic acid pyridinylmethyl-ester, carboxylic acid methyl-piperidinyl-methyl-ester, acetic acid-oxo-ethyl ester, oxo-proprionic acid ethyl ester, oxo-pentanoic acid methyl ester, carbonyl-amino-propionic acid ethyl ester, methyl-sulfonyl, methyl-sulfonyl-methyl-sulfonyl, thiophenyl-sulfonyl, bromo-pyridinyl-sulfonyl";

with the proviso that if R1, R2 together with the nitrogen atom which they are attached to form "heterocyclyl", which is optionally substituted with one or more identical or different substituents Z, "heterocyclyl" is not selected from the group consisting of: "4-piperidine-1-yl-carboxylic acid (4-carboxy-piperidine-1-yl), 3-piperidine-1-yl-carboxylic acid (3-carboxy-piperidine-1-yl), 4-piperidine-1-yl-carboxylic acid ethyl ester (4-ethylcarboxyate-piperidine-1-yl), 3-piperidine-1-yl-carboxylic acid ethyl ester (3-ethylcarboxyate-piperidine-1-yl)";

and the physiologically acceptable salts, derivatives, prodrugs, solvates and stereoisomers thereof, including mixtures thereof in all ratios.

In a yet further preferred embodiment, pyridopyrimidine derivatives according to formula (I) and above embodiments are provided, wherein:
R3 is independently selected from the group consisting of:
(i) "hydrogen, alkyl, methyl, —CF$_3$, —CHO, —COOH, —C(O)NH$_2$, —C(O)NH—X278, —C(O)NX279X280, —C(O)O—X281, —X282-OH, —CH$_2$—OH, —X283-NHX284, —CH$_2$—NHX285, —X286-NX287X288, —CH$_2$—NX289X290";
wherein X278, X279, X280, X281, X282, X283, X284, X285, X286, X287, X288, X289, X290 are independently from each other selected from the group consisting of: "alkyl, (C$_9$-C$_{30}$)alkyl, cycloalkyl, cycloalkyl-alkyl, heterocyclyl, heterocyclylalkyl, aryl, arylalkyl, heteroaryl, heteroarylalkyl";
and the physiologically acceptable salts, derivatives, prodrugs, solvates and stereoisomers thereof, including mixtures thereof in all ratios.
In another preferred embodiment, pyridopyrimidine derivatives according to formula (I) and above embodiments are provided, wherein:
R4 is independently selected from the group consisting of:
(i) "hydrogen, alkyl, methyl, —X291-NHX292, —X293-NX294X295"; wherein X291, X292, X293, X294, X295 are independently from each other selected from the group consisting of: "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl";
and the physiologically acceptable salts, derivatives, prodrugs, solvates and stereoisomers thereof, including mixtures thereof in all ratios.
In yet another preferred embodiment, pyridopyrimidine derivatives according to formula (I) and above embodiments are provided, wherein:
R5, R6 are independently from each other selected from the group consisting of:
(i) "hydrogen, alkyl, methyl";
and the physiologically acceptable salts, derivatives, prodrugs, solvates and stereoisomers thereof, including mixtures thereof in all ratios.
In yet another preferred embodiment, pyridopyrimidine derivatives according to formula (I) and above embodiments are provided, wherein:
n is 1;
and the physiologically acceptable salts, derivatives, prodrugs, solvates and stereoisomers thereof, including mixtures thereof in all ratios.
In yet another preferred embodiment, pyridopyrimidine derivatives according to formula (I) and above embodiments are provided, wherein:
Ar is independently selected from the group consisting of:
(i) "phenyl, pyridinyl";
wherein optionally above substituents of substituents group (i) can in turn independently from each other be substituted with one or more identical or different substituents Z selected from the group consisting of: "halogen, —F, —Cl, alkyl, methyl, —O—X296, methoxy",
wherein X296 is independently from each other selected from the group consisting of: "alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl";
and the physiologically acceptable salts, derivatives, prodrugs, solvates and stereoisomers thereof, including mixtures thereof in all ratios.
In a further preferred embodiment, pyridopyrimidine derivatives according to formula (I) and above embodiments are provided which are selected from the group consisting of:

Compound 1

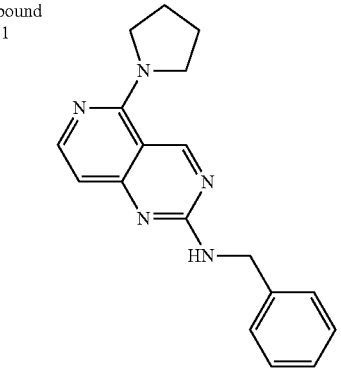

Benzyl-(5-pyrrolidin-1-yl-pyrido[4,3-d]pyrimidin-2-yl)-amine

Compound 2

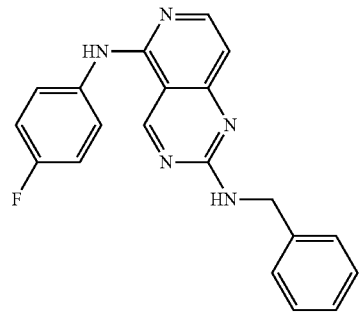 [SMILES: Fc1ccc(Nc2nccc3nc(NCc4ccccc4)ncc23)cc1]

N2-Benzyl-N5-(4-fluoro-phenyl)-pyrido[4,3-d]pyrimidine-2,5-diamine

-continued
| | | |
|---|---|---|
| Compound 3 | 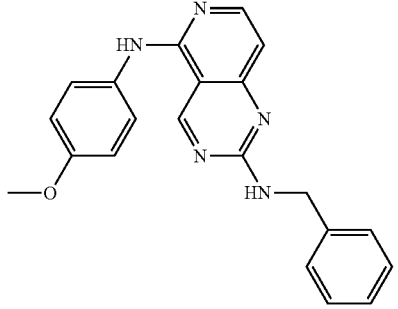 [SMILES: COc1ccc(Nc2nccc3nc(NCc4ccccc4)ncc23)cc1] | N2-Benzyl-N5-(4-methoxy-phenyl)-pyrido[4,3-d]pyrimidine-2,5-diamine |
| Compound 4 | 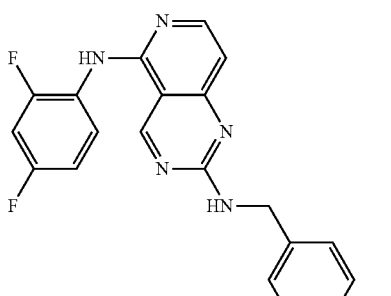 | N2-Benzyl-N5-(2,4-difluoro-phenyl)-pyrido[4,3-d]pyrimidine-2,5-diamine |
| Compound 5 | 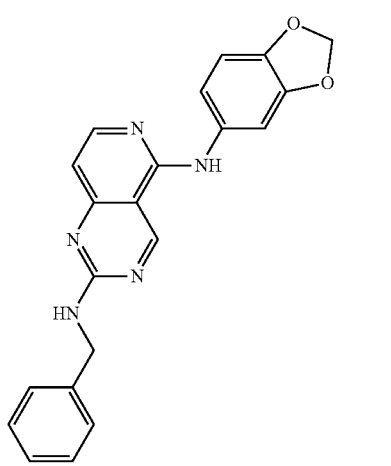 [SMILES: c1ccc(CNc2ncc3c(Nc4ccc5c(c4)OCO5)nccc3n2)cc1] | N5-Benzo[1,3]dioxol-5-yl-N2-benzyl-pyrido[4,3-d]pyrimidine-2,5-diamine |
| Compound 6 | 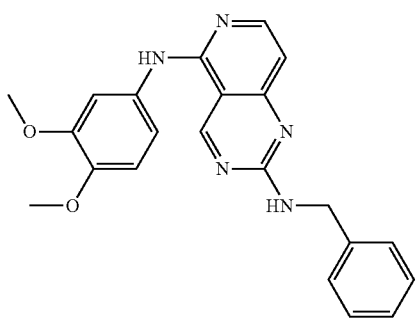 [SMILES: COc1ccc(Nc2nccc3nc(NCc4ccccc4)ncc23)cc1OC] | N2-Benzyl-N5-(3,4-dimethoxy-phenyl)-pyrido[4,3-d]pyrimidine-2,5-diamine |

-continued
| | | |
|---|---|---|
| Compound 7 | 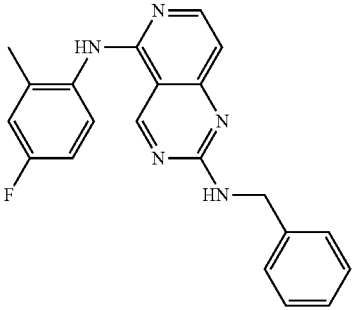 [SMILES: Cc1cc(F)ccc1Nc1nccc2nc(NCc3ccccc3)ncc12] | N2-Benzyl-N5-(4-fluoro-2-methyl-phenyl)-pyrido[4,3-d]pyrimidine-2,5-diamine |
| Compound 8 | 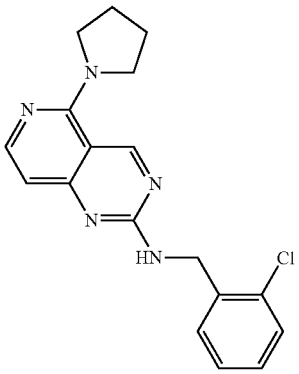 [SMILES: Clc1ccccc1CNc1ncc2c(N3CCCC3)nccc2n1] | (2-Chloro-benzyl)-(5-pyrrolidin-1-yl-pyrido[4,3-d]pyrimidin-2-yl)-amine |
| Compound 9 | 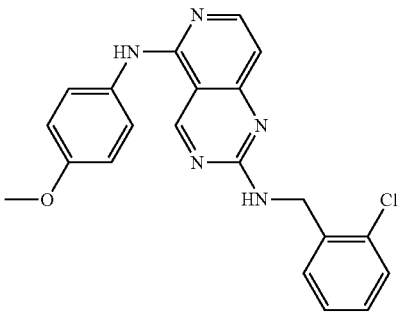 [SMILES: COc1ccc(Nc2nccc3nc(NCc4ccccc4Cl)ncc23)cc1] | N2-(2-Chloro-benzyl)-N5-(4-methoxy-phenyl)-pyrido[4,3-d]pyrimidine-2,5-diamine |
| Compound 10 | 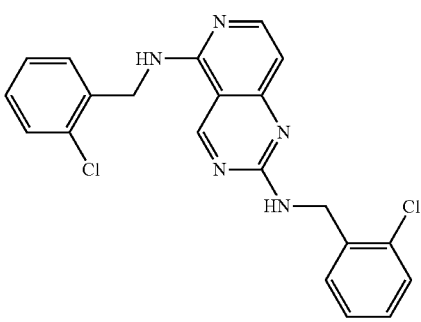 [SMILES: Clc1ccccc1CNc1ncc2c(NCc3ccccc3Cl)nccc2n1] | N2,N5-Bis-(2-chloro-benzyl)-pyrido[4,3-d]pyrimidine-2,5-diamine |
| Compound 11 | 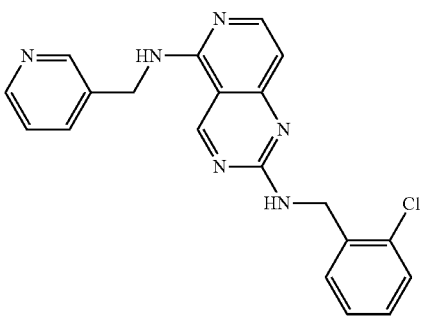 [SMILES: Clc1ccccc1CNc1ncc2c(NCc3cccnc3)nccc2n1] | N2-(2-Chloro-benzyl)-N5-pyridin-3-ylmethyl-pyrido[4,3-d]pyrimidine-2,5-diamine |

| | | |
|---|---|---|
| Compound 12 | 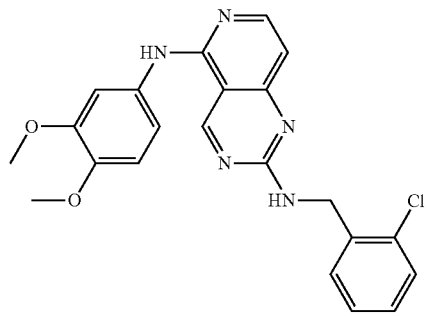 [SMILES: COc1ccc(Nc2nccc3nc(NCc4ccccc4Cl)ncc23)cc1OC] | N2-(2-Chloro-benzyl)-N5-(3,4-dimethoxy-phenyl)-pyrido[4,3-d]pyrimidine-2,5-diamine |
| Compound 13 | 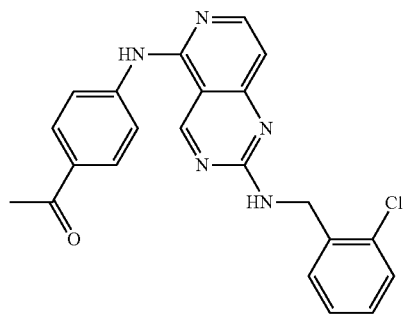 [SMILES: CC(=O)c1ccc(Nc2nccc3nc(NCc4ccccc4Cl)ncc23)cc1] | 1-{4-[2-(2-Chloro-benzylamino)-pyrido[4,3-d]pyrimidin-5-ylamino]-phenyl}-ethanone |
| Compound 14 | 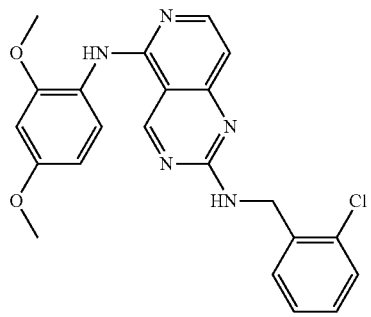 [SMILES: COc1ccc(Nc2nccc3nc(NCc4ccccc4Cl)ncc23)c(OC)c1] | N2-(2-Chloro-benzyl)-N5-(2,4-dimethoxy-phenyl)-pyrido[4,3-d]pyrimidine-2,5-diamine |
| Compound 15 | 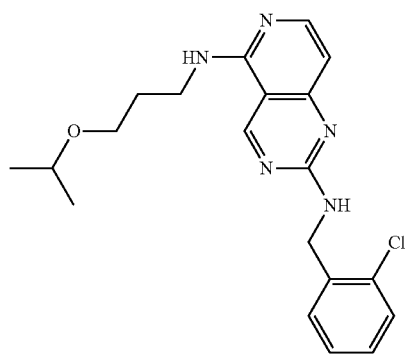 [SMILES: CC(C)OCCCNc1nccc2nc(NCc3ccccc3Cl)ncc12] | N2-(2-Chloro-benzyl)-N5-(3-isopropoxy-propyl)-pyrido[4,3-d]pyrimidine-2,5-diamine |
| Compound 16 | 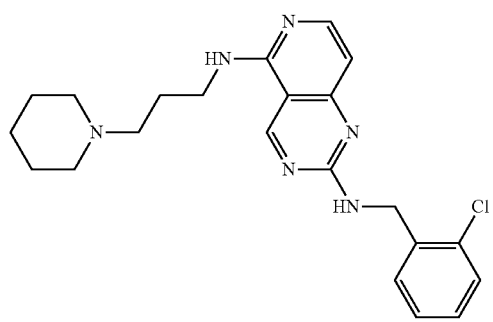 [SMILES: Clc1ccccc1CNc1ncc2c(NCCCN3CCCCC3)nccc2n1] | N2-(2-Chloro-benzyl)-N5-(3-piperidin-1-yl-propyl)-pyrido[4,3-d]pyrimidine-2,5-diamine |

-continued
Compound 17 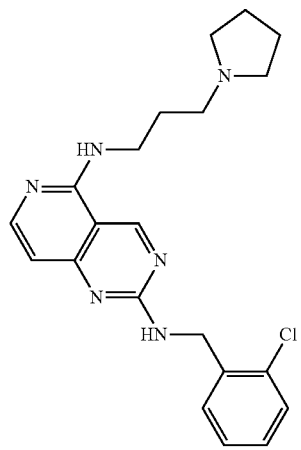 [SMILES: Clc1ccccc1CNc1ncc2c(NCCCN3CCCC3)nccc2n1] N2-(2-Chloro-benzyl)-N5-(3-pyrrolidin-1-yl-propyl)-pyrido[4,3-d]pyrimidine-2,5-diamine
Compound 18 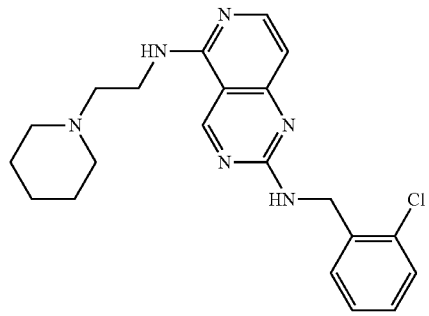 [SMILES: Clc1ccccc1CNc1ncc2c(NCCN3CCCCC3)nccc2n1] N2-(2-Chloro-benzyl)-N5-(2-piperidin-1-yl-ethyl)-pyrido[4,3-d]pyrimidine-2,5-diamine
Compound 19 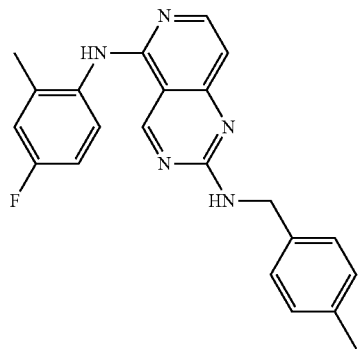 [SMILES: Cc1ccc(CNc2ncc3c(Nc4ccc(F)cc4C)nccc3n2)cc1] N5-(4-Fluoro-2-methyl-phenyl)-N2-(4-methyl-benzyl)-pyrido[4,3-d]pyrimidine-2,5-diamine
Compound 20 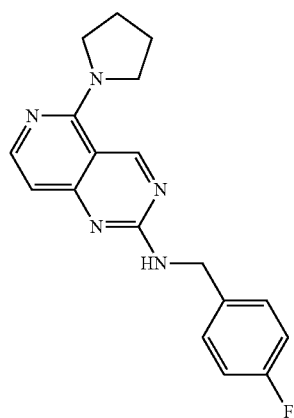 [SMILES: Fc1ccc(CNc2ncc3c(N4CCCC4)nccc3n2)cc1] (4-Fluoro-benzyl)-(5-pyrrolidin-1-yl-pyrido[4,3-d]pyrimidin-2-yl)-amine -continued
| | | |
|---|---|---|
| Compound 21 | 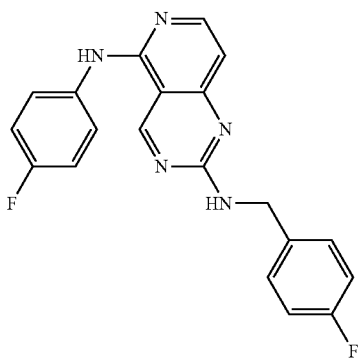 [SMILES: Fc1ccc(CNc2ncc3c(Nc4ccc(F)cc4)nccc3n2)cc1] | N2-(4-Fluoro-benzyl)-N5-(4-fluoro-phenyl)-pyrido[4,3-d]pyrimidine-2,5-diamine |
| Compound 22 | 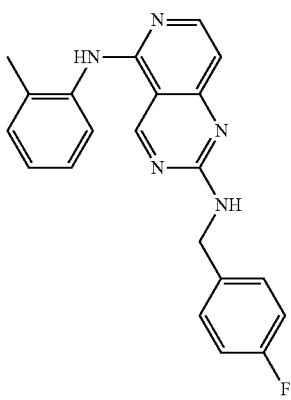 [SMILES: Cc1ccccc1Nc1nccc2nc(NCc3ccc(F)cc3)ncc12] | N2-(4-Fluoro-benzyl)-N5-o-tolyl-pyrido[4,3-d]pyrimidine-2,5-diamine |
| Compound 23 | 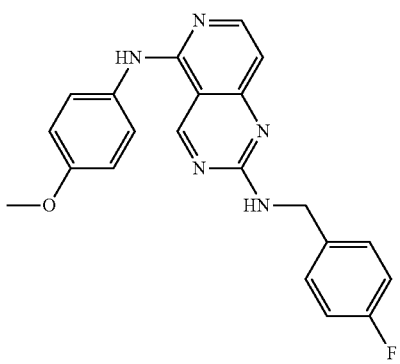 [SMILES: COc1ccc(Nc2nccc3nc(NCc4ccc(F)cc4)ncc23)cc1] | N2-(4-Fluoro-benzyl)-N5-(4-methoxy-phenyl)-pyrido[4,3-d]pyrimidine-2,5-diamine |
| Compound 24 | 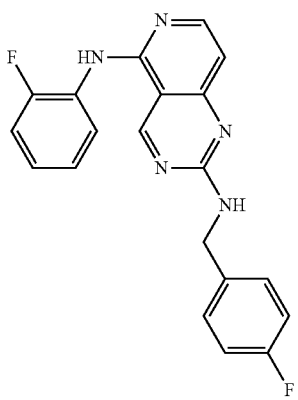 [SMILES: Fc1ccc(CNc2ncc3c(Nc4ccccc4F)nccc3n2)cc1] | N2-(4-Fluoro-benzyl)-N5-(2-fluoro-phenyl)-pyrido[4,3-d]pyrimidine-2,5-diamine |

-continued

| | | |
|---|---|---|
| Compound 25 | | N5-(2,4-Difluoro-phenyl)-N2-(4-fluoro-benzyl)-pyrido[4,3-d]pyrimidine-2,5-diamine |
| Compound 26 | | N5-Benzo[1,3]dioxol-5-yl-N2-(4-fluoro-benzyl)-pyrido[4,3-d]pyrimidine-2,5-diamine |
| Compound 27 | | N5-(3,4-Dimethoxy-phenyl)-N2-(4-fluoro-benzyl)-pyrido[4,3-d]pyrimidine-2,5-diamine |
| Compound 28 | | N2-(4-Fluoro-benzyl)-N5-(4-fluoro-2-methyl-phenyl)-pyrido[4,3-d]pyrimidine-2,5-diamine |

| | | |
|---|---|---|
| Compound 29 | | N5-Benzo[1,2,5]oxadiazol-5-ylmethyl-N2-(4-fluoro-benzyl)-pyrido[4,3-d]pyrimidine-2,5-diamine |
| Compound 30 | | N2-(4-Fluoro-benzyl)-N5-isobutyl-pyrido[4,3-d]pyrimidine-2,5-diamine |
| Compound 31 | | (2-Methoxy-benzyl)-(5-pyrrolidin-1-yl-pyrido[4,3-d]pyrimidin-2-yl)-amine |
| Compound 32 | | N5-(2-Ethoxy-phenyl)-N2-(2-methoxy-benzyl)-pyrido[4,3-d]pyrimidine-2,5-diamine |

-continued
| | | |
|---|---|---|
| Compound 33 | 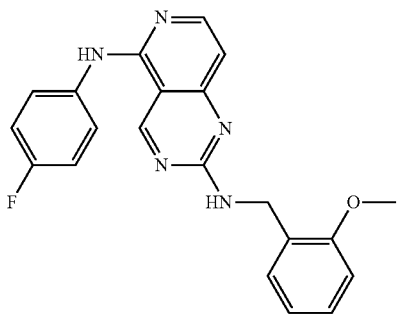 [SMILES: COc1ccccc1CNc1ncc2c(Nc3ccc(F)cc3)nccc2n1] | N5-(4-Fluoro-phenyl)-N2-(2-methoxy-benzyl)-pyrido[4,3-d]pyrimidine-2,5-diamine |
| Compound 34 | 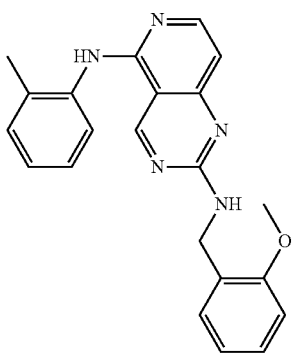 [SMILES: COc1ccccc1CNc1ncc2c(Nc3ccccc3C)nccc2n1] | N2-(2-Methoxy-benzyl)-N5-o-tolyl-pyrido[4,3-d]pyrimidine-2,5-diamine |
| Compound 35 | 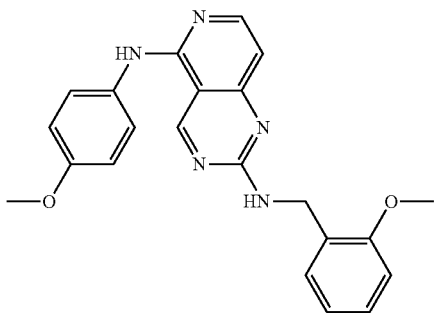 | N2-(2-Methoxy-benzyl)-N5-(4-methoxy-phenyl)-pyrido[4,3-d]pyrimidine-2,5-diamine |
| Compound 36 | 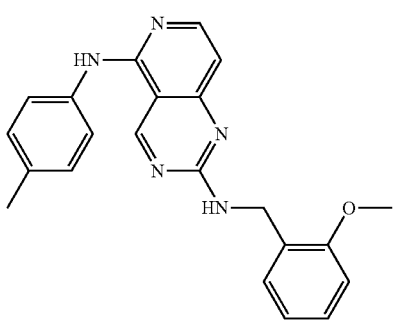 [SMILES: COc1ccccc1CNc1ncc2c(Nc3ccc(C)cc3)nccc2n1] | N2-(2-Methoxy-benzyl)-N5-p-tolyl-pyrido[4,3-d]pyrimidine-2,5-diamine |
| Compound 37 | 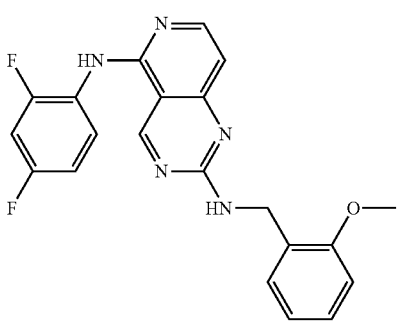 [SMILES: COc1ccccc1CNc1ncc2c(Nc3ccc(F)cc3F)nccc2n1] | N5-(2,4-Difluoro-phenyl)-N2-(2-methoxy-benzyl)-pyrido[4,3-d]pyrimidine-2,5-diamine |

| Compound 38 | | N5-(3,4-Dimethoxy-phenyl)-N2-(2-methoxy-benzyl)-pyrido[4,3-d]pyrimidine-2,5-diamine |
|---|---|---|
| Compound 39 | | N5-(2,3-Dihydro-benzo[1,4]dioxin-6-yl)-N2-(2-methoxy-benzyl)-pyrido[4,3-d]pyrimidine-2,5-diamine |
| Compound 40 | | N5-(2,4-Dimethoxy-phenyl)-N2-(2-methoxy-benzyl)-pyrido[4,3-d]pyrimidine-2,5-diamine |
| Compound 41 | | N5-(4-Fluoro-2-methyl-phenyl)-N2-(2-methoxy-benzyl)-pyrido[4,3-d]pyrimidine-2,5-diamine |
| Compound 42 | | N2-(4-Chloro-benzyl)-N5-(4-fluoro-phenyl)-pyrido[4,3-d]pyrimidine-2,5-diamine |

-continued

| | | |
|---|---|---|
| Compound 43 | | N2-(4-Chloro-benzyl)-N5-o-tolyl-pyrido[4,3-d]pyrimidine-2,5-diamine |
| Compound 44 | | N2-(4-Chloro-benzyl)-N5-(4-methoxy-phenyl)-pyrido[4,3-d]pyrimidine-2,5-diamine |
| Compound 45 | | N2-(4-Chloro-benzyl)-N5-(2,4-difluoro-phenyl)-pyrido[4,3-d]pyrimidine-2,5-diamine |
| Compound 46 | | N5-Benzo[1,3]dioxol-5-yl-N2-(4-chloro-benzyl)-pyrido[4,3-d]pyrimidine-2,5-diamine |

-continued
| Compound 47 | 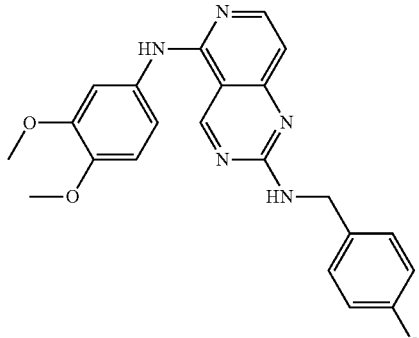 | N2-(4-Chloro-benzyl)-N5-(3,4-dimethoxy-phenyl)-pyrido[4,3-d]pyrimidine-2,5-diamine |
| Compound 48 | 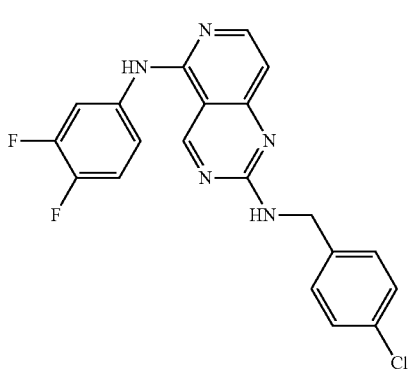 [SMILES: Fc1ccc(Nc2nccc3nc(NCc4ccc(Cl)cc4)ncc23)cc1F] | N2-(4-Chloro-benzyl)-N5-(3,4-difluoro-phenyl)-pyrido[4,3-d]pyrimidine-2,5-diamine |
| Compound 49 | 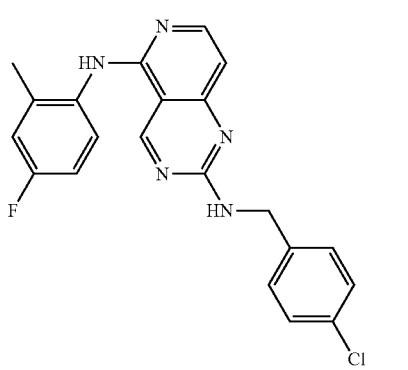 [SMILES: Cc1cc(F)ccc1Nc1nccc2nc(NCc3ccc(Cl)cc3)ncc12] | N2-(4-Chloro-benzyl)-N5-(4-fluoro-2-methyl-phenyl)-pyrido[4,3-d]pyrimidine-2,5-diamine |
| Compound 50 | 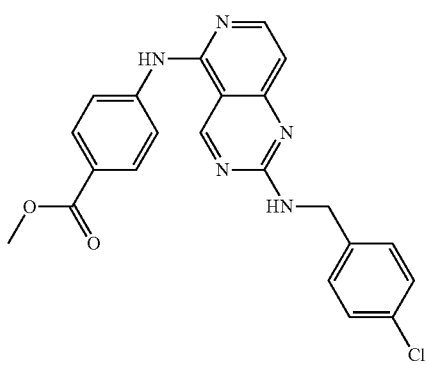 [SMILES: COC(=O)c1ccc(Nc2nccc3nc(NCc4ccc(Cl)cc4)ncc23)cc1] | 4-[2-(4-Chloro-benzylamino)-pyrido[4,3-d]pyrimidin-5-ylamino]-benzoic acid methyl ester |

-continued

| Compound 51 | | N5-(2,5-Dimethoxy-phenyl)-N2-(4-methoxy-benzyl)-pyrido[4,3-d]pyrimidine-2,5-diamine |
|---|---|---|
| Compound 52 | | N5-(2,4-Difluoro-phenyl)-N2-(4-methoxy-benzyl)-pyrido[4,3-d]pyrimidine-2,5-diamine |
| Compound 53 | | N5-Benzo[1,3]dioxol-5-yl-N2-(4-methoxy-benzyl)-pyrido[4,3-d]pyrimidine-2,5-diamine |
| Compound 54 | | N5-(3,4-Dimethoxy-phenyl)-N2-(4-methoxy-benzyl)-pyrido[4,3-d]pyrimidine-2,5-diamine |

-continued
| | | |
|---|---|---|
| Compound 55 | 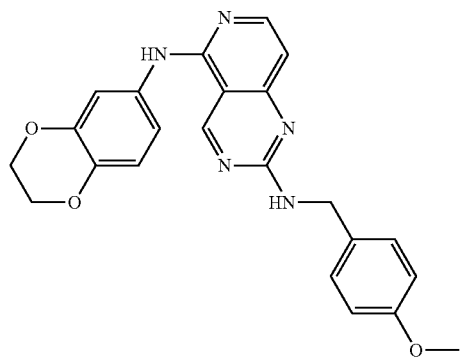 [SMILES: COc1ccc(CNc2ncc3c(Nc4ccc5c(c4)OCCO5)nccc3n2)cc1] | N5-(2,3-Dihydro-benzo[1,4]dioxin-6-yl)-N2-(4-methoxy-benzyl)-pyrido[4,3-d]pyrimidine-2,5-diamine |
| Compound 56 | 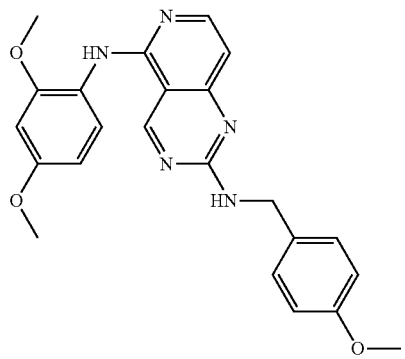 [SMILES: COc1ccc(CNc2ncc3c(Nc4ccc(OC)cc4OC)nccc3n2)cc1] | N5-(2,4-Dimethoxy-phenyl)-N2-(4-methoxy-benzyl)-pyrido[4,3-d]pyrimidine-2,5-diamine |
| Compound 57 | 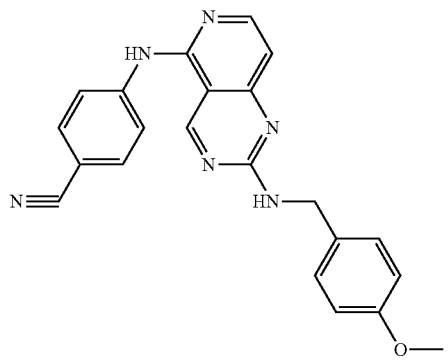 [SMILES: COc1ccc(CNc2ncc3c(Nc4ccc(C#N)cc4)nccc3n2)cc1] | 4-[2-(4-Methoxy-benzylamino)-pyrido[4,3-d]pyrimidin-5-ylamino]-benzonitrile |
| Compound 58 | 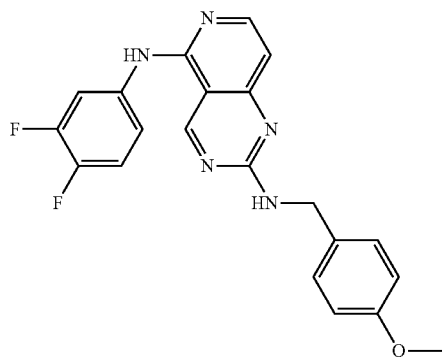 [SMILES: COc1ccc(CNc2ncc3c(Nc4ccc(F)c(F)c4)nccc3n2)cc1] | N5-(3,4-Difluoro-phenyl)-N2-(4-methoxy-benzyl)-pyrido[4,3-d]pyrimidine-2,5-diamine |

| Compound 59 | | N5-(4-Fluoro-2-methyl-phenyl)-N2-(4-methoxy-benzyl)-pyrido[4,3-d]pyrimidine-2,5-diamine |
| Compound 60 | | 1-(2-Benzylamino-pyrido[4,3-d]pyrimidin-5-yl)-piperidine-4-carboxylic acid (furan-2-ylmethyl)-amide |
| Compound 61 | | 1-(2-Benzylamino-pyrido[4,3-d]pyrimidin-5-yl)-piperidine-4-carboxylic acid iso-propylamide |
| Compound 62 | | 1-[2-(2-Chloro-benzylamino)-pyrido[4,3-d]pyrimidin-5-yl]-piperidine-4-carboxylic acid (pyridin-3-ylmethyl)-amide |

| | | |
|---|---|---|
| Compound 63 | 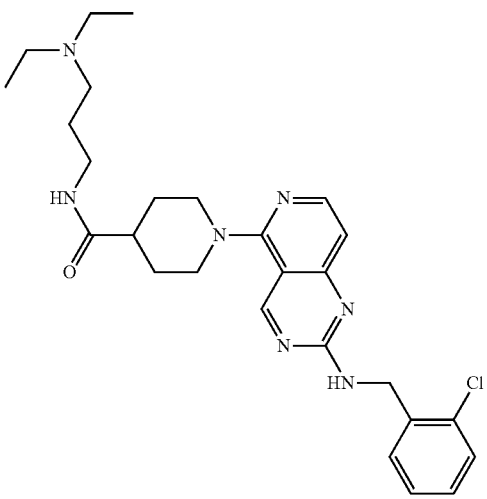 [SMILES: CCN(CC)CCCNC(=O)C1CCN(c2nccc3nc(NCc4ccccc4Cl)ncc23)CC1] | 1-[2-(2-Chloro-benzylamino)-pyrido[4,3-d]pyrimidin-5-yl]-piperidine-4-carboxylic acid (3-diethylamino-propyl)-amide |
| Compound 64 | 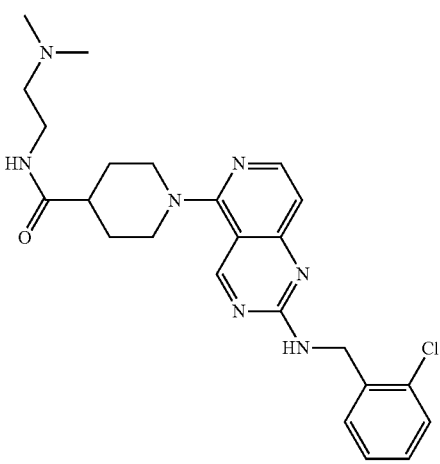 [SMILES: CN(C)CCNC(=O)C1CCN(c2nccc3nc(NCc4ccccc4Cl)ncc23)CC1] | 1-[2-(2-Chloro-benzylamino)-pyrido[4,3-d]pyrimidin-5-yl]-piperidine-4-carboxylic acid (2-dimethylamino-ethyl)-amide |
| Compound 65 | 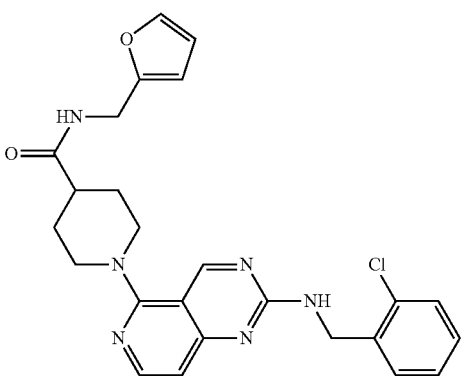 [SMILES: O=C(NCc1ccco1)C1CCN(c2nccc3nc(NCc4ccccc4Cl)ncc23)CC1] | 1-[2-(2-Chloro-benzylamino)-pyrido[4,3-d]pyrimidin-5-yl]-piperidine-4-carboxylic acid (furan-2-ylmethyl)-amide |

-continued
| Compound 66 | 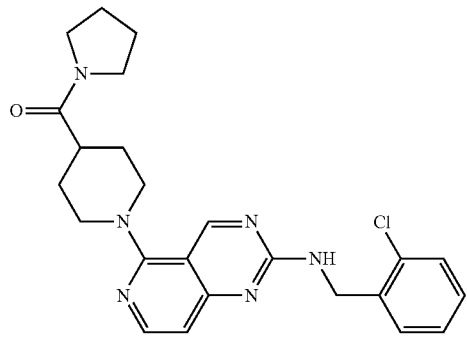 [SMILES: O=C(C1CCN(c2nccc3nc(NCc4ccccc4Cl)ncc23)CC1)N1CCCC1] | {1-[2-(2-Chloro-benzylamino)-pyrido[4,3-d]pyrimidin-5-yl]-piperidin-4-yl}-pyrrolidin-1-yl-methanone |
| Compound 67 | 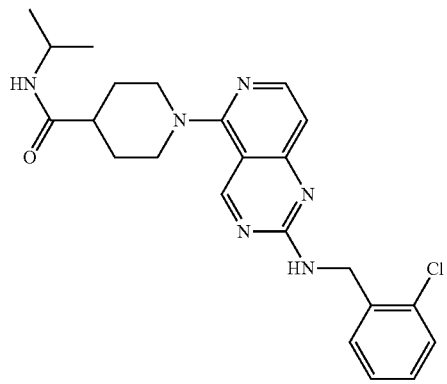 [SMILES: CC(C)NC(=O)C1CCN(c2nccc3nc(NCc4ccccc4Cl)ncc23)CC1] | 1-[2-(2-Chloro-benzylamino)-pyrido[4,3-d]pyrimidin-5-yl]-piperidine-4-carboxylic acid iso-propylamide |
| Compound 68 | 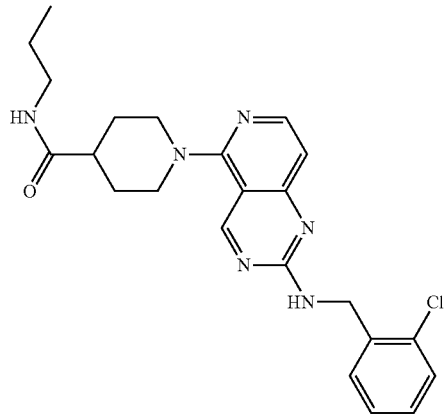 [SMILES: CCCNC(=O)C1CCN(c2nccc3nc(NCc4ccccc4Cl)ncc23)CC1] | 1-[2-(2-Chloro-benzylamino)-pyrido[4,3-d]pyrimidin-5-yl]-piperidine-4-carboxylic acid prop-ylamide |

-continued

| | | |
|---|---|---|
| Compound 69 | | 1-[2-(2-Chloro-benzylamino)-pyrido[4,3-d]pyrimidin-5-yl]-piperidine-4-carboxylic acid cyclopropylamide |
| Compound 70 | | 1-[2-(2-Chloro-benzylamino)-pyrido[4,3-d]pyrimidin-5-yl]-piperidine-4-carboxylic acid (2-methoxy-ethyl)-amide |
| Compound 71 | | 1-[2-(2-Chloro-benzylamino)-pyrido[4,3-d]pyrimidin-5-yl]-piperidine-4-carboxylic acid allylamide |

-continued
| | | |
|---|---|---|
| Compound 72 | 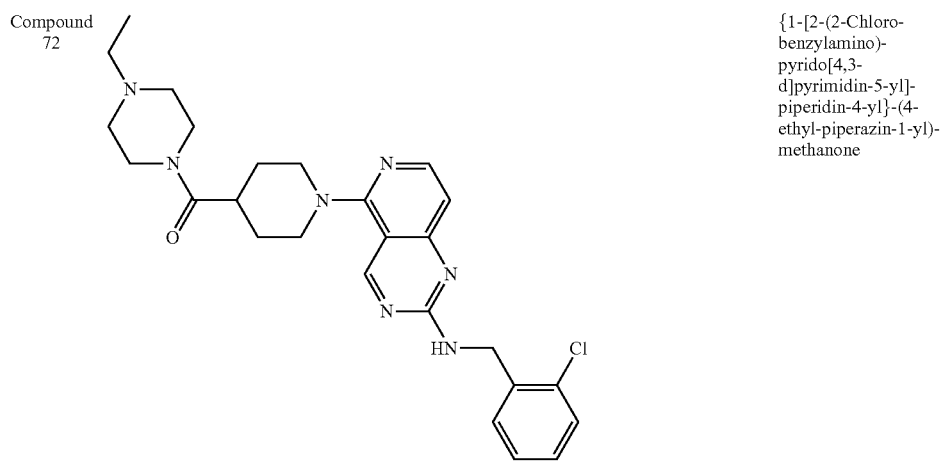 | {1-[2-(2-Chloro-benzylamino)-pyrido[4,3-d]pyrimidin-5-yl]-piperidin-4-yl}-(4-ethyl-piperazin-1-yl)-methanone |
| Compound 73 | 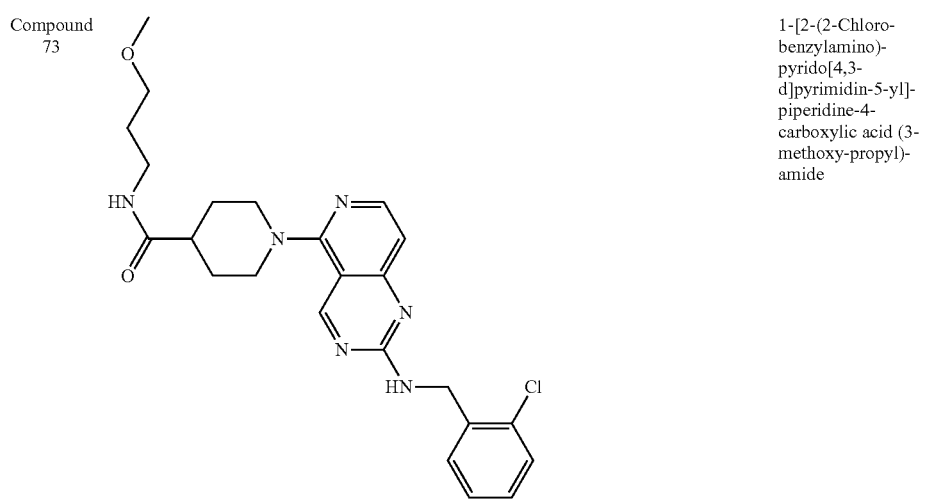 | 1-[2-(2-Chloro-benzylamino)-pyrido[4,3-d]pyrimidin-5-yl]-piperidine-4-carboxylic acid (3-methoxy-propyl)-amide |
| Compound 74 | 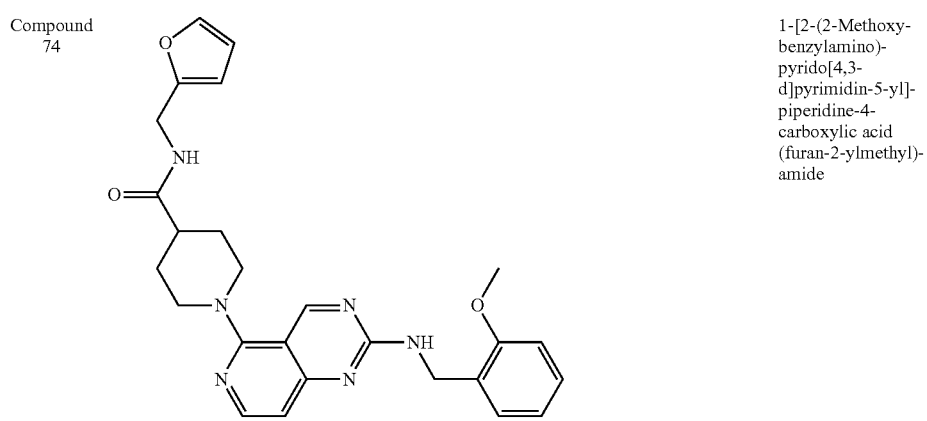 | 1-[2-(2-Methoxy-benzylamino)-pyrido[4,3-d]pyrimidin-5-yl]-piperidine-4-carboxylic acid (furan-2-ylmethyl)-amide |

| | | |
|---|---|---|
| Compound 75 | 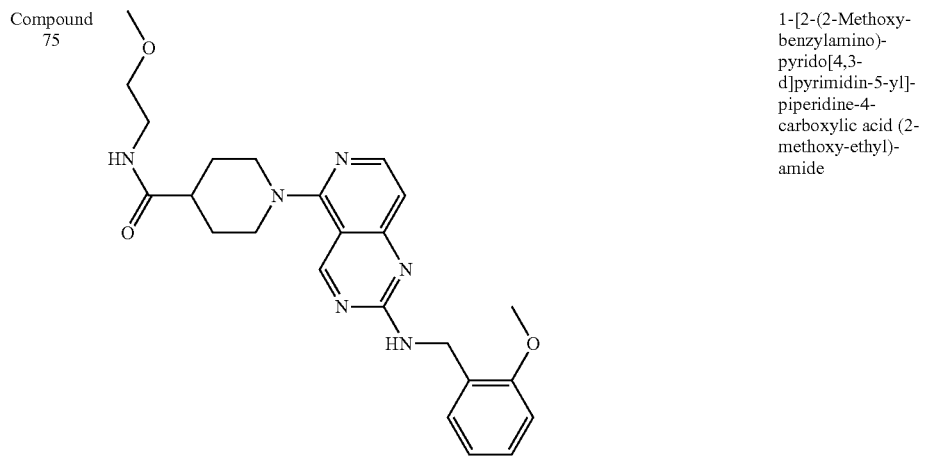 | 1-[2-(2-Methoxy-benzylamino)-pyrido[4,3-d]pyrimidin-5-yl]-piperidine-4-carboxylic acid (2-methoxy-ethyl)-amide |
| Compound 76 | 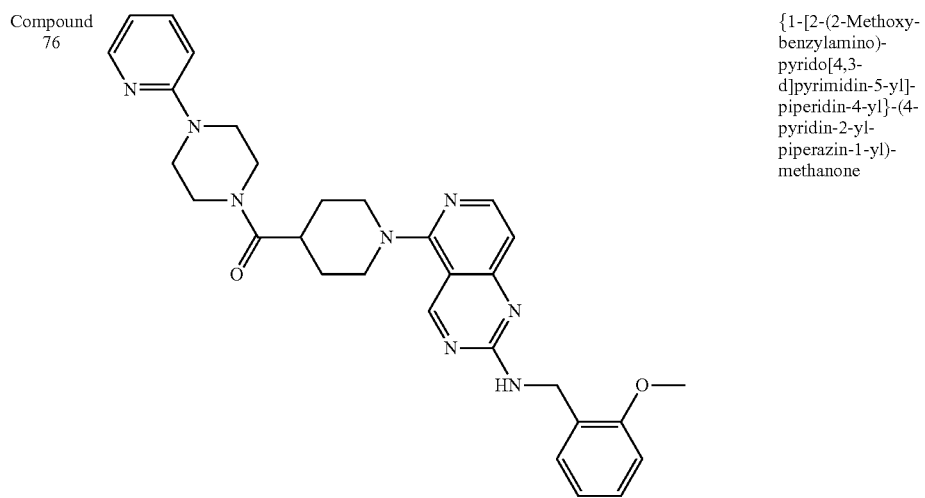 | {1-[2-(2-Methoxy-benzylamino)-pyrido[4,3-d]pyrimidin-5-yl]-piperidin-4-yl}-(4-pyridin-2-yl-piperazin-1-yl)-methanone |
| Compound 77 | 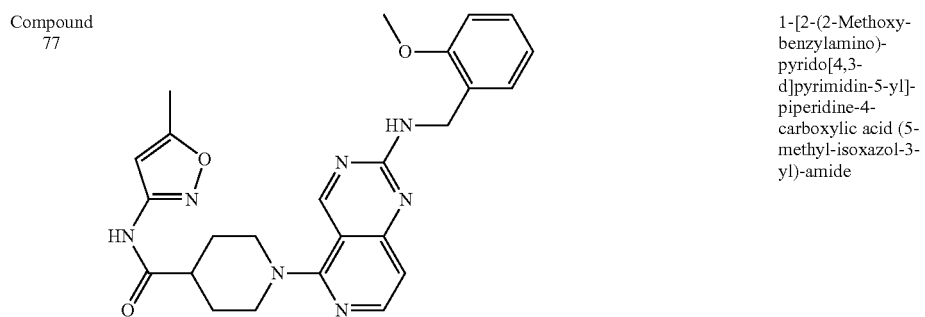 | 1-[2-(2-Methoxy-benzylamino)-pyrido[4,3-d]pyrimidin-5-yl]-piperidine-4-carboxylic acid (5-methyl-isoxazol-3-yl)-amide |

| | | |
|---|---|---|
| Compound 78 | | 1-[2-(4-Chloro-benzylamino)-pyrido[4,3-d]pyrimidin-5-yl]-piperidine-4-carboxylic acid pyridin-3-ylamide |
| Compound 79 | | 1-[2-(4-Chloro-benzylamino)-pyrido[4,3-d]pyrimidin-5-yl]-piperidine-4-carboxylic acid (furan-2-ylmethyl)-amide |
| Compound 80 | | {1-[2-(4-Chloro-benzylamino)-pyrido[4,3-d]pyrimidin-5-yl]-piperidin-4-yl}-pyrrolidin-1-yl-methanone |
| Compound 81 | | 1-[2-(2-Chloro-benzylamino)-pyrido[4,3-d]pyrimidin-5-yl]-piperidine-3-carboxylic acid (pyridin-3-ylmethyl)-amide |

| | | |
|---|---|---|
| Compound 82 | 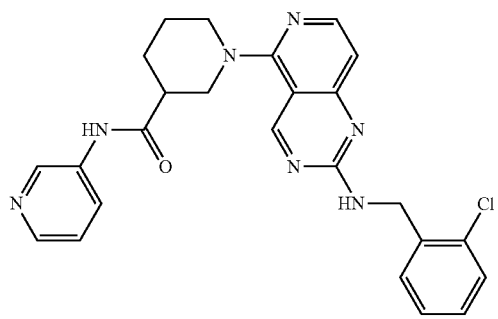 [SMILES: O=C(Nc1cccnc1)C1CCCN(c2nccc3nc(NCc4ccccc4Cl)ncc23)C1] | 1-[2-(2-Chloro-benzylamino)-pyrido[4,3-d]pyrimidin-5-yl]-piperidine-3-carboxylic acid pyridin-3-ylamide |
| Compound 83 | 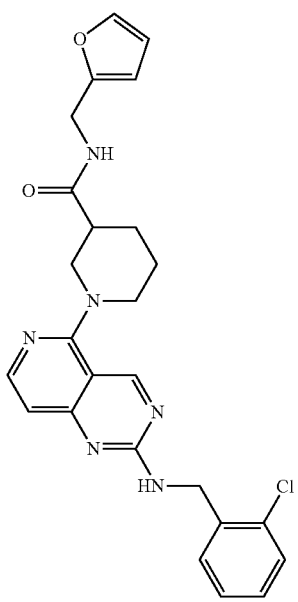 [SMILES: O=C(NCc1ccco1)C1CCCN(c2nccc3nc(NCc4ccccc4Cl)ncc23)C1] | 1-[2-(2-Chloro-benzylamino)-pyrido[4,3-d]pyrimidin-5-yl]-piperidine-3-carboxylic acid (furan-2-ylmethyl)-amide |
| Compound 84 | 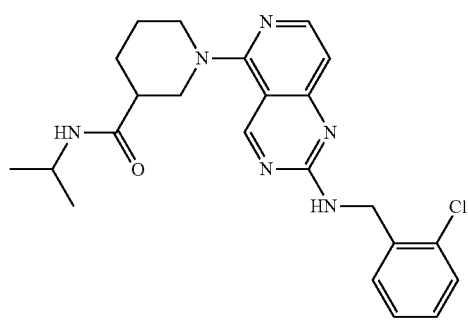 [SMILES: CC(C)NC(=O)C1CCCN(c2nccc3nc(NCc4ccccc4Cl)ncc23)C1] | 1-[2-(2-Chloro-benzylamino)-pyrido[4,3-d]pyrimidin-5-yl]-piperidine-3-carboxylic acid isopropylamide |
| Compound 85 | 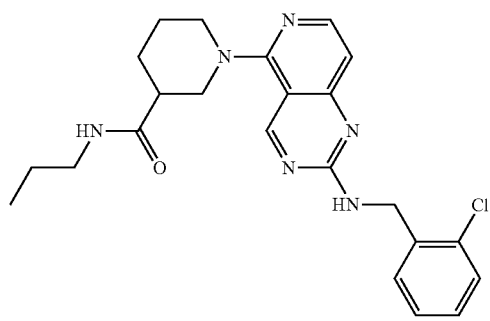 [SMILES: CCCNC(=O)C1CCCN(c2nccc3nc(NCc4ccccc4Cl)ncc23)C1] | 1-[2-(2-Chloro-benzylamino)-pyrido[4,3-d]pyrimidin-5-yl]-piperidine-3-carboxylic acid propylamide |

| | | |
|---|---|---|
| Compound 86 | 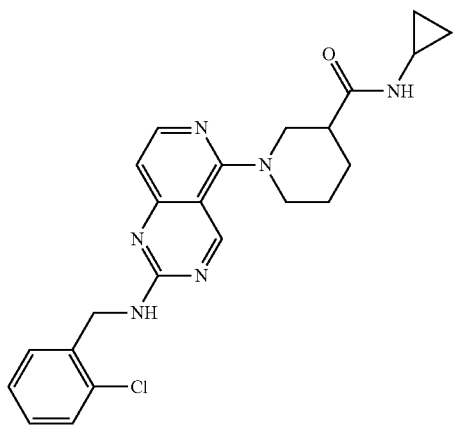 [SMILES: O=C(NC1CC1)C1CCCN(c2nccc3nc(NCc4ccccc4Cl)ncc23)C1] | 1-[2-(2-Chloro-benzylamino)-pyrido[4,3-d]pyrimidin-5-yl]-piperidine-3-carboxylic acid cyclopropylamide |
| Compound 87 | 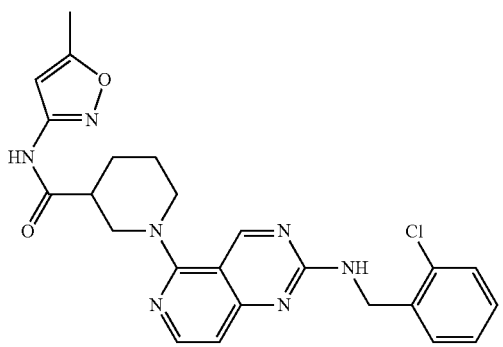 [SMILES: Cc1cc(NC(=O)C2CCCN(c3nccc4nc(NCc5ccccc5Cl)ncc34)C2)no1] | 1-[2-(2-Chloro-benzylamino)-pyrido[4,3-d]pyrimidin-5-yl]-piperidine-3-carboxylic acid (5-methyl-isoxazol-3-yl)-amide |
| Compound 88 | 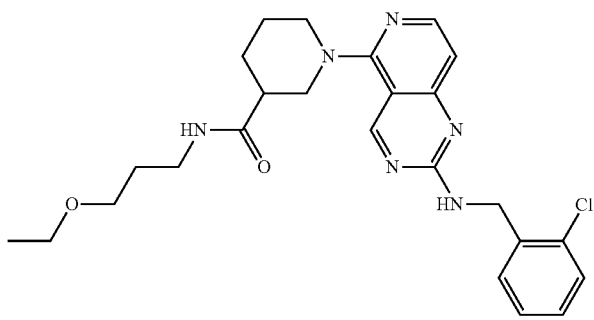 [SMILES: CCOCCCNC(=O)C1CCCN(c2nccc3nc(NCc4ccccc4Cl)ncc23)C1] | 1-[2-(2-Chloro-benzylamino)-pyrido[4,3-d]pyrimidin-5-yl]-piperidine-3-carboxylic acid (3-ethoxy-propyl)-amide |
| Compound 89 | 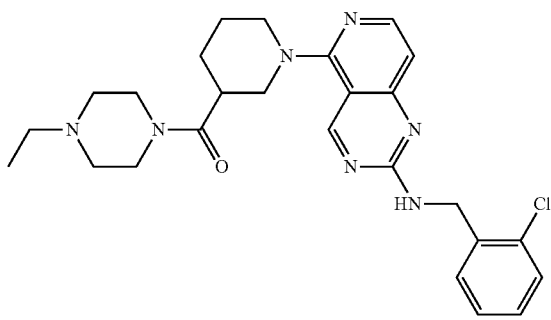 [SMILES: CCN1CCN(C(=O)C2CCCN(c3nccc4nc(NCc5ccccc5Cl)ncc34)C2)CC1] | {1-[2-(2-Chloro-benzylamino)-pyrido[4,3-d]pyrimidin-5-yl]-piperidin-3-yl}-(4-ethyl-piperazin-1-yl)-methanone |

-continued

| | | |
|---|---|---|
| Compound 90 | 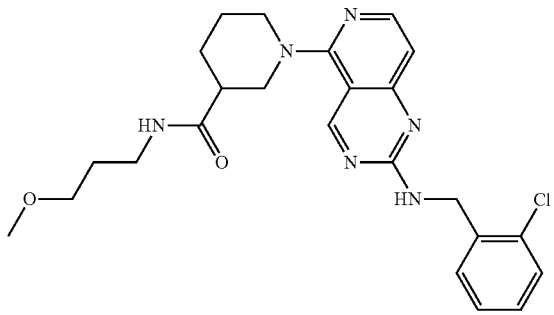 [SMILES: COCCCNC(=O)C1CCCN(c2nccc3nc(NCc4ccccc4Cl)ncc23)C1] | 1-[2-(2-Chloro-benzylamino)-pyrido[4,3-d]pyrimidin-5-yl]-piperidine-3-carboxylic acid (3-methoxy-propyl)-amide |
| Compound 91 | 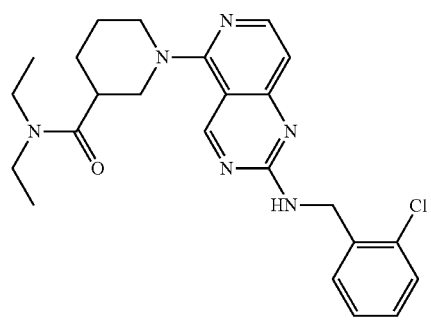 [SMILES: CCN(CC)C(=O)C1CCCN(c2nccc3nc(NCc4ccccc4Cl)ncc23)C1] | 1-[2-(2-Chloro-benzylamino)-pyrido[4,3-d]pyrimidin-5-yl]-piperidine-3-carboxylic acid di-ethylamide |
| Compound 92 | 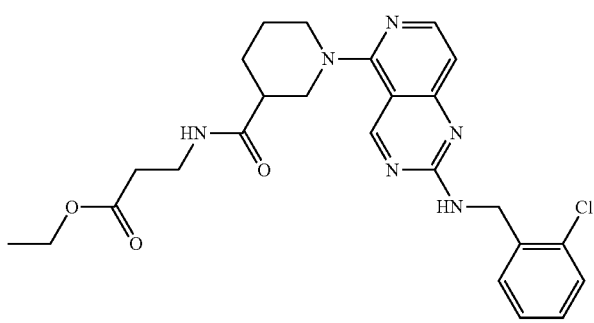 [SMILES: CCOC(=O)CCNC(=O)C1CCCN(c2nccc3nc(NCc4ccccc4Cl)ncc23)C1] | 3-({1-[2-(2-Chloro-benzylamino)-pyrido[4,3-d]pyrimidin-5-yl]-piperidine-3-carbonyl}-amino)-propionic acid ethyl ester |
| Compound 93 | 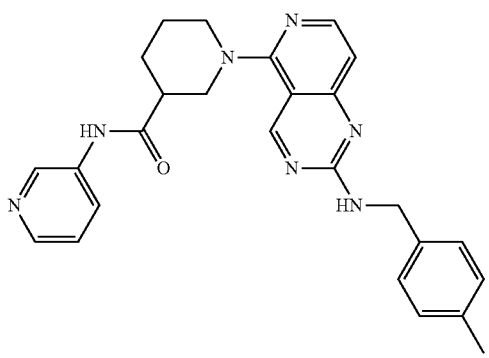 [SMILES: Cc1ccc(CNc2ncc3c(N4CCCC(C(=O)Nc5cccnc5)C4)nccc3n2)cc1] | 1-[2-(4-Methyl-benzylamino)-pyrido[4,3-d]pyrimidin-5-yl]-piperidine-3-carboxylic acid pyri-din-3-ylamide |

| Compound 94 | 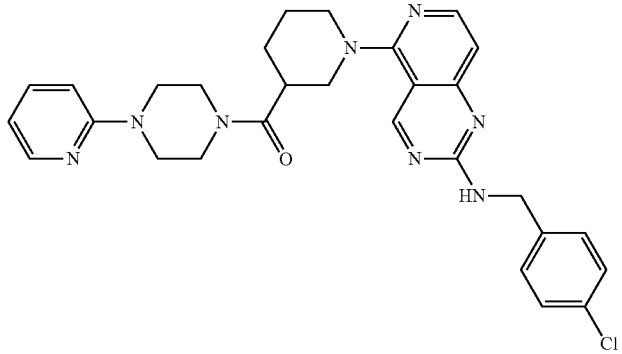 [SMILES: O=C(C1CCCN(c2nccc3nc(NCc4ccc(Cl)cc4)ncc23)C1)N1CCN(c2ccccn2)CC1] | {1-[2-(4-Chloro-benzylamino)-pyrido[4,3-d]pyrimidin-5-yl]-piperidin-3-yl}-(4-pyridin-2-yl-piperazin-1-yl)-methanone |
|---|---|---|
| Compound 95 | 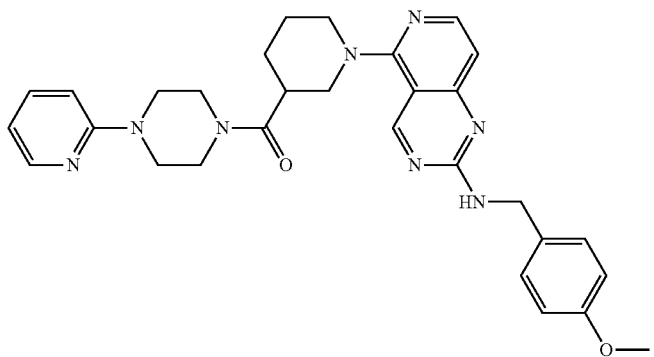 [SMILES: COc1ccc(CNc2ncc3c(N4CCCC(C(=O)N5CCN(c6ccccn6)CC5)C4)nccc3n2)cc1] | {1-[2-(4-Methoxy-benzylamino)-pyrido[4,3-d]pyrimidin-5-yl]-piperidin-3-yl}-(4-pyridin-2-yl-piperazin-1-yl)-methanone |
| Compound 96 | 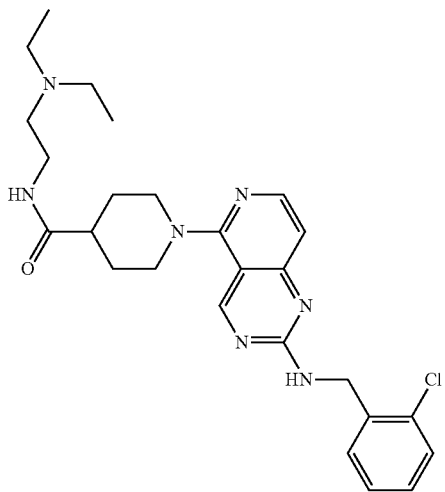 [SMILES: CCN(CC)CCNC(=O)C1CCN(c2nccc3nc(NCc4ccccc4Cl)ncc23)CC1] | 1-[2-(2-Chloro-benzylamino)-pyrido[4,3-d]pyrimidin-5-yl]-piperidine-4-carboxylic acid (2-diethylamino-ethyl)-amide |

-continued

| Compound 97 | | {1-[2-(2-Chloro-benzylamino)-pyrido[4,3-d]pyrimidin-5-yl]-piperidin-4-yl}-(4-propyl-piperazin-1-yl)-methanone |
| Compound 98 | | 1-[2-(2-Chloro-benzylamino)-pyrido[4,3-d]pyrimidin-5-yl]-piperidine-4-carboxylic acid (3-ethoxy-propyl)-amide |
| Compound 99 | | {1-[2-(2-Chloro-benzylamino)-pyrido[4,3-d]pyrimidin-5-yl]-piperidin-3-yl}-(4-pyridin-2-yl-piperazin-1-yl)-methanone |
| Compound 100 | | N2-(2-Chloro-benzyl)-N5-(2-fluoro-phenyl)-pyrido[4,3-d]pyrimidine-2,5-diamine |

| Compound 101 | 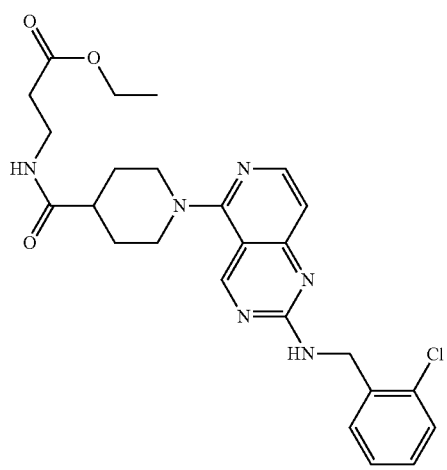 [SMILES: CCOC(=O)CCNC(=O)C1CCN(c2nccc3nc(NCc4ccccc4Cl)ncc23)CC1] | 3-({1-[2-(2-Chloro-benzylamino)-pyrido[4,3-d]pyrimidin-5-yl]-piperidine-4-carbonyl}-amino)-propionic acid ethyl ester |
| Compound 102 | 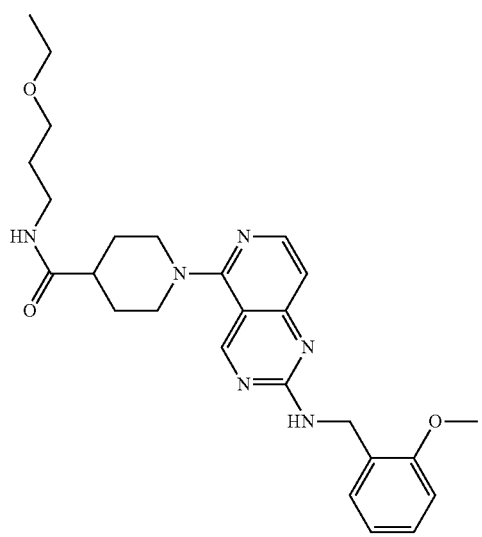 [SMILES: CCOCCCNC(=O)C1CCN(c2nccc3nc(NCc4ccccc4OC)ncc23)CC1] | 1-[2-(2-Methoxy-benzylamino)-pyrido[4,3-d]pyrimidin-5-yl]-piperidine-4-carboxylic acid (3-ethoxy-propyl)-amide |
| Compound 103 | 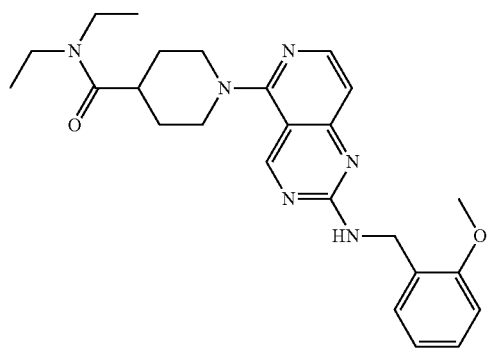 [SMILES: CCN(CC)C(=O)C1CCN(c2nccc3nc(NCc4ccccc4OC)ncc23)CC1] | 1-[2-(2-Methoxy-benzylamino)-pyrido[4,3-d]pyrimidin-5-yl]-piperidine-4-carboxylic acid di-ethylamide |

| | | |
|---|---|---|
| Compound 104 | 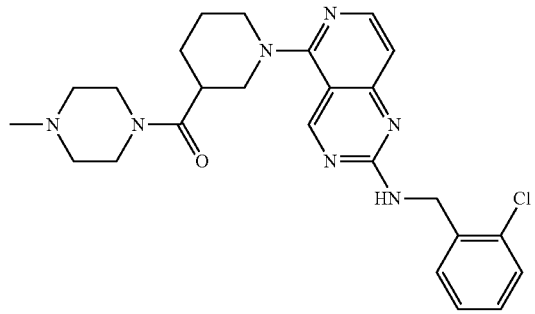 [SMILES: CN1CCN(C(=O)C2CCCN(c3nccc4nc(NCc5ccccc5Cl)ncc34)C2)CC1] | {1-[2-(2-Chloro-benzylamino)-pyrido[4,3-d]pyrimidin-5-yl]-piperidin-3-yl}-(4-methyl-piperazin-1-yl)-methanone |
| Compound 105 | 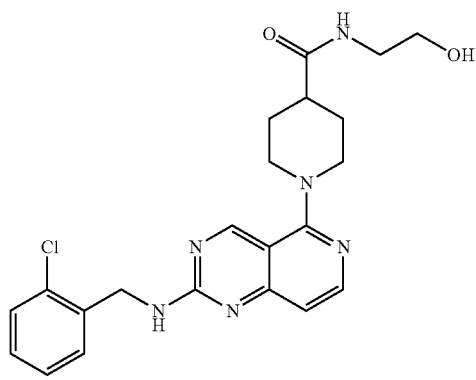 [SMILES: O=C(NCCO)C1CCN(c2nccc3nc(NCc4ccccc4Cl)ncc23)CC1] | 1-[2-(2-Chloro-benzylamino)-pyrido[4,3-d]pyrimidin-5-yl]-piperidine-4-carboxylic acid (2-hydroxy-ethyl)-amide |
| Compound 106 | 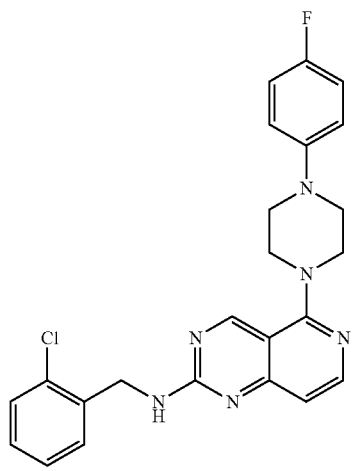 [SMILES: Fc1ccc(N2CCN(c3nccc4nc(NCc5ccccc5Cl)ncc34)CC2)cc1] | (2-Chloro-benzyl)-{5-[4-(4-fluoro-phenyl)-piperazin-1-yl]-pyrido[4,3-d]pyrimidin-2-yl}-amine |
| Compound 107 | 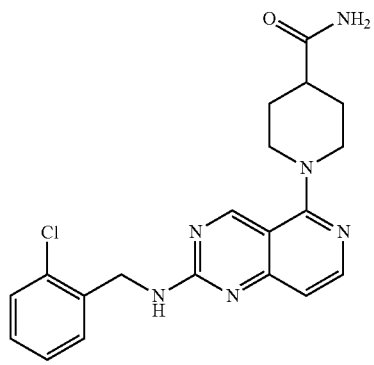 [SMILES: NC(=O)C1CCN(c2nccc3nc(NCc4ccccc4Cl)ncc23)CC1] | 1-[2-(2-Chloro-benzylamino)-pyrido[4,3-d]pyrimidin-5-yl]-piperidine-4-carboxylic acid amide |

| Compound 108 | 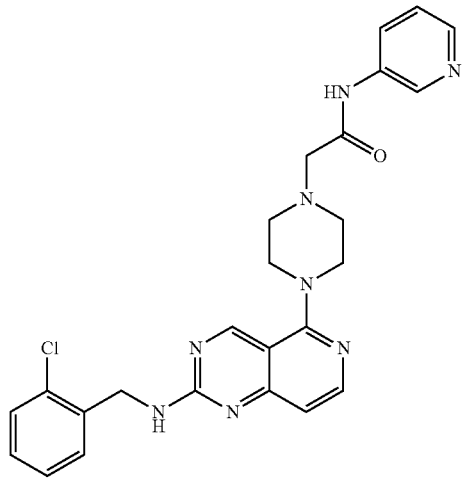 [SMILES: O=C(CN1CCN(c2nccc3nc(NCc4ccccc4Cl)ncc23)CC1)Nc1cccnc1] | 2-{4-[2-(2-Chloro-benzylamino)-pyrido[4,3-d]pyrimidin-5-yl]-piperazin-1-yl}-N-pyridin-3-yl-acetamide |
| Compound 109 | 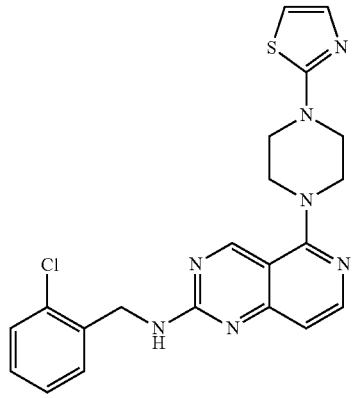 [SMILES: Clc1ccccc1CNc1ncc2c(N3CCN(c4nccs4)CC3)nccc2n1] | (2-Chloro-benzyl)-[5-(4-thiazol-2-yl-piperazin-1-yl)-pyrido[4,3-d]pyrimidin-2-yl]-amine |
| Compound 110 | 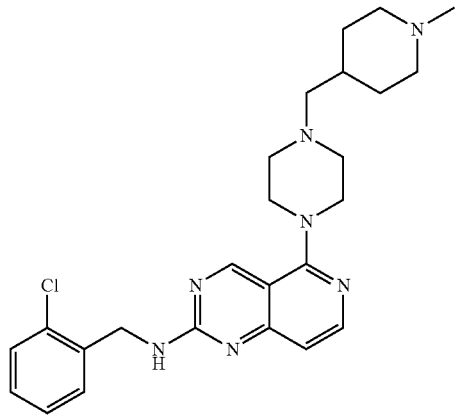 [SMILES: CN1CCC(CN2CCN(c3nccc4nc(NCc5ccccc5Cl)ncc34)CC2)CC1] | (2-Chloro-benzyl)-{5-[4-(1-methyl-piperidin-4-ylmethyl)-piperazin-1-yl]-pyrido[4,3-d]pyrimidin-2-yl}-amine |

-continued
| | | |
|---|---|---|
| Compound 111 | 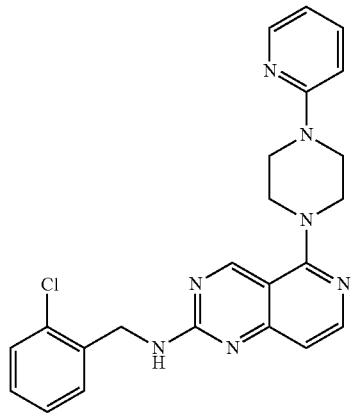 [SMILES: Clc1ccccc1CNc1ncc2c(N3CCN(c4ccccn4)CC3)nccc2n1] | (2-Chloro-benzyl)-[5-(4-pyridin-2-yl-piperazin-1-yl)-pyrido[4,3-d]pyrimidin-2-yl]-amine |
| Compound 112 | 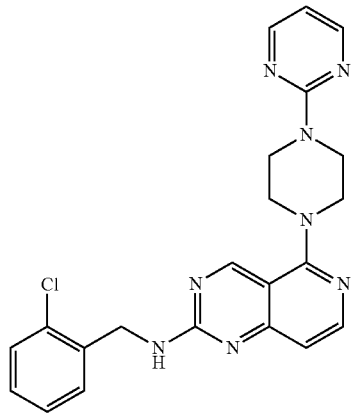 [SMILES: Clc1ccccc1CNc1ncc2c(N3CCN(c4ncccn4)CC3)nccc2n1] | (2-Chloro-benzyl)-[5-(4-pyrimidin-2-yl-piperazin-1-yl)-pyrido[4,3-d]pyrimidin-2-yl]-amine |
| Compound 113 | 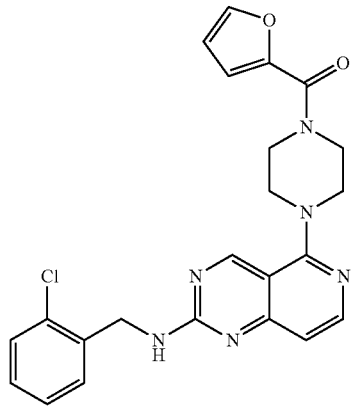 [SMILES: O=C(c1ccco1)N1CCN(c2nccc3nc(NCc4ccccc4Cl)ncc23)CC1] | {4-[2-(2-Chloro-benzylamino)-pyrido[4,3-d]pyrimidin-5-yl]-piperazin-1-yl}-furan-2-yl-methanone |
| Compound 114 | 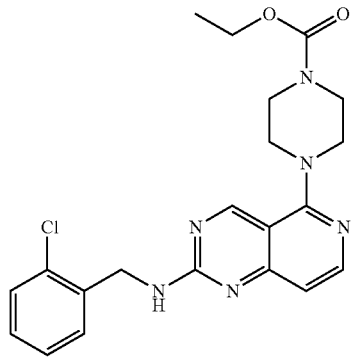 [SMILES: CCOC(=O)N1CCN(c2nccc3nc(NCc4ccccc4Cl)ncc23)CC1] | 4-[2-(2-Chloro-benzylamino)-pyrido[4,3-d]pyrimidin-5-yl]-piperazine-1-carboxylic acid ethyl ester |

| | | |
|---|---|---|
| Compound 115 | 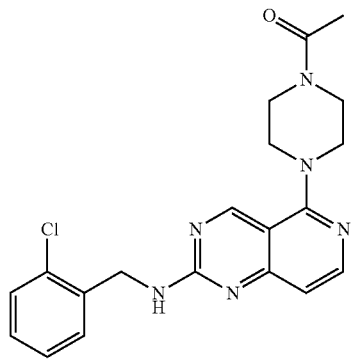 | 1-{4-[2-(2-Chloro-benzylamino)-pyrido[4,3-d]pyrimidin-5-yl]-piperazin-1-yl}-ethanone |
| Compound 116 | 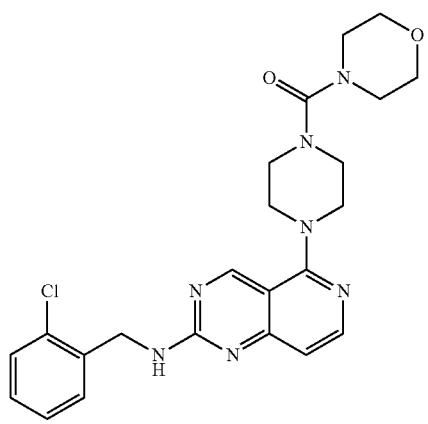 [SMILES: O=C(N1CCOCC1)N1CCN(c2nccc3nc(NCc4ccccc4Cl)ncc23)CC1] | {4-[2-(2-Chloro-benzylamino)-pyrido[4,3-d]pyrimidin-5-yl]-piperazin-1-yl}-morpholin-4-yl-methanone |
| Compound 117 | 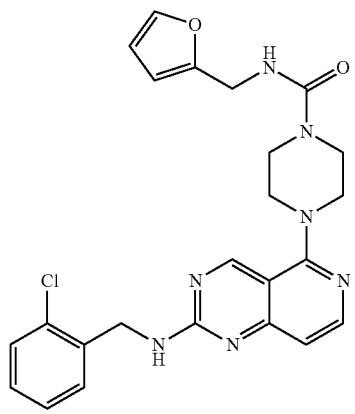 [SMILES: O=C(NCc1ccco1)N1CCN(c2nccc3nc(NCc4ccccc4Cl)ncc23)CC1] | 4-[2-(2-Chloro-benzylamino)-pyrido[4,3-d]pyrimidin-5-yl]-piperazine-1-carboxylic acid (furan-2-ylmethyl)-amide |
| Compound 118 | 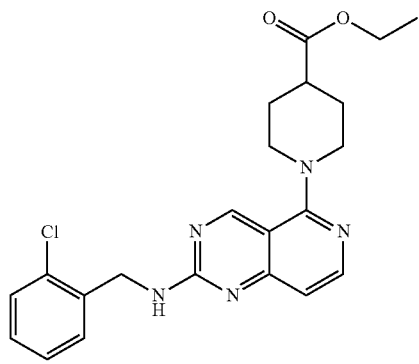 [SMILES: CCOC(=O)C1CCN(c2nccc3nc(NCc4ccccc4Cl)ncc23)CC1] | 1-[2-(2-Chloro-benzylamino)-pyrido[4,3-d]pyrimidin-5-yl]-piperidine-4-carboxylic acid ethyl ester |

| | | |
|---|---|---|
| Compound 119 | 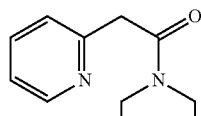 | 1-{4-[2-(2-Chloro-benzylamino)-pyrido[4,3-d]pyrimidin-5-yl]-piperazin-1-yl}-2-pyridin-2-yl-ethanone |
| Compound 120 | 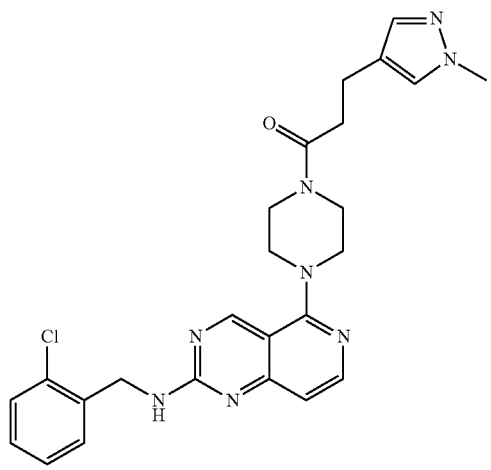 [SMILES: Cn1cc(CCC(=O)N2CCN(c3nccc4nc(NCc5ccccc5Cl)ncc34)CC2)cn1] | 1-{4-[2-(2-Chloro-benzylamino)-pyrido[4,3-d]pyrimidin-5-yl]-piperazin-1-yl}-3-(1-methyl-1H-pyrazol-4-yl)-propan-1-one |
| Compound 121 | 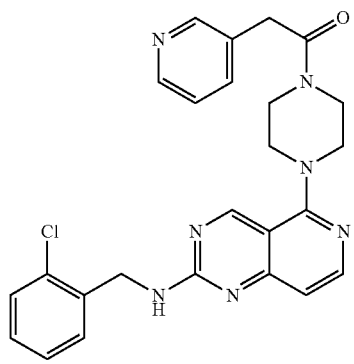 [SMILES: O=C(Cc1cccnc1)N1CCN(c2nccc3nc(NCc4ccccc4Cl)ncc23)CC1] | 1-{4-[2-(2-Chloro-benzylamino)-pyrido[4,3-d]pyrimidin-5-yl]-piperazin-1-yl}-2-pyridin-3-yl-ethanone |
| Compound 122 | 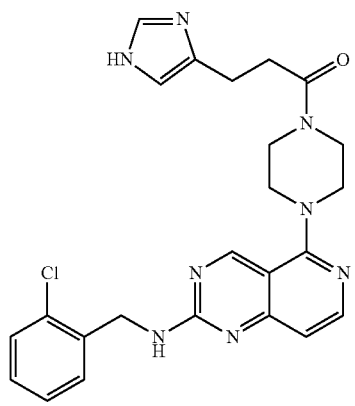 [SMILES: O=C(CCc1c[nH]cn1)N1CCN(c2nccc3nc(NCc4ccccc4Cl)ncc23)CC1] | 1-{4-[2-(2-Chloro-benzylamino)-pyrido[4,3-d]pyrimidin-5-yl]-piperazin-1-yl}-3-(1H-imidazol-4-yl)-propan-1-one |

| | | |
|---|---|---|
| Compound 123 | 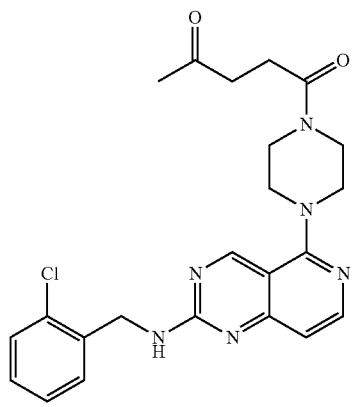 [SMILES: CC(=O)CCC(=O)N1CCN(c2nccc3nc(NCc4ccccc4Cl)ncc23)CC1] | 1-{4-[2-(2-Chloro-benzylamino)-pyrido[4,3-d]pyrimidin-5-yl]-piperazin-1-yl}-pentane-1,4-dione |
| Compound 124 | 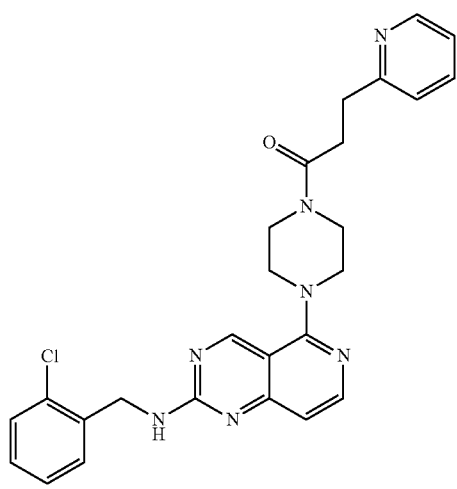 [SMILES: O=C(CCc1ccccn1)N1CCN(c2nccc3nc(NCc4ccccc4Cl)ncc23)CC1] | 1-{4-[2-(2-Chloro-benzylamino)-pyrido[4,3-d]pyrimidin-5-yl]-piperazin-1-yl}-3-pyridin-2-yl-propan-1-one |
| Compound 125 | 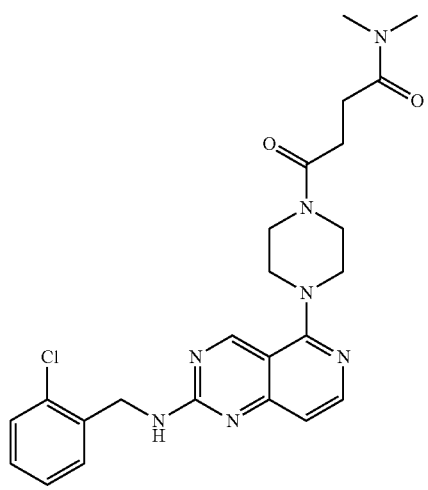 [SMILES: CN(C)C(=O)CCC(=O)N1CCN(c2nccc3nc(NCc4ccccc4Cl)ncc23)CC1] | 4-{4-[2-(2-Chloro-benzylamino)-pyrido[4,3-d]pyrimidin-5-yl]-piperazin-1-yl}-N,N-dimethyl-4-oxo-butyramide |

| | | |
|---|---|---|
| Compound 126 | 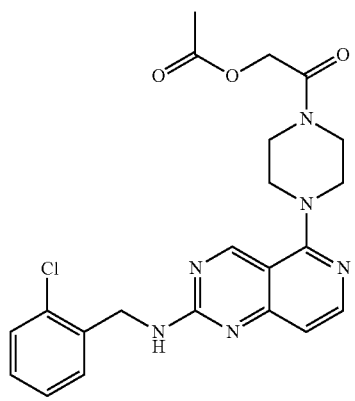 [SMILES: CC(=O)OCC(=O)N1CCN(c2nccc3nc(NCc4ccccc4Cl)ncc23)CC1] | Acetic acid 2-{4-[2-(2-chloro-benzylamino)-pyrido[4,3-d]pyrimidin-5-yl]-piperazin-1-yl}-2-oxo-ethyl ester |
| Compound 128 | 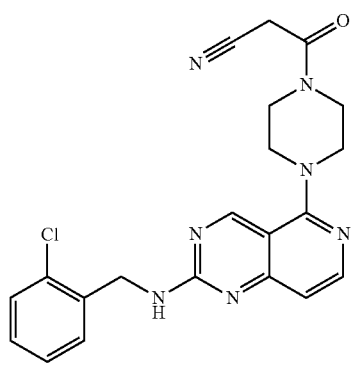 [SMILES: N#CCC(=O)N1CCN(c2nccc3nc(NCc4ccccc4Cl)ncc23)CC1] | 3-{4-[2-(2-Chloro-benzylamino)-pyrido[4,3-d]pyrimidin-5-yl]-piperazin-1-yl}-3-oxo-propionitrile |
| Compound 129 | 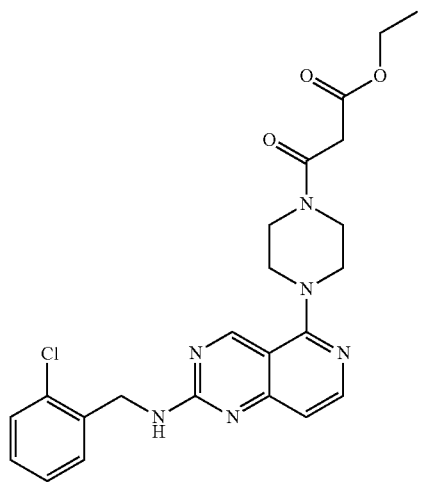 [SMILES: CCOC(=O)CC(=O)N1CCN(c2nccc3nc(NCc4ccccc4Cl)ncc23)CC1] | 3-{4-[2-(2-Chloro-benzylamino)-pyrido[4,3-d]pyrimidin-5-yl]-piperazin-1-yl}-3-oxo-propionic acid ethyl ester |
| Compound 130 | 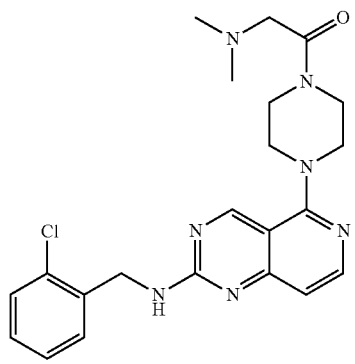 [SMILES: CN(C)CC(=O)N1CCN(c2nccc3nc(NCc4ccccc4Cl)ncc23)CC1] | 1-{4-[2-(2-Chloro-benzylamino)-pyrido[4,3-d]pyrimidin-5-yl]-piperazin-1-yl}-2-dimethylamino-ethanone |

-continued
| | | |
|---|---|---|
| Compound 131 | 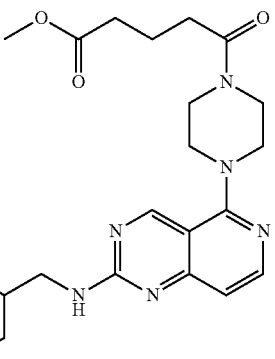 | 5-{4-[2-(2-Chloro-benzylamino)-pyrido[4,3-d]pyrimidin-5-yl]-piperazin-1-yl}-5-oxo-pentanoic acid methyl ester |
| Compound 132 | 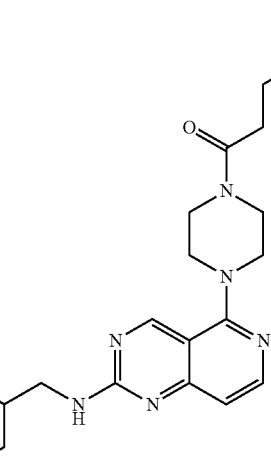 | 4-Amino-1-{4-[2-(2-chloro-benzylamino)-pyrido[4,3-d]pyrimidin-5-yl]-piperazin-1-yl}-butan-1-one |
| Compound 133 | 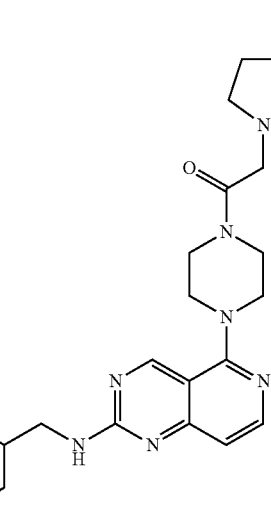 | (S)-3-Amino-1-(2-{4-[2-(2-chloro-benzylamino)-pyrido[4,3-d]pyrimidin-5-yl]-piperazin-1-yl}-2-oxo-ethyl)-pyrrolidin-2-one |
| Compound 134 | 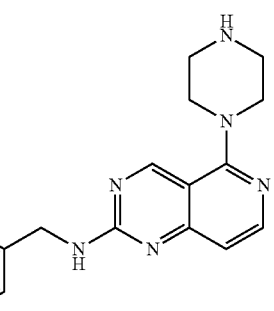 | (2-Chloro-benzyl)-(5-piperazin-1-yl-pyrido[4,3-d]pyrimidin-2-yl)-amine |

| | | |
|---|---|---|
| Compound 135 | 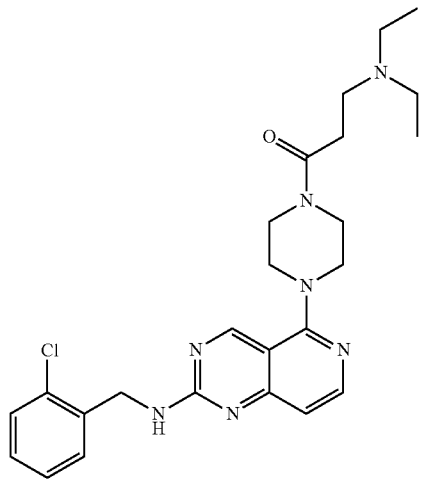 [SMILES: CCN(CC)CCC(=O)N1CCN(c2nccc3nc(NCc4ccccc4Cl)ncc23)CC1] | 1-{4-[2-(2-Chloro-benzylamino)-pyrido[4,3-d]pyrimidin-5-yl]-piperazin-1-yl}-3-diethylamino-propan-1-one |
| Compound 136 | 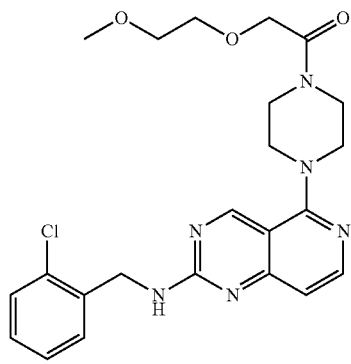 [SMILES: COCCOCC(=O)N1CCN(c2nccc3nc(NCc4ccccc4Cl)ncc23)CC1] | 1-{4-[2-(2-Chloro-benzylamino)-pyrido[4,3-d]pyrimidin-5-yl]-piperazin-1-yl}-2-(2-methoxy-ethoxy)-ethanone |
| Compound 137 | 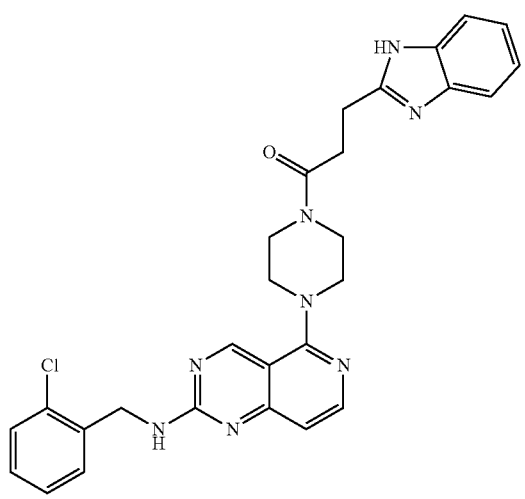 [SMILES: O=C(CCc1nc2ccccc2[nH]1)N1CCN(c2nccc3nc(NCc4ccccc4Cl)ncc23)CC1] | 3-(1H-Benzoimidazol-2-yl)-1-{4-[2-(2-chloro-benzylamino)-pyrido[4,3-d]pyrimidin-5-yl]-piperazin-1-yl}-propan-1-one |

| | | |
|---|---|---|
| Compound 138 | 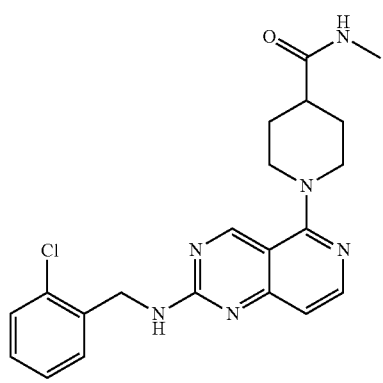 [SMILES: CNC(=O)C1CCN(c2nccc3nc(NCc4ccccc4Cl)ncc23)CC1] | 1-{4-[2-(2-Chloro-benzylamino)-pyrido[4,3-d]pyrimidin-5-yl]-piperazin-1-yl}-2-pyridin-4-yl-ethanone |
| Compound 139 | 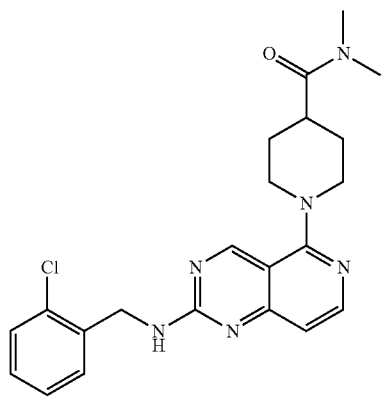 [SMILES: CN(C)C(=O)C1CCN(c2nccc3nc(NCc4ccccc4Cl)ncc23)CC1] | 1-[2-(2-Chloro-benzylamino)-pyrido[4,3-d]pyrimidin-5-yl]-piperidine-4-carboxylic acid methylamide |
| Compound 140 | | 1-[2-(2-Chloro-benzylamino)-pyrido[4,3-d]pyrimidin-5-yl]-piperidine-4-carboxylic acid di-methylamide |
| Compound 141 | 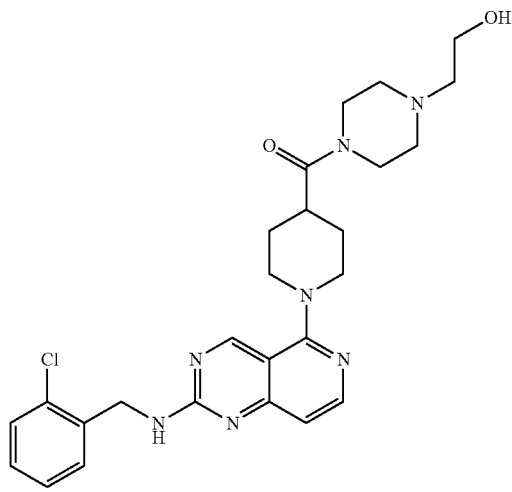 [SMILES: O=C(C1CCN(c2nccc3nc(NCc4ccccc4Cl)ncc23)CC1)N1CCN(CCO)CC1] | {1-[2-(2-Chloro-benzylamino)-pyrido[4,3-d]pyrimidin-5-yl]-piperidin-4-yl}-[4-(2-hydroxy-ethyl)-piperazin-1-yl]-methanone |

| Compound 142 | 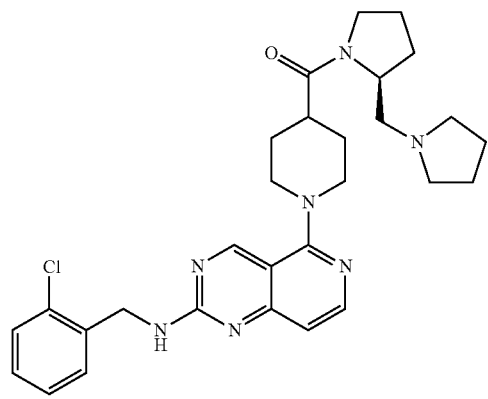 [SMILES: O=C(C1CCN(c2nccc3nc(NCc4ccccc4Cl)ncc23)CC1)N1CCC[C@H]1CN1CCCC1] | {1-[2-(2-Chloro-benzylamino)-pyrido[4,3-d]pyrimidin-5-yl]-piperidin-4-yl}-((S)-2-pyrrolidin-1-ylmethyl-pyrrolidin-1-yl)-methanone |
| --- | --- | --- |
| Compound 143 | 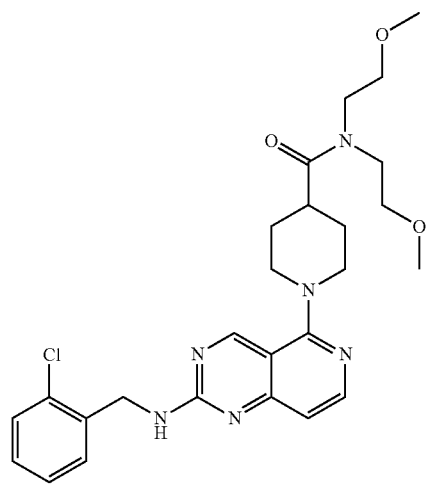 [SMILES: COCCN(CCOC)C(=O)C1CCN(c2nccc3nc(NCc4ccccc4Cl)ncc23)CC1] | 1-[2-(2-Chloro-benzylamino)-pyrido[4,3-d]pyrimidin-5-yl]-piperidine-4-carboxylic acid bis-(2-methoxy-ethyl)-amide |
| Compound 144 | 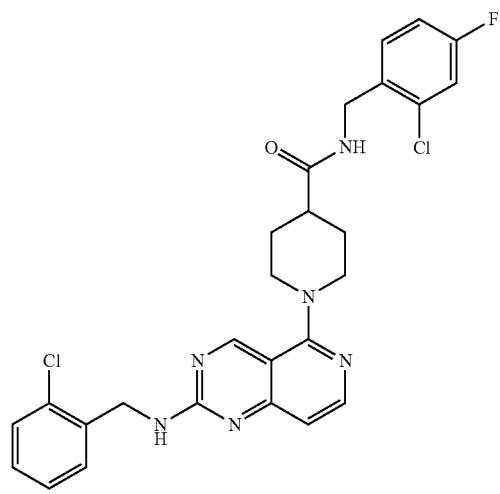 [SMILES: O=C(NCc1ccc(F)cc1Cl)C1CCN(c2nccc3nc(NCc4ccccc4Cl)ncc23)CC1] | 1-[2-(2-Chloro-benzylamino)-pyrido[4,3-d]pyrimidin-5-yl]-piperidine-4-carboxylic acid 2-chloro-4-fluoro-benzylamide |

| Compound 145 | 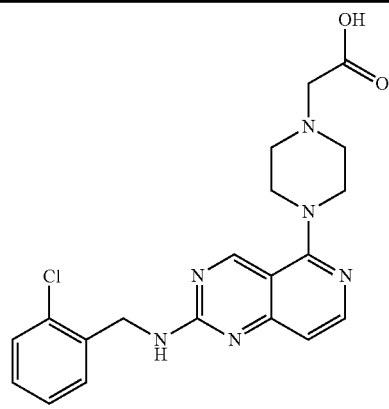 | {4-[2-(2-Chloro-benzylamino)-pyrido[4,3-d]pyrimidin-5-yl]-piperazin-1-yl}-acetic acid |
| Compound 146 | 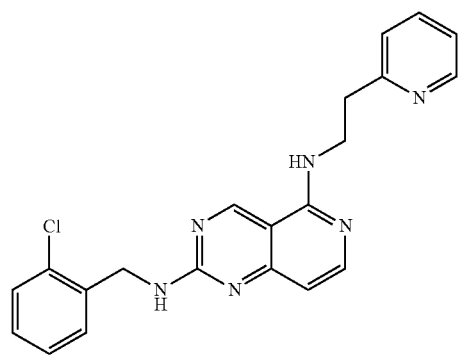 [SMILES: Clc1ccccc1CNc1ncc2c(NCCc3ccccn3)nccc2n1] | N2-(2-Chloro-benzyl)-N5-(2-pyridin-2-yl-ethyl)-pyrido[4,3-d]pyrimidine-2,5-diamine |
| Compound 147 | 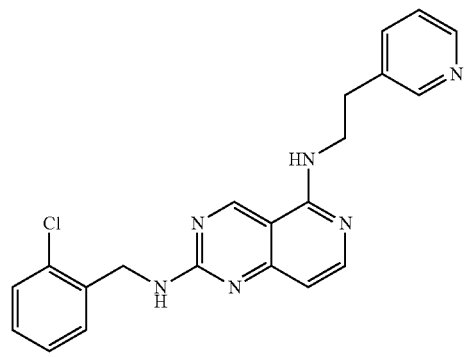 [SMILES: Clc1ccccc1CNc1ncc2c(NCCc3cccnc3)nccc2n1] | N2-(2-Chloro-benzyl)-N5-(2-pyridin-3-yl-ethyl)-pyrido[4,3-d]pyrimidine-2,5-diamine |
| Compound 148 | 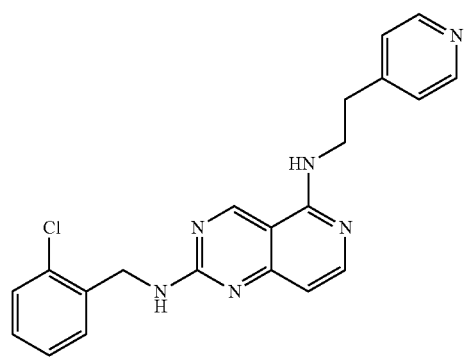 [SMILES: Clc1ccccc1CNc1ncc2c(NCCc3ccncc3)nccc2n1] | N2-(2-Chloro-benzyl)-N5-(2-pyridin-4-yl-ethyl)-pyrido[4,3-d]pyrimidine-2,5-diamine |

-continued
| Compound 149 | 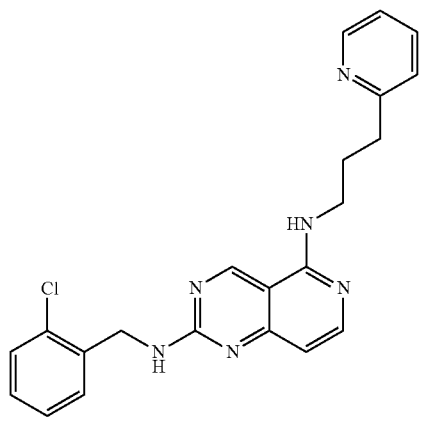 [SMILES: Clc1ccccc1CNc1ncc2c(NCCCc3ccccn3)nccc2n1] | N2-(2-Chloro-benzyl)-N5-(3-pyridin-2-yl-propyl)-pyrido[4,3-d]pyrimidine-2,5-diamine |
| Compound 150 | 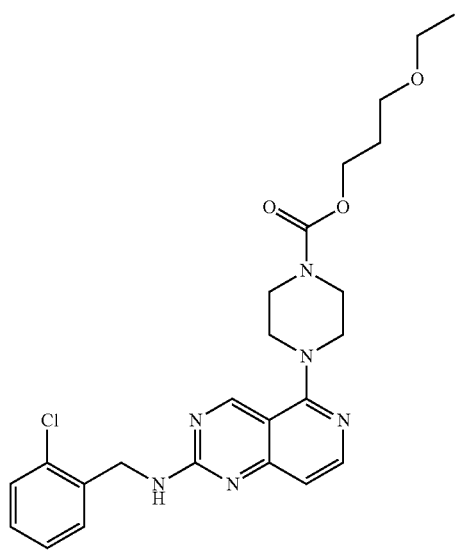 [SMILES: CCOCCCOC(=O)N1CCN(c2nccc3nc(NCc4ccccc4Cl)ncc23)CC1] | 4-[2-(2-Chloro-benzylamino)-pyrido[4,3-d]pyrimidin-5-yl]-piperazine-1-carboxylic acid 3-ethoxy-propyl ester |
| Compound 151 | 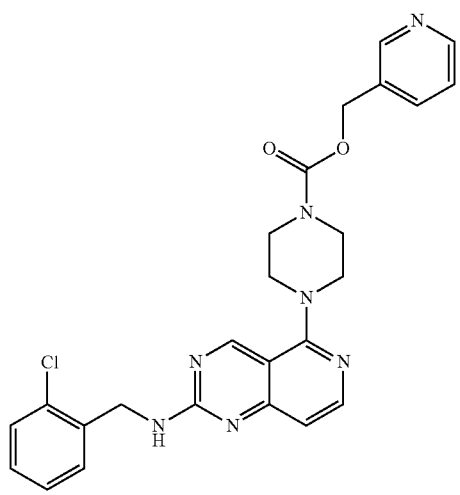 [SMILES: O=C(OCc1cccnc1)N1CCN(c2nccc3nc(NCc4ccccc4Cl)ncc23)CC1] | 4-[2-(2-Chloro-benzylamino)-pyrido[4,3-d]pyrimidin-5-yl]-piperazine-1-carboxylic acid pyridin-3-ylmethyl ester |

| Compound 152 | 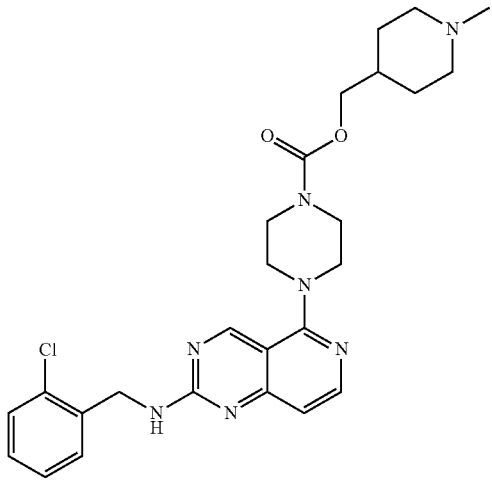 [SMILES: CN1CCC(COC(=O)N2CCN(c3nccc4nc(NCc5ccccc5Cl)ncc34)CC2)CC1] | 4-[2-(2-Chloro-benzylamino)-pyrido[4,3-d]pyrimidin-5-yl]-piperazine-1-carboxylic acid 1-methyl-piperidin-4-ylmethyl ester |
| Compound 153 | 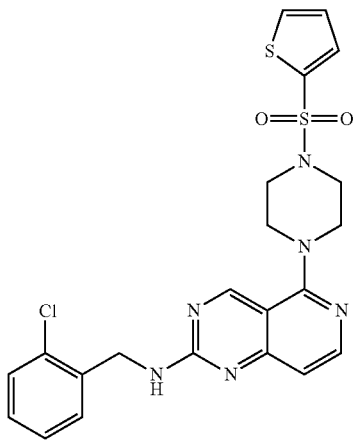 [SMILES: O=S(=O)(c1cccs1)N1CCN(c2nccc3nc(NCc4ccccc4Cl)ncc23)CC1] | (2-Chloro-benzyl)-{5-[4-(thiophene-2-sulfonyl)-piperazin-1-yl]-pyrido[4,3-d]pyrimidin-2-yl}-amine |
| Compound 154 | 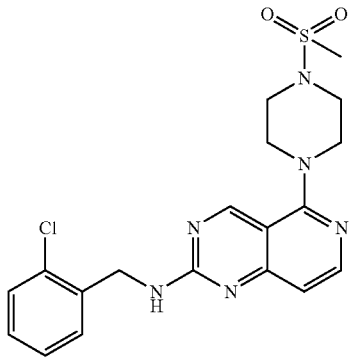 [SMILES: CS(=O)(=O)N1CCN(c2nccc3nc(NCc4ccccc4Cl)ncc23)CC1] | (2-Chloro-benzyl)-[5-(4-methanesulfonyl-piperazin-1-yl)-pyrido[4,3-d]pyrimidin-2-yl]-amine |

| Compound 155 | 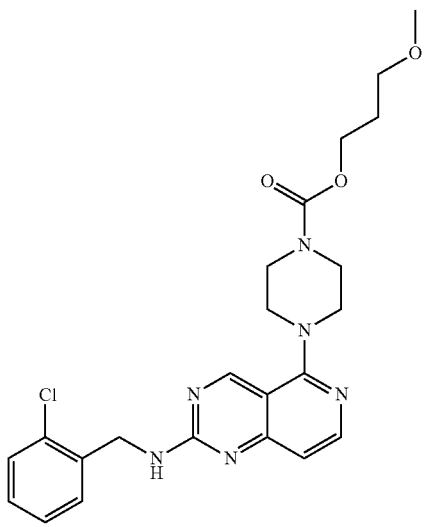 [SMILES: COCCCOC(=O)N1CCN(c2nccc3nc(NCc4ccccc4Cl)ncc23)CC1] | 4-[2-(2-Chloro-benzylamino)-pyrido[4,3-d]pyrimidin-5-yl]-piperazine-1-carboxylic acid 3-methoxy-propyl ester |
| Compound 156 | 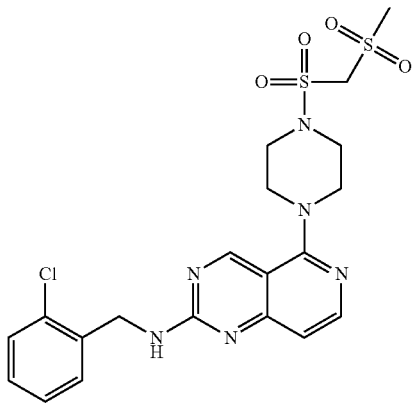 [SMILES: CS(=O)(=O)CS(=O)(=O)N1CCN(c2nccc3nc(NCc4ccccc4Cl)ncc23)CC1] | (2-Chloro-benzyl)-[5-(4-methanesulfonyl-methanesulfonyl-piperazin-1-yl)-pyrido[4,3-d]pyrimidin-2-yl]-amine |
| Compound 157 | 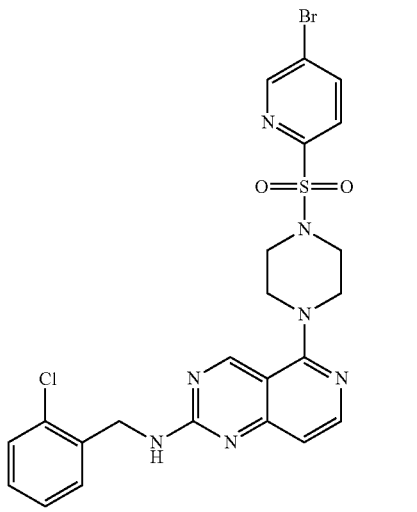 [SMILES: O=S(=O)(c1ccc(Br)cn1)N1CCN(c2nccc3nc(NCc4ccccc4Cl)ncc23)CC1] | {5-[4-(5-Bromo-pyridine-2-sulfonyl)-piperazin-1-yl]-pyrido[4,3-d]pyrimidin-2-yl}-(2-chloro-benzyl)-amine | the physiologically acceptable salts, derivatives, prodrugs, solvates and stereoisomers thereof, including mixtures thereof in all ratios.

For the avoidance of doubt, if chemical name and chemical structure of the above illustrated compounds do not correspond by mistake, the chemical structure is regarded to unambiguously define the compound.

All the above generically or explicitly disclosed pyridopyrimidine derivatives, including preferred subsets/embodiments of the herein disclosed formula (I) and Compounds 1 to 157, are hereinafter referred to as compounds of the (present) invention.

The nomenclature as used herein for defining compounds, especially the compounds according to the invention, is in general based on the rules of the IUPAC organisation for chemical compounds and especially organic compounds.

The terms indicated for explanation of the above compounds of the invention always, unless indicated otherwise in the description or in the claims, have the following meanings:

The term "unsubstituted" means that the corresponding radical, group or moiety has no substituents.

The term "substituted" means that the corresponding radical, group or moiety has one or more substituents. Where a radical has a plurality of substituents, and a selection of various substituents is specified, the substituents are selected independently of one another and do not need to be identical.

The terms "alkyl" or "A" as well as other groups having the prefix "alk" for the purposes of this invention refer to acyclic saturated or unsaturated hydrocarbon radicals which may be branched or straight-chain and preferably have 1 to 8 carbon atoms, i.e. $C_1$-$C_8$-alkenyls, $C_2$-$C_8$-alkenyls and $C_2$-$C_8$-alkynyls. Alkenyls have at least one C—C double bond and alkynyls at least one C—C triple bond. Alkynyls may additionally also have at least one C—C double bond. Examples of suitable alkyl radicals are methyl, ethyl, n-propyl, isopropyl, n-butyl, isobutyl, sec-butyl, tert-butyl, n-pentyl, iso-pentyl, neo-pentyl, tert-pentyl, 2- or 3-methyl-pentyl, n-hexyl, 2-hexyl, isohexyl, n-heptyl, n-octyl, n-nonyl, n-decyl, n-undecyl, n-dodecyl, n-tetradecyl, n-hexadecyl, n-octadecyl, n-icosanyl, n-docosenyl, ethylenyl (vinyl), propenyl (—$CH_2CH$=$CH_2$; —CH=CH—$CH_3$, —C(=$CH_2$)—$CH_3$), butenyl, pentenyl, hexenyl, heptenyl, octenyl, octadienyl, octadecenyl, octadec-9-enyl, icosenyl, icos-11-enyl, (Z)-icos-11-enyl, docosenyl, docos-13-enyl, (Z)-docos-13-enyl, ethynyl, propynyl (—$CH_2$—C≡CH, —C≡C—$CH_3$), butynyl, pentynyl, hexynyl, heptynyl, octynyl. Especially preferred is $C_{1-4}$-alkyl. A $C_{1-4}$-alkyl radical is for example a methyl, ethyl, propyl, isopropyl, butyl, isobutyl, tert-butyl.

The term "($C_9$-$C_{30}$)alkyl" for the purposes of this invention refers to acyclic saturated or unsaturated hydrocarbon radicals which may be branched or straight-chain and have 9 to 30 carbon atoms, i.e. $C_{9-30}$-alkenyls, $C_{9-30}$-alkenyls and $C_{9-30}$-alkynyls. $C_{9-30}$-Alkenyls have at least one C—C double bond and $C_{9-30}$-alkynyls at least one C—C triple bond. $C_{9-30}$-Alkynyls may additionally also have at least one C—C double bond. Examples of suitable ($C_9$-$C_{30}$)alkyl radicals are tetradecyl, hexadecyl, octadecyl, eicosanyl, cis-13-docosenyl (erucyl), trans-13-docosenyl (brassidyl), cis-15-tetracosenyl (nervonyl) and trans-15-tetracosenyl.

The term "cycloalkyl" for the purposes of this invention refers to saturated and partially unsaturated non-aromatic cyclic hydrocarbon groups/radicals, having 1 to 3 rings, that contain 3 to 20, preferably 3 to 12, most preferably 3 to 8 carbon atoms. The cycloalkyl radical may also be part of a bi- or polycyclic system, where, for example, the cycloalkyl radical is fused to an aryl, heteroaryl or heterocyclyl radical as defined herein by any possible and desired ring member(s). The bonding to the compounds of the general formula can be effected via any possible ring member of the cycloalkyl radical. Examples of suitable cycloalkyl radicals are cyclopropyl, cyclobutyl, cyclopentyl, cyclohexyl, cycloheptyl, cyclooctyl, cyclodecyl, cyclohexenyl, cyclopentenyl and cyclooctadienyl. Especially preferred are $C_3$-$C_9$-cycloalkyl and $C_4$-$C_8$-cycloalkyl. A $C_4$-$C_8$-cycloalkyl radical is for example a cyclobutyl, cyclopentyl, cyclohexyl, cycloheptyl, cyclooctyl.

The term "heterocyclyl" for the purposes of this invention refers to a mono- or polycyclic system of 3 to 20, preferably 5 or 6 to 14 ring atoms comprising carbon atoms 1, 2, 3, 4, or 5 heteroatoms, in particular nitrogen, oxygen and/or sulfur which are identical or different. The cyclic system may be saturated, mono- or polyunsaturated but may not be aromatic. In the case of a cyclic system consisting of at least two rings the rings may be fused or spiro- or otherwise connected. Such "heterocyclyl" radicals can be linked via any ring member. The term "heterocyclyl" also includes systems in which the heterocycle is part of a bi- or polycyclic saturated, partially unsaturated and/or aromatic system, such as where the heterocycle is fused to an "aryl", "cycloalkyl", "heteroaryl" or "heterocyclyl" group as defined herein via any desired and possible ring member of the heterocycyl radical. The bonding to the compounds of the general formula can be effected via any possible ring member of the heterocycyl radical. Examples of suitable "heterocyclyl" radicals are pyrrolidinyl, thiapyrrolidinyl, piperidinyl, piperazinyl, oxopiperazinyl, oxopiperidinyl, oxadiazolyl, tetrahydrofuryl, imidazolidinyl, thiazolidinyl, tetrahydropyranyl, morpholinyl, tetrahydrothiophenyl, dihydropyranyl, indolinyl, indolinylmethyl, imidazolidinyl, 2-aza-bicyclo[2.2.2]octanyl.

The term "aryl" for the purposes of this invention refers to a mono- or polycyclic aromatic hydrocarbon systems having 3 to 14, preferably 5 to 14, more preferably 6 to 10 carbon atoms. The term "aryl" also includes systems in which the aromatic cycle is part of a bi- or polycyclic saturated, partially unsaturated and/or aromatic system, such as where the aromatic cycle is fused to an "aryl", "cycloalkyl", "heteroaryl" or "heterocyclyl" group as defined herein via any desired and possible ring member of the aryl radical. The bonding to the compounds of the general formula can be effected via any possible ring member of the aryl radical. Examples of suitable "aryl" radicals are phenyl, biphenyl, naphthyl, 1-naphthyl, 2-naphthyl and anthracenyl, but likewise indanyl, indenyl, or 1,2,3,4-tetrahydronaphthyl. The most preferred aryl is phenyl.

The term "heteroaryl" for the purposes of this invention refers to a 3 to 15, preferably 5 to 14, more preferably 5-, 6- or 7-membered mono- or polycyclic aromatic hydrocarbon radical which comprises at least 1, where appropriate also 2, 3, 4 or 5 heteroatoms, preferably nitrogen, oxygen and/or sulfur, where the heteroatoms are identical or different. The number of nitrogen atoms is preferably 0, 1, 2, or 3, and that of the oxygen and sulfur atoms is independently 0 or 1. The term "heteroaryl" also includes systems in which the aromatic cycle is part of a bi- or polycyclic saturated, partially unsaturated and/or aromatic system, such as where the aromatic cycle is fused to an "aryl", "cycloalkyl", "heteroaryl" or "heterocyclyl" group as defined herein via any desired and possible ring member of the heteroaryl radical. The bonding to the compounds of the general formula can be effected via any possible ring member of the heteroaryl radical. Examples of suitable "heteroaryl" are acridinyl, benzodioxinyl, benzimidazolyl, benzisoxazolyl, benzodioxolyl, benzofuranyl, benzothiadiazolyl, benzothiazolyl, benzothienyl, benzoxazolyl, carbazolyl, cinnolinyl, dibenzofuranyl, dihydrobenzothienyl, furanyl, furazanyl, furyl, imidazolyl, indazolyl, indolinyl, indolizinyl, indolyl, isobenzylfuranyl, isoindolyl, isoquinolinyl, isoquinolyl, isothiazolyl, isoxazolyl, naphthyridinyl, oxadiazolyl, oxazolyl, phenazinyl, phenothiazinyl, phenoxazinyl, phthalazinyl, pteridinyl, purinyl, pyrazinyl, pyrazolyl, pyridazinyl, pyridinyl, pyridyl, pyrimidinyl, pyrimidyl, pyrrolyl, quinazolinyl, quinolinyl, quinolyl, quinoxalinyl, tetrazolyl, thiadiazolyl, thiazolyl, thienyl, thiophenyl, triazinyl, triazolyl.

For the purposes of the present invention, the terms "alkyl-cycloalkyl", "cycloalkylalkyl", "alkyl-heterocyclyl", "heterocyclylalkyl", "alkyl-aryl", "arylalkyl", "alkyl-heteroaryl" and "heteroarylalkyl" mean that alkyl, cycloalkyl, heterocycyl, aryl and heteroaryl are each as defined above, and the cycloalkyl, heterocyclyl, aryl and heteroaryl radical is bonded to the compounds of the general formula via an alkyl radical, preferably $C_1$-$C_8$-alkyl radical, more preferably $C_1$-$C_4$-alkyl radical.

The term "alkyloxy" or "alkoxy" for the purposes of this invention refers to an alkyl radical according to above definition that is attached to an oxygen atom. The attachment to the compounds of the general formula is via the oxygen atom. Examples are methoxy, ethoxy and n-propyloxy, propoxy, isopropoxy. Preferred is "$C_1$-$C_4$-alkyloxy" having the indicated number of carbon atoms.

The term "cycloalkyloxy" or "cycloalkoxy" for the purposes of this invention refers to a cycloalkyl radical according to above definition that is attached to an oxygen atom. The attachment to the compounds of the general formula is via the oxygen atom. Examples are cyclopropyloxy, cyclobutyloxy, cyclopentyloxy, cyclohexyloxy, cycloheptyloxy, cyclooctyloxy. Preferred is "$C_3$-$C_9$cycloalkyloxy" having the indicated number of carbon atoms.

The term "heterocyclyloxy" for the purposes of this invention refers to a heterocyclyl radical according to above definition that is attached to an oxygen atom. The attachment to the compounds of the general formulae is via the oxygen atom. Examples are pyrrolidinyloxy, thiapyrrolidinyloxy, piperidinyloxy, piperazinyloxy.

The term "aryloxy" for the purposes of this invention refers to an aryl radical according to above definition that is attached to an oxygen atom. The attachment to the compounds of the general formula is via the oxygen atom. Examples are phenyloxy, 2-naphthyloxy, 1-naphthyloxy, biphenyloxy, indanyloxy. Preferred is phenyloxy.

The term "heteroaryloxy" for the purposes of this invention refers to a heteroaryl radical according to above definition that is attached to an oxygen atom. The attachment to the compounds of the general formula is via the oxygen atom. Examples are pyrrolyloxy, thienyloxy, furyloxy, imidazolyloxy, thiazolyloxy.

The term "carbonyl" or "carbonyl moiety" for the purposes of this invention refers to a —C(O)— group.

The term "alkylcarbonyl" for the purposes of this invention refers to a "alkyl-C(O)—" group, wherein alkyl is as defined herein.

The term "alkoxycarbonyl" or "alkyloxycarbonyl" for the purposes of this invention refers to a "alkyl-O—C(O)—" group, wherein alkyl is as defined herein.

The term "alkoxyalkyl" for the purposes of this invention refers to a "alkyl-O-alkyl-" group, wherein alkyl is as defined herein.

The term "haloalkyl" for the purposes of this invention refers to an alkyl group as defined herein comprising at least one carbon atom substituent with at least one halogen as defined herein.

The term "halogen", "halogen atom", "halogen substituent" or "Hal" for the purposes of this invention refers to one or, where appropriate, a plurality of fluorine (F, fluoro), bromine (Br, bromo), chlorine (Cl, chloro), or iodine (I, iodo) atoms. The designations "dihalogen", "trihalogen" and "perhalogen" refer respectively to two, three and four substituents, where each substituent can be selected independently from the group consisting of fluorine, chlorine, bromine and iodine. "Halogen" preferably means a fluorine, chlorine or bromine atom. Fluorine is most preferred, when the halogens are substituted on an alkyl (haloalkyl) or alkoxy group (e.g. $CF_3$ and $CF_3O$).

The term "hydroxyl" or "hydroxy" means an OH group.

The term "composition", as in pharmaceutical composition, for the purposes of this invention is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

The terms "administration of" and "administering a" compound should be understood to mean providing a compound of the invention or a prodrug of a compound of the invention to the individualist need.

As used herein, the term "effective amount" refers to any amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

All stereoisomers of the compounds of the invention are contemplated, either in a mixture or in pure or substantially pure form. The compounds of the invention can have asymmetric centers at any of the carbon atoms. Consequently, they can exist in the form of their racemates, in the form of the pure enantiomers and/or diastereomers or in the form of mixtures of these enantiomers and/or diastereomers. The mixtures may have any desired mixing ratio of the stereoisomers.

Thus, for example, the compounds of the invention which have one or more centers of chirality and which occur as racemates or as diastereomer mixtures can be fractionated by methods known per se into their optical pure isomers, i.e. enantiomers or diastereomers. The separation of the compounds of the invention can take place by column separation on chiral or nonchiral phases or by recrystallization from an optionally optically active solvent or with use of an optically active acid or base or by derivatization with an optically active reagent such as, for example, an optically active alcohol, and subsequent elimination of the radical.

The compounds of the invention may be present in the form of their double bond isomers as "pure" E or Z isomers, or in the form of mixtures of these double bond isomers.

Where possible, the compounds of the invention may be in the form of the tautomers, such as keto-enol tautomers.

It is likewise possible for the compounds of the invention to be in the form of any desired prodrugs such as, for example, esters, carbonates, carbamates, ureas, amides phosphates, in which cases the actually biologically active form is released only through metabolism. Any compound that can be converted in vivo to provide the bioactive agent (i.e. compounds of the invention) is a prodrug within the scope and spirit of the invention.

Various forms of prodrugs are well known in the art and are described for instance in:
 (i) Wermuth C G et al., Chapter 31: 671-696, The Practice of Medicinal Chemistry, Academic Press 1996;
 (ii) Bundgaard H, Design of Prodrugs, Elsevier 1985; and
 (iii) Bundgaard H, Chapter 5: 131-191, A Textbook of Drug Design and Development, Harwood Academic Publishers 1991.

Said references are incorporated herein by reference.

It is further known that chemical substances are converted in the body into metabolites which may where appropriate likewise elicit the desired biological effect—in some circumstances even in more pronounced form.

Any biologically active compound that was converted in vivo by metabolism from any of the compounds of the invention is a metabolite within the scope and spirit of the invention.

The compounds of the invention can, if they have a sufficiently basic group such as, for example, a secondary or tertiary amine, be converted with inorganic and organic acids into salts. The pharmaceutically acceptable salts of the compounds of the invention are preferably formed with hydrochloric acid, hydrobromic acid, iodic acid, sulfuric acid, phosphoric acid, methanesulfonic acid, p-toluenesulfonic acid, carbonic acid, formic acid, acetic acid, sulfoacetic acid, trifluoroacetic acid, oxalic acid, malonic acid, maleic acid, succinic acid, tartaric acid, racemic acid, malic acid, embonic acid, mandelic acid, fumaric acid, lactic acid, citric acid, taurocholic acid, glutaric acid, stearic acid, glutamic acid or aspartic acid. The salts which are formed are, inter alia, hydrochlorides, chlorided, hydrobromides, bromides, iodides, sulfates, phosphates, methanesulfonates, tosylates, carbonates, bicarbonates, formates, acetates, sulfoacetates, triflates, oxalates, malonates, maleates, succinates, tartrates, malates, embonates, mandelates, fumarates, lactates, citrates, glutarates, stearates, aspartates and glutamates. The stoichiometry of the salts formed from the compounds of the invention may moreover be an integral or non-integral multiple of one.

The compounds of the invention can, if they contain a sufficiently acidic group such as, for example, the carboxy, sulfonic acid, phosphoric acid or a phenolic group, be converted with inorganic and organic bases into their physiologically tolerated salts. Examples of suitable inorganic bases are ammonium, sodium hydroxide, potassium hydroxide, calcium hydroxide, and of organic bases are ethanolamine, diethanolamine, triethanolamine, ethylenediamine, t-butylamine, t-octylamine, dehydroabietylamine, cyclohexylamine, dibenzylethylene-diamine and lysine. The stoichiometry of the salts formed from the compounds of the invention can moreover be an integral or non-integral multiple of one.

It is likewise possible for the compounds of the invention to be in the form of their solvates and, in particular, hydrates which can be obtained for example by crystallization from a solvent or from aqueous solution. It is moreover possible for one, two, three or any number of solvate or water molecules to combine with the compounds of the invention to give solvates and hydrates.

By the term "solvate" is meant a hydrate, an alcoholate, or other solvate of crystallization.

It is known that chemical substances form solids which exist in different order states which are referred to as polymorphic forms or modifications. The various modifications of a polymorphic substance may differ greatly in their physical properties. The compounds of the invention can exist in various polymorphic forms and certain modifications may moreover be metastable. All these polymorphic forms of the compounds are to be regarded as belonging to the invention.

The compounds of the invention are surprisingly characterized by a strong and/or selective inhibition of autotaxin.

Due to their surprisingly strong and/or selective enzyme inhibition, the compounds of the invention can be advantageously administered at lower doses compared to other less potent or selective inhibitors of the prior art while still achieving equivalent or even superior desired biological effects. In addition, such a dose reduction may advantageously lead to less or even no medicinal adverse effects. Further, the high inhibition selectivity of the compounds of the invention may translate into a decrease of undesired side effects on its own regardless of the dose applied.

The compounds of the invention being autotaxin inhibitors generally have an inhibition constant $IC_{50}$ of less than about 30 µM, and preferably less than about 5 µM.

The object of the present invention has surprisingly been solved in another aspect by providing the use of a compound of the invention as autotaxin inhibitor.

The terms "inhibiting, inhibition and/or retardation" are intended to refer for the purposes of the present invention to as follows: "partial or complete inhibiting, inhibition and/or retardation". In this case, it is within the specialist knowledge of the average person skilled in the art to measure and determine such inhibiting, inhibition, and/or retardation by means of the usual methods of measurement and determination. Thus, a partial inhibiting, inhibition and/or retardation, for example, can be measured and determined in relation to a complete inhibiting, inhibition and/or retardation.

In a preferred embodiment, the use of a compound of the invention as autotaxin inhibitor is provided, characterized in that the following pyridopyrimidine derivatives are additionally comprised:
  i) pyridopyrimidine derivatives according to formula (I) and the herein disclosed preferred embodiments characterized in that if R1, R2 together with the nitrogen atom which they are attached to form "heterocyclyl", which is optionally substituted with one or more identical or different substituents Z, "heterocyclyl" does additionally comprise "4-piperidine-1-yl-carboxylic acid (4-carboxy-piperidine-1-yl), 3-piperidine-1-yl-carboxylic acid (3-carboxy-piperidine-1-yl), 4-piperidine-1-yl-carboxylic acid ethyl ester (4-ethylcarboxyate-piperidine-1-yl), 3-piperidine-1-yl-carboxylic acid ethyl ester (3-ethylcarboxyate-piperidine-1-yl)";
  ii)

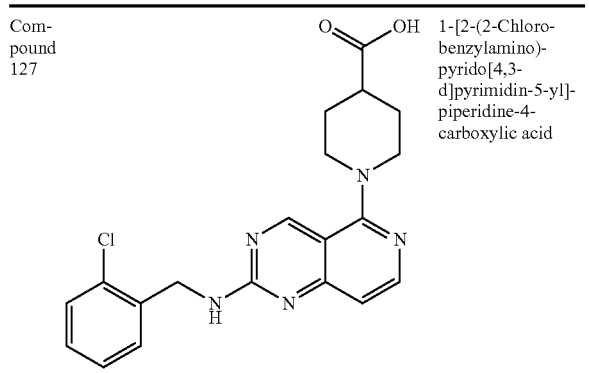

Compound 127 — 1-[2-(2-Chloro-benzylamino)-pyrido[4,3-d]pyrimidin-5-yl]-piperidine-4-carboxylic acid For the purpose of medicaments, medical uses and methods of treatments above pyridopyrimidine derivatives (i) and (ii) are intended to be comprised by the term "compounds of the (present) invention".

The object of the present invention has surprisingly been solved in another aspect by providing a process for the preparation of a compound of the invention, comprising the steps:
  a) reacting ethyl 2-acetyl-3-ethoxy-2-propenoate (1), {[amino(imino)methyl]-sufanyl}methane (2) and a base, preferably an organic or inorganic base, most preferably triethylamine, in an organic solvent, preferably ethanol, to obtain 4-methyl-2-methylsulfanyl-pyrimidine-5-carboxylic acid ethyl ester (3), b) reacting 4-methyl-2-methylsulfanyl-pyrimidine-5-carboxylic acid ethyl ester (3) obtained in step a) with N,N-dimethyl-R3-formamide-dimethylacetal (4), wherein R3 is as defined herein, in an organic solvent, preferably DMF, to yield 4-((E)-2-dimethylamino-R3-vinyl)-2-methylsulfanyl-pyrimidine-5-carboxylic acid ethyl ester (5), wherein R3 is as defined herein, c) cyclizising 4-((E)-2-dimethylamino-R3-vinyl)-2-methylsulfanyl-pyrimidine-5-carboxylic acid ethyl ester (5), wherein R3 is as defined herein, yielded in step b) in the presence of ammonia or a salt thereof, preferably ammonium acetate, in an organic solvent, preferably DMF, to 7-R3-2-methylsulfanyl-6H-pyrido[4,3-d]pyrimidin-5-one (6), wherein R3 is as defined herein, d) reacting 7-R3-2-methylsulfanyl-6H-pyrido[4,3-d]pyrimidin-5-one (6), wherein R3 is as defined herein, obtained in step c) with a compound of formula (II) (7),

wherein Ar, R4, R5, R6, n are as defined herein, to obtain a compound of formula (III) (8),

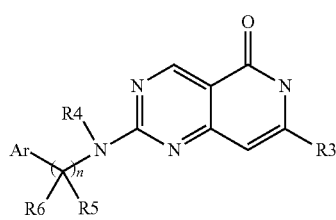

wherein Ar, R3, R4, R5, R6, n are as defined herein, e) reacting the compound of formula (III) (8) obtained in step d) with a chlorination agent, preferably POCl₃ or SO₂Cl₂, to yield a compound of formula (IV) (9)

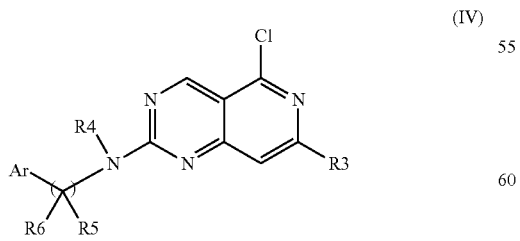

wherein Ar, R3, R4, R5, R6, n are as defined herein f) reacting the compound of formula (IV) (9) obtained in step e) with a compound of formula (V) (10)

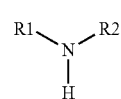

wherein R1, R2 are as defined herein to obtain a compound of formula (I) (11) as defined herein.

The object of the present invention has surprisingly been solved in another aspect by providing a process for the preparation of a compound of the invention, comprising the steps:

d) reacting 7-R3-2-methylsulfanyl-6H-pyrido[4,3-d]pyrimidin-5-one (6), wherein R3 is as defined herein, with a compound of formula (II) (7),

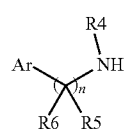

wherein Ar, R4, R5, R6, n are as defined herein, to obtain a compound of formula (III) (8),

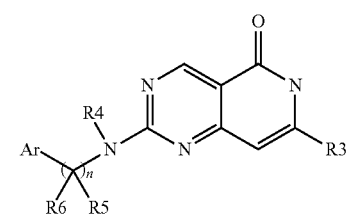

wherein Ar, R3, R4, R5, R6, n are as defined herein, e) reacting the compound of formula (III) (8) obtained in step d) with a chlorination agent, preferably POCl₃ or SO₂Cl₂, to yield a compound of formula (IV) (9)

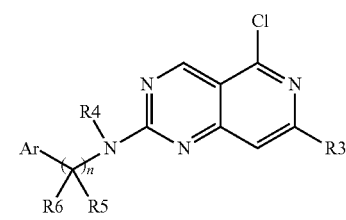

wherein Ar, R3, R4, R5, R6, n are as defined herein, f) reacting the compound of formula (IV) (9) obtained in step e) with a compound of formula (V) (10)

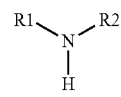

wherein R1, R2 are as defined herein to obtain a compound of formula (I) (11) as defined herein.

The object of the present invention has surprisingly been solved in another aspect by providing a process for the preparation of a compound of the invention, comprising the steps:

f) reacting the compound of formula (IV) (9) wherein Ar, R3, R4, R5, R6, n are as defined herein,

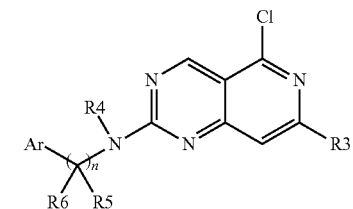

with a compound of formula (V) (10)

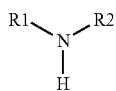

wherein R1, R2 are as defined herein to obtain a compound of formula (I) (11) as defined herein.

The following overview is the corresponding general synthesis scheme of the above disclosed process:

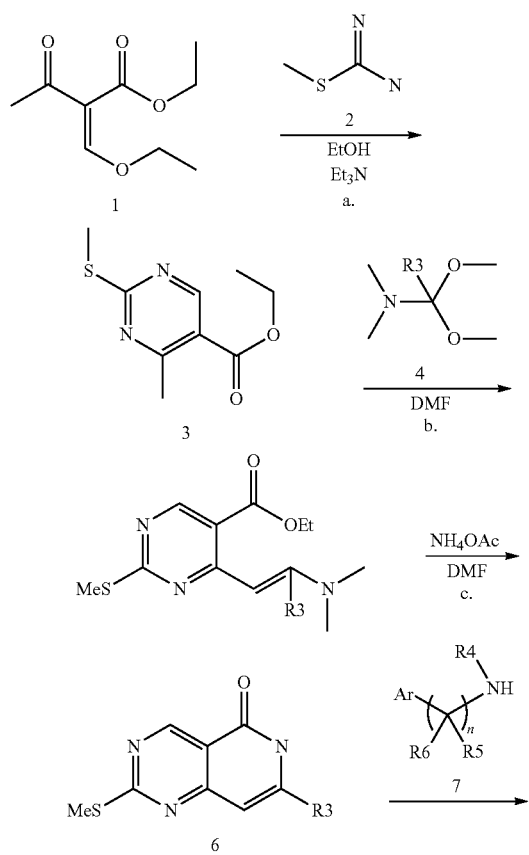

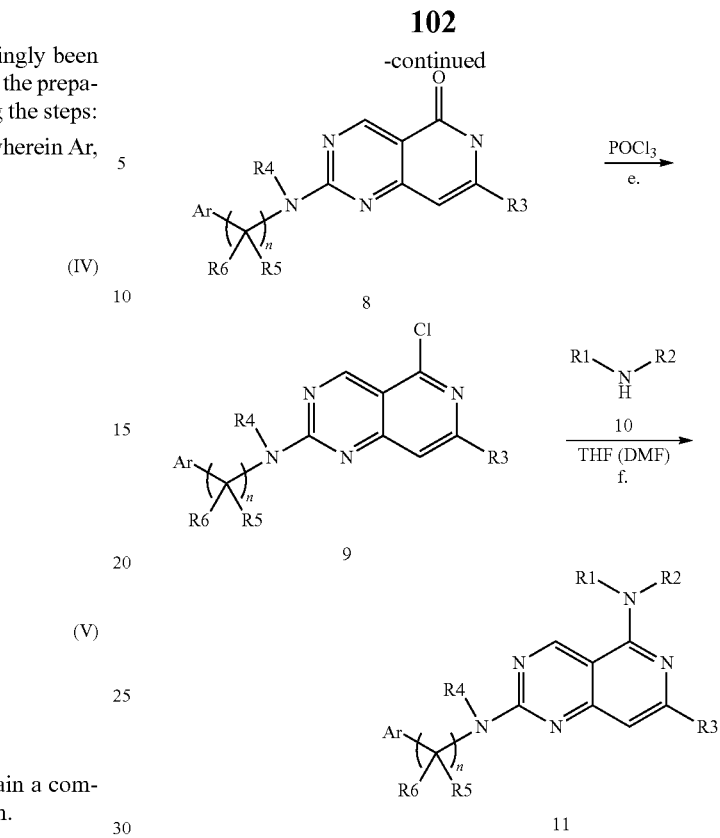

All crude products were subjected to standard chromatography using solvent mixtures containing methanol, ethanol, isopropanol, n-hexane, cyclohexane or petrol ether, respectively.

For a further detailed description of the manufacturing processes, please refer also to the examples and the following general description of the preferred conditions.

A physiologically acceptable salt of a compound of the invention can also be obtained by isolating and/or treating the compound of the invention obtained by the described reaction with an acid or a base.

The compounds of the invention and also the starting materials for their preparation are, are prepared by methods as described in the examples or by methods known per se, as described in the literature (for example in standard works, such as Houben-Weyl, Methoden der Organischen Chemie [Methods of Organic Chemistry], Georg Thieme Verlag, Stuttgart; Organic Reactions, John Wiley & Sons, Inc., New York), to be precise under reaction conditions which are known and suitable for the said reactions. Use can also be made here of variants which are known per se, but are not mentioned here in greater detail.

The starting materials for the claimed process may, if desired, also be formed in situ by not isolating them from the reaction mixture, but instead immediately converting them further into the compounds of the invention. On the other hand, it is possible to carry out the reaction stepwise.

Preferably, the reaction of the compounds is carried out in the presence of a suitable solvent, which is preferably inert under the respective reaction conditions. Examples of suitable solvents are hydrocarbons, such as hexane, petroleum ether, benzene, toluene or xylene; chlorinated hydrocarbons, such as trichlorethylene, 1,2-dichloroethane, tetrachloromethane, chloroform or dichloromethane; alcohols, such as methanol, ethanol, isopropanol, n-propanol, n-butanol or tertbutanol; ethers, such as diethyl ether, diisopropyl ether, tetrahydrofuran (THF) or dioxane; glycol ethers, such as ethylene glycol monomethyl or monoethyl ether or ethylene glycol dimethyl ether (diglyme); ketones, such as acetone or butanone; amides, such as acetamide, dimethylacetamide, dimethylformamide (DMF) or N-methylpyrrolidinone (NMP); nitriles, such as acetonitrile; sulfoxides, such as dimethyl sulfoxide (DMSO); nitro compounds, such as nitromethane or nitrobenzene; esters, such as ethyl acetate, or mixtures of the said solvents or mixtures with water. Polar solvents are in general preferred. Examples for suitable polar solvents are chlorinated hydrocarbons, alcohols, glycol ethers, nitriles, amides and sulfoxides or mixtures thereof. More preferred are amides, especially dimethylformamide (DMF).

As stated above, the reaction temperature is between about −100° C. and 300° C., depending on the reaction step and the conditions used.

Reaction times are generally in the range between some minutes and several days, depending on the reactivity of the respective compounds and the respective reaction conditions. Suitable reaction times are readily determinable by methods known in the art, for example reaction monitoring. Based on the reaction temperatures given above, suitable reaction times generally lie in the range between 10 min and 48 hrs.

A base of a compound of the invention can be converted into the associated acid-addition salt using an acid, for example by reaction of equivalent amounts of the base and the acid in a preferably inert solvent, such as ethanol, followed by evaporation. Suitable acids for this reaction are, in particular, those which give physiologically acceptable salts. Thus, it is possible to use inorganic acids, for example sulfuric acid, sulfurous acid, dithionic acid, nitric acid, hydrohalic acids, such as hydrochloric acid or hydrobromic acid, phosphoric acids, such as, for example, orthophosphoric acid, sulfamic acid, furthermore organic acids, in particular aliphatic, alicyclic, aralphatic, aromatic or heterocyclic monobasic or polybasic carboxylic, sulfonic or sulfuric acids, for example formic acid, acetic acid, propionic acid, hexanoic acid, octanoic acid, decanoic acid, hexadecanoic acid, octadecanoic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, trimethoxybenzoic acid, adamantanecarboxylic acid, p-toluenesulfonic acid, glycolic acid, embonic acid, chlorophenoxyacetic acid, aspartic acid, glutamic acid, proline, glyoxylic acid, palmitic acid, parachlorophenoxyisobutyric acid, cyclohexanecarboxylic acid, glucose 1-phosphate, naphthalenemono- and -disulfonic acids or laurylsulfuric acid.

Salts with physiologically unacceptable acids, for example picrates, can be used to isolate and/or purify the compounds of the invention.

On the other hand, compounds of the invention can be converted into the corresponding metal salts, in particular alkali metal salts or alkaline earth metal salts, or into the corresponding ammonium salts, using bases (for example sodium hydroxide, potassium hydroxide, sodium carbonate or potassium carbonate). Suitable salts are furthermore substituted ammonium salts, for example the dimethyl-, diethyl- and diisopropylammonium salts, monoethanol-, diethanol- and diisopropanolammonium salts, cyclohexyl- and dicyclohexylammonium salts, dibenzylethylenediammonium salts, furthermore, for example, salts with arginine or lysine.

If desired, the free bases of the compounds of the invention can be liberated from their salts by treatment with strong bases, such as sodium hydroxide, potassium hydroxide, sodium carbonate or potassium carbonate, so long as no further acidic groups are present in the molecule. In the cases where the compounds of the invention have free acid groups, salt formation can likewise be achieved by treatment with bases. Suitable bases are alkali metal hydroxides, alkaline earth metal hydroxides or organic bases in the form of primary, secondary or tertiary amines.

Every reaction step described herein can optionally be followed by one or more working up procedures and/or isolating procedures. Suitable such procedures are known in the art, for example from standard works, such as Houben-Weyl, Methoden der organischen Chemie [Methods of Organic Chemistry], Georg-Thieme-Verlag, Stuttgart). Examples for such procedures include, but are not limited to evaporating a solvent, distilling, crystallization, fractionised crystallization, extraction procedures, washing procedures, digesting procedures, filtration procedures, chromatography, chromatography by HPLC and drying procedures, especially drying procedures in vacuo and/or elevated temperature.

The object of the present invention has surprisingly been solved in another aspect by providing a medicament comprising at least one compound of the invention.

The object of the present invention has surprisingly been solved in another aspect by providing a medicament comprising at least one compound of the invention for use in the treatment and/or prophylaxis of physiological and/or pathophysiological conditions, which are caused, mediated and/or propagated by increased lysophosphatic acid levels and/or the activation of autotaxin. A corresponding use for the preparation of a medicament for the treatment and/or prophylaxis of the aforementioned conditions is intended to be comprised.

The object of the present invention has surprisingly been solved in another aspect by providing a medicament comprising at least one compound of the invention for use in the treatment and/or prophylaxis of physiological and/or pathophysiological conditions selected from the group consisting of: "cancer, tumour, malignant tumours, benign tumours, solid tumours, sarcomas, carcinomas, hyperproliferative disorders, carcinoids, Ewing sarcomas, Kaposi sarcomas, brain tumours, tumours originating from the brain and/or the nervous system and/or the meninges, gliomas, glioblastomas, neuroblastomas, stomach cancer, kidney cancer, kidney cell carcinomas, prostate cancer, prostate carcinomas, connective tissue tumours, soft tissue sarcomas, pancreas tumours, liver tumours, head tumours, neck tumours, laryngeal cancer, oesophageal cancer, thyroid cancer, osteosarcomas, retinoblastomas, thymoma, testicular cancer, lung cancer, lung adenocarcinoma, small cell lung carcinoma, bronchial carcinomas, breast cancer, mamma carcinomas, intestinal cancer, colorectal tumours, colon carcinomas, rectum carcinomas, gynecological tumours, ovary tumours/ovarian tumours, uterine cancer, cervical cancer, cervix carcinomas, cancer of body of uterus, corpus carcinomas, endometrial carcinomas, urinary bladder cancer, urogenital tract cancer, bladder cancer, skin cancer, epithelial tumours, squamous epithelial carcinoma, basaliomas, spinaliomas, melanomas, intraocular melanomas, leukaemias, monocyte leukaemia, chronic leukaemias, chronic myelotic leukaemia, chronic lymphatic leukemia, acute leukaemias, acute myelotic leukaemia, acute lymphatic leukemia, lymphomas, angiogenesis, arteriosclerosis, ophthalmic diseases, choroidal neovascularization, diabetic retinopathy, inflammatory diseases, arthritis, neurodegeneration, restenosis, wound healing and/or transplant rejection". A corresponding use for the preparation of a medicament for the treatment and/or prophylaxis of the aforementioned conditions is intended to be comprised.

Compounds of the invention may be used in combination with one or more other active substances (ingredients, drugs) in the treatment, prevention, suppression or amelioration of diseases or conditions for which compounds of the invention or the other substances have utility. Typically the combination of the drugs is safer or more effective than either drug alone, or the combination is safer or more effective than would it be expected based on the additive properties of the individual drugs. Such other drug(s) may be administered, by a route and in an amount commonly used contemporaneously or sequentially with a compound of the invention. When a compound of the invention is used contemporaneously with one or more other drugs, a combination product containing such other drug(s) and the compound of the invention is preferred. However, combination therapy also includes therapies in which the compound of the invention and one or more other drugs are administered on different overlapping schedules. It is contemplated that when used in combination with other active ingredients, the compound of the present invention or the other active ingredient or both may be used effectively in lower doses than when each is used alone. Accordingly, the pharmaceutical compositions of the present invention include those that contain one or more other active ingredients, in addition to a compound of the invention.

Examples of other active substances (ingredients, drugs) that may be administered in combination with a compound of the invention, and either administered separately or in the same pharmaceutical composition, include, but are not limited to the compounds classes and specific compounds listed in Table 1:

TABLE 1

| | | |
|---|---|---|
| Alkylating agents | Cyclophosphamide | Lomustine |
| | Busulfane | Procarbazine |
| | Ifosfamide | Altretamine |
| | Melphalane | Estramustinphosphate |
| | Hexamethylmelamine | Mechlorethamine |
| | Thiotepa | Streptozocine |
| | Chlorambucil | Temozolomide |
| | Dacarbazine | Semustine |
| | Carmustine | |
| Platinum agents | Cisplatin | Carboplatin |
| | Oxaliplatin | ZD-0473 (AnorMED) |
| | Spiroplatin | Lobaplatin (AeternaZentaris) |
| | Carboxyphthalatoplatinum | Satraplatin (Johnson Matthey) |
| | Tetraplatin | BBR-3464 (Hoffmann-La Roche) |
| | Ormiplatin | |
| | Iproplatin | SM-11355 (Sumitomo) |
| | | AP-5280 (Access) |
| Antimetabolites | Azacytidine | Tomudex |
| | Gemcitabine | Trimetrexate |
| | Capecitabine | Deoxycoformycine |
| | 5-Fluoruracil | Fludarabine |
| | Floxuridine | Pentostatine |
| | 2-Chlordesoxyadenosine | Raltitrexede |
| | 6-Mercaptopurine | Hydroxyurea |
| | 6-Thioguanine | Decitabine (SuperGen) |
| | Cytarabine | Clofarabine (Bioenvision) |
| | 2-Fluordesoxycytidine | Irofulven (MGI Pharma) |
| | Methotrexate | DMDC (Hoffmann-La Roche) |
| | Idatrexate | Ethinylcytidine (Taiho) |
| Topoisomerase inhibitors | Amsacrine | Rubitecane (SuperGen) |
| | Epirubicine | Exatecanmesylate (Daiichi) |
| | Etoposide | Quinamed (ChemGenex) |
| | Teniposide or Mitoxantrone | Gimatecane (Sigma-Tau) |
| | Irinotecane (CPT-11) | Diflomotecane (Beaufour-Ipsen) |
| | 7-Ethyl-10-hydroxycamptothecine | TAS-103 (Taiho) |
| | Topotecane | Elsamitrucine (Spectrum) |
| | Dexrazoxanet (TopoTarget) | J-107088 (Merck & Co) |
| | Pixantrone (Novuspharrna) | BNP-1350 (BioNumerik) |
| | Rebeccamycin-Analogue (Exelixis) | CKD-602 (Chong Kun Dang) |
| | BBR-3576 (Novuspharrna) | KW-2170 (Kyowa Hakko) |
| Antitumor antibiotics | Dactinomycin (Actinomycin D) | Amonafide |
| | Doxorubicin (Adriamycin) | Azonafide |
| | Deoxyrubicin | Anthrapyrazole |
| | Valrubicin | Oxantrazole |
| | Daunorubicin (Daunomycin) | Losoxantrone |
| | Epirubicin | Bleomycinsulfate (Blenoxan) |
| | Therarubicin | Bleomycinacid |
| | Idarubicin | Bleomycin A |
| | Rubidazone | Bleomycin B |
| | Plicamycinp | Mitomycin C |
| | Porfiromycin | MEN-10755 (Menarini) |
| | Cyanomorpholinodoxorubicin | GPX-100 (Gem Pharmaceuticals) |
| | Mitoxantron (Novantron) | |
| Antimitotic agents | Paclitaxel | SB 408075 (Glaxo SmithKline) |
| | Docetaxel | |
| | Colchicin | E7010 (Abbott) |

TABLE 1-continued

| | | |
|---|---|---|
| | Vinblastine | PG-TXL (Cell Therapeutics) |
| | Vincristine | IDN 5109 (Bayer) |
| | Vinorelbine | A 105972 (Abbott) |
| | Vindesine | A 204197 (Abbott) |
| | Dolastatine 10 (NCI) | LU 223651 (BASF) |
| | Rhizoxine (Fujisawa) | D 24851 (ASTA Medica) |
| | Mivobuline (Warner-Lambert) | ER-86526 (Eisai) |
| | Cemadotine (BASF) | Combretastatine A4 (BMS) |
| | RPR 109881A (Aventis) | Isohomohalichondrin-B |
| | TXD 258 (Aventis) | (PharmaMar) |
| | Epothilon B (Novartis) | ZD 6126 (AstraZeneca) |
| | T 900607 (Tularik) | PEG-Paclitaxel (Enzon) |
| | T 138067 (Tularik) | AZ10992 (Asahi) |
| | Cryptophycin 52 (Eli Lilly) | !DN-5109 (Indena) |
| | Vinflunine (Fabre) | AVLB (Prescient NeuroPharma) |
| | Auristatine PE (Teikoku Hormone) | Azaepothilon B (BMS) |
| | BMS 247550 (BMS) | BNP-7787 (BioNumerik) |
| | BMS 184476 (BMS) | CA-4-Prodrug (OXiGENE) |
| | BMS 188797 (BMS) | Dolastatin-10 (NrH) |
| | Taxoprexine (Protarga) | CA-4 (OXiGENE) |
| Aromatase inhibitors | Aminoglutethimide | Exemestane |
| | Letrozole | Atamestane (BioMedicines) |
| | Anastrazole | YM-511 (Yamanouchi) |
| | Formestane | |
| Thymidylatesynthase inhibitors | Pemetrexed (Eli Lilly) | Nolatrexed (Eximias) |
| | ZD-9331 (BTG) | CoFactor™ (BioKeys) |
| DNA antagonists | Trabectedine (PharmaMar) | Mafosfamide (Baxter International) |
| | Glufosfamide (Baxter International) | Apaziquone (Spectrum Pharmaceuticals) |
| | Albumin + 32P (Isotope Solutions) | O6-Benzylguanine (Paligent) |
| | Thymectacine (NewBiotics) | |
| | Edotreotide (Novartis) | |
| Farnesyltransferase inhibitors | Arglabine (NuOncology Labs) | Tipifarnibe (Johnson & Johnson) |
| | Ionafarnibe (Schering-Plough) | Perillylalcohol (DOR Bio-Pharma) |
| | BAY-43-9006 (Bayer) | |
| Pump inhibitors | CBT-1 (CBA Pharma) | Zosuquidar-Trihydrochloride (Eli Lilly) |
| | Tariquidar (Xenova) | |
| | MS-209 (Schering AG) | Biricodar-Dicitrate (Vertex) |
| Histoneacetyltransferase inhibitors | Tacedinaline (Pfizer) | Pivaloyloxymethylbutyrate (Titan) |
| | SAHA (Aton Pharma) | |
| | MS-275 (Schering AG) | Depsipeptide (Fujisawa) |
| Metalloproteinase inhibitors/ Ribonucleosidereduktase inhibitors | Neovastat (Aeterna Laboratories) | CMT-3 (CollaGenex) |
| | | BMS-275291 (Celltech) |
| | Marimastat (British Biotech) | Tezacitabine (Aventis) |
| | Galliummaltolate (Titan) | Didox (Molecules for Health) |
| | Triapine (Vion) | |
| TNF-alpha agonists/ antagonists | Virulizine (Lorus Therapeutics) | Revimide (Celgene) |
| | CDC-394 (Celgene) | |
| Endotheline-A receptor antagonists | Atrasentane (Abbot) | YM-598 (Yamanouchi) |
| | ZD-4054 (AstraZeneca) | |
| Retinoic acid receptor agonists | Fenretinide (Johnson & Johnson) | Alitretinoin (Ligand) |
| | LGD-1550 (Ligand) | |
| Immunomodulators | Interferon | Dexosome therapy (Anosys) |
| | Oncophage (Antigenics) | Pentrix (Australian Cancer Technology) |
| | GMK (Progenics) | |
| | Adenocarzinoma vaccine (Biomira) | JSF-154 (Tragen) |
| | | Cancer vaccine (Intercell) |
| | CTP-37 (AVI BioPharma) | Noreline (Biostar) |
| | JRX-2 (Immuno-Rx) | BLP-25 (Biomira) |
| | PEP-005 (Peplin Biotech) | MGV (Progenics) |
| | Synchrovax vaccine (CTL Immuno) | 13-Alethine (Dovetail) |
| | | CLL-Thera (Vasogen) |
| | Melanoma vaccine (CTL Immuno) | |
| | p21-RAS vaccine (GemVax) | |
| Hormonal and anti-hormonal agents | Estrogens | Prednisone |
| | Conjugated Estrogens | Methylprednisolone |
| | Ethinylestradiole | Prednisolone |
| | Chlorotrianisen | Aminoglutethimide |
| | Idenestrole | Leuprolide |
| | Hydroxyprogesteroncaproate | Goserelin |
| | Medroxyprogesterone | Leuporelin |
| | Testosterone | Cetrorelix |
| | Testosteronpropionate | Bicalutamide |
| | Fluoxymesterone | Flutamide |
| | Methyltestosterone | Octreotide |
| | Diethylstilbestrole | Nilutamide |
| | Megestrole | Mitotane |

TABLE 1-continued

| | | |
|---|---|---|
| | Tamoxifen | P-04 (Novogen) |
| | Toremofine | 2-Methoxyestradiol (Entre-Med) |
| | Dexamethasone | |
| | | Arzoxifen (Eli Lilly) |
| Photodynamic agents | Talaporfine (Light Sciences) | Pd-Bacteriopheophorbide (Yeda) |
| | Theralux (Theratechnologies) | Lutetium-Texaphyrine (Pharmacyclics) |
| | Motexafin Gadolinium (Pharmacyclics) | Hypericine |
| Tyrosinkinase inhibitors | Imatinib (Novartis) | Kahalid F (PharmaMar) |
| | Leflunomid (Sugen/Pharmacia) | CEP-701 (Cephalon) |
| | | CEP-751 (Cephalon) |
| | ZDI839 (AstraZeneca) | MLN518 (Millenium) |
| | Erlotinib (Oncogene Science) | PKC412 (Novartis) |
| | Canertjnib (Pfizer) | Phenoxodiol O |
| | Squalamin (Genaera) | Trastuzumab (Genentech) |
| | SU5416 (Pharmacia) | C225 (ImClone) |
| | SU6668 (Pharmacia) | rhu-Mab (Genentech) |
| | ZD4190 (AstraZeneca) | MDX-H210 (Medarex) |
| | ZD6474 (AstraZeneca) | 2C4 (Genentech) |
| | Vatalanib (Novartis) | MDX-447 (Medarex) |
| | PKI166 (Novartis) | ABX-EGF (Abgenix) |
| | GW2016 (GlaxoSmithKline) | IMC-1C11 (ImClone) |
| | EKB-509 (Wyeth) | |
| | EKB-569 (Wyeth) | |
| Different agents | SR-27897 (CCK-A inhibitor, Sanofi-Synthelabo) | BCX-1777 (PNP inhibitor, BioCryst) |
| | Tocladesine (cyclic-AMP agonist, Ribapharm) | Ranpirnase (Ribonuclease stimulans, Alfacell) |
| | Alvocidib (CDK inhibitor, Aventis) | Galarubicin (RNA synthesis inhibitor, Dong-A) |
| | CV-247 (COX-2-Inhibitor, Ivy Medical) | Tirapazamin (reducing agent, SRI International) |
| | P54 (COX-2 inhibitor, Phytopharm) | N-Acetylcystein (reducing agent, Zambon) |
| | CapCell ™ (CYP450 stimulans, Bavarian Nordic) | R-Flurbiprofen (NF-kappaB inhibitor, Encore) |
| | GCS-IOO (gal3 antagonist, GlycoGenesys) | 3CPA (NF-kappaB inhibitor, Active Biotech) |
| | G17DT immunogen (Gastrin inhibitor, Aphton) | Seocalcitol (Vitamin-D receptor agonist, Leo) |
| | Efaproxiral (Oxygenator, Allos Therapeutics) | 131-I-TM-601 (DNA antagonist, TransMolecular) |
| | PI-88 (Heparanase inhibitor, Progen) | Eflornithin (ODC inhibitor, ILEX Oncology) |
| | Tesmilifen (Histamine antagonist, YM BioSciences) | Minodronic acid (Osteoclasts inhibitor, Yamanouchi) |
| | Histamine (Histamine-H2 receptor agonist, Maxim) | Indisulam (p53 stimulans, Eisai) |
| | Tiazofurin (IMPDH inhibitor, Ribapharm) | Aplidin (PPT inhibitor, Pharma Mar) |
| | Cilengitide (Integrine antagonist, Merck KGaA) | Rituximab (CD20 antibody, Genentech) |
| | SR-31747 (IL-1 antagonist, Sanofi-Synthelabo) | Gemtuzumab (CD33 antibody, Wyeth Ayerst) |
| | CCI-779 (mTOR kinase inhibitor, Wyeth) | PG2 (Hematopoesis enhancer, Pharmagenesis) |
| | Exisulind (PDE-V inhibitor, Cell Pathways) | Immunol ™ (Triclosan oral irrigation, Endo) |
| | CP-461 (PDE-V inhibitor, Cell Pathways) | Triacetyluridine (Uridine pro-drug, Wellstat) |
| | AG-2037 (GART inhibitor, Pfizer) | SN-4071 (sarcoma agent, Signature BioScience) |
| | WX-UK1 (Plasminogen activator inhibitor, Wilex) | TransMID-107 ™ (Immunotoxine, KS Biomedix) |
| | PBI-1402 (PMN stimulans, ProMetic LifeSciences) | PCK-3145 (Apoptosis enhancer, Procyon) |
| | Bortezomib (Proteasome inhibitor, Millennium) | Doranidazole (Apoptosis enhancer, Pola) |
| | SRL-172 (T-cell stimulans, SR Pharma) | CHS-828 (cytotoxic agent, Leo) |
| | TLK-286 (Glutathione-S-transferase inhibitor, Telik) | trans-Retinoic acid (Differentiator, NIH) |
| | PT-100 (Growth factor agonist, Point Therapeutics) | MX6 (Apoptosis enhancer, MAXIA) |
| | Midostaurin (PKC inhibitor, Novartis) | Apomin (Apoptosis enhancer, ILEX Oncology) |
| | Bryostatin-1 (PKC stimulans, GPC Biotech) | Urocidine (Apoptosis enhancer, Bioniche) |
| | CDA-II (Apoptosis enhancer, Everlife) | Ro-31-7453 (Apoptosis enhancer, |

TABLE 1-continued

| | |
|---|---|
| SDX-101 (Apoptosis enhancer, Salmedix) | La Roche) |
| Ceflatonin (Apoptosis enhancer, ChemGenex) | Brostallicin (Apoptosis enhancer, Pharmacia) |

In a preferred embodiment, a compound of the invention is administered in combination with one or more known antitumor agents, such as the following: estrogen receptor modulators, androgen receptor modulators, retinoid receptor modulators, cytotoxics, antiproliferative agents, prenyl proteintransferase inhibitors, HMG-CoA-reductase inhibitors, HIV protease inhibitors, reverse transcriptase inhibitors, angiogenesis inhibitors.

The compounds of the invention are in particular well suited for administration in combination with radiotherapy. The synergistic effects of VEGF inhibition in combination with radiotherapy are known to the skilled artisan (WO 00/61186).

The term "estrogen receptor modulators" in the course of the present invention refers to compounds that interfere with or inhibit the binding of estrogen to estrogen receptor—independently from the mode of action. Non-limiting examples of estrogen receptor modulators are tamoxifen, raloxifen, idoxifen, LY353381, LY 117081, toremifen, fulvestrant, 4-[7-(2, 2-Dimethyl-1-oxopropoxy-4-methyl-2-[4-[2-(1-piperidinyl) ethoxy]phenyl]-2H-1-benzopyran-3-yl]phenyl-2,2-dimethyl-propanoate, 4,4'-Dihydroxybenzophenon-2,4-dinitrophenylhydrazone and SH646.

The term "androgen receptor modulators" in the course of the present invention refers to compounds that interfere with or inhibit the binding of androgens to androgen receptor—independently from the mode of action. Non-limiting examples of androgen receptor modulators are finasteride and other 5alpha-reductase inhibitors, nilutamide, flutamide, bicalutamide, liarozole and abirateron acetate.

The term "retinoid receptor modulators" in the course of the present invention refers to compounds that interfere with or inhibit the binding of retinoids to retinoid receptor—independently from the mode of action. Non-limiting examples of retinoid receptor modulators are bexaroten, tretinoin, 13-cis-retinoic acid, 9-cis-retinoic acid, alpha-difluoromethylornithine, ILX23-7553, trans-N-(4'-Hydroxyphenyl)retinamide and N-4-carboxyphenylretinamide.

The term "cytotoxics" in the course of the present invention refers to compounds that primarily trigger cell death through direct action on cell function(s) or which interfere with or inhibit cell myosis, such as alkylating agents, tumor necrosis factors, intercalating agents, microtubule inhibitors and topoisomerase inhibitors. Non-limiting examples of cytotoxics are tirapazimin, sertenef, cachectine, ifosfamide, tasonermine, lonidamine, carboplatin, altretamine, prednimustine, dibromodulcit, ranimustine, fotemustine, nedaplatin, oxaliplatin, temozolomide, heptaplatin, estramustin, improsulfantosylate, trofosfamide, nimustine, dibrospidium-chloride, pumitepa, lobaplatin, satraplatin, profiromycin, cisplatin, irofulven, dexifosfamide, cis-am indichloro(2-methylpyridine)platin, benzylguanine, glufosfamide, GPX100, (trans, trans,trans)-bis-mu-(hexane-1,6-diamine)-mu-[diamine-platin(II)]bis-[diamine(chloro)platin(II)]-tetrachloride, diarizidinylspermine, arsenium trioxide, 1-(11-Dodecylamino-10-hydroxyundecyl)-3,7-dimethylxanthine, zorubicin, idarubicin, daunorubicin, bisantren, mitoxantron, pirarubicin, pinafide, valrubicine, amrubicine, antineoplaston, 3'-desamino-3'-morpholino-13-desoxo-10-hydroxycaminomycin, annamycin, galarubicin, elinafide, MEN10755 and 4-desmethoxy-3-desamino-3-aziridinyl-4-methylsulfonyl-daunorubicin (WO 00/50032).

Non-limiting examples of microtubule inhibitors are paclitaxel, vindesine-sulfate, 3',4'-dideshydro-4'-desoxy-8'-norv-incaleukoblastine, docetaxol, rhizoxine, dolastatine, mivobuline-isethionate, auristatine, cemadotine, RPR109881, BMS184476, vinflunine, cryptophycine, 2,3,4,5,6-pentafluoro-N-(3-fluoro-4-methoxyphenyl)-benzenesulfonamide, anhydrovinblastine, N,N-dimethyl-L-valyl-L-valyl-N-methyl-L-valyl-L-prolyl-L-proline-t-butylamide, TDX258 and BMS188797.

Non-limiting examples of topoisomerase inhibitors are topotecane, hycaptamine, irinotecane, rubitecane, 6-ethoxypropionyl-3',4'-O-exo-benzylidene-chartreusine, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo-[de]-pyrano-[3',4':b,7] indolizino[1,2b]quinoline-10,13(9H,15H)-dione, lurtotecane, 7-[2-(N-isopropylamino)ethyl]-(20S)camptothecine, BNP1350, BNPI1100, BN80915, BN80942, etoposide-phosphate, teniposide, sobuzoxane, 2'-dimethylamino-2'-desoxy-etoposide, GL331, N-[2-(dimethylamino)ethyl]-9-hydroxy-5,6-dimethyl-6H-pyrido[4,3-b]carbazole-1-carboxamide, asulacrine, (5a,5aB,8aa,9b)-9-[2-[N-[2-(dimethylamino)ethyl]-N-methylamino]ethyl]-5-[4-hydroxy-3,5-dimethoxyphenyl]-5,5a,6,8,8a,9-hexohydrofuro(3',4':6,7)naphtho(2,3-d)-1,3-dioxol-6-one, 2,3-(methylendioxy)-5-methyl-7-hydroxy-8-methoxybenzo [c]phenanthridinium, 6,9-bis[(2-aminoethyl)amino]-benzo [g]isoquinoline-5,10-dione, 5-(3-aminopropylamino)-7,10-dihydroxy-2-(2-hydroxyethylaminomethyl)-6H-pyrazolo[4, 5,1-de]-acridine-6-one, N-[1-[2(diethylamino)ethylamino]-7-methoxy-9-oxo-9H-thioxane-then-4-ylmethyl] formamide, N-(2-(dimethyl-amino)-ethyl)acridine-4-carboxamide, 6-[[2-(dimethylamino)-ethyl]amino]-3-hydroxy-7H-indeno[2,1-c]quinolin-7-one and dimesna.

Non-limiting examples of antiproliferative agents are antisense RNA- and antisense-DNA oligonucleotides, such as G3139, ODN698, RVASKRAS, GEM231 and INX3001, as well as antimetabolites such as enocitabine, carmofur, tegafur, pentostatine, doxifluridine, trimetrexate, fludarabine, capecitabine, galocitabine, cytarabinocfosfate, fosteabine sodiumhydrate, raltitrexed, paltitrexide, emitefur, tiazofurine, decitabine, nolatrexed, pemetrexed, nelzarabine, 2'-desoxy-2'-methylidencytidine, 2'-fluoromethylen-2'-desoxycytidine, N-[5-(2,3-dihydrobenzofuryl)sulfonyl]-N'-(3,4-dichlorophenyl)urea, N6-[4-desoxy-4-[N2-[2(E),4(E)-tetradecadienoyl]glycylamino]-L-glycero-B-L-manno-heptopyranosyl]adenine, aplidine, ecteinascidine, troxacitabine, 4-[2-amino-4-oxo-4,6,7,8-tetrahydro-3H-pyrimidino[5,4-b][1,4]thiazine-6-yl-(S)-ethyl]-2,5-thienoyl-L-glutaminic acid, aminopterine, 5-fluorouracil, alanosine, 11-acetyl-8-(carbamoyloxymethyl)-4-formyl-6-methoxy-14-oxa-1,11-diaza-tetracyclo-(7.4.1.0.0)-tetradeca-2,4,6-trien-9-ylacetic acid ester, swainsonine, lometrexole, dexrazoxane, methioninase, 2'-cyan-2'-desoxy-N4-palmitoyl-1-B-D-arabinofuranosylcytosine and 3-aminopyridine-2-carboxaldehyde-thiosemicarbazone.

"Antiproliferative agents" also comprises monoclonal antibodies against growth factors that have not been listed under "angiogenesis inhibitors", such as trastuzumab, as well as tumor suppressor genes, such as p53.

In another aspect of the invention, a medicament according to above aspects and embodiments is provided, wherein in such medicament comprises at least one additional pharmacologically active substance (drug, ingredient).

In a preferred embodiment the at least one pharmacologically active substance is a substance as described herein.

In another aspect of the invention, a medicament according to above aspects and embodiments is provided, wherein the medicament is applied before and/or during and/or after treatment with at least one additional pharmacologically active substance.

In a preferred embodiment the at least one pharmacologically active substance is a substance as described herein.

In another aspect of the invention, a pharmaceutical composition comprising a therapeutically effective amount of at least one compound of the invention is provided.

In a preferred embodiment, the pharmaceutical composition contains at least one additional compound selected from the group consisting of physiologically acceptable excipients, auxiliaries, adjuvants, diluents, carriers and/or additional pharmaceutically active substance other than the compounds of the invention.

In another aspect of the invention, a pharmaceutical composition is disclosed which comprises at least one compound of the invention, at least one pharmacologically active substance other than the compounds of the invention as described herein; and a pharmaceutically acceptable carrier.

A further embodiment of the present invention is a process for the manufacture of said pharmaceutical compositions, characterized in that one or more compounds according to the invention and one or more compounds selected from the group consisting of solid, liquid or semiliquid excipients, auxiliaries, adjuvants, diluents, carriers and pharmaceutically active agents other than the compounds according to the invention, are converted in a suitable dosage form.

In another aspect of the invention, a kit is provided comprising a therapeutically effective amount of at least one compound of the invention and/or at least one pharmaceutical composition as described herein and a therapeutically effective amount of at least one further pharmacologically active substance other than the compounds of the invention.

The pharmaceutical compositions of the present invention may be administered by any means that achieve their intended purpose. For example, administration may be by oral, parenteral, topical, enteral, intravenous, intramuscular, inhalant, nasal, intraarticular, intraspinal, transtracheal, transocular, subcutaneous, intraperitoneal, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the effect desired. Parenteral administration is preferred. Oral administration is especially preferred.

Suitable dosage forms include, but are not limited to capsules, tablets, pellets, dragees, semi-solids, powders, granules, suppositories, ointments, creams, lotions, inhalants, injections, cataplasms, gels, tapes, eye drops, solution, syrups, aerosols, suspension, emulsion, which can be produced according to methods known in the art, for example as described below:

tablets: mixing of active ingredient/s and auxiliaries, compression of said mixture into tablets (direct compression), optionally granulation of part of mixture before compression.

capsules: mixing of active ingredient/s and auxiliaries to obtain a flowable powder, optionally granulating powder, filling powders/granulate into opened capsules, capping of capsules.

semi-solids (ointments, gels, creams): dissolving/dispersing active ingredient/s in an aqueous or fatty carrier; subsequent mixing of aqueous/fatty phase with complementary fatty/aqueous phase, homogenization (creams only).

suppositories (rectal and vaginal): dissolving/dispersing active ingredient/s in carrier material liquified by heat (rectal: carrier material normally a wax; vaginal: carrier normally a heated solution of a gelling agent), casting said mixture into suppository forms, annealing and withdrawal suppositories from the forms.

aerosols: dispersing/dissolving active agent/s in a propellant, bottling said mixture into an atomizer.

In general, non-chemical routes for the production of pharmaceutical compositions and/or pharmaceutical preparations comprise processing steps on suitable mechanical means known in the art that transfer one or more compounds of the invention into a dosage form suitable for administration to a patient in need of such a treatment. Usually, the transfer of one or more compounds of the invention into such a dosage form comprises the addition of one or more compounds, selected from the group consisting of carriers, excipients, auxiliaries and pharmaceutical active ingredients other than the compounds of the invention. Suitable processing steps include, but are not limited to combining, milling, mixing, granulating, dissolving, dispersing, homogenizing, casting and/or compressing the respective active and non-active ingredients. Mechanical means for performing said processing steps are known in the art, for example from Ullmann's Encyclopedia of Industrial Chemistry, 5th Edition. In this respect, active ingredients are preferably at least one compound of the invention and one or more additional compounds other than the compounds of the invention, which show valuable pharmaceutical properties, preferably those pharmaceutical active agents other than the compounds of the invention, which are disclosed herein.

Particularly suitable for oral use are tablets, pills, coated tablets, capsules, powders, granules, syrups, juices or drops, suitable for rectal use are suppositories, suitable for parenteral use are solutions, preferably oil-based or aqueous solutions, furthermore suspensions, emulsions or implants, and suitable for topical use are ointments, creams or powders. The compounds of the invention may also be lyophilised and the resultant lyophilisates used, for example, for the preparation of injection preparations. The preparations indicated may be sterilised and/or comprise assistants, such as lubricants, preservatives, stabilisers and/or wetting agents, emulsifiers, salts for modifying the osmotic pressure, buffer substances, dyes, flavours and/or a plurality of further active ingredients, for example one or more vitamins.

Suitable excipients are organic or inorganic substances, which are suitable for enteral (for example oral), parenteral or topical administration and do not react with the compounds of the invention, for example water, vegetable oils, benzyl alcohols, alkylene glycols, polyethylene glycols, glycerol triacetate, gelatine, carbohydrates, such as lactose, sucrose, mannitol, sorbitol or starch (maize starch, wheat starch, rice starch, potato starch), cellulose preparations and/or calcium phosphates, for example tricalcium phosphate or calcium hydrogen phosphate, magnesium stearate, talc, gelatine, tragacanth, methyl cellulose, hydroxypropylmethylcellulose, sodium carboxymethylcellulose, polyvinyl pyrrolidone and/or vaseline.

If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries include, without limitation, flow-regulating agents and lubricants, for example, silica, talc, stearic acid or salts thereof, such as magnesium stearate or calcium stearate, and/or polyethylene glycol. Dragee cores are provided with suitable coatings, which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices or to provide a dosage form affording the advantage of prolonged action, the tablet, dragee or pill can comprise an inner dosage and an outer dosage component me latter being in the form of an envelope over the former. The two components can be separated by an enteric layer, which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, acetyl alcohol, solutions of suitable cellulose preparations such as acetyl-cellulose phthalate, cellulose acetate or hydroxypropylmethyl-cellulose phthalate, are used. Dye stuffs or pigments may be added to the tablets or dragee coatings, for example, for identification or in order to characterize combinations of active compound doses.

Suitable carrier substances are organic or inorganic substances which are suitable for enteral (e.g. oral) or parenteral administration or topical application and do not react with the novel compounds, for example water, vegetable oils, benzyl alcohols, polyethylene glycols, gelatin, carbohydrates such as lactose or starch, magnesium stearate, talc and petroleum jelly. In particular, tablets, coated tablets, capsules, syrups, suspensions, drops or suppositories are used for enteral administration, solutions, preferably oily or aqueous solutions, furthermore suspensions, emulsions or implants, are used for parenteral administration, and ointments, creams or powders are used for topical application. The compounds of the invention can also be lyophilized and the lyophilizates obtained can be used, for example, for the production of injection preparations.

The preparations indicated can be sterilized and/or can contain excipients such as lubricants, preservatives, stabilizers and/or wetting agents, emulsifiers, salts for affecting the osmotic pressure, buffer substances, colorants, flavourings and/or aromatizers. They can, if desired, also contain one or more further active compounds, e.g. one or more vitamins.

Other pharmaceutical preparations, which can be used orally include push-fit capsules made of gelatine, as well as soft, sealed capsules made of gelatine and a plasticizer such as glycerol or sorbitol. The push-fit capsules can contain the active compounds in the form of granules, which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

The liquid forms in which the novel compositions of the present invention may be incorporated for administration orally include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatine.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400).

Aqueous injection suspensions may contain substances, which increase the viscosity of the suspension, including, for example, sodium carboxymethyl cellulose, sorbitol, and/or dextran, optionally, the suspension may also contain stabilizers.

For administration as an inhalation spray, it is possible to use sprays in which the active ingredient is either dissolved or suspended in a propellant gas or propellant gas mixture (for example $CO_2$ or chlorofluorocarbons). The active ingredient is advantageously used here in micronized form, in which case one or more additional physiologically acceptable solvents may be present, for example ethanol. Inhalation solutions can be administered with the aid of conventional inhalers.

Possible pharmaceutical preparations, which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatine rectal capsules, which consist of a combination of the active compounds with a base. Possible base materials include, for example, liquid triglycerides, polyethylene glycols, or paraffin hydrocarbons.

For use in medicine, the compounds of the present invention will be in the form of pharmaceutically acceptable salts. Other salts may, however, be useful in the preparation of the compounds of the invention or of their pharmaceutically acceptable salts. Suitable pharmaceutically acceptable salts of the compounds of this invention include acid addition salts which may, for example be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic bases, e.g. quaternary ammonium salts.

The pharmaceutical preparations can be employed as medicaments in human and veterinary medicine. As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function. Said therapeutic effective amount of one or more of the compounds of the invention is known to the skilled artisan or can be easily determined by standard methods known in the art.

The compounds of the invention and the additional active substances are generally administered analogously to commercial preparations. Usually, suitable doses that are therapeutically effective lie in the range between 0.0005 mg and 1000 mg, preferably between 0.005 mg and 500 mg and especially between 0.5 mg and 100 mg per dose unit. The daily dose is preferably between about 0.001 mg/kg and 10 mg/kg of body weight.

Those of skill will readily appreciate that dose levels can vary as a function of the specific compound, the severity of the symptoms and the susceptibility of the subject to side effects. Some of the specific compounds are more potent than others. Preferred dosages for a given compound are readily determinable by those of skill in the art by a variety of means. A preferred means is to measure the physiological potency of a given compound.

For the purpose of the present invention, all mammalian species are regarded as being comprised. In a preferred embodiment, such mammals are selected from the group consisting of "primate, human, rodent, equine, bovine, canine, feline, domestic animals, cattle, livestock, pets, cow, sheep, pig, goat, horse, pony, donkey, hinny, mule, hare, rabbit, cat, dog, guinea pig, hamster, rat, mouse". More preferably, such mammals are humans. Animal models are of interest for experimental investigations, providing a model for treatment of human diseases.

The specific dose for the individual patient depends, however, on the multitude of factors, for example on the efficacy of the specific compounds employed, on the age, body weight, general state of health, the sex, the kind of diet, on the time and route of administration, on the excretion rate, the kind of administration and the dosage form to be administered, the pharmaceutical combination and severity of the particular disorder to which the therapy relates. The specific therapeutic effective dose for the individual patient can readily be determined by routine experimentation, for example by the doctor or physician, which advises or attends the therapeutic treatment.

In the case of many disorders, the susceptibility of a particular cell to treatment with the subject compounds may be determined by in vitro testing. Typically a culture of the cell is combined with a subject compound at varying concentrations for a period of time sufficient to allow the active agents to show a relevant reaction, usually between about one hour and one week. For in vitro testing, cultured cells from a biopsy sample may be used.

Even without further details, it is assumed that a person skilled in the art will be able to utilise the above description in the broadest scope. The preferred embodiments should therefore merely be regarded as descriptive disclosure, which is absolutely not limiting in any way.

Above and below, all temperatures are indicated in ° C. In the following examples, "conventional work-up" means that, if necessary, the solvent is removed, water is added if necessary, the pH is adjusted, if necessary, to between 2 and 10, depending on the constitution of the end product, the mixture is extracted with ethyl acetate or dichloromethane, the phases are separated, the organic phase is washed with saturated NaHCO$_3$ solution, if desired with water and saturated NaCl solution, is dried over sodium sulfate, filtered and evaporated, and the product is purified by chromatography on silica gel, by preparative HPLC and/or by crystallisation. The purified compounds are, if desired, freeze-dried.

Mass spectrometry (MS):ESI (electrospray ionisation) (M+H)$^+$

List of Abbreviations and Acronyms:

AcOH acetic acid, anh anhydrous, atm atmosphere(s), BOC tert-butoxycarbonyl CDI 1,1'-carbonyl diimidazole, conc concentrated, d day(s), dec decomposition, DMAC N,N-dimethylacetamide, DMPU 1,3-dimethyl-3,4,5,6-tetrahydro-2(1H)-pyrimidinone, DMF N,N-dimethylformamide, DMSO dimethylsulfoxide, DPPA diphenylphosphoryl azide, EDCI 1-(3-dimethylaminopropyl)-3-ethylcarbodiimide, EtOAc ethyl acetate, EtOH ethanol (100%), Et$_2$O diethyl ether, Et$_3$N triethylamine, h hour(s), MeOH methanol, pet. ether petroleum ether (boiling range 30-60° C.), temp. temperature, THF tetrahydrofuran, TFA trifluoroAcOH, Tf trifluoromethanesulfonyl.

The contents of all cited references are hereby incorporated by reference in their entirety. The invention is explained in more detail by means of the following examples without, however, being restricted thereto.

EXAMPLES

I. Synthesis of Selected Compounds of the Invention

Example 1

Synthesis of {1-[2-(2-chloro-benzylamino)-pyrido[4,3-d]pyrimidin-5-yl]-piperidin-4-yl}-(4-ethyl-piperazin-1-yl)-methanone 11 (Compound 72)

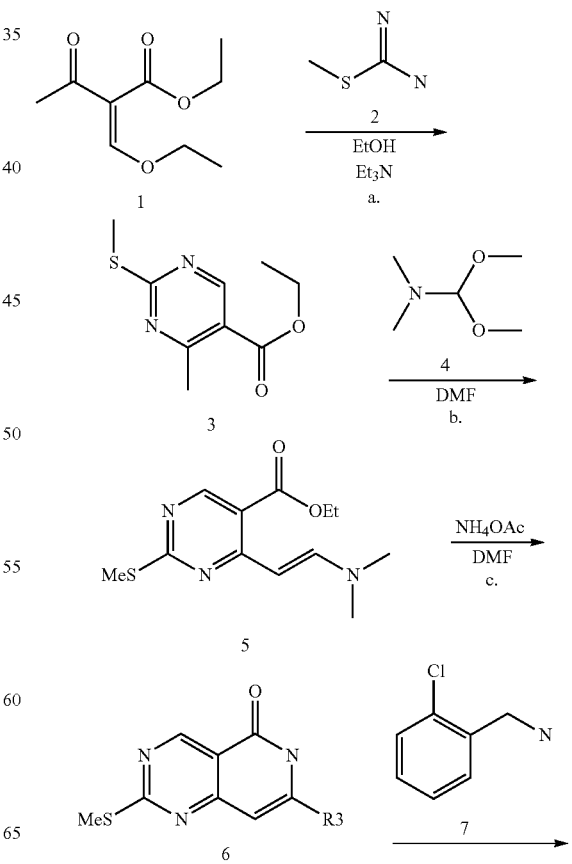

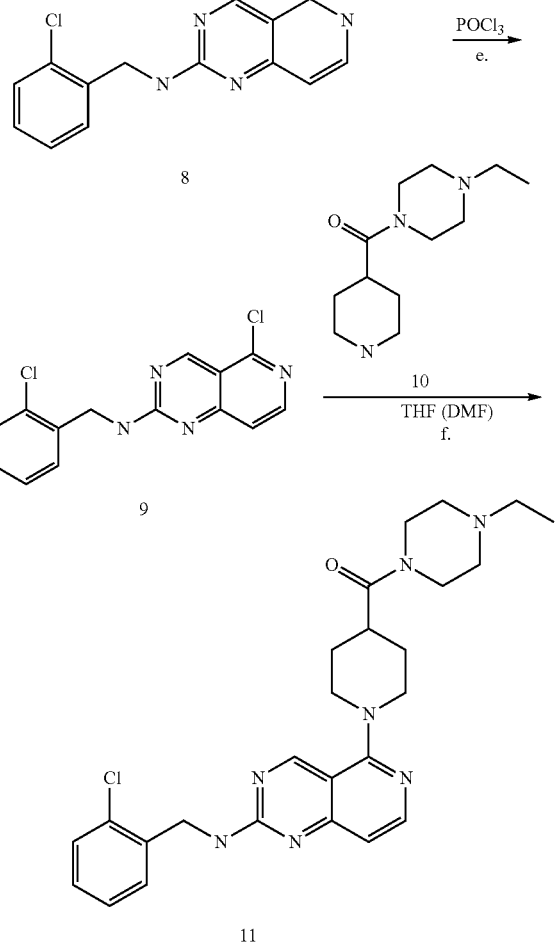

a. Preparation of 4-Methyl-2-methylsulfanyl-pyrimidine-5-carboxylic acid ethyl ester 3

Equimolar quantities of ethyl 2-acetyl-3-ethoxy-2-propenoate 1 (20.0 g, 107 mmol), ((amino(imino)methyl)-sulfanyl)methane 2 (9.68 g, 107 mmol) and triethylamine (10.8 g, 107 mmol) in EtOH (100 mL) were stirred at reflux for 48 hours. Then reaction mixture was concentrated and diluted with water. The biphasic mixture was transferred into a separatory funnel and extracted with DCM. Organic extract was washed with water, dried, filtered, and concentrated. The product was purified by crystallization from ethanol/water to yield in a colorless solid (18.4 g, 86.7 mmol, 81%).

b. Preparation of 4-((E)-2-Dimethylamino-vinyl)-2-methylsulfanyl-pyrimidine-5-carboxylic acid ethyl ester 5

4-Methyl-2-methylsulfanyl-pyrimidine-5-carboxylic acid ethyl ester 3 (18.0 g, 84.8 mmol) was dissolved in DMF (50 mL), N,N-Dimethylformamidedimethylacetal (22.5 mL, 170 mmol) and stirred at reflux for 3 hours. Then mixture was concentrated, the residue was dissolved in TCM, washed with water, dried, filtered, and concentrated. The product was purified by crystallization from ether to yield in a colorless solid (14.0 g, 52.5 mmol, 62%).

c. Preparation of 2-Methylsulfanyl-6H-pyrido[4,3-d]pyrimidin-5-one 6

4-((E)-2-Dimethylamino-vinyl)-2-methylsulfanyl-pyrimidine-5-carboxylic acid ethyl ester 5 (13.5 g, 50.5 mmol) and NH₄OAc (38.9 g, 505 mmol) were dissolved in DMF (250 mL) and stirred at reflux for about four days. Then mixture was concentrated, residue dissolved in TCM, washed with water, dried, filtered, and concentrated. The product was purified by crystallization from ethanol to obtain a colorless solid (7.60 g, 39.4 mmol, 78%).

d. Preparation of 2-(2-Chloro-benzylamino)-6H-pyrido[4,3-d]pyrimidin-5-one 8

2-Methylsulfanyl-6H-pyrido[4,3-d]pyrimidin-5-one 6 (3.00 g, 15.5 mmol) and 2-Chlorobenzyl amine 7 (9.40 mL, 77.6 mmol) were stirred at 150° C. for two days. To the recooled mixture Methanol/water (1:1, 100 mL) was added and left at RT overnight. The precipitate was filtered off and dried in vacuo. The product was purified by crystallization from ethanol to yield in a colorless solid (4.00 g, 14.0 mmol, 90%).

e. Preparation of (2-Chloro-benzyl)-(5-chloro-pyrido[4,3-d]pyrimidin-2-yl)-amine 9

2-(2-Chloro-benzylamino)-6H-pyrido[4,3-d]pyrimidin-5-one 8 (3.00 g, 10.5 mmol) was dissolved in POCl₃ (30 mL) and stirred at 90° C. for 15 h. The reaction mixture was carefully poured into ice water and the pH was adjusted to 8 adding 2 N NaOH solution. The precipitate formed was filtered off and dried in vacuo. The product was purified by crystallization from diethyl ether to yield in a colorless solid (3.18 g, 10.4 mmol, 100%).

f. Preparation of {1-[2-(2-Chloro-benzylamino)-pyrido[4,3-d]pyrimidin-5-yl]-piperidin-4-yl}-(4-ethyl-piperazin-1-yl)-methanone 11

(2-Chloro-benzyl)-(5-chloro-pyrido[4,3-d]pyrimidin-2-yl)-amine 9 (100 mg, 0.33 mmol), Isonipocetamide 10 (83.0 mg, 0.66 mmol) and NH₃ (25% solution in water, 45 µL, 0.66 mmol) were dissolved in THF (3 mL) and stirred at 100° C. in a high pressure flask for 15 hours. The mixture was poured into water and the precipitate formed was filtered off and dried in vacuo. The residue was crystallized from DCM/diethyl ether to yield in a colorless solid (86 mg, 0.22 mmol, 67%).

Analogous to above instructions further compounds were synthesized.

Instead of precursor 7 the following amine precursors were used in addition:

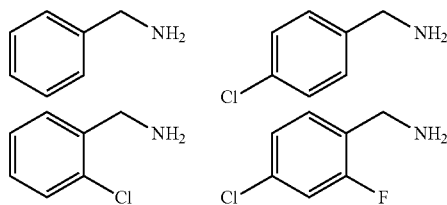

-continued

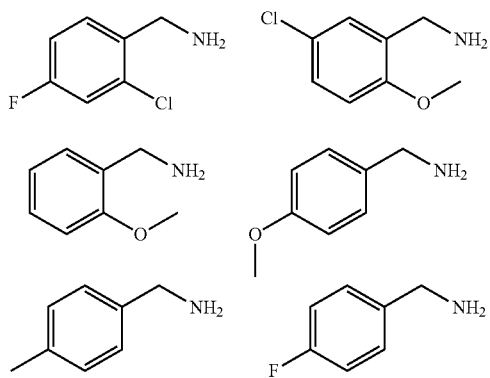

Example 2

Synthesis of {1-[2-(2-Chloro-benzylamino)-pyrido[4,3-d]pyrimidin-5-yl]-piperidin-4-yl}-[4-(2-hydroxy-ethyl)-piperazin-1-yl]-methanone 15 (Compound 141)

g. Preparation of 1-[2-(2-Chloro-benzylamino)-pyrido[4,3-d]pyrimidin-5-yl]-piperidine-4-carboxylic acid ethyl ester 13

(2-Chloro-benzyl)-(5-chloro-pyrido[4,3-d]pyrimidin-2-yl)-amine 9 (500 mg, 1.64 mmol), Piperidine-4-carboxylic acid ethyl ester 12 (0.51 mL, 3.28 mmol) and $NH_3$ (25% solution in water, 0.22 mL, 3.28 mmol) were dissolved in THF (5 mL) and stirred at 100° C. in a high pressure flask for 15 hours. To the mixture water (5 mL) was added and the precipitate formed was filtered off and dried in vacuo. The obtained colorless solid (583 mg, 1.37 mmol, 84%) was used without further purification.

h. Preparation of 1-[2-(2-Chloro-benzylamino)-pyrido[4,3-d]pyrimidin-5-yl]-piperidine-4-carboxylic acid 14

1-[2-(2-Chloro-benzylamino)-pyrido[4,3-d]pyrimidin-5-yl]-piperidine-4-carboxylic acid ethyl ester 13 (583 mg, 1.37 mmol) was dissolved in THF (10 mL), 2 N NaOH solution (5 mL) were added and the mixture was stirred for 3 h at 50° C. The mixture was evaporated to dryness, water was added and the pH was adjusted to 7 adding 2 N HCl solution. The aqueous layer was extracted twice with ethyl acetate and

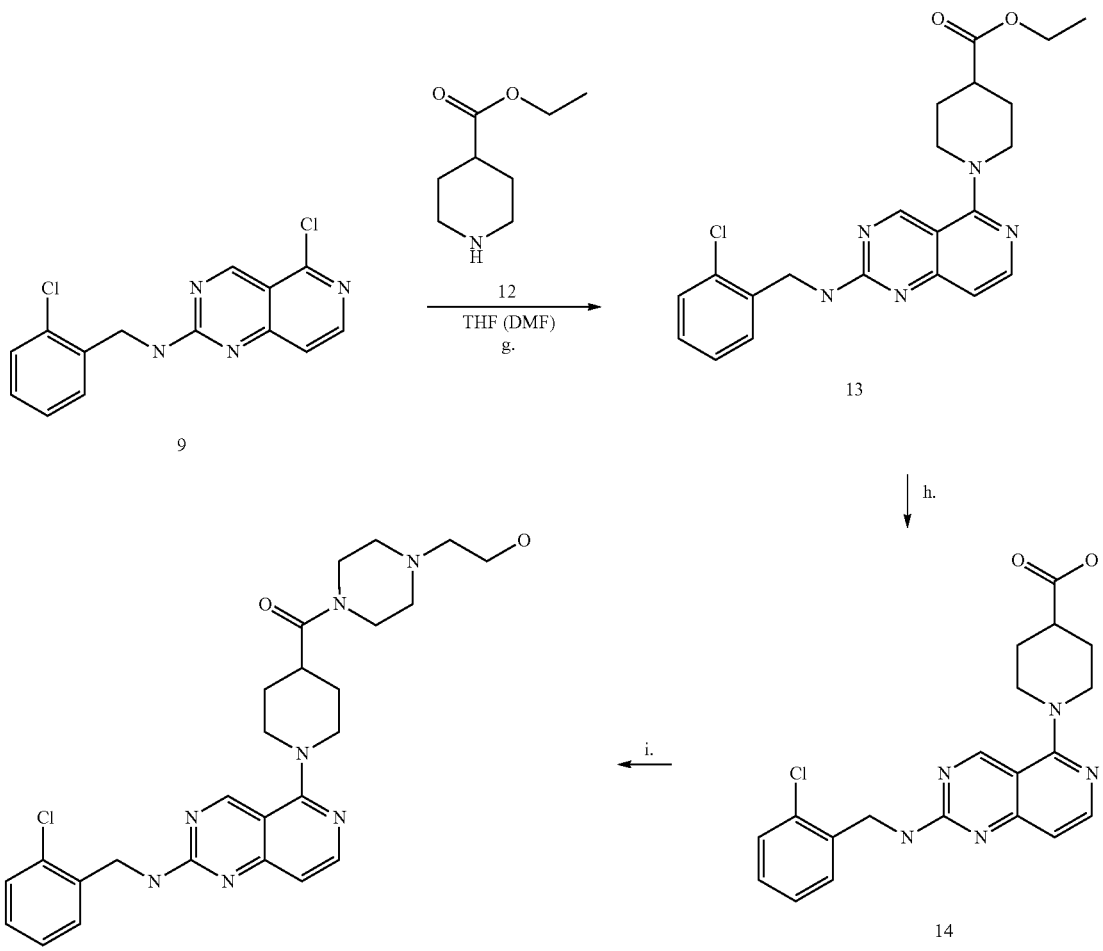

DCM. The combined organic layers were dried over sodium sulfate, filtered and evaporated to dryness. The obtained colorless solid (447 mg, 1.12 mmol, 82%) was used without further purification.

i. Preparation of {1-[2-(2-Chloro-benzylamino)-pyrido[4,3-d]pyrimidin-5-yl]-piperidin-4-yl}-[4-(2-hydroxy-ethyl)-piperazin-1-yl]-methanone 15

1-[2-(2-Chloro-benzylamino)-pyrido[4,3-d]pyrimidin-5-yl]-piperidine-4-carboxylic acid 14 (50 mg, 0.13 mmol), 2-piperazin-1-yl-ethanol (17.0 mg, 0.13 mmol) and 4-Methylmorpholine (70 µL, 0.64 mmol) were dissolved in DMF (3 mL). To this mixture hydroxybenzotriazole (17.0 mg, 0.13 mmol) and N-(3-dimethylaminopropyl)-N'-ethylcarbodiimide×HCl (24.0 mg, 0.13 mmol) were added and the mixture was stirred for 48 h at room temperature. Water was added to the mixture and the precipitate formed was filtered off and dried in vacuo. The residue was purified by silica chromatography (ethyl acetate/cyclohexane) to yield in a colorless solid (27.8 mg, 0.05 mmol, 43%) characterized as 15.

Example 3

Synthesis of derivatives of (2-Chloro-benzyl)-(5-piperazin-1-yl-pyrido[4,3-d]pyrimidin-2-yl)-amine 18 (Compound 134)

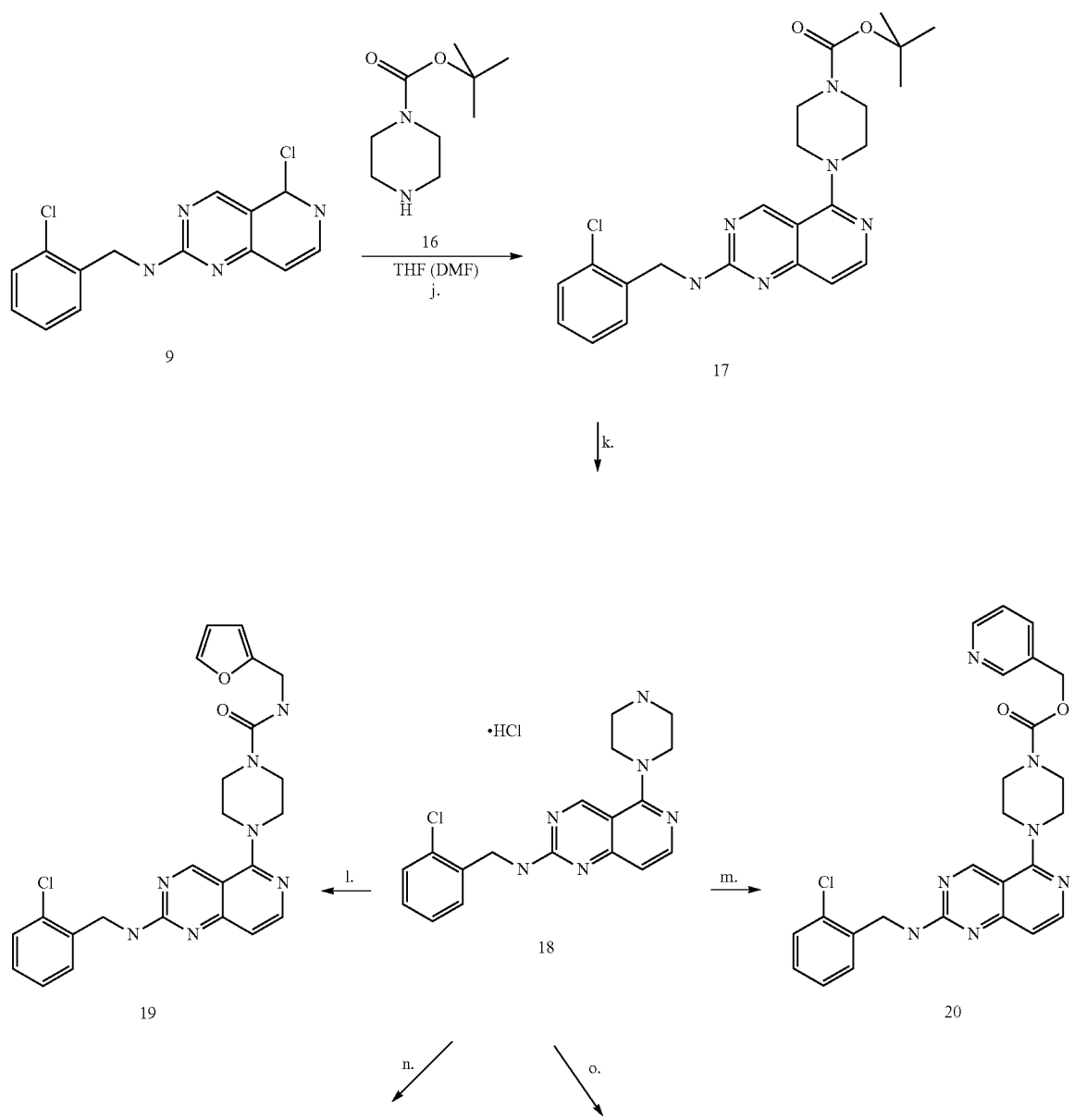

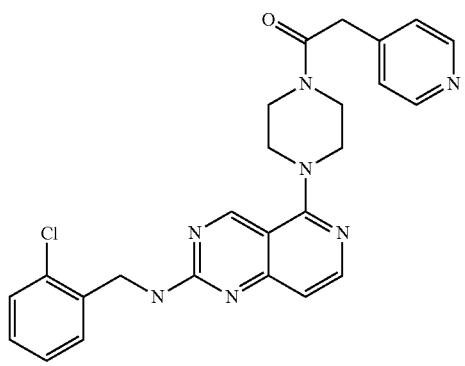

21

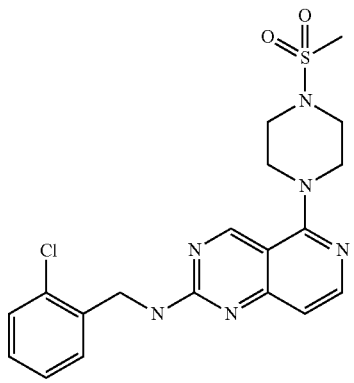

22 j. Preparation of 4-[2-(2-Chloro-benzylamino)-pyrido[4,3-d]pyrimidin-5-yl]-piperazine-1-carboxylic acid tert-butyl ester 17

(2-Chloro-benzyl)-(5-chloro-pyrido[4,3-d]pyrimidin-2-yl)-amine 9 (500 mg, 1.64 mmol), Piperidine-4-carboxylic acid ethyl ester 12 (610 mg, 3.28 mmol) and $NH_3$ (25% solution in water, 0.22 mL, 3.28 mmol) were dissolved in THF (5 mL) and stirred at 100° C. in a high pressure flask for 15 hours. To the mixture water (5 mL) was added and the precipitate formed was filtered off and dried in vacuo. The obtained colorless solid (605 mg, 1.33 mmol, 81%) was used without further purification.

k. Preparation of (2-Chloro-benzyl)-(5-piperazin-1-yl-pyrido[4,3-d]pyrimidin-2-yl)-amines Hydrochloride 18

4-[2-(2-Chloro-benzylamino)-pyrido[4,3-d]pyrimidin-5-yl]-piperazine-1-carboxylic acid tert-butyl ester 17 (605 mg, 1.33 mmol) was dissolve in 5-6 N HCl solution in Dioxan (10 mL) and stirred at RT for 1 h. The reaction mixture was evaporated to dryness and the residue was crystallized front her to result in a colorless (510 mg, 1.30 mmol, 98%) was used without further purification.

l. Preparation of 4-[2-(2-Chloro-benzylamino)-pyrido[4,3-d]pyrimidin-5-yl]-piperazine-1-carboxylic acid (furan-2-ylmethyl)-amide 19

(2-Chloro-benzyl)-(5-piperazin-1-yl-pyrido[4,3-d]pyrimidin-2-yl)-amines Hydrochloride 18 (50 mg, 0.13 mmol) was suspended in DCM (3 mL), furfuryl isocyanate (14 µL, 0.13 mmol) and triethylamine (37 µL, 0.26 mmol) added and stirred at room temperature for 15 hours. The mixture was evaporated to dryness and crystallized from methanol/diethyl ether. After drying a colorless solid (28.1 mg, 0.06 mmol, 46%) was obtained.

m. Preparation of 4-[2-(2-Chloro-benzylamino)-pyrido[4,3-d]pyrimidin-5-yl]-piperazine-1-carboxylic acid pyridin-3-ylmethyl ester 20

Pyridin-3-yl-methanol (23.8 mg, 0.13 mmol) was dissolved in THF (3 mL), 1,1'-Carbonyldiimidazol (20.8 mg, 0.13 mmol) was added and the mixture was stirred for 3 h at Room temperature. To this mixture (2-Chloro-benzyl)-(5-piperazin-1-yl-pyrido[4,3-d]pyrimidin-2-yl)-amines hydrochloride 18 (50 mg, 0.13 mmol) was added and stirring was continued for 18 h at room temperature. Water was added to the mixture and the precipitate formed was filtered off and dried in vacuo. A colorless solid (45.2 mg, 0.09 mmol, 72%) with high purity was obtained, characterized as 20.

n. Preparation of 1-{4-[2-(2-Chloro-benzylamino)-pyrido[4,3-d]pyrimidin-5-yl]-piperazin-1-yl}-2-pyridin-4-yl-ethanone 21

(2-Chloro-benzyl)-(5-piperazin-1-yl-pyrido[4,3-d]pyrimidin-2-yl)-amines Hydrochloride 18 (50 mg, 0.13 mmol), 4-pyridyl acetic acid hydrochloride (22.2 mg, 0.13 mmol) and 4-Methylmorpholine (70 µL, 0.64 mmol) were dissolved in DMF (3 mL). To this mixture hydroxybenzotriazole (17.3 mg, 0.13 mmol) and N-(3-dimethylaminopropyl)-N'-ethylcarbodiimide×HCl (24.5 mg, 0.13 mmol) were added and the mixture was stirred for 15 h at room temperature. Water was added to the mixture and the precipitate formed was filtered off and dried in vacuo. A colorless solid (25.9 mg, 0.06 mmol, 43%) with high purity was obtained, characterized as 21.

o. Preparation of (2-Chloro-benzyl)-[5-(4-methanesulfonyl-piperazin-1-yl)-pyrido[4,3-d]pyrimidin-2-yl]-amine 22

(2-Chloro-benzyl)-(5-piperazin-1-yl-pyrido[4,3-d]pyrimidin-2-yl)-amines hydrochloride 18 (50 mg, 0.13 mmol) was dissolved in THF (3 mL) mesylchloride (17.6 mg, 0.15 mmol) and triethyl amine (39 µL, 0.28 mmol) were added and stirring was continued for 6 h at room temperature. Water was added to the mixture and the precipitate formed was filtered off and dried in vacuo. A colorless solid (51.0 mg, 0.12 mmol, 92%) with high purity was obtained, characterized as 22.

An overview about further analogously synthesized compounds of the invention including physico-chemical parameters for all compounds of the invention is given in Table 2.

TABLE 2

| Compound | Chemical Name | ESI [M + 1]+ | HPLC Rt [min] | HPLC/MS Rt [min] |
|---|---|---|---|---|
| 1 | Benzyl-(5-pyrrolidin-1-yl-pyrido[4,3-d]pyrimidin-2-yl)-amine | 306 | | 2.16 |
| 2 | N2-Benzyl-N5-(4-fluoro-phenyl)-pyrido[4,3-d]pyrimidine-2,5-diamine | 346 | | 2.21 |
| 3 | N2-Benzyl-N5-(4-methoxy-phenyl)-pyrido[4,3-d]pyrimidine-2,5-diamine | 358 | | 2.18 |
| 4 | N2-Benzyl-N5-(2,4-difluoro-phenyl)-pyrido[4,3-d]pyrimidine-2,5-diamine | 364 | | 2.32 |
| 5 | N5-Benzo[1,3]dioxol-5-yl-N2-benzyl-pyrido[4,3-d]pyrimidine-2,5-diamine | 372 | | 2.26 |
| 6 | N2-Benzyl-N5-(3,4-dimethoxy-phenyl)-pyrido[4,3-d]pyrimidine-2,5-diamine | 388 | | 2.24 |
| 7 | N2-Benzyl-N5-(4-fluoro-2-methyl-phenyl)-pyrido[4,3-d]pyrimidine-2,5-diamine | 360 | | 2.23 |
| 8 | (2-Chloro-benzyl)-(5-pyrrolidin-1-yl-pyrido[4,3-d]pyrimidin-2-yl)-amine | 341 | | 2.10 |
| 9 | N2-(2-Chloro-benzyl)-N5-(4-methoxy-phenyl)-pyrido[4,3-d]pyrimidine-2,5-diamine | 393 | | 2.34 |
| 10 | N2,N5-Bis-(2-chloro-benzyl)-pyrido[4,3-d]pyrimidine-2,5-diamine | 411 | | 2.52 |
| 11 | N2-(2-Chloro-benzyl)-N5-pyridin-3-ylmethyl-pyrido[4,3-d]pyrimidine-2,5-diamine | 378 | | 1.78 |
| 12 | N2-(2-Chloro-benzyl)-N5-(3,4-dimethoxy-phenyl)-pyrido[4,3-d]pyrimidine-2,5-diamine | 423 | | 2.29 |
| 13 | 1-{4-[2-(2-Chloro-benzylamino)-pyrido[4,3-d]pyrimidin-5-ylamino]-phenyl}-ethanone | 405 | | 2.54 |
| 14 | N2-(2-Chloro-benzyl)-N5-(2,4-dimethoxy-phenyl)-pyrido[4,3-d]pyrimidine-2,5-diamine | 423 | | 2.39 |
| 15 | N2-(2-Chloro-benzyl)-N5-(3-isopropoxy-propyl)-pyrido[4,3-d]pyrimidine-2,5-diamine | 387 | | 2.35 |
| 16 | N2-(2-Chloro-benzyl)-N5-(3-piperidin-1-yl-propyl)-pyrido[4,3-d]pyrimidine-2,5-diamine | 412 | | 1.74 |
| 17 | N2-(2-Chloro-benzyl)-N5-(3-pyrrolidin-1-yl-propyl)-pyrido[4,3-d]pyrimidine-2,5-diamine | 398 | | 2.67 |
| 18 | N2-(2-Chloro-benzyl)-N5-(2-piperidin-1-yl-ethyl)-pyrido[4,3-d]pyrimidine-2,5-diamine | 398 | | 1.82 |
| 19 | N5-(4-Fluoro-2-methyl-phenyl)-N2-(4-methyl-benzyl)-pyrido[4,3-d]pyrimidine-2,5-diamine | 374 | | 2.66 |
| 20 | (4-Fluoro-benzyl)-(5-pyrrolidin-1-yl-pyrido[4,3-d]pyrimidin-2-yl)-amine | 324 | | 2.17 |
| 21 | N2-(4-Fluoro-benzyl)-N5-(4-fluoro-phenyl)-pyrido[4,3-d]pyrimidine-2,5-diamine | 364 | | 2.23 |
| 22 | N2-(4-Fluoro-benzyl)-N5-o-tolyl-pyrido[4,3-d]pyrimidine-2,5-diamine | 360 | | 2.11 |
| 23 | N2-(4-Fluoro-benzyl)-N5-(4-methoxy-phenyl)-pyrido[4,3-d]pyrimidine-2,5-diamine | 376 | | 2.34 |
| 24 | N2-(4-Fluoro-benzyl)-N5-(2-fluoro-phenyl)-pyrido[4,3-d]pyrimidine-2,5-diamine | 364 | | 2.23 |
| 25 | N5-(2,4-Difluoro-phenyl)-N2-(4-fluoro-benzyl)-pyrido[4,3-d]pyrimidine-2,5-diamine | 382 | | 2.28 |
| 26 | N5-Benzo[1,3]dioxol-5-yl-N2-(4-fluoro-benzyl)-pyrido[4,3-d]pyrimidine-2,5-diamine | 390 | | 2.22 |

TABLE 2-continued

| Compound | Chemical Name | ESI [M + 1]+ | HPLC Rt [min] | HPLC/MS Rt [min] |
|---|---|---|---|---|
| 27 | N5-(3,4-Dimethoxy-phenyl)-N2-(4-fluoro-benzyl)-pyrido[4,3-d]pyrimidine-2,5-diamine | 406 | | 2.32 |
| 28 | N2-(4-Fluoro-benzyl)-N5-(4-fluoro-2-methyl-phenyl)-pyrido[4,3-d]pyrimidine-2,5-diamine | 378 | | 2.14 |
| 29 | N5-Benzo[1,2,5]oxadiazol-5-ylmethyl-N2-(4-fluoro-benzyl)-pyrido[4,3-d]pyrimidine-2,5-diamine | 402 | | 2.52 |
| 30 | N2-(4-Fluoro-benzyl)-N5-isobutyl-pyrido[4,3-d]pyrimidine-2,5-diamine | 326 | | 2.18 |
| 31 | (2-Methoxy-benzyl)-(5-pyrrolidin-1-yl-pyrido[4,3-d]pyrimidin-2-yl)-amine | 336 | | 2.20 |
| 32 | N5-(2-Ethoxy-phenyl)-N2-(2-methoxy-benzyl)-pyrido[4,3-d]pyrimidine-2,5-diamine | 402 | | 2.47 |
| 33 | N5-(4-Fluoro-phenyl)-N2-(2-methoxy-benzyl)-pyrido[4,3-d]pyrimidine-2,5-diamine | 376 | | 2.15 |
| 34 | N2-(2-Methoxy-benzyl)-N5-o-tolyl-pyrido[4,3-d]pyrimidine-2,5-diamine | 372 | | 2.26 |
| 35 | N2-(2-Methoxy-benzyl)-N5-(4-methoxy-phenyl)-pyrido[4,3-d]pyrimidine-2,5-diamine | 388 | | 2.15 |
| 36 | N2-(2-Methoxy-benzyl)-N5-p-tolyl-pyrido[4,3-d]pyrimidine-2,5-diamine | 372 | | 2.43 |
| 37 | N5-(2,4-Difluoro-phenyl)-N2-(2-methoxy-benzyl)-pyrido[4,3-d]pyrimidine-2,5-diamine | 394 | | 2.20 |
| 38 | N5-(3,4-Dimethoxy-phenyl)-N2-(2-methoxy-benzyl)-pyrido[4,3-d]pyrimidine-2,5-diamine | 418 | | 2.31 |
| 39 | N5-(2,3-Dihydro-benzo[1,4]dioxin-6-yl)-N2-(2-methoxy-benzyl)-pyrido[4,3-d]pyrimidine-2,5-diamine | 416 | | 2.36 |
| 40 | N5-(2,4-Dimethoxy-phenyl)-N2-(2-methoxy-benzyl)-pyrido[4,3-d]pyrimidine-2,5-diamine | 418 | | 2.29 |
| 41 | N5-(4-Fluoro-2-methyl-phenyl)-N2-(2-methoxy-benzyl)-pyrido[4,3-d]pyrimidine-2,5-diamine | 390 | | 2.24 |
| 42 | N2-(4-Chloro-benzyl)-N5-(4-fluoro-phenyl)-pyrido[4,3-d]pyrimidine-2,5-diamine | 381 | | 2.35 |
| 43 | N2-(4-Chloro-benzyl)-N5-o-tolyl-pyrido[4,3-d]pyrimidine-2,5-diamine | 377 | | 2.40 |
| 44 | N2-(4-Chloro-benzyl)-N5-(4-methoxy-phenyl)-pyrido[4,3-d]pyrimidine-2,5-diamine | 393 | | 2.26 |
| 45 | N2-(4-Chloro-benzyl)-N5-(2,4-difluoro-phenyl)-pyrido[4,3-d]pyrimidine-2,5-diamine | 399 | | 2.68 |
| 46 | N5-Benzo[1,3]dioxol-5-yl-N2-(4-chloro-benzyl)-pyrido[4,3-d]pyrimidine-2,5-diamine | 407 | | 2.38 |
| 47 | N2-(4-Chloro-benzyl)-N5-(3,4-dimethoxy-phenyl)-pyrido[4,3-d]pyrimidine-2,5-diamine | 423 | | 2.33 |
| 48 | N2-(4-Chloro-benzyl)-N5-(3,4-difluoro-phenyl)-pyrido[4,3-d]pyrimidine-2,5-diamine | 399 | | 2.58 |
| 49 | N2-(4-Chloro-benzyl)-N5-(4-fluoro-2-methyl-phenyl)-pyrido[4,3-d]pyrimidine-2,5-diamine | 395 | | 2.65 |
| 50 | 4-[2-(4-Chloro-benzylamino)-pyrido[4,3-d]pyrimidin-5-ylamino]-benzoic acid methyl ester | 421 | | 3.68 |

TABLE 2-continued

| Compound | Chemical Name | ESI [M + 1]+ | HPLC Rt [min] | HPLC/MS Rt [min] |
|---|---|---|---|---|
| 51 | N5-(2,5-Dimethoxy-phenyl)-N2-(4-methoxy-benzyl)-pyrido[4,3-d]pyrimidine-2,5-diamine | 418 | | 2.45 |
| 52 | N5-(2,4-Difluoro-phenyl)-N2-(4-methoxy-benzyl)-pyrido[4,3-d]pyrimidine-2,5-diamine | 394 | | 2.43 |
| 53 | N5-Benzo[1,3]dioxol-5-yl-N2-(4-methoxy-benzyl)-pyrido[4,3-d]pyrimidine-2,5-diamine | 402 | | 2.23 |
| 54 | N5-(3,4-Dimethoxy-phenyl)-N2-(4-methoxy-benzyl)-pyrido[4,3-d]pyrimidine-2,5-diamine | 418 | | 2.16 |
| 55 | N5-(2,3-Dihydro-benzo[1,4]dioxin-6-yl)-N2-(4-methoxy-benzyl)-pyrido[4,3-d]pyrimidine-2,5-diamine | 416 | | 2.24 |
| 56 | N5-(2,4-Dimethoxy-phenyl)-N2-(4-methoxy-benzyl)-pyrido[4,3-d]pyrimidine-2,5-diamine | 418 | | 2.44 |
| 57 | 4-[2-(4-Methoxy-benzylamino)-pyrido[4,3-d]pyrimidin-5-ylamino]-benzonitrile | 383 | | 2.57 |
| 58 | N5-(3,4-Difluoro-phenyl)-N2-(4-methoxy-benzyl)-pyrido[4,3-d]pyrimidine-2,5-diamine | 394 | | 2.51 |
| 59 | N5-(4-Fluoro-2-methyl-phenyl)-N2-(4-methoxy-benzyl)-pyrido[4,3-d]pyrimidine-2,5-diamine | 390 | | 2.45 |
| 60 | 1-(2-Benzylamino-pyrido[4,3-d]pyrimidin-5-yl)-piperidine-4-carboxylic acid (furan-2-ylmethyl)-amide | 444 | | 2.44 |
| 61 | 1-(2-Benzylamino-pyrido[4,3-d]pyrimidin-5-yl)-piperidine-4-carboxylic acid isopropylamide | 406 | | 2.24 |
| 62 | 1-[2-(2-Chloro-benzylamino)-pyrido[4,3-d]pyrimidin-5-yl]-piperidine-4-carboxylic acid (pyridin-3-ylmethyl)-amide | 489 | | 1.84 |
| 63 | 1-[2-(2-Chloro-benzylamino)-pyrido[4,3-d]pyrimidin-5-yl]-piperidine-4-carboxylic acid (3-diethylamino-propyl)-amide | 511 | | |
| 64 | 1-[2-(2-Chloro-benzylamino)-pyrido[4,3-d]pyrimidin-5-yl]-piperidine-4-carboxylic acid (2-dimethylamino-ethyl)-amide | 469 | | 2.07 |
| 65 | 1-[2-(2-Chloro-benzylamino)-pyrido[4,3-d]pyrimidin-5-yl]-piperidine-4-carboxylic acid (furan-2-ylmethyl)-amide | 478 | | 2.26 |
| 66 | {1-[2-(2-Chloro-benzylamino)-pyrido[4,3-d]pyrimidin-5-yl]-piperidin-4-yl}-pyrrolidin-1-yl-methanone | 452 | | 2.45 |
| 67 | 1-[2-(2-Chloro-benzylamino)-pyrido[4,3-d]pyrimidin-5-yl]-piperidine-4-carboxylic acid isopropylamide | 440 | | 2.35 |
| 68 | 1-[2-(2-Chloro-benzylamino)-pyrido[4,3-d]pyrimidin-5-yl]-piperidine-4-carboxylic acid propylamide | 440 | | 2.35 |
| 69 | 1-[2-(2-Chloro-benzylamino)-pyrido[4,3-d]pyrimidin-5-yl]-piperidine-4-carboxylic acid cyclopropylamide | 438 | | 2.41 |
| 70 | 1-[2-(2-Chloro-benzylamino)-pyrido[4,3-d]pyrimidin-5-yl]-piperidine-4-carboxylic acid (2-methoxy-ethyl)-amide | 456 | | 2.21 |
| 71 | 1-[2-(2-Chloro-benzylamino)-pyrido[4,3-d]pyrimidin-5-yl]-piperidine-4-carboxylic acid allylamide | 438 | | 2.47 |

TABLE 2-continued

| Compound | Chemical Name | ESI [M + 1]+ | HPLC Rt [min] | HPLC/MS Rt [min] |
|---|---|---|---|---|
| 72 | {1-[2-(2-Chloro-benzylamino)-pyrido[4,3-d]pyrimidin-5-yl]-piperidin-4-yl}-(4-ethyl-piperazin-1-yl)-methanone | 495 | | 2.28 |
| 73 | 1-[2-(2-Chloro-benzylamino)-pyrido[4,3-d]pyrimidin-5-yl]-piperidine-4-carboxylic acid (3-methoxy-propyl)-amide | 470 | | 2.37 |
| 74 | 1-[2-(2-Methoxy-benzylamino)-pyrido[4,3-d]pyrimidin-5-yl]-piperidine-4-carboxylic acid (furan-2-ylmethyl)-amide | 474 | | 3.63 |
| 75 | 1-[2-(2-Methoxy-benzylamino)-pyrido[4,3-d]pyrimidin-5-yl]-piperidine-4-carboxylic acid (2-methoxy-ethyl)-amide | 452 | | 3.48 |
| 76 | {1-[2-(2-Methoxy-benzylamino)-pyrido[4,3-d]pyrimidin-5-yl]-piperidin-4-yl}-(4-pyridin-2-yl-piperazin-1-yl)-methanone | 540 | | 3.38 |
| 77 | 1-[2-(2-Methoxy-benzylamino)-pyrido[4,3-d]pyrimidin-5-yl]-piperidine-4-carboxylic acid (5-methyl-isoxazol-3-yl)-amide | 475 | | 3.66 |
| 78 | 1-[2-(4-Chloro-benzylamino)-pyrido[4,3-d]pyrimidin-5-yl]-piperidine-4-carboxylic acid pyridin-3-ylamide | 475 | | 2.05 |
| 79 | 1-[2-(4-Chloro-benzylamino)-pyrido[4,3-d]pyrimidin-5-yl]-piperidine-4-carboxylic acid (furan-2-ylmethyl)-amide | 478 | | 2.36 |
| 80 | {1-[2-(4-Chloro-benzylamino)-pyrido[4,3-d]pyrimidin-5-yl]-piperidin-4-yl}-pyrrolidin-1-yl-methanone | 452 | | 2.27 |
| 81 | 1-[2-(2-Chloro-benzylamino)-pyrido[4,3-d]pyrimidin-5-yl]-piperidine-3-carboxylic acid (pyridin-3-ylmethyl)-amide | 489 | | 2.05 |
| 82 | 1-[2-(2-Chloro-benzylamino)-pyrido[4,3-d]pyrimidin-5-yl]-piperidine-3-carboxylic acid pyridin-3-ylamide | 475 | | 2.31 |
| 83 | 1-[2-(2-Chloro-benzylamino)-pyrido[4,3-d]pyrimidin-5-yl]-piperidine-3-carboxylic acid (furan-2-ylmethyl)-amide | 478 | | 2.61 |
| 84 | 1-[2-(2-Chloro-benzylamino)-pyrido[4,3-d]pyrimidin-5-yl]-piperidine-3-carboxylic acid isopropylamide | 440 | | 2.68 |
| 85 | 1-[2-(2-Chloro-benzylamino)-pyrido[4,3-d]pyrimidin-5-yl]-piperidine-3-carboxylic acid propylamide | 440 | | 2.68 |
| 86 | 1-[2-(2-Chloro-benzylamino)-pyrido[4,3-d]pyrimidin-5-yl]-piperidine-3-carboxylic acid cyclopropylamide | 438 | | 2.54 |
| 87 | 1-[2-(2-Chloro-benzylamino)-pyrido[4,3-d]pyrimidin-5-yl]-piperidine-3-carboxylic acid (5-methyl-isoxazol-3-yl)-amide | 479 | | 2.55 |
| 88 | 1-[2-(2-Chloro-benzylamino)-pyrido[4,3-d]pyrimidin-5-yl]-piperidine-3-carboxylic acid (3-ethoxy-propyl)-amide | 484 | | 2.48 |
| 89 | {1-[2-(2-Chloro-benzylamino)-pyrido[4,3-d]pyrimidin-5-yl]-piperidin-3-yl}-(4-ethyl-piperazin-1-yl)-methanone | 495 | | 2.12 |
| 90 | 1-[2-(2-Chloro-benzylamino)-pyrido[4,3-d]pyrimidin-5-yl]-piperidine-3-carboxylic acid (3-methoxy-propyl)-amide | 470 | | 2.48 |

TABLE 2-continued

| Compound | Chemical Name | ESI [M + 1]+ | HPLC Rt [min] | HPLC/MS Rt [min] |
|---|---|---|---|---|
| 91 | 1-[2-(2-Chloro-benzylamino)-pyrido[4,3-d]pyrimidin-5-yl]-piperidine-3-carboxylic acid diethylamide | 454 | | 2.66 |
| 92 | 3-({1-[2-(2-Chloro-benzylamino)-pyrido[4,3-d]pyrimidin-5-yl]-piperidine-3-carbonyl}-amino)-propionic acid ethyl ester | 498 | | 2.48 |
| 93 | 1-[2-(4-Methyl-benzylamino)-pyrido[4,3-d]pyrimidin-5-yl]-piperidine-3-carboxylic acid pyridin-3-ylamide | 455 | | 2.05 |
| 94 | {1-[2-(4-Chloro-benzylamino)-pyrido[4,3-d]pyrimidin-5-yl]-piperidin-3-yl}-(4-pyridin-2-yl-piperazin-1-yl)-methanone | 544 | | 2.07 |
| 95 | {1-[2-(4-Methoxy-benzylamino)-pyrido[4,3-d]pyrimidin-5-yl]-piperidin-3-yl}-(4-pyridin-2-yl-piperazin-1-yl)-methanone | 540 | | 1.93 |
| 96 | 1-[2-(2-Chloro-benzylamino)-pyrido[4,3-d]pyrimidin-5-yl]-piperidine-4-carboxylic acid (2-diethylamino-ethyl)-amide | 497 | | |
| 97 | {1-[2-(2-Chloro-benzylamino)-pyrido[4,3-d]pyrimidin-5-yl]-piperidin-4-yl}-(4-propyl-piperazin-1-yl)-methanone | 509 | | 1.42 |
| 98 | 1-[2-(2-Chloro-benzylamino)-pyrido[4,3-d]pyrimidin-5-yl]-piperidine-4-carboxylic acid (3-ethoxy-propyl)-amide | 484 | 3.28 | 1.74 |
| 99 | {1-[2-(2-Chloro-benzylamino)-pyrido[4,3-d]pyrimidin-5-yl]-piperidin-3-yl}-(4-pyridin-2-yl-piperazin-1-yl)-methanone | 544 | | 1.53 |
| 100 | N2-(2-Chloro-benzyl)-N5-(2-fluoro-phenyl)-pyrido[4,3-d]pyrimidine-2,5-diamine | 381 | | 2.54 |
| 101 | 3-({1-[2-(2-Chloro-benzylamino)-pyrido[4,3-d]pyrimidin-5-yl]-piperidine-4-carbonyl}-amino)-propionic acid ethyl ester | 498 | | |
| 102 | 1-[2-(2-Methoxy-benzylamino)-pyrido[4,3-d]pyrimidin-5-yl]-piperidine-4-carboxylic acid (3-ethoxy-propyl)-amide | 480 | | 3.55 |
| 103 | 1-[2-(2-Methoxy-benzylamino)-pyrido[4,3-d]pyrimidin-5-yl]-piperidine-4-carboxylic acid diethylamide | 450 | | 3.61 |
| 104 | {1-[2-(2-Chloro-benzylamino)-pyrido[4,3-d]pyrimidin-5-yl]-piperidin-3-yl}-(4-methyl-piperazin-1-yl)-methanone | 481 | | 2.07 |
| 105 | 1-[2-(2-Chloro-benzylamino)-pyrido[4,3-d]pyrimidin-5-yl]-piperidine-4-carboxylic acid (2-hydroxy-ethyl)-amide | 442 | 2.85 | 1.587* |
| 106 | (2-Chloro-benzyl)-{5-[4-(4-fluoro-phenyl)-piperazin-1-yl]-pyrido[4,3-d]pyrimidin-2-yl}-amine | 450 | 4.05 | 2.037* |
| 107 | 1-[2-(2-Chloro-benzylamino)-pyrido[4,3-d]pyrimidin-5-yl]-piperidine-4-carboxylic acid amide | 398 | 2.91 | 1.597* |
| 108 | 2-{4-[2-(2-Chloro-benzylamino)-pyrido[4,3-d]pyrimidin-5-yl]-piperazin-1-yl}-N-pyridin-3-yl-acetamide | 490 | 2.56 | 1.486* |
| 109 | (2-Chloro-benzyl)-[5-(4-thiazol-2-yl-piperazin-1-yl)-pyrido[4,3-d]pyrimidin-2-yl]-amine | 439 | 2.88 | 1.577* |
| 110 | (2-Chloro-benzyl)-{5-[4-(1-methyl-piperidin-4-ylmethyl)-piperazin-1-yl]pyrido[4,3-d]pyrimidin-2-yl}-amine | 467 | 2.48 | 1.476* |

TABLE 2-continued

| Compound | Chemical Name | ESI [M + 1]+ | HPLC Rt [min] | HPLC/MS Rt [min] |
|---|---|---|---|---|
| 111 | (2-Chloro-benzyl)-[5-(4-pyridin-2-yl-piperazin-1-yl)-pyrido[4,3-d]pyrimidin-2-yl]-amine | 433 | 2.72 | 1.533* |
| 112 | (2-Chloro-benzyl)-[5-(4-pyrimidin-2-yl-piperazin-1-yl)-pyrido[4,3-d]pyrimidin-2-yl]-amine | 434 | 3.28 | 1.729* |
| 113 | {4-[2-(2-Chloro-benzylamino)-pyrido[4,3-d]pyrimidin-5-yl]-piperazin-1-yl}-furan-2-yl-methanone | 450 | 3.31 | 1.744* |
| 114 | 4-[2-(2-Chloro-benzylamino)-pyrido[4,3-d]pyrimidin-5-yl]-piperazine-1-carboxylic acid ethyl ester | 428 | 3.49 | 1.800* |
| 115 | 1-{4-[2-(2-Chloro-benzylamino)-pyrido[4,3-d]pyrimidin-5-yl]-piperazin-1-yl}-ethanone | 398 | 2.96 | 1.614* |
| 116 | {4-[2-(2-Chloro-benzylamino)-pyrido[4,3-d]pyrimidin-5-yl]-piperazin-1-yl}-morpholin-4-yl-methanone | 469 | 3.15 | 1.666* |
| 117 | 4-[2-(2-Chloro-benzylamino)-pyrido[4,3-d]pyrimidin-5-yl]-piperazine-1-carboxylic acid (furan-2-ylmethyl)-amide | 479 | 3.41 | 1.772* |
| 118 | 1-[2-(2-Chloro-benzylamino)-pyrido[4,3-d]pyrimidin-5-yl]-piperidine-4-carboxylic acid ethyl ester | 427 | 3.73 | 1.896* |
| 119 | 1-{4-[2-(2-Chloro-benzylamino)-pyrido[4,3-d]pyrimidin-5-yl]-piperazin-1-yl}-2-pyridin-2-yl-ethanone | 475 | 2.72 | 1.542* |
| 120 | 1-{4-[2-(2-Chloro-benzylamino)-pyrido[4,3-d]pyrimidin-5-yl]-piperazin-1-yl}-3-(1-methyl-1H-pyrazol-4-yl)-propan-1-one | 492 | 3.15 | 1.642* |
| 121 | 1-{4-[2-(2-Chloro-benzylamino)-pyrido[4,3-d]pyrimidin-5-yl]-piperazin-1-yl}-2-pyridin-3-yl-ethanone | 475 | 2.77 | 1.532* |
| 122 | 1-{4-[2-(2-Chloro-benzylamino)-pyrido[4,3-d]pyrimidin-5-yl]-piperazin-1-yl}-3-(1H-imidazol-4-yl)-propan-1-one | 478 | 2.77 | 1.535* |
| 123 | 1-{4-[2-(2-Chloro-benzylamino)-pyrido[4,3-d]pyrimidin-5-yl]-piperazin-1-yl}-pentane-1,4-dione | 454 | 3.15 | 1.658* |
| 124 | 1-{4-[2-(2-Chloro-benzylamino)-pyrido[4,3-d]pyrimidin-5-yl]-piperazin-1-yl}-3-pyridin-2-yl-propan-1-one | 489 | 2.80 | 1.531* |
| 125 | 4-{4-[2-(2-Chloro-benzylamino)-pyrido[4,3-d]pyrimidin-5-yl]-piperazin-1-yl}-N,N-dimethyl-4-oxo-butyramide | 483 | 2.88 | 1.61 |
| 126 | Acetic acid 2-{4-[2-(2-chloro-benzylamino)-pyrido[4,3-d]pyrimidin-5-yl]-piperazin-1-yl}-2-oxo-ethyl ester | 456 | 3.01 | 1.72 |
| 127 | 1-[2-(2-Chloro-benzylamino)-pyrido[4,3-d]pyrimidin-5-yl]-piperidine-4-carboxylic acid | 399 | 3.15 | 1.59 |
| 128 | 3-{4-[2-(2-Chloro-benzylamino)-pyrido[4,3-d]pyrimidin-5-yl]-piperazin-1-yl}-3-oxo-propionitrile | 423 | 3.04 | 1.74 |
| 129 | 3-{4-[2-(2-Chloro-benzylamino)-pyrido[4,3-d]pyrimidin-5-yl]-piperazin-1-yl}-3-oxo-propionic acid ethyl ester | 470 | | 1.83 |
| 130 | 1-{4-[2-(2-Chloro-benzylamino)-pyrido[4,3-d]pyrimidin-5-yl]-piperazin-1-yl}-2-dimethylamino-ethanone | 441 | | 1.500* |

TABLE 2-continued

| Compound | Chemical Name | ESI [M + 1]+ | HPLC Rt [min] | HPLC/MS Rt [min] |
|---|---|---|---|---|
| 131 | 5-{4-[2-(2-Chloro-benzylamino)-pyrido[4,3-d]pyrimidin-5-yl]-piperazin-1-yl}-5-oxo-pentanoic acid methyl ester | 484 | 3.25 | 1.82 |
| 132 | 4-Amino-1-{4-[2-(2-chloro-benzylamino)-pyrido[4,3-d]pyrimidin-5-yl]-piperazin-1-yl}-butan-1-one | 441 | 2.64 | 1.36 |
| 133 | (S)-3-Amino-1-(2-{4-[2-(2-chloro-benzylamino)-pyrido[4,3-d]pyrimidin-5-yl]-piperazin-1-yl}-2-oxo-ethyl)-pyrrolidin-2-one | 496 | 2.59 | 1.38 |
| 134 | (2-Chloro-benzyl)-(5-piperazin-1-yl-pyrido[4,3-d]pyrimidin-2-yl)-amine | 356 | 2.35 | 1.493* |
| 135 | 1-{4-[2-(2-Chloro-benzylamino)-pyrido[4,3-d]pyrimidin-5-yl]-piperazin-1-yl}-3-diethylamino-propan-1-one | 483 | 2.67 | 1.42 |
| 136 | 1-{4-[2-(2-Chloro-benzylamino)-pyrido[4,3-d]pyrimidin-5-yl]-piperazin-1-yl}-2-(2-methoxy-ethoxy)-ethanone | 472 | 2.96 | 1.68 |
| 137 | 3-(1H-Benzoimidazol-2-yl)-1-{4-[2-(2-chloro-benzylamino)-pyrido[4,3-d]pyrimidin-5-yl]-piperazin-1-yl}-propan-1-one | 528 | 2.91 | 1.52 |
| 138 | 1-{4-[2-(2-Chloro-benzylamino)-pyrido[4,3-d]pyrimidin-5-yl]-piperazin-1-yl}-2-pyridin-4-yl-ethanone | 475 | 2.64 | 1.44 |
| 139 | 1-[2-(2-Chloro-benzylamino)-pyrido[4,3-d]pyrimidin-5-yl]-piperidine-4-carboxylic acid methylamide | 412 | 3.01 | 1.51 |
| 140 | 1-[2-(2-Chloro-benzylamino)-pyrido[4,3-d]pyrimidin-5-yl]-piperidine-4-carboxylic acid dimethylamide | 426 | 3.17 | 1.57 |
| 141 | {1-[2-(2-Chloro-benzylamino)-pyrido[4,3-d]pyrimidin-5-yl]-piperidin-4-yl}-[4-(2-hydroxy-ethyl)-piperazin-1-yl]-methanone | 511 | 2.83 | 1.30 |
| 142 | {1-[2-(2-Chloro-benzylamino)-pyrido[4,3-d]pyrimidin-5-yl]-piperidin-4-yl}-((S)-2-pyrrolidin-1-ylmethyl-pyrrolidin-1-yl)-methanone | 535 | 2.99 | 1.39 |
| 143 | 1-[2-(2-Chloro-benzylamino)-pyrido[4,3-d]pyrimidin-5-yl]-piperidine-4-carboxylic acid bis-(2-methoxy-ethyl)-amide | 514 | 3.41 | 1.68 |
| 144 | 1-[2-(2-Chloro-benzylamino)-pyrido[4,3-d]pyrimidin-5-yl]-piperidine-4-carboxylic acid 2-chloro-4-fluoro-benzylamide | 540 | 4.00 | 1.93 |
| 145 | {4-[2-(2-Chloro-benzylamino)-pyrido[4,3-d]pyrimidin-5-yl]-piperazin-1-yl}-acetic acid | 414 | 2.59 | 1.63 |
| 146 | N2-(2-Chloro-benzyl)-N5-(2-pyridin-2-yl-ethyl)-pyrido[4,3-d]pyrimidine-2,5-diamine | 392 | 2.77 | 1.47 |
| 147 | N2-(2-Chloro-benzyl)-N5-(2-pyridin-3-yl-ethyl)-pyrido[4,3-d]pyrimidine-2,5-diamine | 392 | 2.75 | 1.32 |
| 148 | N2-(2-Chloro-benzyl)-N5-(2-pyridin-4-yl-ethyl)-pyrido[4,3-d]pyrimidine-2,5-diamine | 392 | 2.77 | 1.31 |
| 149 | N2-(2-Chloro-benzyl)-N5-(3-pyridin-2-yl-propyl)-pyrido[4,3-d]pyrimidine-2,5-diamine | 406 | 2.83 | 1.40 |
| 150 | 4-[2-(2-Chloro-benzylamino)-pyrido[4,3-d]pyrimidin-5-yl]-piperazine-1-carboxylic acid 3-ethoxy-propyl ester | 486 | 3.63 | 2.02 |

TABLE 2-continued

| Compound | Chemical Name | ESI [M + 1]+ | HPLC Rt [min] | HPLC/MS Rt [min] |
|---|---|---|---|---|
| 151 | 4-[2-(2-Chloro-benzylamino)-pyrido[4,3-d]pyrimidin-5-yl]-piperazine-1-carboxylic acid pyridin-3-ylmethyl ester | 491 | 2.88 | 1.68 |
| 152 | 4-[2-(2-Chloro-benzylamino)-pyrido[4,3-d]pyrimidin-5-yl]-piperazine-1-carboxylic acid 1-methyl-piperidin-4-ylmethyl ester | 511 | | 1.48 |
| 153 | (2-Chloro-benzyl)-{5-[4-(thiophene-2-sulfonyl)-piperazin-1-yl]-pyrido[4,3-d]pyrimidin-2-yl}-amine | 502 | 3.92 | 2.31 |
| 154 | (2-Chloro-benzyl)-[5-(4-methanesulfonyl-piperazin-1-yl)-pyrido[4,3-d]pyrimidin-2-yl]-amine | 434 | 3.31 | 1.88 |
| 155 | 4-[2-(2-Chloro-benzylamino)-pyrido[4,3-d]pyrimidin-5-yl]-piperazine-1-carboxylic acid 3-methoxy-propyl ester | 472 | 3.47 | 1.91 |
| 156 | (2-Chloro-benzyl)-[5-(4-methanesulfonylmethanesulfonyl-piperazin-1-yl)-pyrido[4,3-d]pyrimidin-2-yl]-amine | 512 | 3.44 | 1.95 |
| 157 | {5-[4-(5-Bromo-pyridine-2-sulfonyl)-piperazin-1-yl]-pyrido[4,3-d]pyrimidin-2-yl}-(2-chloro-benzyl)-amine | 574/576 | 4.03 | 2.33 |

In the following $^1$H-NMR data for selected compounds of the invention are displayed:

Compound 98, $C_{25}H_{31}ClN_6O_2$

1H-NMR (DMSO-d6): δ [ppm]=1.11 (t, 3H), 1.60-1.66 (m, 2H), 1.79 (s(b), 4H), 2.34-2.40 (m, 1H), 2.98-3.05 (m, 2H), 3.08-3.14 (m, 2H), 3.35-3.43 (m, 4H), 3.92 (d, 2H), 4.67 (d, 2H), 6.67 (d, 1H), 7.27-7.32 (m, 2H); 7.38-7.48 (m, 2H), 7.78 (s(b), 1H), 8.09 (d, 1H), 8.29 (s(b), 1H), 9.07 (s, 1H).

Compound 106, $C_{24}H_{22}ClFN_6$

1H-NMR (DMSO-d6): δ [ppm]=3.32 (s(b), 4H), 3.59 (s(b), 4H), 4.69 (d, 2H), 6.82 (d, 1H), 6.98 (s(b), 2H), 7.08 (t, 2H); 7.30 (t, 2H), 7.40-7.50 (m, 2H), 8.13 (d, 1H), 8.33 (s(b), 1H), 9.19 (s, 1H).

Compound 109, $C_{21}H_{20}ClN_7S$

1H-NMR (DMSO-d6): δ[ppm]=3.57 (s(b), 4H), 3.64 (s(b), 4H), 4.68 (d, 2H), 6.85 (d, 1H), 6.90 (d, 1H), 7.21 (d, 1H); 7.25-7.33 (m, 2H), 7.38-7.4050 (m, 2H), 8.14 (d, 1H), 8.37 (t, 1H), 9.22 (s, 1H).

Compound 114, $C_{21}H_{23}ClN_6O_2$

1H-NMR (DMSO-d6): δ [ppm]=1.21 (t, 3H), 3.43 (s(b), 4H), 3.60 (s(b), 4H), 4.07 (d, 2H), 4.68 (s(b), 2H), 6.82 (d, 1H), 7.25-7.33 (m, 2H); 7.36-7.49 (m, 2H), 8.12 (d, 1H), 8.35 (s(b), 1H), 9.16 (s, 1H).

Compound 116, $C_{23}H_{26}ClN_7O_2$

1H-NMR (DMSO-d6): δ [ppm]=3.16 (s(b), 4H), 3.39 (s(b), 4H), 3.44 (s(b), 4H), 3.58 (s(b), 4H), 4.67 (d, 2H), 6.80 (d, 1H), 7.26-7.31 (m, 2H); 7.37-7.48 (m, 2H), 8.09 (d, 1H), 8.32 (s(b), 1H), 9.16 (s, 1H).

Compound 118, $C_{22}H_{24}ClN_5O_2$

1H-NMR (DMSO-d6): δ [ppm]=1.21 (t, 3H), 1.82 (q, 2H), 1.95 (d, 2H), 2.58-2.66 (m, 1H), 3.11 (t, 2H), 3.84 (dt, 2H), 4.11 (q, 2H), 4.68 (d, 2H), 6.78 (d, 1H), 7.25-7.33 (m, 2H); 7.38-7.48 (m, 2H), 8.08 (d, 1H), 8.29 (s(b), 1H), 9.08 (s, 1H).

Compound 127, $C_{20}H_{20}ClN_5O_2$ $^1$H-NMR (DMSO-d6): δ [ppm]=1.72-1.97 (m, 5H), 3.06-3.14 (m, 2H), 3.83 (dt, 2H), 4.67 (d, 2H), 6.76 (d, 1H), 7.27-7.32 (m, 2H); 7.38-7.48 (m, 2H), 8.08 (d, 1H), 8.28 (s(b), 1H), 9.08 (s, 1H), 12.2 (s(b), 1H).

Compound 138, $C_{25}H_{24}ClN_7O$

1H-NMR (DMSO-d6): δ [ppm]=3.42 (s(b), 4H), 3.72 (s(b), 4H), 3.84 (s(b), 2H), 4.67 (d, 2H), 6.81 (d, 1H), 7.23-7.30 (m, 4H); 7.37-7.47 (m, 2H), 8.10 (d, 1H), 8.32 (s(b), 1H), 8.48 (d, 2H), 9.16 (s, 1H).

Compound 142, $C_{26}H_{32}ClN_7O_2$

1H-NMR (DMSO-d6, d-TFA exchanged): δ [ppm]=1.89 (s(b), 4H), 2.95-3.30 (m, 6H), 3.49-3.68 (m, 5H), 3.76-3.81 (m, 2H), 4.11 (d, 2H), 4.22-4.30 (m, 1H), 4.43-4.53 (m, 1H), 4.78 (d, 2H), 6.86 (dd, 1H), 7.28-7.33 (m, 2H); 7.42-7.50 (m, 2H), 7.87 (d, 1H), 9.22 (s, 1H).

Compound 155, $C_{23}H_{27}ClN_6O_3$

1H-NMR (DMSO-d6): δ [ppm]=1.82 (quintet, 2H), 3.24 (s, 3H), 3.38-3.44 (m, 6H), 3.59 (s(b), 4H), 4.08 (t, 2H), 4.68 (d, 2H), 6.81 (d, 1H), 7.25-7.47 (m, 4H), 8.11 (d, 1H), 8.28-8.35 (m, 1H), 9.16 (s, 1H).

Compound 157, $C_{23}H_{21}BrClN_7O_2S$

1H-NMR (DMSO-d6): δ [ppm]=3.41 (s(b), 4H), 3.48 (s(b), 4H), 4.65 (d, 2H), 6.81 (d, 1H), 7.25-7.30 (m, 2H);

7.35-7.40 (m, 1H), 7.42-7.47 (m, 1H), 7.91 (d, 1H), 8.08 (d, 1H), 8.28-8.35 (m, 1H), 8.40 (d, 1H), 8.88 (s, 1H), 9.12 (s, 1H).

The following analytical methods were use for determining above illustrated physicochemical parameters:
ESI: Electrospray Ionization Mass Spectrometry (M+H)⁺
Method HPLC/MS:
Device: Agilent LC/MS 1100
ELSD: Sedex 75
Column: Chromolith RP18e 50-4.6 mm
Solvent A: Water+0.05% formic acid
Solvent B: Acetonitrile+0.04% formic acid
Flow: 2.4 mL/min
Gradient:
0.0 min 4% B
2.8 min 100% B
3.3 min 100% B
UV detection at 220 nm
ELSD Detection
MS mass range: m/z—85-1000 positive mode
Method HPLC:
A) HPLC System for analysis of multicomponent organic mixtures which includes: HPLC D-7000 Hitachi
B) Column: Chromolith Performance RP18e 100-4.6 mm
C) solvent:
A: $H_2O$ with 0.1% TFA
B: ACN with 0.08% TFA
D) Gradient:
0.0 min. 20% B
5.0 min. 100% B
5.5 min. 100% B
6.0 min. 20% B
6.5 min. 20% B
E) Detector: Diode Array L-7450A Hitachi
F) Flow-rate 1.5 mL
*Method LC/MS:
A) LC-MS System for analysis of multicomponent organic mixtures witch includes:
HPLC: 1200er series, MS: Single Quad API-ESI 6100er series
B) Column: Chromolith SpeedROD RP-18e 50-4.6 mm
C) solvent:
A: $H_2O$ with 0.05% formic acid
B: ACN with 0.04% formic acid
D) Gradient:

|   | time | % B |
|---|------|-----|
| 1 | 0    | 4   |
| 2 | 2, 8 | 100 |
| 3 | 3, 3 | 100 |
| 4 | 3, 4 | 4   |

E) UV-Detection, MS-range, m/z—100 . . . 1000 positive mode
F) UV-detection wave-length 220 nm
G) Flow-rate 2.4 mL
Method LC/MS
A) LCMS system for analysis of multicomponent organic mixtures which includes:
HPLC: Shimadzu Analytical 10Avp series, autosampler: Gilson 215, ELSD: Sedex 75, mass-spectrometer: PE SCIEX API 150:
B) Column: Synergi 2u Hydro-RP Mercury, 20×2.0 mm:
C) Solvent A—water with 0.05% of TFA, solvent B—acetonitrile with 0.05% TFA;
D) Gradient (4 min) time program: water:acetonitrile:
0.01 min—5% B;
2.60 min—95% B;
3.70 min—95% B;
3.95 min—5% B;
4.02 min—controller stop;
E) UV detection;
ELSD;
MS—mass range, m/z—100 . . . 1000 positive mode;
F) UV detection wave-length, nM—215, 254;
G) Flow rate—0.500 mL/min.

II. Autotaxin Assay

Assay Description

Autotaxin activity is measured indirectly by means of Amplex Red Reagent. In this course, Amplex Red is measured as fluorogenic indicator for generated $H_2O_2$. Autotaxin converts substrate lysophosphatidylcholine (LPC) to phosphocholine and lysophosphatidylic acid (LPA). After the conversion phosphocholine is reacted with alkaline phosphatase to obtain inorganic phosphate and choline. During the next step choline is oxidized with choline oxidase to yield betaine, whereby $H_2O_2$ is generated. $H_2O_2$ reacts with Amplex Red Reagent in the presence of peroxidase (Horseradish peroxidase) in an 1:1 stochiometry and yields highly fluorescent resorufin. The generated fluorescence is measured in a reaction-dependent kinetic mode in order to enable subtraction of fluorescence signals of possible other fluorescent compounds that are not part of the reaction from total measured fluorescence.

Performing the Assay 1.5 μl of a standard solution or of the compounds of the invention are dissolved in 20 mM Hepes pH 7.2 with maximally 7.7% DMSO in individual concentrations. The resulting solution is pre-incubated together with 10 μl (16 ng) of highly purified recombinant autotaxin in a black 384-hole microtiter plate for 30 min at 22° C. Thereafter, the reaction is started through the addition of 5 μL-a-lysophosphatidylcholine (LPC), whereby the final concentration of LPC is 75 μM. The mixture is incubated for 90 min. at 37° C. After the incubation Amplex Red Reagent, peroxidase (Horseradish peroxidase) and choline oxidase are added. The fluorescence is immediately measured at a wavelength of 612 nm with an excitation wavelength of 485 nm in a "Tecan Ultra multimode" fluorescence reader. The activity of autotaxin is indirectly calculated via the amount of detected generated $H_2O_2$.

For $IC_{50}$ analysis, ten serial 1:3 dilutions starting at 30 μM for each compound were run in duplicates.

$IC_{50}$ values were calculated on normalized data. For normalization, control wells were added to each assay plate and the signal of uninhibited control wells was set to 100%, whereas the signal inhibited by 500 μM C14 LPA, (Avanti Polar Lipids, Cat# 857120P) was set to 0%. Curves were fitted and $IC_{50}$ values calculated by the following model using proprietary analysis software:

$$Y=\text{Bottom}+(100-\text{Bottom})/(1+10^{((\text{LogIC}_{50}-X)*\text{Hill-Slope})})$$

Where X is the logarithm of concentration. Y is the response; Y starts at Bottom and goes to Top with a sigmoid shape.

Material

Microtiter plate: PS-Microplate, 384-hole, small volume, black Corning, Cat#3677

Protein: Recombinant autotaxin (baculoviral Hi5 expression)

Substrate: L-a-lysophosphatidyl choline (chicken egg); Avanti Polar Lipids #830071 P Standard: C14 LPA, Avanti Polar Lipids, Cat# 857120P Detection Reagent Amplex Red Reagent; Invitrogen #A12222; dissolved in 1.923 ml of DMSO peroxidase Type VI-A (horseradish), Sigma #P6782; dissolved in 7.45 ml of test buffer, Choline Oxidase; Sigma #C5896; dissolved in 2.47 ml test buffer Detection Reagent Mix: 1:100 dilution of Amplex Red Regent in test buffer Test buffer: 200 mM Tris-HCl, Merck, Cat # 1.08219, pH 7.9; 0.1% BSA, lipid free, Roche Cat#775835

TABLE 3

| Compound | Chemical Name | $IC_{50}$ value [M] |
| --- | --- | --- |
| 1 | Benzyl-(5-pyrrolidin-1-yl-pyrido[4,3-d]pyrimidin-2-yl)-amine | <3E−5 |
| 2 | N2-Benzyl-N5-(4-fluoro-phenyl)-pyrido[4,3-d]pyrimidine-2,5-diamine | <3E−5 |
| 3 | N2-Benzyl-N5-(4-methoxy-phenyl)-pyrido[4,3-d]pyrimidine-2,5-diamine | <3E−5 |
| 4 | N2-Benzyl-N5-(2,4-difluoro-phenyl)-pyrido[4,3-d]pyrimidine-2,5-diamine | <3E−5 |
| 5 | N5-Benzo[1,3]dioxol-5-yl-N2-benzyl-pyrido[4,3-d]pyrimidine-2,5-diamine | <3E−5 |
| 6 | N2-Benzyl-N5-(3,4-dimethoxy-phenyl)-pyrido[4,3-d]pyrimidine-2,5-diamine | <3E−5 |
| 7 | N2-Benzyl-N5-(4-fluoro-2-methyl-phenyl)-pyrido[4,3-d]pyrimidine-2,5-diamine | <3E−5 |
| 8 | (2-Chloro-benzyl)-(5-pyrrolidin-1-yl-pyrido[4,3-d]pyrimidin-2-yl)-amine | <5E−6 |
| 9 | N2-(2-Chloro-benzyl)-N5-(4-methoxy-phenyl)-pyrido[4,3-d]pyrimidine-2,5-diamine | <3E−5 |
| 10 | N2,N5-Bis-(2-chloro-benzyl)-pyrido[4,3-d]pyrimidine-2,5-diamine | <3E−5 |
| 11 | N2-(2-Chloro-benzyl)-N5-pyridin-3-ylmethyl-pyrido[4,3-d]pyrimidine-2,5-diamine | <3E−5 |
| 12 | N2-(2-Chloro-benzyl)-N5-(3,4-dimethoxy-phenyl)-pyrido[4,3-d]pyrimidine-2,5-diamine | <3E−5 |
| 13 | 1-{4-[2-(2-Chloro-benzylamino)-pyrido[4,3-d]pyrimidin-5-ylamino]-phenyl}-ethanone | <3E−5 |
| 14 | N2-(2-Chloro-benzyl)-N5-(2,4-dimethoxy-phenyl)-pyrido[4,3-d]pyrimidine-2,5-diamine | <3E−5 |
| 15 | N2-(2-Chloro-benzyl)-N5-(3-isopropoxy-propyl)-pyrido[4,3-d]pyrimidine-2,5-diamine | <3E−5 |
| 16 | N2-(2-Chloro-benzyl)-N5-(3-piperidin-1-yl-propyl)-pyrido[4,3-d]pyrimidine-2,5-diamine | <3E−5 |
| 17 | N2-(2-Chloro-benzyl)-N5-(3-pyrrolidin-1-yl-propyl)-pyrido[4,3-d]pyrimidine-2,5-diamine | <3E−5 |
| 18 | N2-(2-Chloro-benzyl)-N5-(2-piperidin-1-yl-ethyl)-pyrido[4,3-d]pyrimidine-2,5-diamine | <3E−5 |
| 19 | N5-(4-Fluoro-2-methyl-phenyl)-N2-(4-methyl-benzyl)-pyrido[4,3-d]pyrimidine-2,5-diamine | <3E−5 |
| 20 | (4-Fluoro-benzyl)-(5-pyrrolidin-1-yl-pyrido[4,3-d]pyrimidin-2-yl)-amine | <3E−5 |

TABLE 3-continued

| Compound | Chemical Name | $IC_{50}$ value [M] |
| --- | --- | --- |
| 21 | N2-(4-Fluoro-benzyl)-N5-(4-fluoro-phenyl)-pyrido[4,3-d]pyrimidine-2,5-diamine | <3E−5 |
| 22 | N2-(4-Fluoro-benzyl)-N5-o-tolyl-pyrido[4,3-d]pyrimidine-2,5-diamine | <3E−5 |
| 23 | N2-(4-Fluoro-benzyl)-N5-(4-methoxy-phenyl)-pyrido[4,3-d]pyrimidine-2,5-diamine | <3E−5 |
| 24 | N2-(4-Fluoro-benzyl)-N5-(2-fluoro-phenyl)-pyrido[4,3-d]pyrimidine-2,5-diamine | <3E−5 |
| 25 | N5-(2,4-Difluoro-phenyl)-N2-(4-fluoro-benzyl)-pyrido[4,3-d]pyrimidine-2,5-diamine | <3E−5 |
| 26 | N5-Benzo[1,3]dioxol-5-yl-N2-(4-fluoro-benzyl)-pyrido[4,3-d]pyrimidine-2,5-diamine | <3E−5 |
| 27 | N5-(3,4-Dimethoxy-phenyl)-N2-(4-fluoro-benzyl)-pyrido[4,3-d]pyrimidine-2,5-diamine | <3E−5 |
| 28 | N2-(4-Fluoro-benzyl)-N5-(4-fluoro-2-methyl-phenyl)-pyrido[4,3-d]pyrimidine-2,5-diamine | <3E−5 |
| 29 | N5-Benzo[1,2,5]oxadiazol-5-ylmethyl-N2-(4-fluoro-benzyl)-pyrido[4,3-d]pyrimidine-2,5-diamine | <3E−5 |
| 30 | N2-(4-Fluoro-benzyl)-N5-isobutyl-pyrido[4,3-d]pyrimidine-2,5-diamine | <3E−5 |
| 31 | (2-Methoxy-benzyl)-(5-pyrrolidin-1-yl-pyrido[4,3-d]pyrimidin-2-yl)-amine | <3E−5 |
| 32 | N5-(2-Ethoxy-phenyl)-N2-(2-methoxy-benzyl)-pyrido[4,3-d]pyrimidine-2,5-diamine | <3E−5 |
| 33 | N5-(2-Fluoro-phenyl)-N2-(2-methoxy-benzyl)-pyrido[4,3-d]pyrimidine-2,5-diamine | <3E−5 |
| 34 | N2-(2-Methoxy-benzyl)-N5-o-tolyl-pyrido[4,3-d]pyrimidine-2,5-diamine | <3E−5 |
| 35 | N2-(2-Methoxy-benzyl)-N5-(4-methoxy-phenyl)-pyrido[4,3-d]pyrimidine-2,5-diamine | <3E−5 |
| 36 | N2-(2-Methoxy-benzyl)-N5-p-tolyl-pyrido[4,3-d]pyrimidine-2,5-diamine | <3E−5 |
| 37 | N5-(2,4-Difluoro-phenyl)-N2-(2-methoxy-benzyl)-pyrido[4,3-d]pyrimidine-2,5-diamine | <3E−5 |
| 38 | N5-(3,4-Dimethoxy-phenyl)-N2-(2-methoxy-benzyl)-pyrido[4,3-d]pyrimidine-2,5-diamine | <3E−5 |
| 39 | N5-(2,3-Dihydro-benzo[1,4]dioxin-6-yl)-N2-(2-methoxy-benzyl)-pyrido[4,3-d]pyrimidine-2,5-diamine | <3E−5 |
| 40 | N5-(2,4-Dimethoxy-phenyl)-N2-(2-methoxy-benzyl)-pyrido[4,3-d]pyrimidine-2,5-diamine | <3E−5 |
| 41 | N5-(4-Fluoro-2-methyl-phenyl)-N2-(2-methoxy-benzyl)-pyrido[4,3-d]pyrimidine-2,5-diamine | <3E−5 |
| 42 | N2-(4-Chloro-benzyl)-N5-(4-fluoro-phenyl)-pyrido[4,3-d]pyrimidine-2,5-diamine | <3E−5 |
| 43 | N2-(4-Chloro-benzyl)-N5-o-tolyl-pyrido[4,3-d]pyrimidine-2,5-diamine | <3E−5 |
| 44 | N2-(4-Chloro-benzyl)-N5-(4-methoxy-phenyl)-pyrido[4,3-d]pyrimidine-2,5-diamine | <3E−5 |

TABLE 3-continued

| Compound | Chemical Name | IC$_{50}$ value [M] |
|---|---|---|
| 45 | N2-(4-Chloro-benzyl)-N5-(2,4-difluoro-phenyl)-pyrido[4,3-d]pyrimidine-2,5-diamine | <3E−5 |
| 46 | N5-Benzo[1,3]dioxol-5-yl-N2-(4-chloro-benzyl)-pyrido[4,3-d]pyrimidine-2,5-diamine | <3E−5 |
| 47 | N2-(4-Chloro-benzyl)-N5-(3,4-dimethoxy-phenyl)-pyrido[4,3-d]pyrimidine-2,5-diamine | <3E−5 |
| 48 | N2-(4-Chloro-benzyl)-N5-(3,4-difluoro-phenyl)-pyrido[4,3-d]pyrimidine-2,5-diamine | <3E−5 |
| 49 | N2-(4-Chloro-benzyl)-N5-(4-fluoro-2-methyl-phenyl)-pyrido[4,3-d]pyrimidine-2,5-diamine | <3E−5 |
| 50 | 4-[2-(4-Chloro-benzylamino)-pyrido[4,3-d]pyrimidin-5-ylamino]-benzoic acid methyl ester | <3E−5 |
| 51 | N5-(2,5-Dimethoxy-phenyl)-N2-(4-methoxy-benzyl)-pyrido[4,3-d]pyrimidine-2,5-diamine | <3E−5 |
| 52 | N5-(2,4-Difluoro-phenyl)-N2-(4-methoxy-benzyl)-pyrido[4,3-d]pyrimidine-2,5-diamine | <3E−5 |
| 53 | N5-Benzo[1,3]dioxol-5-yl-N2-(4-methoxy-benzyl)-pyrido[4,3-d]pyrimidine-2,5-diamine | <3E−5 |
| 54 | N5-(3,4-Dimethoxy-phenyl)-N2-(4-methoxy-benzyl)-pyrido[4,3-d]pyrimidine-2,5-diamine | <3E−5 |
| 55 | N5-(2,3-Dihydro-benzo[1,4]dioxin-6-yl)-N2-(4-methoxy-benzyl)-pyrido[4,3-d]pyrimidine-2,5-diamine | <3E−5 |
| 56 | N5-(2,4-Dimethoxy-phenyl)-N2-(4-methoxy-benzyl)-pyrido[4,3-d]pyrimidine-2,5-diamine | <3E−5 |
| 57 | 4-[2-(4-Methoxy-benzylamino)-pyrido[4,3-d]pyrimidin-5-ylamino]-benzonitrile | <3E−5 |
| 58 | N5-(3,4-Difluoro-phenyl)-N2-(4-methoxy-benzyl)-pyrido[4,3-d]pyrimidine-2,5-diamine | <3E−5 |
| 59 | N5-(4-Fluoro-2-methyl-phenyl)-N2-(4-methoxy-benzyl)-pyrido[4,3-d]pyrimidine-2,5-diamine | <1E−5 |
| 60 | 1-(2-Benzylamino-pyrido[4,3-d]pyrimidin-5-yl)-piperidine-4-carboxylic acid (furan-2-ylmethyl)-amide | <3E−5 |
| 61 | 1-(2-Benzylamino-pyrido[4,3-d]pyrimidin-5-yl)-piperidine-4-carboxylic acid isopropylamide | <3E−5 |
| 62 | 1-[2-(2-Chloro-benzylamino)-pyrido[4,3-d]pyrimidin-5-yl]-piperidine-4-carboxylic acid (pyridin-3-ylmethyl)-amide | <5E−6 |
| 63 | 1-[2-(2-Chloro-benzylamino)-pyrido[4,3-d]pyrimidin-5-yl]-piperidine-4-carboxylic acid (3-diethylamino-propyl)-amide | <1E−5 |
| 64 | 1-[2-(2-Chloro-benzylamino)-pyrido[4,3-d]pyrimidin-5-yl]-piperidine-4-carboxylic acid (2-dimethylamino-ethyl)-amide | <1E−5 |
| 65 | 1-[2-(2-Chloro-benzylamino)-pyrido[4,3-d]pyrimidin-5-yl]-piperidine-4-carboxylic acid (furan-2-ylmethyl)-amide | <5E−6 |
| 66 | {1-[2-(2-Chloro-benzylamino)-pyrido[4,3-d]pyrimidin-5-yl]-piperidin-4-yl}-pyrrolidin-1-yl-methanone | <5E−6 |
| 67 | 1-[2-(2-Chloro-benzylamino)-pyrido[4,3-d]pyrimidin-5-yl]-piperidine-4-carboxylic acid isopropylamide | <5E−6 |
| 68 | 1-[2-(2-Chloro-benzylamino)-pyrido[4,3-d]pyrimidin-5-yl]-piperidine-4-carboxylic acid propylamide | <1E−5 |
| 69 | 1-[2-(2-Chloro-benzylamino)-pyrido[4,3-d]pyrimidin-5-yl]-piperidine-4-carboxylic acid cyclopropylamide | <1E−5 |
| 70 | 1-[2-(2-Chloro-benzylamino)-pyrido[4,3-d]pyrimidin-5-yl]-piperidine-4-carboxylic acid (2-methoxy-ethyl)-amide | <5E−6 |
| 71 | 1-[2-(2-Chloro-benzylamino)-pyrido[4,3-d]pyrimidin-5-yl]-piperidine-4-carboxylic acid allylamide | <3E−5 |
| 72 | {1-[2-(2-Chloro-benzylamino)-pyrido[4,3-d]pyrimidin-5-yl]-piperidin-4-yl}-(4-ethyl-piperazin-1-yl)-methanone | <5E−6 |
| 73 | 1-[2-(2-Chloro-benzylamino)-pyrido[4,3-d]pyrimidin-5-yl]-piperidine-4-carboxylic acid (3-methoxy-propyl)-amide | <5E−6 |
| 74 | 1-[2-(2-Methoxy-benzylamino)-pyrido[4,3-d]pyrimidin-5-yl]-piperidine-4-carboxylic acid (furan-2-ylmethyl)-amide | <3E−5 |
| 75 | 1-[2-(2-Methoxy-benzylamino)-pyrido[4,3-d]pyrimidin-5-yl]-piperidine-4-carboxylic acid (2-methoxy-ethyl)-amide | <3E−5 |
| 76 | {1-[2-(2-Methoxy-benzylamino)-pyrido[4,3-d]pyrimidin-5-yl]-piperidin-4-yl}-(4-pyridin-2-yl-piperazin-1-yl)-methanone | <3E−5 |
| 77 | 1-[2-(2-Methoxy-benzylamino)-pyrido[4,3-d]pyrimidin-5-yl]-piperidine-4-carboxylic acid (5-methyl-isoxazol-3-yl)-amide | <3E−5 |
| 78 | 1-[2-(4-Chloro-benzylamino)-pyrido[4,3-d]pyrimidin-5-yl]-piperidine-4-carboxylic acid pyridin-3-ylamide | <5E−6 |
| 79 | 1-[2-(4-Chloro-benzylamino)-pyrido[4,3-d]pyrimidin-5-yl]-piperidine-4-carboxylic acid (furan-2-ylmethyl)-amide | <3E−5 |
| 80 | {1-[2-(4-Chloro-benzylamino)-pyrido[4,3-d]pyrimidin-5-yl]-piperidin-4-yl}-pyrrolidin-1-yl-methanone | <5E−6 |
| 81 | 1-[2-(2-Chloro-benzylamino)-pyrido[4,3-d]pyrimidin-5-yl]-piperidine-3-carboxylic acid (pyridin-3-ylmethyl)-amide | <5E−6 |
| 82 | 1-[2-(2-Chloro-benzylamino)-pyrido[4,3-d]pyrimidin-5-yl]-piperidine-3-carboxylic acid pyridin-3-ylamide | <5E−6 |
| 83 | 1-[2-(2-Chloro-benzylamino)-pyrido[4,3-d]pyrimidin-5-yl]-piperidine-3-carboxylic acid (furan-2-ylmethyl)-amide | <3E−5 |
| 84 | 1-[2-(2-Chloro-benzylamino)-pyrido[4,3-d]pyrimidin-5-yl]-piperidine-3-carboxylic acid isopropylamide | <5E−6 |
| 85 | 1-[2-(2-Chloro-benzylamino)-pyrido[4,3-d]pyrimidin-5-yl]-piperidine-3-carboxylic acid propylamide | <3E−5 |

TABLE 3-continued

| Compound | Chemical Name | IC$_{50}$ value [M] |
|---|---|---|
| 86 | 1-[2-(2-Chloro-benzylamino)-pyrido[4,3-d]pyrimidin-5-yl]-piperidine-3-carboxylic acid cyclopropylamide | <5E−6 |
| 87 | 1-[2-(2-Chloro-benzylamino)-pyrido[4,3-d]pyrimidin-5-yl]-piperidine-3-carboxylic acid (5-methyl-isoxazol-3-yl)-amide | <3E−5 |
| 88 | 1-[2-(2-Chloro-benzylamino)-pyrido[4,3-d]pyrimidin-5-yl]-piperidine-3-carboxylic acid (3-ethoxy-propyl)-amide | <1E−5 |
| 89 | {1-[2-(2-Chloro-benzylamino)-pyrido[4,3-d]pyrimidin-5-yl]-piperidin-3-yl}-(4-ethyl-piperazin-1-yl)-methanone | <5E−6 |
| 90 | 1-[2-(2-Chloro-benzylamino)-pyrido[4,3-d]pyrimidin-5-yl]-piperidine-3-carboxylic acid (3-methoxy-propyl)-amide | <3E−5 |
| 91 | 1-[2-(2-Chloro-benzylamino)-pyrido[4,3-d]pyrimidin-5-yl]-piperidine-3-carboxylic acid diethylamide | <3E−5 |
| 92 | 3-({1-[2-(2-Chloro-benzylamino)-pyrido[4,3-d]pyrimidin-5-yl]-piperidine-3-carbonyl}-amino)-propionic acid ethyl ester | <1E−5 |
| 93 | 1-[2-(4-Methyl-benzylamino)-pyrido[4,3-d]pyrimidin-5-yl]-piperidine-3-carboxylic acid pyridin-3-ylamide | <3E−5 |
| 94 | {1-[2-(4-Chloro-benzylamino)-pyrido[4,3-d]pyrimidin-5-yl]-piperidin-3-yl}-(4-pyridin-2-yl-piperazin-1-yl)-methanone | <1E−5 |
| 95 | {1-[2-(4-Methoxy-benzylamino)-pyrido[4,3-d]pyrimidin-5-yl]-piperidin-3-yl}-(4-pyridin-2-yl-piperazin-1-yl)-methanone | <3E−5 |
| 96 | 1-[2-(2-Chloro-benzylamino)-pyrido[4,3-d]pyrimidin-5-yl]-piperidine-4-carboxylic acid (2-diethylamino-ethyl)-amide | <5E−6 |
| 97 | {1-[2-(2-Chloro-benzylamino)-pyrido[4,3-d]pyrimidin-5-yl]-piperidin-4-yl}-(4-propyl-piperazin-1-yl)-methanone | <1E−5 |
| 98 | 1-[2-(2-Chloro-benzylamino)-pyrido[4,3-d]pyrimidin-5-yl]-piperidine-4-carboxylic acid (3-ethoxy-propyl)-amide | <5E−6 |
| 99 | {1-[2-(2-Chloro-benzylamino)-pyrido[4,3-d]pyrimidin-5-yl]-piperidin-3-yl}-(4-pyridin-2-yl-piperazin-1-yl)-methanone | <5E−6 |
| 100 | N2-(2-Chloro-benzyl)-N5-(2-fluoro-phenyl)-pyrido[4,3-d]pyrimidine-2,5-diamine | <1E−5 |
| 101 | 3-({1-[2-(2-Chloro-benzylamino)-pyrido[4,3-d]pyrimidin-5-yl]-piperidine-4-carbonyl}-amino)-propionic acid ethyl ester | <3E−5 |
| 102 | 1-[2-(2-Methoxy-benzylamino)-pyrido[4,3-d]pyrimidin-5-yl]-piperidine-4-carboxylic acid (3-ethoxy-propyl)-amide | <3E−5 |
| 103 | 1-[2-(2-Methoxy-benzylamino)-pyrido[4,3-d]pyrimidin-5-yl]-piperidine-4-carboxylic acid diethylamide | <1E−5 |
| 104 | {1-[2-(2-Chloro-benzylamino)-pyrido[4,3-d]pyrimidin-5-yl]-piperidin-3-yl}-(4-methyl-piperazin-1-yl)-methanone | <3E−5 |
| 105 | 1-[2-(2-Chloro-benzylamino)-pyrido[4,3-d]pyrimidin-5-yl]-piperidine-4-carboxylic acid (2-hydroxy-ethyl)-amide | <3E−5 |
| 106 | (2-Chloro-benzyl)-{5-[4-(4-fluoro-phenyl)-piperazin-1-yl]-pyrido[4,3-d]pyrimidin-2-yl}-amine | <5E−6 |
| 107 | 1-[2-(2-Chloro-benzylamino)-pyrido[4,3-d]pyrimidin-5-yl]-piperidine-4-carboxylic acid amide | <5E−6 |
| 108 | 2-{4-[2-(2-Chloro-benzylamino)-pyrido[4,3-d]pyrimidin-5-yl]-piperazin-1-yl}-N-pyridin-3-yl-acetamide | <1E−5 |
| 109 | (2-Chloro-benzyl)-[5-(4-thiazol-2-yl-piperazin-1-yl)-pyrido[4,3-d]pyrimidin-2-yl]amine | <1E−5 |
| 112 | (2-Chloro-benzyl)-[5-(4-pyrimidin-2-yl-piperazin-1-yl)-pyrido[4,3-d]pyrimidin-2-yl]-amine | <3E−5 |
| 113 | {4-[2-(2-Chloro-benzylamino)-pyrido[4,3-d]pyrimidin-5-yl]-piperazin-1-yl}-furan-2-yl-methanone | <5E−6 |
| 114 | 4-[2-(2-Chloro-benzylamino)-pyrido[4,3-d]pyrimidin-5-yl]-piperazine-1-carboxylic acid ethyl ester | <5E−6 |
| 115 | 1-{4-[2-(2-Chloro-benzylamino)-pyrido[4,3-d]pyrimidin-5-yl]-piperazin-1-yl}-ethanone | <3E−5 |
| 116 | {4-[2-(2-Chloro-benzylamino)-pyrido[4,3-d]pyrimidin-5-yl]-piperazin-1-yl}-morpholin-4-yl-methanone | <5E−6 |
| 117 | 4-[2-(2-Chloro-benzylamino)-pyrido[4,3-d]pyrimidin-5-yl]-piperazine-1-carboxylic acid (furan-2-ylmethyl)-amide | <3E−5 |
| 119 | 1-{4-[2-(2-Chloro-benzylamino)-pyrido[4,3-d]pyrimidin-5-yl]-piperazin-1-yl}-2-pyridin-2-yl-ethanone | <5E−6 |
| 120 | 1-{4-[2-(2-Chloro-benzylamino)-pyrido[4,3-d]pyrimidin-5-yl]-piperazin-1-yl}-3-(1-methyl-1H-pyrazol-4-yl)-propan-1-one | <3E−5 |
| 121 | 1-{4-[2-(2-Chloro-benzylamino)-pyrido[4,3-d]pyrimidin-5-yl]-piperazin-1-yl}-2-pyridin-3-yl-ethanone | <5E−6 |
| 122 | 1-{4-[2-(2-Chloro-benzylamino)-pyrido[4,3-d]pyrimidin-5-yl]-piperazin-1-yl}-3-(1H-imidazol-4-yl)-propan-1-one | <5E−6 |
| 123 | 1-{4-[2-(2-Chloro-benzylamino)-pyrido[4,3-d]pyrimidin-5-yl]-piperazin-1-yl}-pentane-1,4-dione | <3E−5 |
| 125 | 4-{4-[2-(2-Chloro-benzylamino)-pyrido[4,3-d]pyrimidin-5-yl]-piperazin-1-yl}-N,N-dimethyl-4-oxo-butyramide | <3E−5 |
| 126 | Acetic acid 2-{4-[2-(2-chloro-benzylamino)-pyrido[4,3-d]pyrimidin-5-yl]-piperazin-1-yl}-2-oxo-ethyl ester | <5E−6 |
| 127 | 1-[2-(2-Chloro-benzylamino)-pyrido[4,3-d]pyrimidin-5-yl]-piperidine-4-carboxylic acid | <5E−6 |
| 128 | 3-{4-[2-(2-Chloro-benzylamino)-pyrido[4,3-d]pyrimidin-5-yl]-piperazin-1-yl}-3-oxo-propionitrile | <3E−5 |
| 133 | (S)-3-Amino-1-(2-{4-[2-(2-chloro-benzylamino)-pyrido[4,3-d]pyrimidin-5-yl]-piperazin-1-yl}-2-oxo-ethyl)-pyrrolidin-2-one | <3E−5 |

TABLE 3-continued

| Compound | Chemical Name | IC$_{50}$ value [M] |
|---|---|---|
| 136 | 1-{4-[2-(2-Chloro-benzylamino)-pyrido[4,3-d]pyrimidin-5-yl]-piperazin-1-yl}-2-(2-methoxy-ethoxy)-ethanone | <3E−5 |
| 138 | 1-{4-[2-(2-Chloro-benzylamino)-pyrido[4,3-d]pyrimidin-5-yl]-piperazin-1-yl}-2-pyridin-4-yl-ethanone | <3E−5 |
| 139 | 1-[2-(2-Chloro-benzylamino)-pyrido[4,3-d]pyrimidin-5-yl]-piperidine-4-carboxylic acid methylamide | <3E−5 |
| 140 | 1-[2-(2-Chloro-benzylamino)-pyrido[4,3-d]pyrimidin-5-yl]-piperidine-4-carboxylic acid dimethylamide | <3E−5 |
| 142 | {1-[2-(2-Chloro-benzylamino)-pyrido[4,3-d]pyrimidin-5-yl]-piperidin-4-yl}-((S)-2-pyrrolidin-1-ylmethyl-pyrrolidin-1-yl)-methanone | <3E−5 |
| 144 | 1-[2-(2-Chloro-benzylamino)-pyrido[4,3-d]pyrimidin-5-yl]-piperidine-4-carboxylic acid 2-chloro-4-fluoro-benzylamide | <3E−5 |
| 145 | {4-[2-(2-Chloro-benzylamino)-pyrido[4,3-d]pyrimidin-5-yl]-piperazin-1-yl}-acetic acid | <1E−5 |
| 146 | N2-(2-Chloro-benzyl)-N5-(2-pyridin-2-yl-ethyl)-pyrido[4,3-d]pyrimidine-2,5-diamine | <3E−5 |
| 147 | N2-(2-Chloro-benzyl)-N5-(2-pyridin-3-yl-ethyl)-pyrido[4,3-d]pyrimidine-2,5-diamine | <3E−5 |
| 148 | N2-(2-Chloro-benzyl)-N5-(2-pyridin-4-yl-ethyl)-pyrido[4,3-d]pyrimidine-2,5-diamine | <3E−5 |
| 151 | 4-[2-(2-Chloro-benzylamino)-pyrido[4,3-d]pyrimidin-5-yl]-piperazine-1-carboxylic acid pyridin-3-ylmethyl ester | <3E−5 |
| 156 | (2-Chloro-benzyl)-[5-(4-methanesulfonylmethanesulfonyl-piperazin-1-yl)-pyrido[4,3-d]pyrimidin-2-yl]-amine | <3E−5 |

The invention claimed is:

1. A pyridopyrimidine compound according to formula (I)

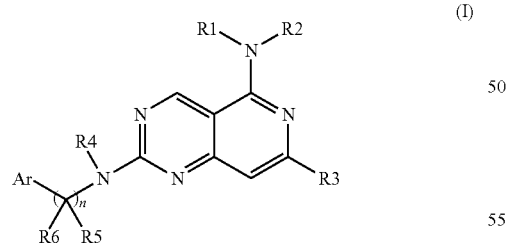

(I)

wherein:
Ar is phenyl which is unsubstituted or substituted with one or more identical or different substituents selected from halogen, alkyl, and —O—X296;
X296 is in each case independently selected from alkyl, cycloalkyl, and cycloalkylalkyl;
R1, R2 are independently from each other selected from hydrogen, alkyl, aryl, arylalkyl, heteroarylalkyl, heterocyclyl, and heterocyclylalkyl, which in each case is unsubstituted or substituted with one or more identical or different substituents selected from —F, —Cl, —CN, —O—X243, —C(O)—X244, and —C(O)O—X245, wherein X243, X244, and X245 are independently from each other selected from the group consisting of: alkyl, cycloalkyl, cycloalkylalkyl, heterocyclyl, heterocyclylalkyl, aryl, arylalkyl, heteroaryl, and heteroarylalkyl; or
R1, R2 can, together with the nitrogen atom to which they are attached, form "heterocyclyl", which is unsubstituted or substituted with one or more identical or different substituents Z,
with the proviso that if R1, R2, together with the nitrogen atom to which they are attached, form "heterocyclyl", which is unsubstituted or substituted with one or more identical or different substituents Z, "heterocyclyl" is not 4-piperidine-1-yl-carboxylic acid (4-carboxy-piperidine-1-yl), 3-piperidine-1-yl-carboxylic acid (3-carboxy-piperidine-1-yl), 4-piperidine-1-yl-carboxylic acid ethyl ester (4-ethylcarboxyate-piperidine-1-yl), or 3-piperidine-1-yl-carboxylic acid ethyl ester (3-ethylcarboxyate-piperidine-1-yl);
R3 is hydrogen;
R4 is independently selected hydrogen, alkyl, —X291—NHX292, and —X293—NX294X295, wherein X291, X292, X293, X294, and X295 are independently from each other alkyl;
R5, R6 are each independently from each other selected from hydrogen and alkyl;
Z is independently selected from selected from COOH, —C(O)NH$_2$, heteroaryl, alkyl-COOH, alkyl-NX246X247, aryl-halogen, heterocyclylalkyl-X248, —C(O)—X249, —C(O)-alkyl-NH$_2$, —C(O)-alkyl-CN, —C(O)-alkyl-C(O)—X250, —C(O)-alkyl-C(O)—NX251X252, —C(O)-alkyl-O-alkyl-O-X253, —C(O)—alkyl-O—C(O)—X254, —C(O)-alkyl-C(O)O—X255, —C(O)-alkyl-NX256X257, —C(O)-heteroarylalkyl, —C(O)-heteroarylalkyl-X258, —C(O)-heterocyclyl-X259, —C(O)-heterocyclyl-X260-OH, —C(O)-heterocyclylalkyl(-NH$_2$)(=O), —C(O)O—X261, —C(O)O-alkyl-O—X262, —C(O)O-heterocyclylalkyl-X263, —C(O)NX264X265, —C(O)NH—X266, —C(O)NH-alkyl-OH, —C(O)NH-alkyl-O—X267, —C(O)NH-alkyl-C(O)O—X268, —C(O)NH-alkyl-NX269X270, —C(O)NH-arylalkyl(-halogen)(-halogen), —C(O)NH-heteroaryl-X271, —C(O)N(X272-O—X273)(X274-O—X275), —S(O$_2$)—X276, —S(O$_2$)-alkyl-S(O$_2$)—X277, and —S(O$_2$)-heteroaryl-halogen;
wherein X246, X247, X248, X249, X250, X251, X252, X253, X254, X255, X256, X257, X258, X259, X260, X261, X262, X263, X264, X265, X266, X267, X268, X269, X270, X271, X272, X273, X274, X275, X276, and X277 are independently from each other selected from the group consisting of: alkyl, (C$_9$-C$_{30}$)alkyl, cycloalkyl, cycloalkylalkyl, heterocyclyl, heterocyclylalkyl, aryl, arylalkyl, heteroaryl, and heteroarylalkyl, and wherein alternatively X246, X247 and/or X251, X252 and/or X256, X257 and/or X264, X265 and/or X269, X270 respectively, together with the nitrogen atom to which they are attached, can also form "heterocyclyl"; and
n is 1;
or a physiologically acceptable salt, prodrug, solvate or stereoisomer thereof, including mixtures thereof in all ratios.

2. A pyridopyrimidine compound according to claim 1, wherein:

R1, R2 are independently from each other selected from hydrogen, propyl, isobutyl, phenyl, benzyl, benzo[1,3]dioxolyl, pyridinylmethyl, piperidinylethyl, piperidinylpropyl, pyrrolidinylpropyl, and 2,3-dihydro-benzo[1,4]dioxinyl, which in each case is unsubstituted or substituted with one or more identical or different substituents selected from —F, —Cl, —CN, methyl, methoxy, ethoxy, methylcarbonyl, methylcarboxyate-yl (carboxoic acid methyl ester), and isopropoxy; or R1, R2, together with the nitrogen atom to which they are attached, form "heterocyclyl" selected from pyrrolidinyl, piperidinyl, and piperazinyl, which in each case is unsubstituted or substituted with one or more identical or different substituents; and Z is —COOH, fluoro-phenyl, thiazolyl, pyridinyl, pyrimidinyl, methyl-piperidinyl-methyl, N,N-dimethyl-oxo-butyramide, amino-butanone-yl, carboxy-methyl, pyridinyl-ethyl-amino-yl, pyridinyl-propyl-amino-yl, methyl-carbonyl, cyano-methyl-carbonyl, butanonyl-carbonyl, methoxy-ethoxy-methyl-carbonyl, dimethyl-amino-methyl-carbonyl, diethyl-amino-ethyl-carbonyl, furanyl-carbonyl, morpholinyl-carbonyl, pyridinyl-methyl-carbonyl, pyridinyl-ethyl-carbonyl, methyl-pyrazolyl-ethyl-carbonyl, imidazolyl-ethyl-carbonyl, pyrrolidinyl-carbonyl, methyl-piperazinyl-carbonyl, ethyl-piperazinyl-carbonyl, propyl-piperazinyl-carbonyl, pyridinyl-piperazinyl-carbonyl, amino-pyrrolidone-methyl-carbonyl, benzoimidazolyl-ethyl-carbonyl, hydroxyl-ethyl-piperazinyl-carbonyl, pyrrolidinyl-methyl-pyrrolidinyl-carbonyl, pyridinyl-acetamide-yl, methyl-carboxylic acid amide-yl, carboxylic acid methylamide-yl, carboxylic acid dimethylamide-yl, carboxylic acid diethylamide-yl, carboxylic acid hydroxy-ethylamide-yl, carboxylic acid propylamide-yl, carboxylic acid isopropylamide-yl, carboxylic acid cyclopropylamide-yl, carboxylic acid allylamide-yl, carboxylic acid (furanylmethyl)-amide-yl, carboxylic acid pyridinyl-amide-yl, carboxylic acid (pyridinylmethyl)-amide-yl, carboxylic acid (dimethylaminoethyl)-amide-yl, carboxylic acid (diethylaminoethyl)-amide-yl, carboxylic acid (diethylamino-propyl)-amide-yl, carboxylic acid (methoxy-ethyl)-amide-yl, carboxylic acid (methoxy-propyl)-amide-yl, carboxylic acid (ethoxy-propyl)-amide-yl, carboxylic acid (methyl-isoxazolyl)-amide-yl, carboxylic acid bis(methoxy-ethyl)amide-yl, carboxylic acid (chloro)(fluoro)benzylamide-yl, carboxylic acid ethyl ester, carboxylic acid methoxy-propyl-ester, carboxylic acid ethoxy-propyl-ester, carboxylic acid pyridinylmethyl-ester, carboxylic acid methyl-piperidinyl-methyl-ester, acetic acid-oxo-ethyl ester, oxo-proprionic acid ethyl ester, oxo-pentanoic acid methyl ester, carbonyl-amino-propionic acid ethyl ester, methyl-sulfonyl, methyl-sulfonyl-methyl-sulfonyl, thiophenyl-sulfonyl, and bromo-pyridinyl-sulfonyl;

with the proviso that if R1, R2, together with the nitrogen atom to which they are attached, form "heterocyclyl", which is unsubstituted or substituted with one or more identical or different substituents Z, "heterocyclyl" is not 4-piperidine-1-yl-carboxylic acid (4-carboxy-piperidine-1-yl), 3-piperidine-1-yl-carboxylic acid (3-carboxy-piperidine-1-yl), 4-piperidine-1-yl-carboxylic acid ethyl ester (4-ethylcarboxyate-piperidine-1-yl), or 3-piperidine-1-yl-carboxylic acid ethyl ester (3-ethylcarboxyate-piperidine-1-yl).

3. A pyridopyrimidine compound selected from:

Compound 1

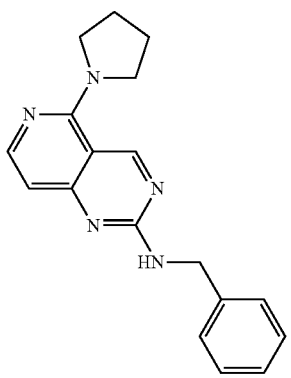 [SMILES: c1ccc(CNc2ncc3c(N4CCCC4)nccc3n2)cc1]

Benzyl-(5-pyrrolidin-1-yl-pyrido[4,3-d]pyrimidin-2-yl)-amine

Compound 2

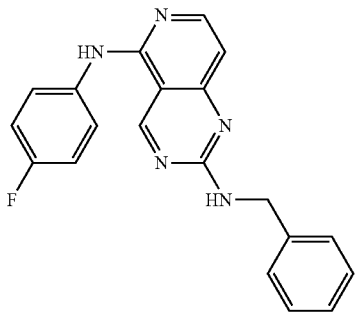 [SMILES: Fc1ccc(Nc2nccc3nc(NCc4ccccc4)ncc23)cc1]

N2-Benzyl-N5-(4-fluoro-phenyl)-pyrido[4,3-d]pyrimidine-2,5-diamine

-continued
| Compound 3 | 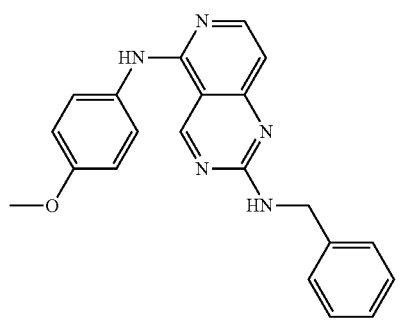 [SMILES: COc1ccc(Nc2nccc3nc(NCc4ccccc4)ncc23)cc1] | N2-Benzyl-N5-(4-methoxy-phenyl)-pyrido[4,3-d]pyrimidine-2,5-diamine |
| Compound 4 | 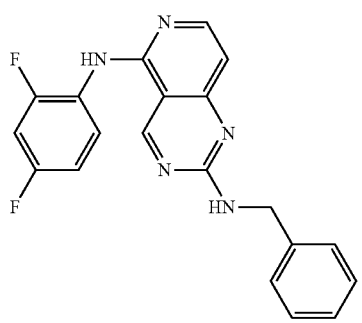 | N2-Benzyl-N5-(2,4-difluoro-phenyl)-pyrido[4,3-d]pyrimidine-2,5-diamine |
| Compound 5 | 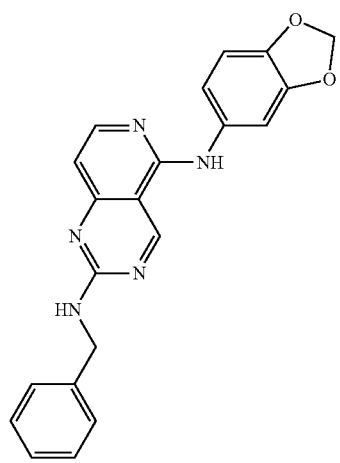 [SMILES: c1ccc(CNc2ncc3c(Nc4ccc5c(c4)OCO5)nccc3n2)cc1] | N5-Benzo[1,3]dioxol-5-yl-N2-benzyl-pyrido[4,3-d]pyrimidine-2,5-diamine |
| Compound 6 | 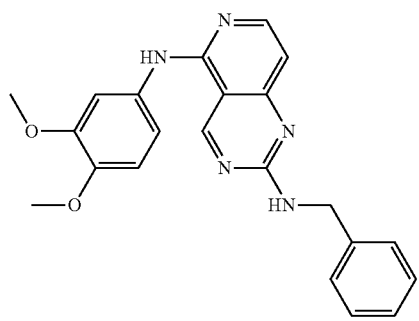 [SMILES: COc1ccc(Nc2nccc3nc(NCc4ccccc4)ncc23)cc1OC] | N2-Benzyl-N5-(3,4-dimethoxy-phenyl)-pyrido[4,3-d]pyrimidine-2,5-diamine |

-continued

| | | |
|---|---|---|
| Compound 7 | | N2-Benzyl-N5-(4-fluoro-2-methyl-phenyl)-pyrido[4,3-d]pyrimidine-2,5-diamine |
| Compound 8 | | (2-Chloro-benzyl)-(5-pyrrolidin-1-yl-pyrido[4,3-d]pyrimidin-2-yl)-amine |
| Compound 9 | | N2-(2-Chloro-benzyl)-N5-(4-methoxy-phenyl)-pyrido[4,3-d]pyrimidine-2,5-diamine |
| Compound 10 | | N2,N5-Bis-(2-chloro-benzyl) pyrido[4,3-d]pyrimidine-2,5-diamine |
| Compound 11 | | N2-(2-Chloro-benzyl)-N5-pyridin-3-ylmethyl-pyrido[4,3-d]pyrimidine-2,5-diamine |

-continued

Compound 12 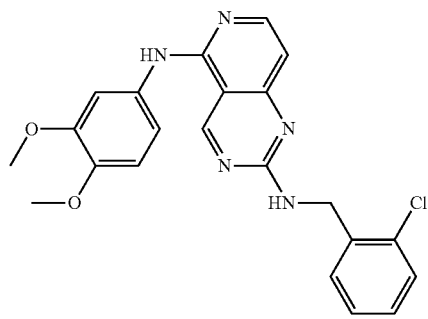 [SMILES: COc1ccc(Nc2nccc3nc(NCc4ccccc4Cl)ncc23)cc1OC] N2-(2-Chloro-benzyl)-N5-(3,4-dimethoxy-phenyl)-pyrido[4,3-d]pyrimidine-2,5-diamine Compound 13 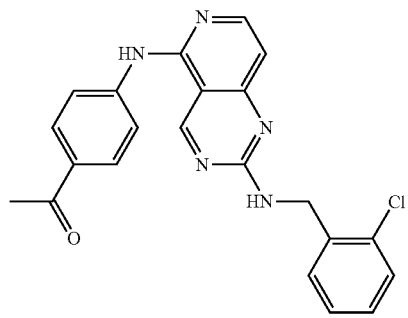 [SMILES: CC(=O)c1ccc(Nc2nccc3nc(NCc4ccccc4Cl)ncc23)cc1] 1-{4-[2-(2-Chloro-benzylamino)-pyrido[4,3-d]pyrimidin-5-ylamino]-phenyl}-ethanone Compound 14 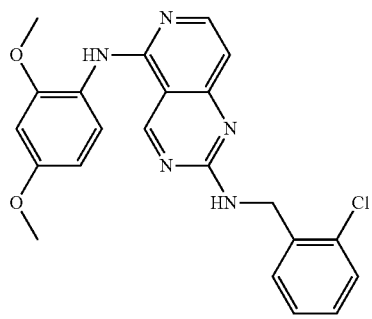 [SMILES: COc1ccc(Nc2nccc3nc(NCc4ccccc4Cl)ncc23)c(OC)c1] N2-(2-Chloro-benzyl)-N5-(2,4-dimethoxy-phenyl)-pyrido[4,3-d]pyrimidine-2,5-diamine Compound 15 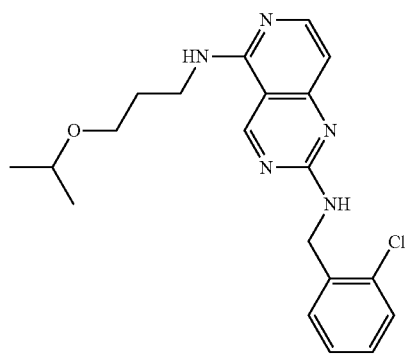 [SMILES: CC(C)OCCCNc1nccc2nc(NCc3ccccc3Cl)ncc12] N2-(2-Chloro-benzyl)-N5-(3-isopropoxy-propyl)-pyrido[4,3-d]pyrimidine-2,5-diamine Compound 16 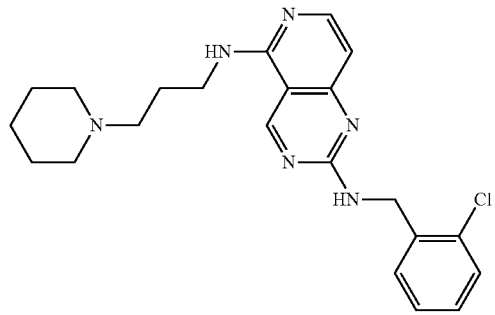 [SMILES: Clc1ccccc1CNc1ncc2c(NCCCN3CCCCC3)nccc2n1] N2-(2-Chloro-benzyl)-N5-(3-piperidin-1-yl-propyl)-pyrido[4,3-d]pyrimidine-2,5-diamine

| Compound | | |
|---|---|---|
| Compound 17 | 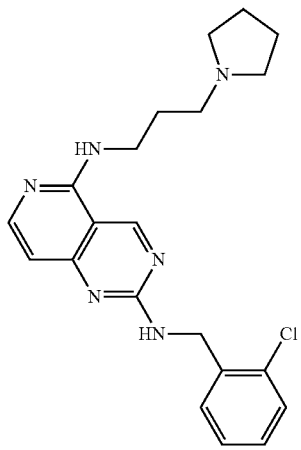 [SMILES: Clc1ccccc1CNc1ncc2c(NCCCN3CCCC3)nccc2n1] | N2-(2-Chloro-benzyl)-N5-(3-pyrrolidin-1-yl-propyl)-pyrido[4,3-d]pyrimidine-2,5-diamine |
| Compound 18 | 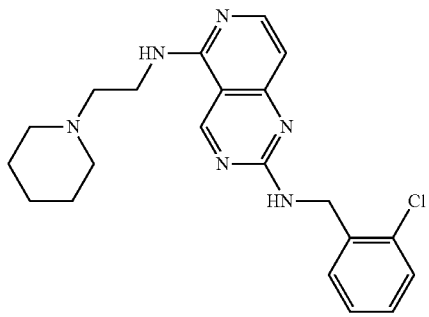 [SMILES: Clc1ccccc1CNc1ncc2c(NCCN3CCCCC3)nccc2n1] | N2-(2-Chloro-benzyl)-N5-(2-piperidin-1-yl-ethyl)-pyrido[4,3-d]pyrimidine-2,5-diamine |
| Compound 19 | 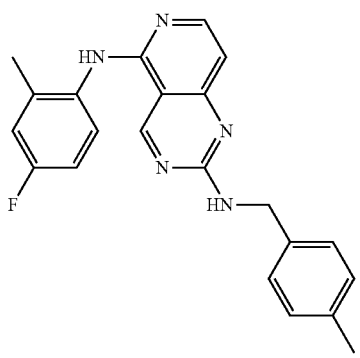 [SMILES: Cc1ccc(CNc2ncc3c(Nc4ccc(F)cc4C)nccc3n2)cc1] | N5-(4-Fluoro-2-methyl-phenyl)-N2-(4-methyl-benzyl)-pyrido[4,3-d]pyrimidine-2,5-diamine |
| Compound 20 | 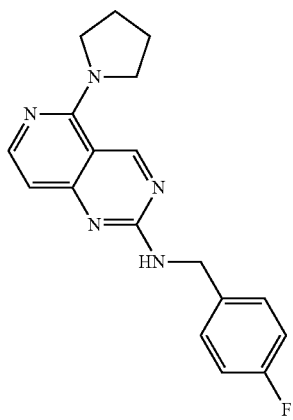 [SMILES: Fc1ccc(CNc2ncc3c(N4CCCC4)nccc3n2)cc1] | (4-Fluoro-benzyl)-(5-pyrrolidin-1-yl-pyrido[4,3-d]pyrimidin-2-yl)-amine |

-continued
| | | |
|---|---|---|
| Compound 21 | 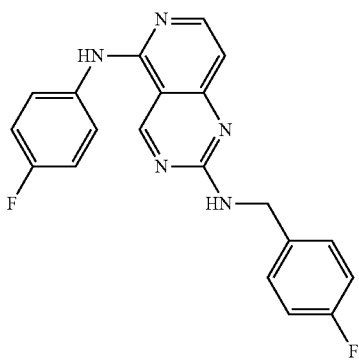 [SMILES: Fc1ccc(CNc2ncc3c(Nc4ccc(F)cc4)nccc3n2)cc1] | N2-(4-Fluoro-benzyl)-N5-(4-fluoro-phenyl)-pyrido[4,3-d]pyrimidine-2,5-diamine |
| Compound 22 | 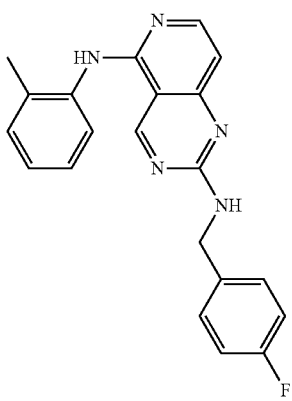 [SMILES: Cc1ccccc1Nc1nccc2nc(NCc3ccc(F)cc3)ncc12] | N2-(4-Fluoro-benzyl)-N5-o-tolyl-pyrido[4,3-d]pyrimidine-2,5-diamine |
| Compound 23 | 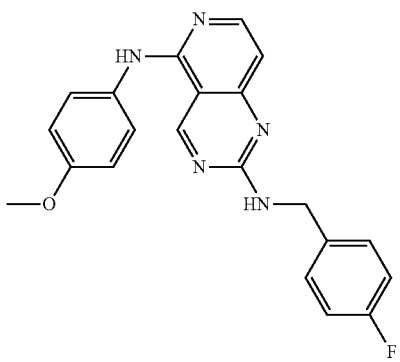 [SMILES: COc1ccc(Nc2nccc3nc(NCc4ccc(F)cc4)ncc23)cc1] | N2-(4-Fluoro-benzyl)-N5-(4-methoxy-phenyl)-pyrido[4,3-d]pyrimidine-2,5-diamine |
| Compound 24 | 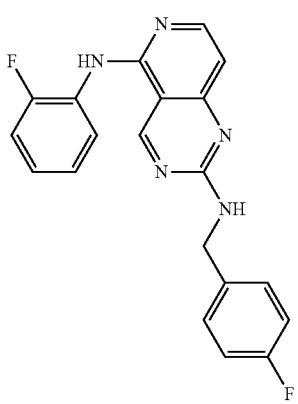 [SMILES: Fc1ccc(CNc2ncc3c(Nc4ccccc4F)nccc3n2)cc1] | N2-(4-Fluoro-benzyl)-N5-(2-fluoro-phenyl)-pyrido[4,3-d]pyrimidine-2,5-diamine |

-continued
| | | |
|---|---|---|
| Compound 25 | 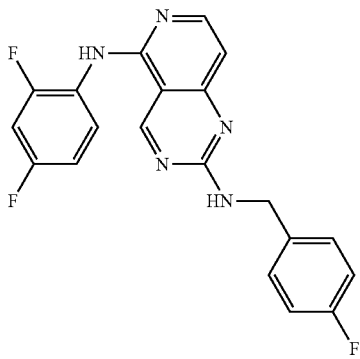 [SMILES: Fc1ccc(CNc2ncc3c(Nc4ccc(F)cc4F)nccc3n2)cc1] | N5-(2,4-Difluoro-phenyl)-N2-(4-fluoro-benzyl)-pyrido[4,3-d]pyrimidine-2,5-diamine |
| Compound 26 | 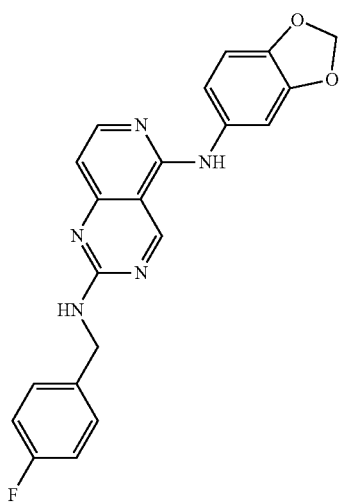 [SMILES: Fc1ccc(CNc2ncc3c(Nc4ccc5c(c4)OCO5)nccc3n2)cc1] | N5-Benzo[1,3]dioxol-5-yl-N2-(4-fluoro-benzyl)-pyrido[4,3-d]pyrimidine-2,5-diamine |
| Compound 27 | 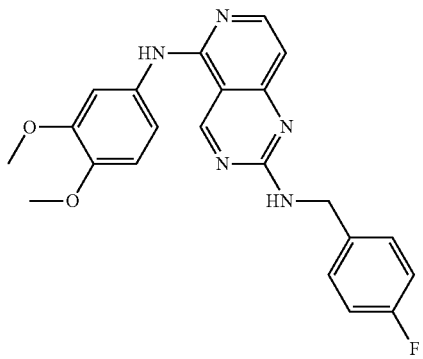 [SMILES: COc1ccc(Nc2nccc3nc(NCc4ccc(F)cc4)ncc23)cc1OC] | N5-(3,4-Dimethoxy-phenyl)-N2-(4-fluoro-benzyl)-pyrido[4,3-d]pyrimidine-2,5-diamine |
| Compound 28 | 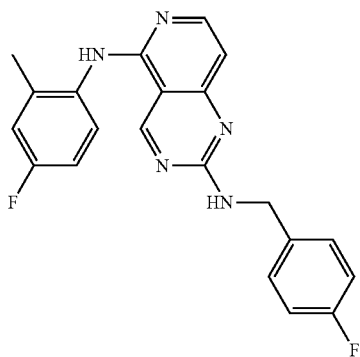 [SMILES: Cc1cc(F)ccc1Nc1nccc2nc(NCc3ccc(F)cc3)ncc12] | N2-(4-Fluoro-benzyl)-N5-(4-fluoro-2-methyl-phenyl)-pyrido[4,3-d]pyrimidine-2,5-diamine |

-continued
| | | |
|---|---|---|
| Compound 29 | 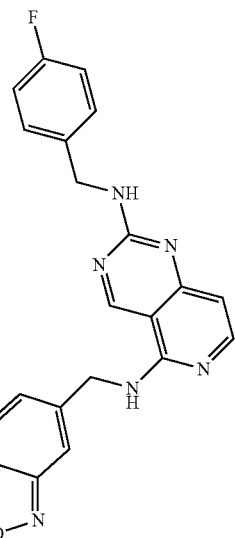 | N5-Benzo[1,2,5]oxa-diazol-5-ylmethyl-N2-(4-fluoro-benzyl)-pyrido[4,3-d]pyrimidine-2,5-diamine |
| Compound 30 | 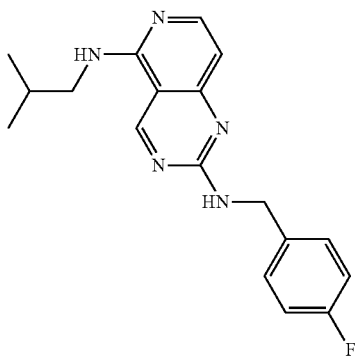 [SMILES: CC(C)CNc1nccc2nc(NCc3ccc(F)cc3)ncc12] | N2-(4-Fluoro-benzyl)-N5-isobutyl-pyrido[4,3-d]pyrimidine-2,5-diamine |
| Compound 31 | 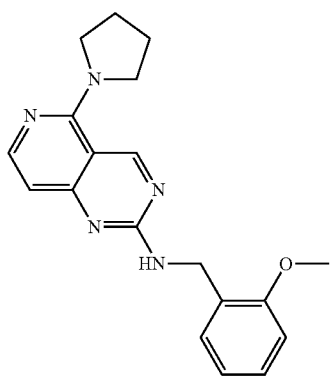 [SMILES: COc1ccccc1CNc1ncc2c(N3CCCC3)nccc2n1] | (2-Methoxy-benzyl)-(5-pyrrolidin-1-yl-pyrido[4,3-d]pyrimidin-2-yl)-amine |
| Compound 32 | 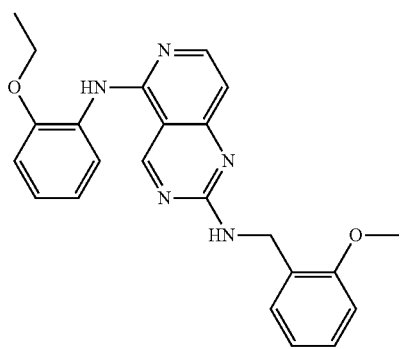 [SMILES: CCOc1ccccc1Nc1nccc2nc(NCc3ccccc3OC)ncc12] | N5-(2-Ethoxy-phenyl)-N2-(2-methoxy-benzyl)-pyrido[4,3-d]pyrimidine-2,5-diamine |

-continued
| | | |
|---|---|---|
| Compound 33 | 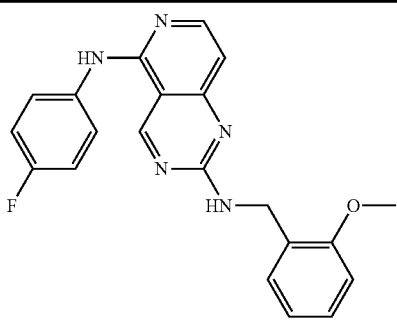 | N5-(4-Fluoro-phenyl)-N2-(2-methoxy-benzyl)-pyrido[4,3-d]pyrimidine-2,5-diamine |
| Compound 34 | 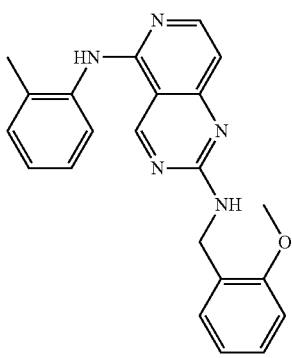 [SMILES: COc1ccccc1CNc1ncc2c(Nc3ccccc3C)nccc2n1] | N2-(2-Methoxy-benzyl)-N5-o-tolyl-pyrido[4,3-d]pyrimidine-2,5-diamine |
| Compound 35 | 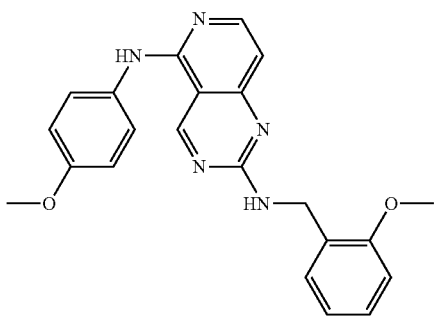 | N2-(2-Methoxy-benzyl)-N5-(4-methoxy-phenyl)-pyrido[4,3-d]pyrimidine-2,5-diamine |
| Compound 36 | 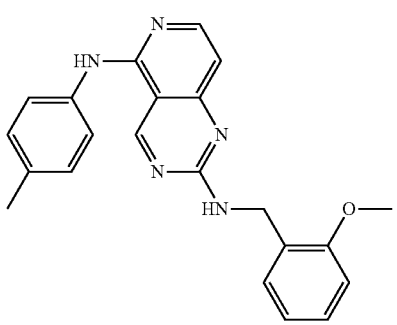 [SMILES: COc1ccccc1CNc1ncc2c(Nc3ccc(C)cc3)nccc2n1] | N2-(2-Methoxy-benzyl)-N5-p-tolyl-pyrido[4,3-d]pyrimidine-2,5-diamine |
| Compound 37 | 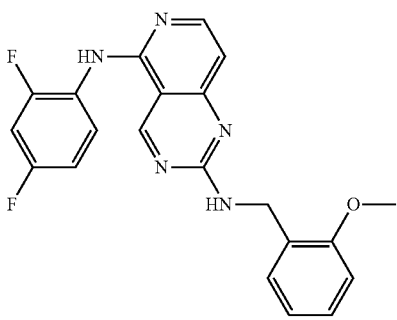 [SMILES: COc1ccccc1CNc1ncc2c(Nc3ccc(F)cc3F)nccc2n1] | N5-(2,4-Difluoro-phenyl)-N2-(2-methoxy-benzyl)-pyrido[4,3-d]pyrimidine-2,5-diamine |

-continued

| | | |
|---|---|---|
| Compound 38 | | N5-(3,4-Dimethoxy-phenyl)-N2-(2-methoxy-benzyl)-pyrido[4,3-d]pyrimidine-2,5-diamine |
| Compound 39 | | N5-(2,3-Dihydro-benzo[1,4]dioxin-6-yl)-N2-(2-methoxy-benzyl)-pyrido[4,3-d]pyrimidine-2,5-diamine |
| Compound 40 | | N5-(2,4-Dimethoxy-phenyl)-N2-(2-methoxy-benzyl)-pyrido[4,3-d]pyrimidine-2,5-diamine |
| Compound 41 | | N5-(4-Fluoro-2-methyl-phenyl)-N2-(2-methoxy-benzyl)-pyrido[4,3-d]pyrimidine-2,5-diamine |
| Compound 42 | | N2-(4-Chloro-benzyl)-N5-(4-fluoro-phenyl)-pyrido[4,3-d]pyrimidine-2,5-diamine |

-continued
| | | |
|---|---|---|
| Compound 43 | 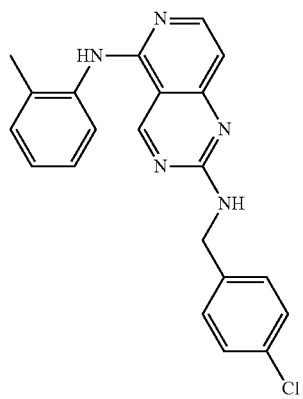 [SMILES: Cc1ccccc1Nc1nccc2nc(NCc3ccc(Cl)cc3)ncc12] | N2-(4-Chloro-benzyl)-N5-o-tolyl-pyrido[4,3-d]pyrimidine-2,5-diamine |
| Compound 44 | 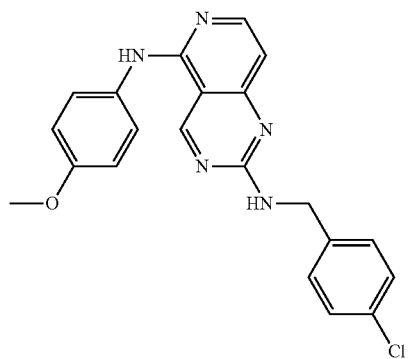 [SMILES: COc1ccc(Nc2nccc3nc(NCc4ccc(Cl)cc4)ncc23)cc1] | N2-(4-Chloro-benzyl)-N5-(4-methoxy-phenyl)-pyrido[4,3-d]pyrimidine-2,5-diamine |
| Compound 45 | 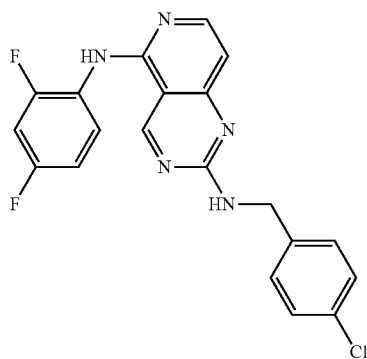 [SMILES: Fc1ccc(Nc2nccc3nc(NCc4ccc(Cl)cc4)ncc23)c(F)c1] | N2-(4-Chloro-benzyl)-N5-(2,4-difluoro-phenyl)-pyrido[4,3-d]pyrimidine-2,5-diamine |
| Compound 46 | 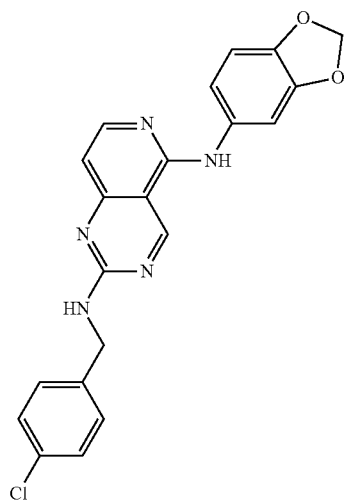 [SMILES: Clc1ccc(CNc2ncc3c(Nc4ccc5c(c4)OCO5)nccc3n2)cc1] | N5-Benzo[1,3]dioxol-5-yl-N2-(4-chloro-benzyl)-pyrido[4,3-d]pyrimidine-2,5-diamine |

-continued
| Compound 47 | 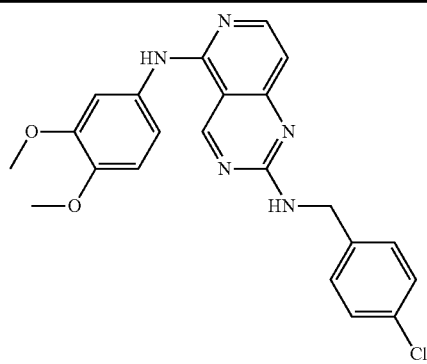 | N2-(4-Chloro-benzyl)-N5-(3,4-dimethoxy-phenyl)-pyrido[4,3-d]pyrimidine-2,5-diamine |
| Compound 48 | 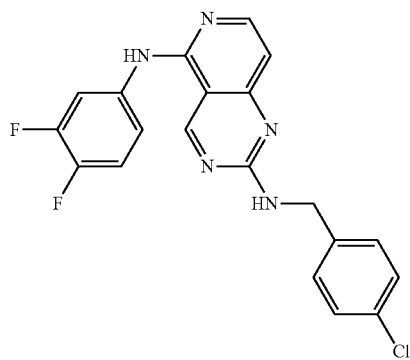 [SMILES: Fc1ccc(Nc2nccc3nc(NCc4ccc(Cl)cc4)ncc23)cc1F] | N2-(4-Chloro-benzyl)-N5-(3,4-difluoro-phenyl)-pyrido[4,3-d]pyrimidine-2,5-diamine |
| Compound 49 | 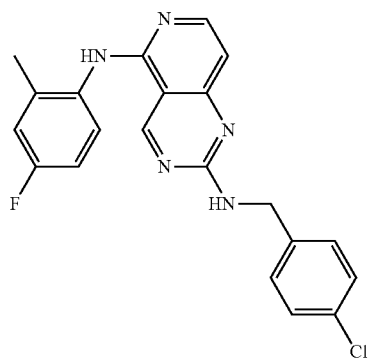 [SMILES: Cc1cc(F)ccc1Nc1nccc2nc(NCc3ccc(Cl)cc3)ncc12] | N2-(4-Chloro-benzyl)-N5-(4-fluoro-2-methyl-phenyl)-pyrido[4,3-d]pyrimidine-2,5-diamine |
| Compound 50 | 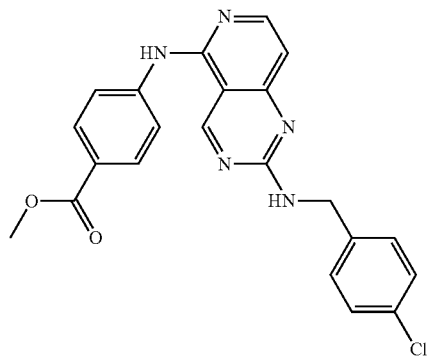 [SMILES: COC(=O)c1ccc(Nc2nccc3nc(NCc4ccc(Cl)cc4)ncc23)cc1] | 4-[2-(4-Chloro-benzylamino)-pyrido[4,3-d]pyrimidin-5-ylamino]-benzoic acid methyl ester |

-continued
| Compound 51 | 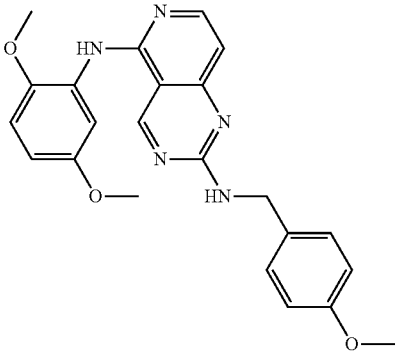 [SMILES: COc1ccc(CNc2ncc3c(Nc4cc(OC)ccc4OC)nccc3n2)cc1] | N5-(2,5-Dimethoxy-phenyl)-N2-(4-methoxy-benzyl)-pyrido[4,3-d]pyrimidine-2,5-diamine |
| Compound 52 | 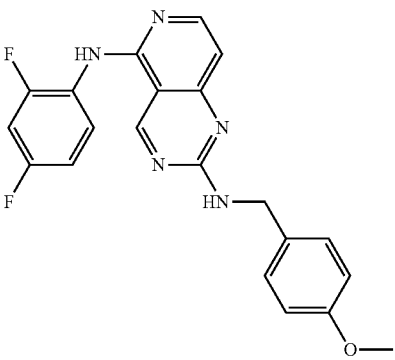 [SMILES: COc1ccc(CNc2ncc3c(Nc4ccc(F)cc4F)nccc3n2)cc1] | N5-(2,4-Difluoro-phenyl)-N2-(4-methoxy-benzyl)-pyrido[4,3-d]pyrimidine-2,5-diamine |
| Compound 53 | 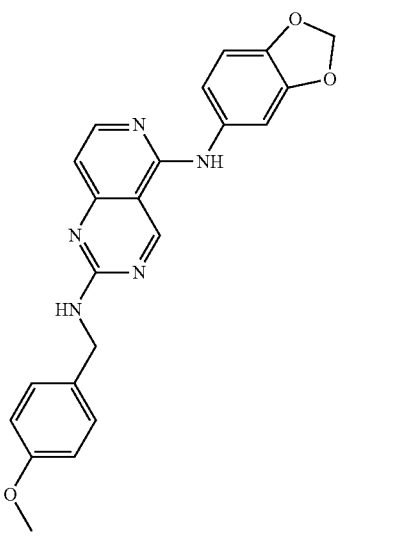 [SMILES: COc1ccc(CNc2ncc3c(Nc4ccc5c(c4)OCO5)nccc3n2)cc1] | N5-Benzo[1,3]dioxol-5-yl-N2-(4-methoxy-benzyl)-pyrido[4,3-d]pyrimidine-2,5-diamine |
| Compound 54 | 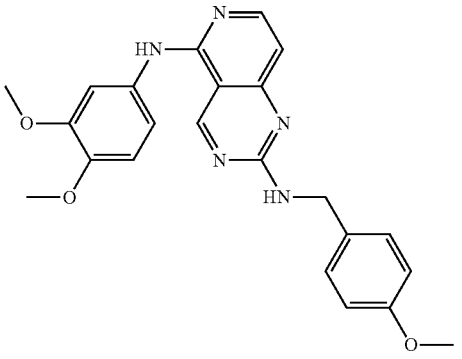 | N5-(3,4-Dimethoxy-phenyl)-N2-(4-methoxy-benzyl)-pyrido[4,3-d]pyrimidine-2,5-diamine |

-continued
| Compound 55 | 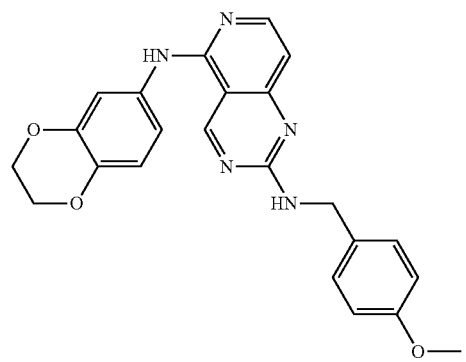 [SMILES: COc1ccc(CNc2ncc3c(Nc4ccc5c(c4)OCCO5)nccc3n2)cc1] | N5-(2,3-Dihydro-benzo[1,4]dioxin-6-yl)-N2-(4-methoxy-benzyl)-pyrido[4,3-d]pyrimidine-2,5-diamine |
| Compound 56 | 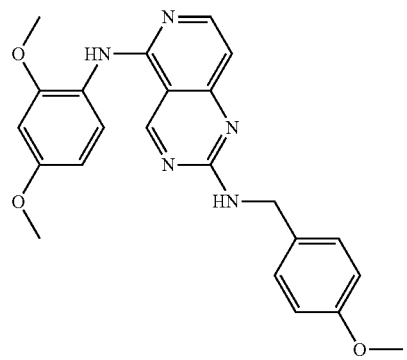 [SMILES: COc1ccc(CNc2ncc3c(Nc4ccc(OC)cc4OC)nccc3n2)cc1] | N5-(2,4-Dimethoxy-phenyl)-N2-(4-methoxy-benzyl)-pyrido[4,3-d]pyrimidine-2,5-diamine |
| Compound 57 | 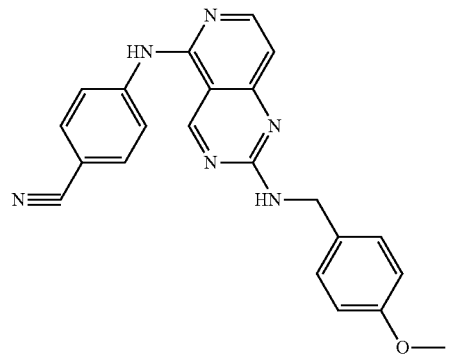 [SMILES: COc1ccc(CNc2ncc3c(Nc4ccc(C#N)cc4)nccc3n2)cc1] | 4-[2-(4-Methoxy-benzylamino)-pyrido[4,3-d]pyrimidin-5-ylamino]-benzonitrile |
| Compound 58 | 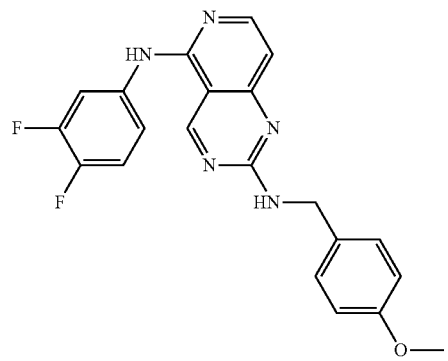 [SMILES: COc1ccc(CNc2ncc3c(Nc4ccc(F)c(F)c4)nccc3n2)cc1] | N5-(3,4-Difluoro-phenyl)-N2-(4-methoxy-benzyl)-pyrido[4,3-d]pyrimidine-2,5-diamine |

-continued

| | | |
|---|---|---|
| Compound 59 | *[structure]* | N5-(4-Fluoro-2-methyl-phenyl)-N2-(4-methoxy-benzyl)-pyrido[4,3-d]pyrimidine-2,5-diamine |
| Compound 60 | *[structure]* | 1-(2-Benzylamino-pyrido[4,3-d]pyrimidin-5-yl)-piperidine-4-carboxylic acid (furan-2-ylmethyl)-amide |
| Compound 61 | *[structure]* | 1-(2-Benzylamino-pyrido[4,3-d]pyrimidin-5-yl)-piperidine-4-carboxylic acid isopropylamide |
| Compound 62 | *[structure]* | 1-[2-(2-Chloro-benzylamino)-pyrido[4,3-d]pyrimidin-5-yl]-piperidine-4-carboxylic acid (pyridin-3-ylmethyl)-amide |

| | | |
|---|---|---|
| Compound 63 | 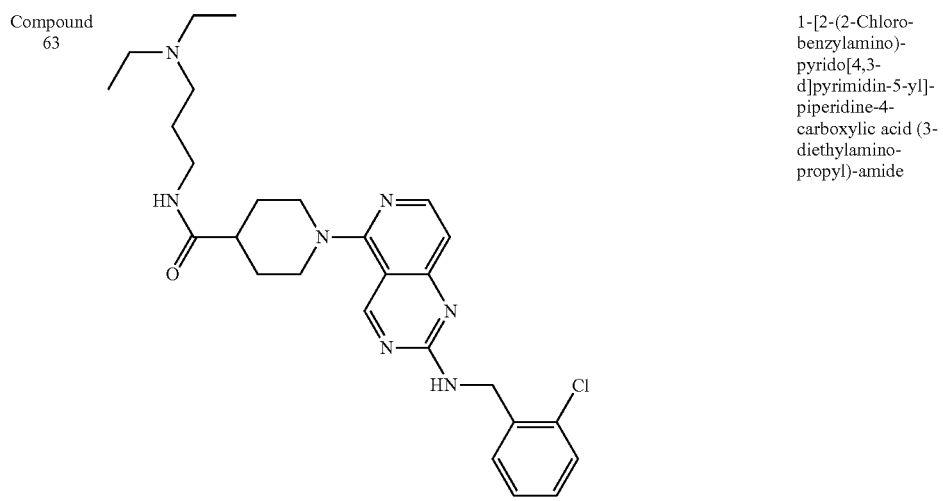 | 1-[2-(2-Chloro-benzylamino)-pyrido[4,3-d]pyrimidin-5-yl]-piperidine-4-carboxylic acid (3-diethylamino-propyl)-amide |
| Compound 64 | 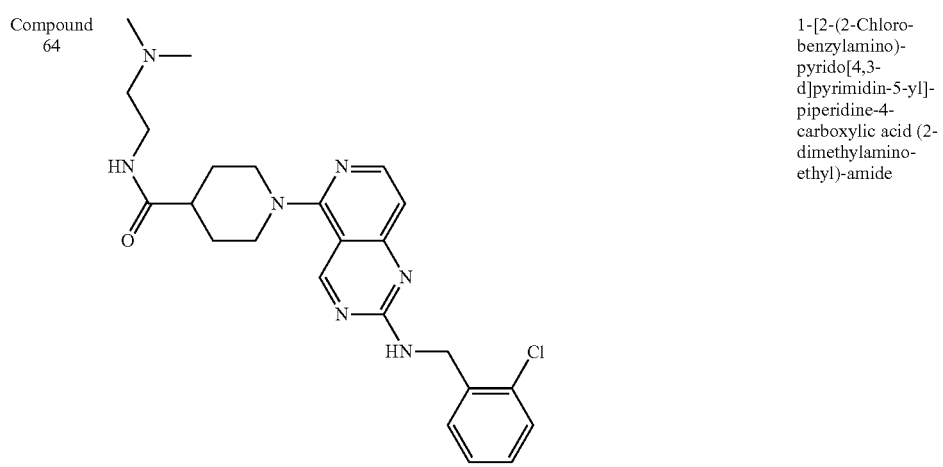 | 1-[2-(2-Chloro-benzylamino)-pyrido[4,3-d]pyrimidin-5-yl]-piperidine-4-carboxylic acid (2-dimethylamino-ethyl)-amide |
| Compound 65 | 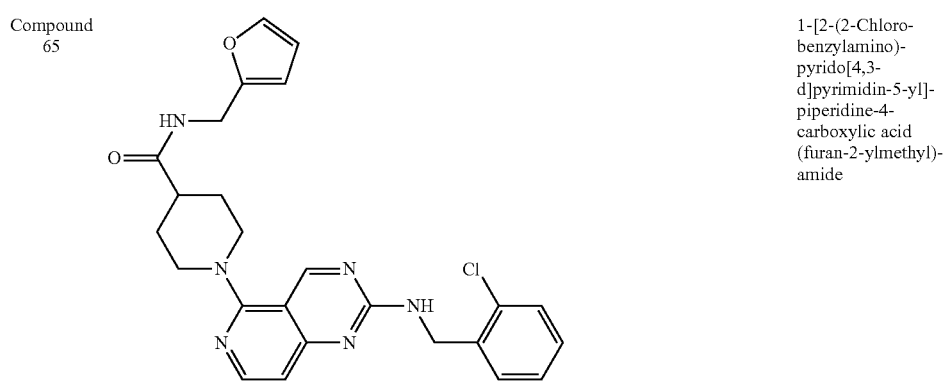 | 1-[2-(2-Chloro-benzylamino)-pyrido[4,3-d]pyrimidin-5-yl]-piperidine-4-carboxylic acid (furan-2-ylmethyl)-amide |

| Compound 66 | 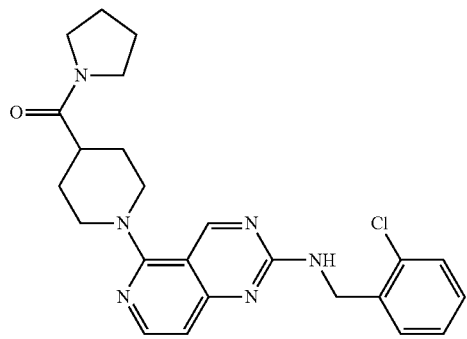 [SMILES: O=C(C1CCN(c2nccc3nc(NCc4ccccc4Cl)ncc23)CC1)N1CCCC1] | {1-[2-(2-Chloro-benzylamino)-pyrido[4,3-d]pyrimidin-5-yl]-piperidin-4-yl}-pyrrolidin-1-yl-methanone |
| Compound 67 | 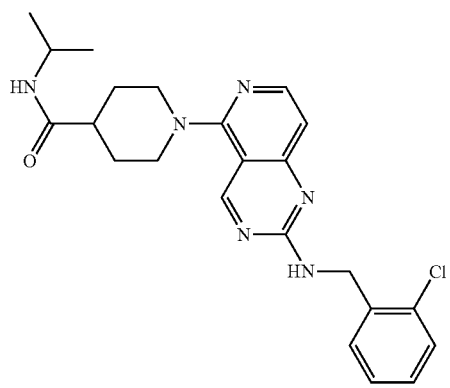 [SMILES: CC(C)NC(=O)C1CCN(c2nccc3nc(NCc4ccccc4Cl)ncc23)CC1] | 1-[2-(2-Chloro-benzylamino)-pyrido[4,3-d]pyrimidin-5-yl]-piperidine-4-carboxylic acid isopropylamide |
| Compound 68 | 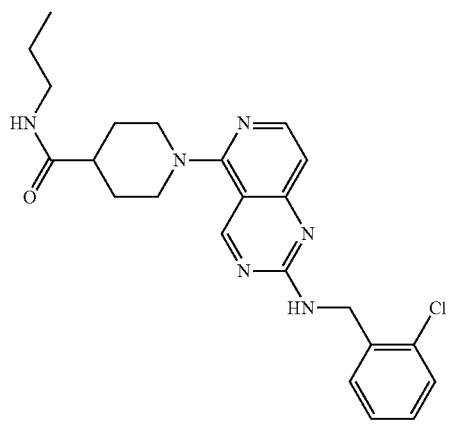 [SMILES: CCCNC(=O)C1CCN(c2nccc3nc(NCc4ccccc4Cl)ncc23)CC1] | 1-[2-(2-Chloro-benzylamino)-pyrido[4,3-d]pyrimidin-5-yl]-piperidine-4-carboxylic acid propylamide |

| | | |
|---|---|---|
| Compound 69 | 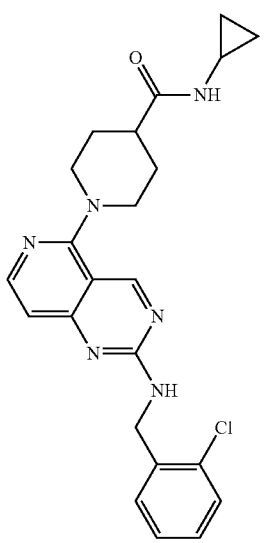 [SMILES: O=C(NC1CC1)C1CCN(c2nccc3nc(NCc4ccccc4Cl)ncc23)CC1] | 1-[2-(2-Chloro-benzylamino)-pyrido[4,3-d]pyrimidin-5-yl]-piperidine-4-carboxylic acid cyclopropylamide |
| Compound 70 | 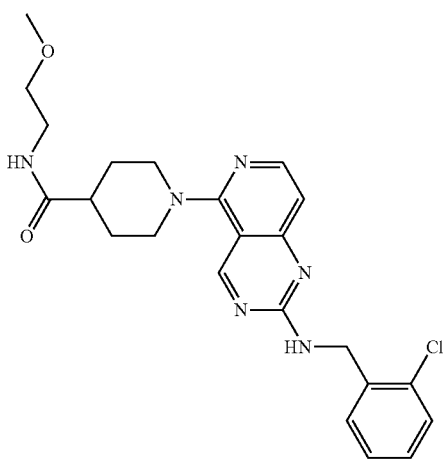 [SMILES: COCCNC(=O)C1CCN(c2nccc3nc(NCc4ccccc4Cl)ncc23)CC1] | 1-[2-(2-Chloro-benzylamino)-pyrido[4,3-d]pyrimidin-5-yl]-piperidine-4-carboxylic acid (2-methoxy-ethyl)-amide |
| Compound 71 | 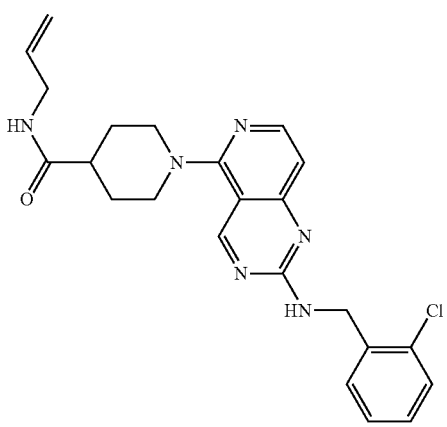 [SMILES: C=CCNC(=O)C1CCN(c2nccc3nc(NCc4ccccc4Cl)ncc23)CC1] | 1-[2-(2-Chloro-benzylamino)-pyrido[4,3-d]pyrimidin-5-yl]-piperidine-4-carboxylic acid allylamide |

-continued
| Compound 72 | 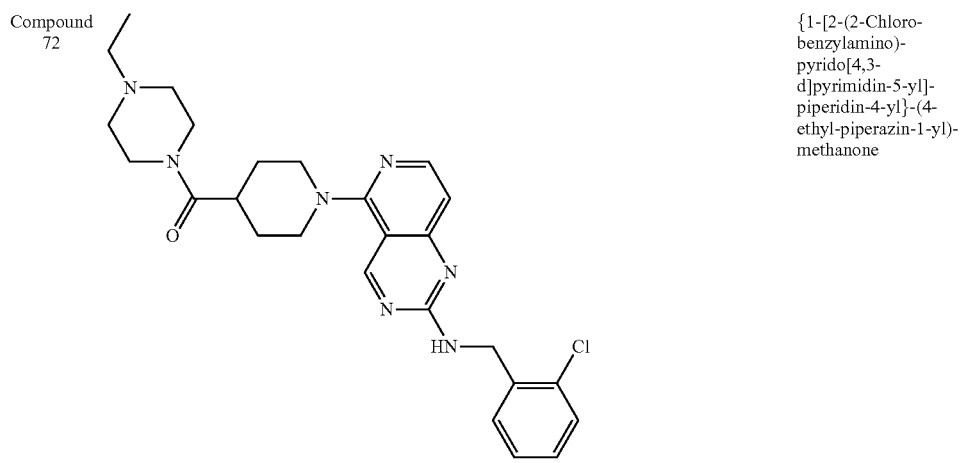 | {1-[2-(2-Chloro-benzylamino)-pyrido[4,3-d]pyrimidin-5-yl]-piperidin-4-yl}-(4-ethyl-piperazin-1-yl)-methanone |
| Compound 73 | 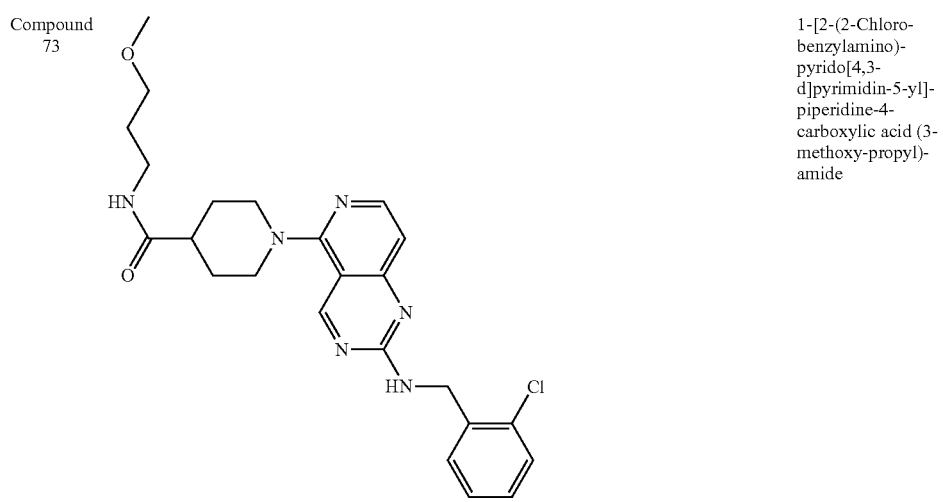 | 1-[2-(2-Chloro-benzylamino)-pyrido[4,3-d]pyrimidin-5-yl]-piperidine-4-carboxylic acid (3-methoxy-propyl)-amide |
| Compound 74 | 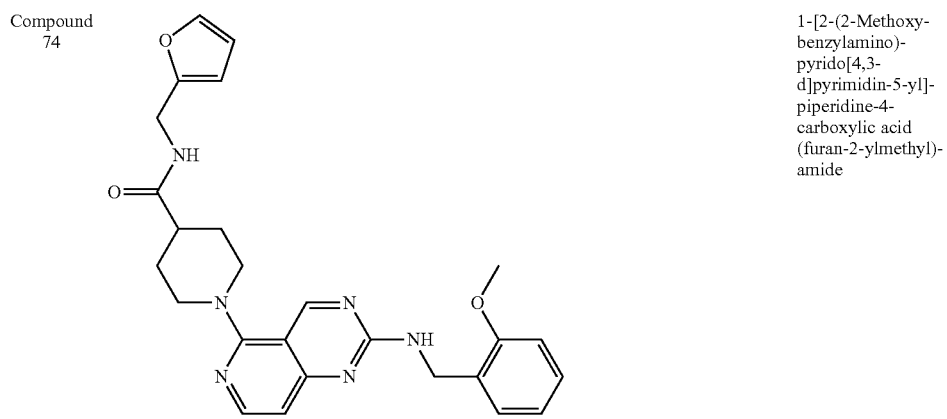 | 1-[2-(2-Methoxy-benzylamino)-pyrido[4,3-d]pyrimidin-5-yl]-piperidine-4-carboxylic acid (furan-2-ylmethyl)-amide |

| | | |
|---|---|---|
| Compound 75 | 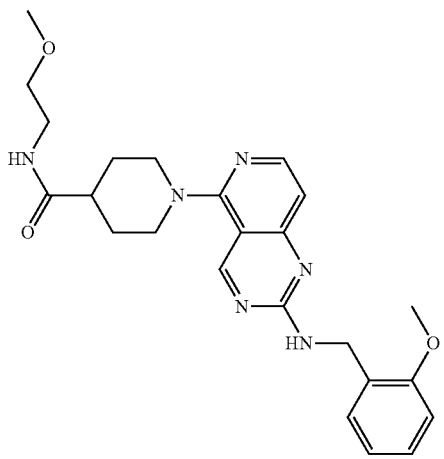 [SMILES: COCCNC(=O)C1CCN(c2nccc3nc(NCc4ccccc4OC)ncc23)CC1] | 1-[2-(2-Methoxy-benzylamino)-pyrido[4,3-d]pyrimidin-5-yl]-piperidine-4-carboxylic acid (2-methoxy-ethyl)-amide |
| Compound 76 | 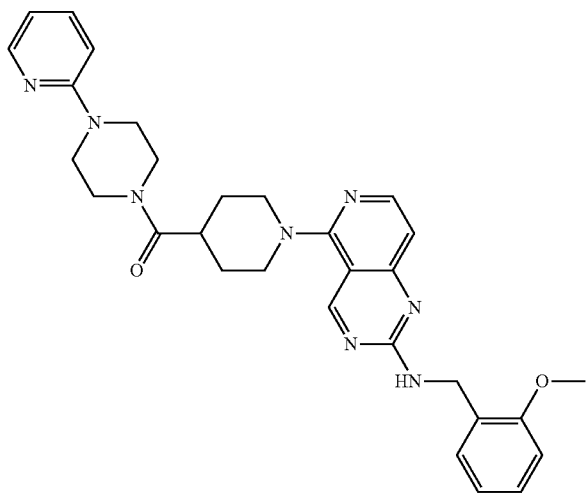 [SMILES: COc1ccccc1CNc1ncc2c(N3CCC(C(=O)N4CCN(c5ccccn5)CC4)CC3)nccc2n1] | {1-[2-(2-Methoxy-benzylamino)-pyrido[4,3-d]pyrimidin-5-yl]-piperidin-4-yl}-(4-pyridin-2-yl-piperazin-1-yl)-methanone |
| Compound 77 | 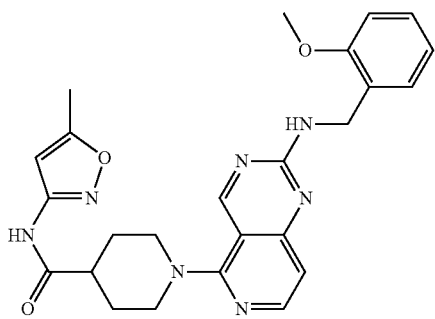 [SMILES: COc1ccccc1CNc1ncc2c(N3CCC(C(=O)Nc4cc(C)on4)CC3)nccc2n1] | 1-[2-(2-Methoxy-benzylamino)-pyrido[4,3-d]pyrimidin-5-yl]-piperidine-4-carboxylic acid (5-methyl-isoxazol-3-yl)-amide |

| | | |
|---|---|---|
| Compound 78 | | 1-[2-(4-Chloro-benzylamino)-pyrido[4,3-d]pyrimidin-5-yl]-piperidine-4-carboxylic acid pyridin-3-ylamide |
| Compound 79 | | 1-[2-(4-Chloro-benzylamino)-pyrido[4,3-d]pyrimidin-5-yl]-piperidine-4-carboxylic acid (furan-2-ylmethyl)-amide |
| Compound 80 | | {1-[2-(4-Chloro-benzylamino)-pyrido[4,3-d]pyrimidin-5-yl]-piperidin-4-yl}-pyrrolidin-1-yl-methanone |
| Compound 81 | | 1-[2-(2-Chloro-benzylamino)-pyrido[4,3-d]pyrimidin-5-yl]-piperidine-3-carboxylic acid (pyridin-3-ylmethyl)-amide |

-continued

| | | |
|---|---|---|
| Compound 82 | 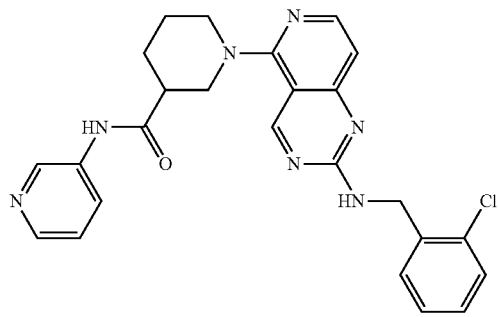 [SMILES: O=C(Nc1cccnc1)C1CCCN(c2nccc3nc(NCc4ccccc4Cl)ncc23)C1] | 1-[2-(2-Chloro-benzylamino)-pyrido[4,3-d]pyrimidin-5-yl]-piperidine-3-carboxylic acid pyridin-3-ylamide |
| Compound 83 | 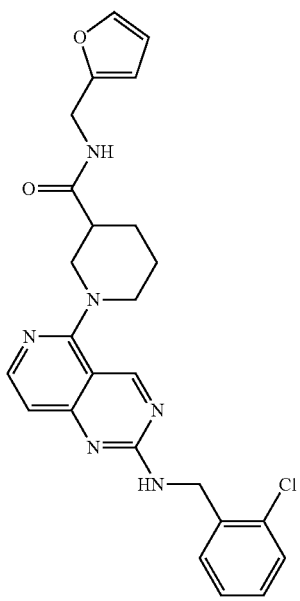 [SMILES: O=C(NCc1ccco1)C1CCCN(c2nccc3nc(NCc4ccccc4Cl)ncc23)C1] | 1-[2-(2-Chloro-benzylamino)-pyrido[4,3-d]pyrimidin-5-yl]-piperidine-3-carboxylic acid (furan-2-ylmethyl)-amide |
| Compound 84 | 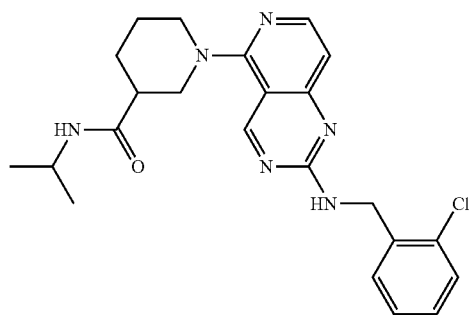 [SMILES: CC(C)NC(=O)C1CCCN(c2nccc3nc(NCc4ccccc4Cl)ncc23)C1] | 1-[2-(2-Chloro-benzylamino)-pyrido[4,3-d]pyrimidin-5-yl]-piperidine-3-carboxylic acid isopropylamide |
| Compound 85 | 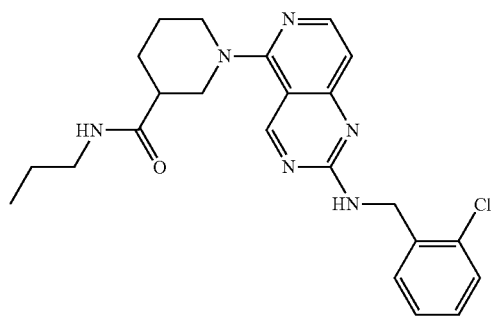 [SMILES: CCCNC(=O)C1CCCN(c2nccc3nc(NCc4ccccc4Cl)ncc23)C1] | 1-[2-(2-Chloro-benzylamino)-pyrido[4,3-d]pyrimidin-5-yl]-piperidine-3-carboxylic acid propylamide |

| | | |
|---|---|---|
| Compound 86 | 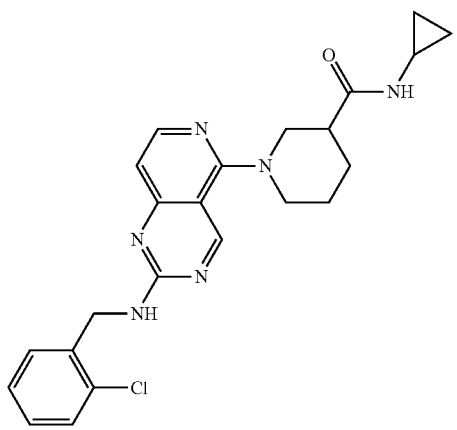 [SMILES: O=C(NC1CC1)C1CCCN(c2nccc3nc(NCc4ccccc4Cl)ncc23)C1] | 1-[2-(2-Chloro-benzylamino)-pyrido[4,3-d]pyrimidin-5-yl]-piperidine-3-carboxylic acid cyclopropylamide |
| Compound 87 | 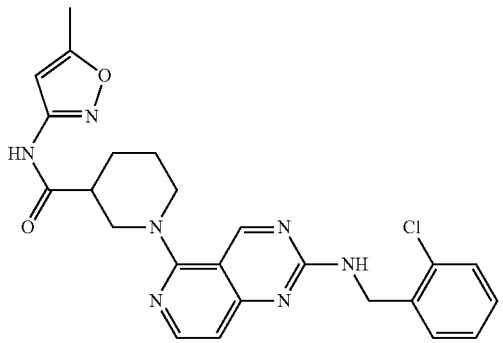 [SMILES: Cc1cc(NC(=O)C2CCCN(c3nccc4nc(NCc5ccccc5Cl)ncc34)C2)no1] | 1-[2-(2-Chloro-benzylamino)-pyrido[4,3-d]pyrimidin-5-yl]-piperidine-3-carboxylic acid (5-methyl-isoxazol-3-yl)-amide |
| Compound 88 | 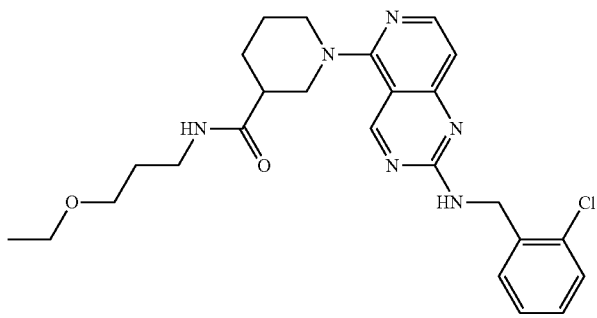 [SMILES: CCOCCCNC(=O)C1CCCN(c2nccc3nc(NCc4ccccc4Cl)ncc23)C1] | 1-[2-(2-Chloro-benzylamino)-pyrido[4,3-d]pyrimidin-5-yl]-piperidine-3-carboxylic acid (3-ethoxy-propyl)-amide |
| Compound 89 | 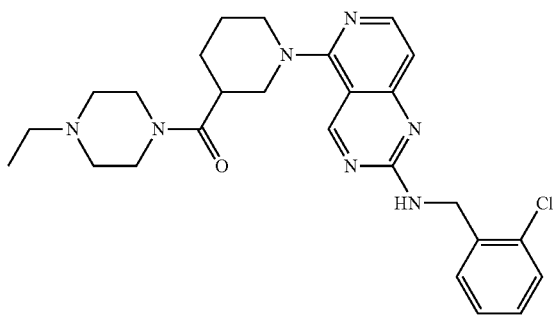 [SMILES: CCN1CCN(C(=O)C2CCCN(c3nccc4nc(NCc5ccccc5Cl)ncc34)C2)CC1] | {1-[2-(2-Chloro-benzylamino)-pyrido[4,3-d]pyrimidin-5-yl]-piperidin-3-yl}-(4-ethyl-piperazin-1-yl)-methanone |

| | | |
|---|---|---|
| Compound 90 | 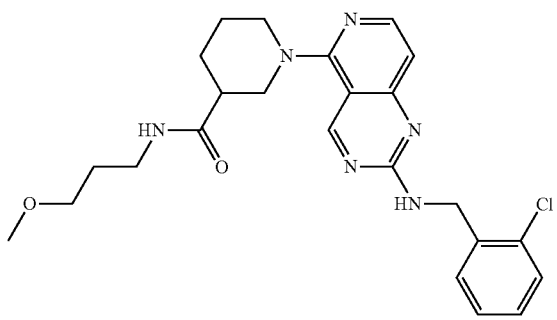 [SMILES: COCCCNC(=O)C1CCCN(c2nccc3nc(NCc4ccccc4Cl)ncc23)C1] | 1-[2-(2-Chloro-benzylamino)-pyrido[4,3-d]pyrimidin-5-yl]-piperidine-3-carboxylic acid (3-methoxy-propyl)-amide |
| Compound 91 | 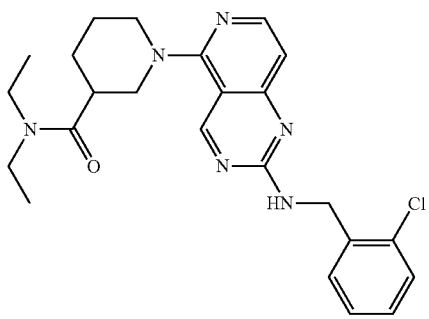 [SMILES: CCN(CC)C(=O)C1CCCN(c2nccc3nc(NCc4ccccc4Cl)ncc23)C1] | 1-[2-(2-Chloro-benzylamino)-pyrido[4,3-d]pyrimidin-5-yl]-piperidine-3-carboxylic acid diethylamide |
| Compound 92 | 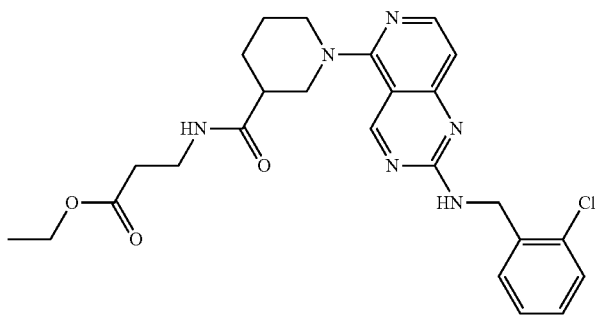 [SMILES: CCOC(=O)CCNC(=O)C1CCCN(c2nccc3nc(NCc4ccccc4Cl)ncc23)C1] | 3-({1-[2-(2-Chloro-benzylamino)-pyrido[4,3-d]pyrimidin-5-yl]-piperidine-3-carbonyl}-amino)-propionic acid ethyl ester |
| Compound 93 | 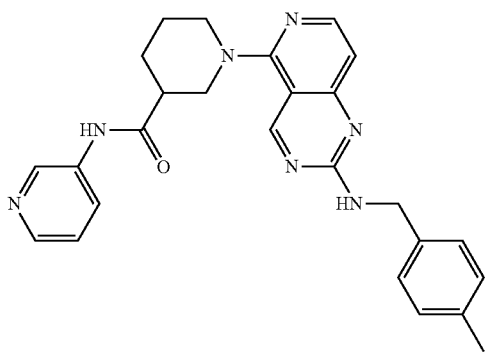 [SMILES: Cc1ccc(CNc2ncc3c(N4CCCC(C(=O)Nc5cccnc5)C4)nccc3n2)cc1] | 1-[2-(4-Methyl-benzylamino)-pyrido[4,3-d]pyrimidin-5-yl]-piperidine-3-carboxylic acid pyridin-3-ylamide |

-continued
| | | |
|---|---|---|
| Compound 94 | 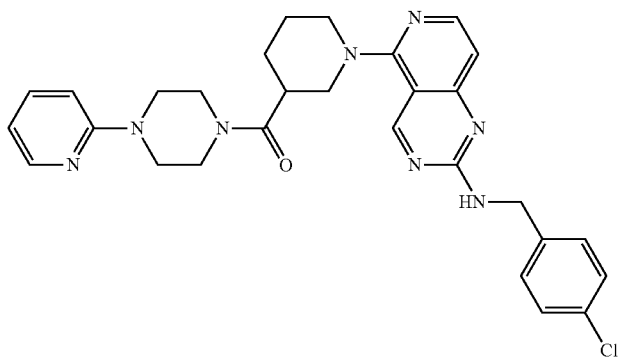 [SMILES: O=C(C1CCCN(c2nccc3nc(NCc4ccc(Cl)cc4)ncc23)C1)N1CCN(c2ccccn2)CC1] | {1-[2-(4-Chloro-benzylamino)-pyrido[4,3-d]pyrimidin-5-yl]-piperidin-3-yl}-(4-pyridin-2-yl-piperazin-1-yl)-methanone |
| Compound 95 | 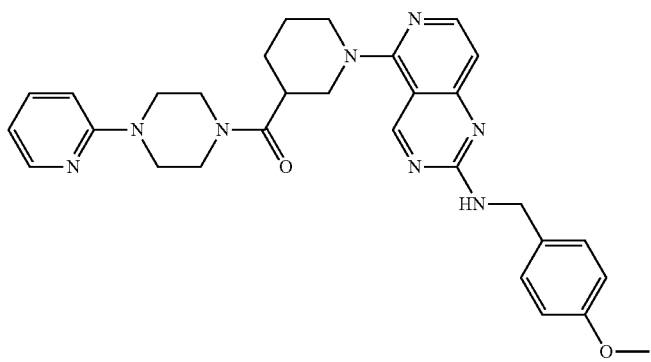 [SMILES: COc1ccc(CNc2ncc3c(N4CCCC(C(=O)N5CCN(c6ccccn6)CC5)C4)nccc3n2)cc1] | {1-[2-(4-Methoxy-benzylamino)-pyrido[4,3-d]pyrimidin-5-yl]-piperidin-3-yl}-(4-pyridin-2-yl-piperazin-1-yl)-methanone |
| Compound 96 | 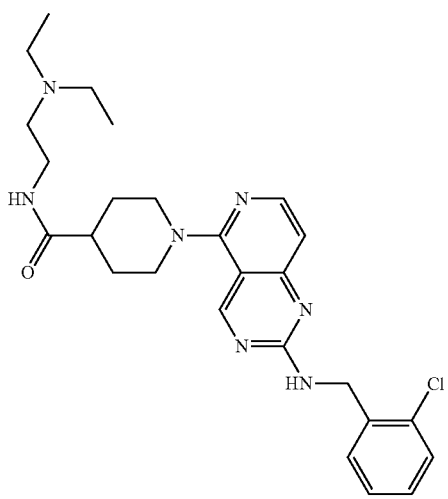 [SMILES: CCN(CC)CCNC(=O)C1CCN(c2nccc3nc(NCc4ccccc4Cl)ncc23)CC1] | 1-[2-(2-Chloro-benzylamino)-pyrido[4,3-d]pyrimidin-5-yl]-piperidine-4-carboxylic acid (2-diethylamino-ethyl)-amide |

-continued

| Compound 97 | | {1-[2-(2-Chloro-benzylamino)-pyrido[4,3-d]pyrimidin-5-yl]-piperidin-4-yl}-(4-propyl-piperazin-1-yl)-methanone |
|---|---|---|
| Compound 98 | | 1-[2-(2-Chloro-benzylamino)-pyrido[4,3-d]pyrimidin-5-yl]-piperidine-4-carboxylic acid (3-ethoxy-propyl)-amide |
| Compound 99 | | {1-[2-(2-Chloro-benzylamino)-pyrido[4,3-d]pyrimidin-5-yl]-piperidin-3-yl}-(4-pyridin-2-yl-piperazin-1-yl)-methanone |
| Compound 100 | | N2-(2-Chloro-benzyl)-N5-(2-fluoro-phenyl)-pyrido[4,3-d]pyrimidine-2,5-diamine |

| | | |
|---|---|---|
| Compound 101 | 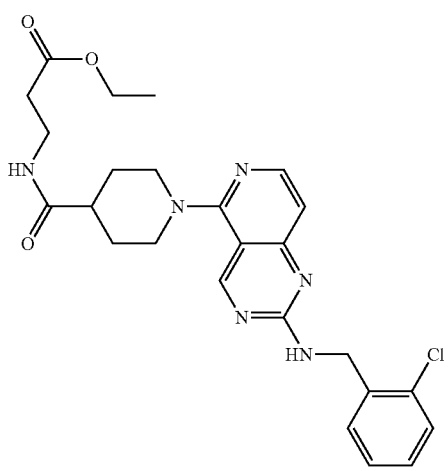 [SMILES: CCOC(=O)CCNC(=O)C1CCN(c2nccc3nc(NCc4ccccc4Cl)ncc23)CC1] | 3-({1-[2-(2-Chloro-benzylamino)-pyrido[4,3-d]pyrimidin-5-yl]-piperidine-4-carbonyl}-amino)-propionic acid ethyl ester |
| Compound 102 | 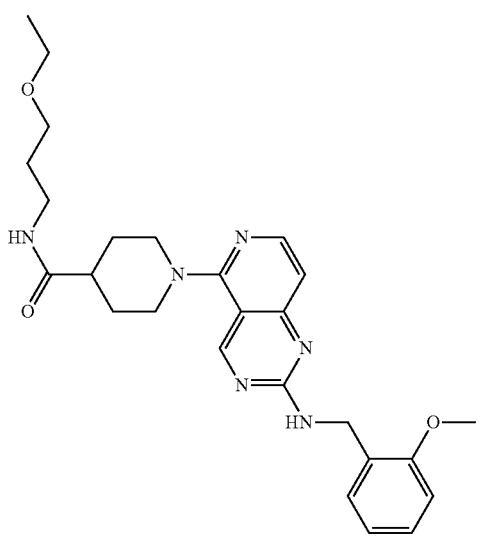 [SMILES: CCOCCCNC(=O)C1CCN(c2nccc3nc(NCc4ccccc4OC)ncc23)CC1] | 1-[2-(2-Methoxy-benzylamino)-pyrido[4,3-d]pyrimidin-5-yl]-piperidine-4-carboxylic acid (3-ethoxy-propyl)-amide |
| Compound 103 | 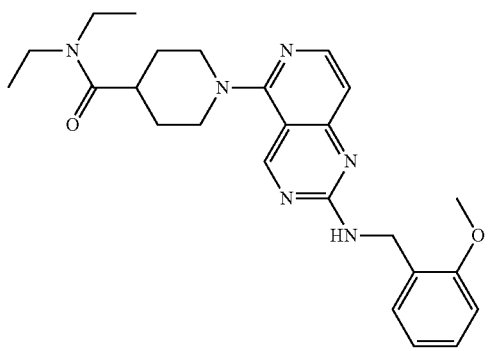 | 1-[2-(2-Methoxy-benzylamino)-pyrido[4,3-d]pyrimidin-5-yl]-piperidine-4-carboxylic acid diethylamide |

| | | |
|---|---|---|
| Compound 104 | 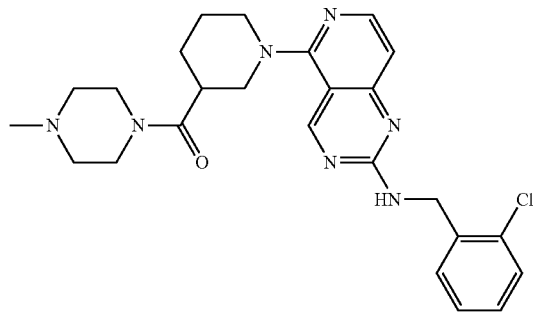 [SMILES: CN1CCN(C(=O)C2CCCN(c3nccc4nc(NCc5ccccc5Cl)ncc34)C2)CC1] | {1-[2-(2-Chloro-benzylamino)-pyrido[4,3-d]pyrimidin-5-yl]-piperidin-3-yl}-(4-methyl-piperazin-1-yl)-methanone |
| Compound 105 | 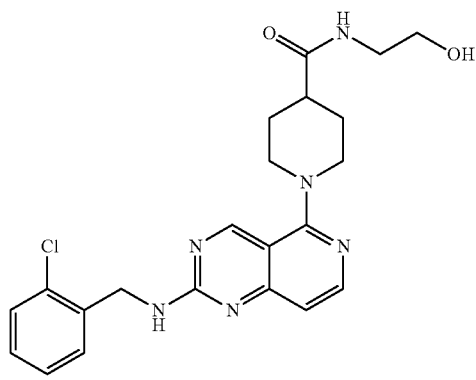 [SMILES: O=C(NCCO)C1CCN(c2nccc3nc(NCc4ccccc4Cl)ncc23)CC1] | 1-[2-(2-Chloro-benzylamino)-pyrido[4,3-d]pyrimidin-5-yl]-piperidine-4-carboxylic acid (2-hydroxy-ethyl)-amide |
| Compound 106 | 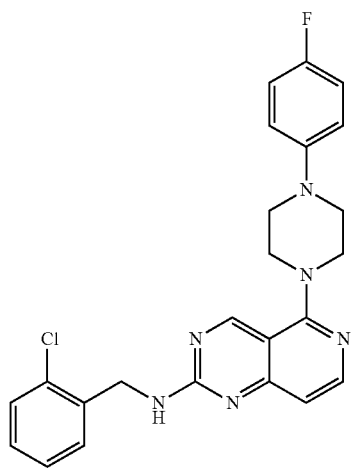 [SMILES: Fc1ccc(N2CCN(c3nccc4nc(NCc5ccccc5Cl)ncc34)CC2)cc1] | (2-Chloro-benzyl)-{5-[4-(4-fluoro-phenyl)-piperazin-1-yl]-pyrido[4,3-d]pyrimidin-2-yl}-amine |
| Compound 107 | 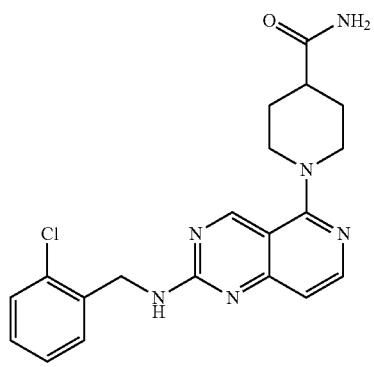 [SMILES: NC(=O)C1CCN(c2nccc3nc(NCc4ccccc4Cl)ncc23)CC1] | 1-[2-(2-Chloro-benzylamino)-pyrido[4,3-d]pyrimidin-5-yl]-piperidine-4-carboxylic acid amide |

| Compound 108 | 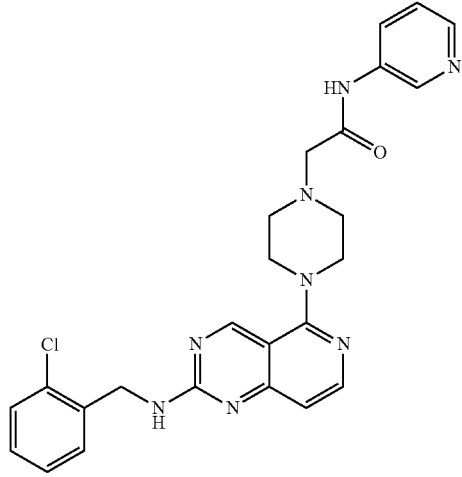 [SMILES: O=C(CN1CCN(c2nccc3nc(NCc4ccccc4Cl)ncc23)CC1)Nc1cccnc1] | 2-{4-[2-(2-Chloro-benzylamino)-pyrido[4,3-d]pyrimidin-5-yl]-piperazin-1-yl}-N-pyridin-3-yl-acetamide |
|---|---|---|
| Compound 109 | 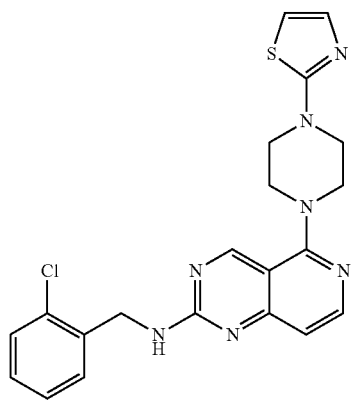 [SMILES: Clc1ccccc1CNc1ncc2c(N3CCN(c4nccs4)CC3)nccc2n1] | (2-Chloro-benzyl)-[5-(4-thiazol-2-yl-piperazin-1-yl)-pyrido[4,3-d]pyrimidin-2-yl]-amine |
| Compound 110 | 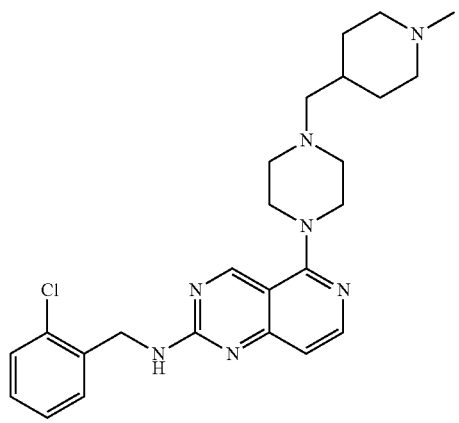 [SMILES: CN1CCC(CN2CCN(c3nccc4nc(NCc5ccccc5Cl)ncc34)CC2)CC1] | (2-Chloro-benzyl)-{5-[4-(1-methyl-piperidin-4-ylmethyl)-piperazin-1-yl]-pyrido[4,3-d]pyrimidin-2-yl}-amine |

| | | |
|---|---|---|
| Compound 111 | 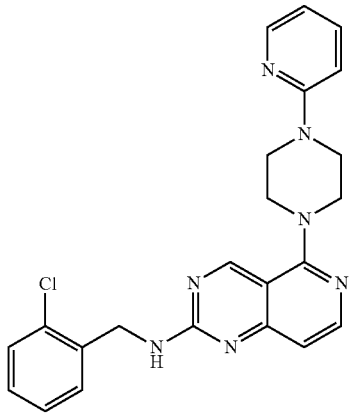 [SMILES: Clc1ccccc1CNc1ncc2c(N3CCN(c4ccccn4)CC3)nccc2n1] | (2-Chloro-benzyl)-[5-(4-pyridin-2-yl-piperazin-1-yl)-pyrido[4,3-d]pyrimidin-2-yl]-amine |
| Compound 112 | 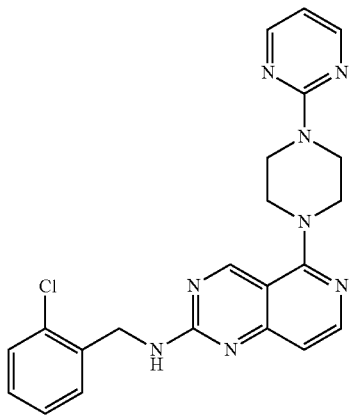 [SMILES: Clc1ccccc1CNc1ncc2c(N3CCN(c4ncccn4)CC3)nccc2n1] | (2-Chloro-benzyl)-[5-(4-pyrimidin-2-yl-piperazin-1-yl)-pyrido[4,3-d]pyrimidin-2-yl]-amine |
| Compound 113 | 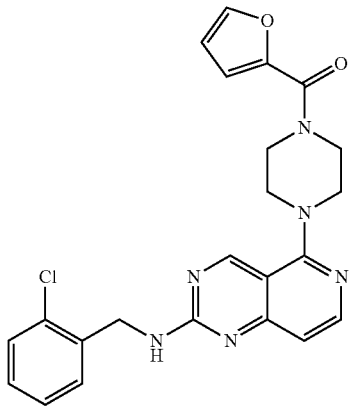 [SMILES: O=C(c1ccco1)N1CCN(c2nccc3nc(NCc4ccccc4Cl)ncc23)CC1] | {4-[2-(2-Chloro-benzylamino)-pyrido[4,3-d]pyrimidin-5-yl]-piperazin-1-yl}-furan-2-yl-methanone |
| Compound 114 | 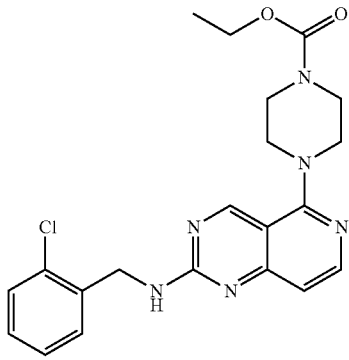 [SMILES: CCOC(=O)N1CCN(c2nccc3nc(NCc4ccccc4Cl)ncc23)CC1] | 4-[2-(2-Chloro-benzylamino)-pyrido[4,3-d]pyrimidin-5-yl]-piperazine-1-carboxylic acid ethyl ester |

-continued

| | | |
|---|---|---|
| Compound 115 | 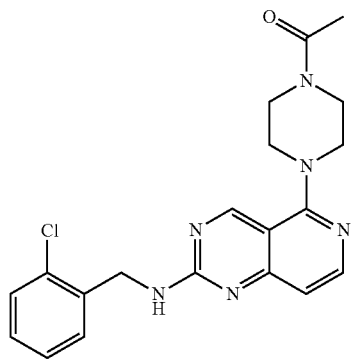 [SMILES: CC(=O)N1CCN(c2nccc3nc(NCc4ccccc4Cl)ncc23)CC1] | 1-{4-[2-(2-Chloro-benzylamino)-pyrido[4,3-d]pyrimidin-5-yl]-piperazin-1-yl}-ethanone |
| Compound 116 | 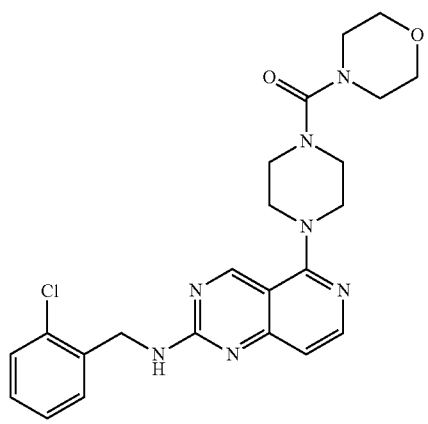 [SMILES: O=C(N1CCOCC1)N1CCN(c2nccc3nc(NCc4ccccc4Cl)ncc23)CC1] | {4-[2-(2-Chloro-benzylamino)-pyrido[4,3-d]pyrimidin-5-yl]-piperazin-1-yl}-morpholin-4-yl-methanone |
| Compound 117 | 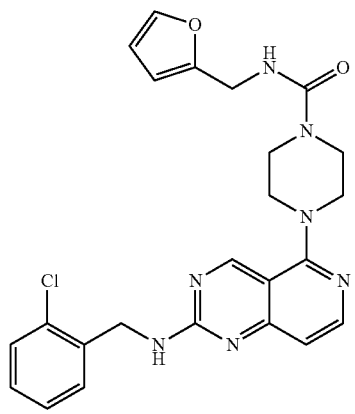 [SMILES: O=C(NCc1ccco1)N1CCN(c2nccc3nc(NCc4ccccc4Cl)ncc23)CC1] | 4-[2-(2-Chloro-benzylamino)-pyrido[4,3-d]pyrimidin-5-yl]-piperazine-1-carboxylic acid (furan-2-ylmethyl)-amide |
| Compound 118 | 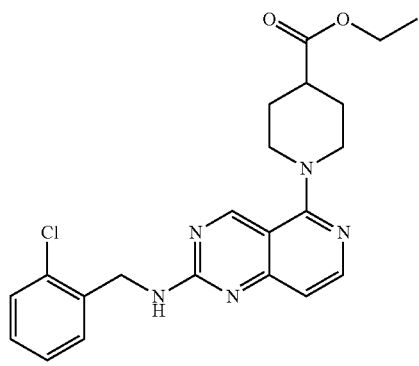 [SMILES: CCOC(=O)C1CCN(c2nccc3nc(NCc4ccccc4Cl)ncc23)CC1] | 1-[2-(2-Chloro-benzylamino)-pyrido[4,3-d]pyrimidin-5-yl]-piperidine-4-carboxylic acid ethyl ester |

-continued

| | | |
|---|---|---|
| Compound 119 | 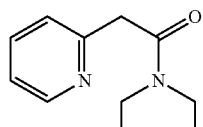 | 1-{4-[2-(2-Chloro-benzylamino)-pyrido[4,3-d]pyrimidin-5-yl]-piperazin-1-yl}-2-pyridin-2-yl-ethanone |
| Compound 120 | 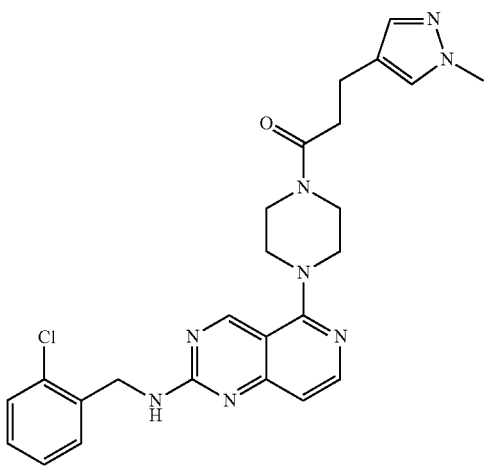 [SMILES: Cn1cc(CCC(=O)N2CCN(c3nccc4nc(NCc5ccccc5Cl)ncc34)CC2)cn1] | 1-{4-[2-(2-Chloro-benzylamino)-pyrido[4,3-d]pyrimidin-5-yl]-piperazin-1-yl}-3-(1-methyl-1H-pyrazol-4-yl)-propan-1-one |
| Compound 121 | 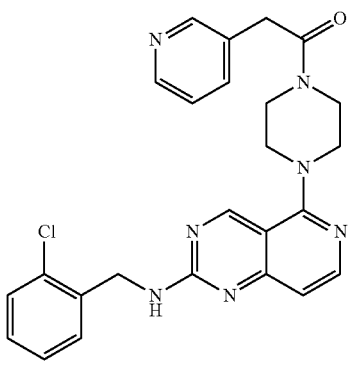 [SMILES: O=C(Cc1cccnc1)N1CCN(c2nccc3nc(NCc4ccccc4Cl)ncc23)CC1] | 1-{4-[2-(2-Chloro-benzylamino)-pyrido[4,3-d]pyrimidin-5-yl]-piperazin-1-yl}-2-pyridin-3-yl-ethanone |
| Compound 122 | 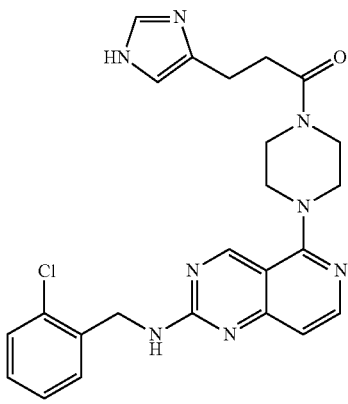 [SMILES: O=C(CCc1c[nH]cn1)N1CCN(c2nccc3nc(NCc4ccccc4Cl)ncc23)CC1] | 1-{4-[2-(2-Chloro-benzylamino)-pyrido[4,3-d]pyrimidin-5-yl]-piperazin-1-yl}-3-(1H-imidazol-4-yl)-propan-1-one |

| | | |
|---|---|---|
| Compound 123 | 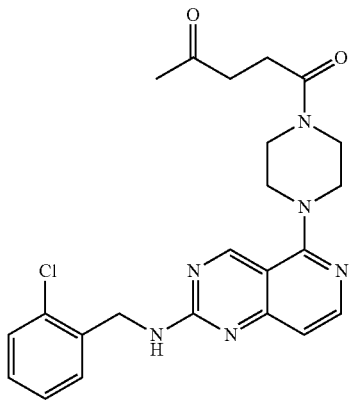 [SMILES: CC(=O)CCC(=O)N1CCN(c2nccc3nc(NCc4ccccc4Cl)ncc23)CC1] | 1-{4-[2-(2-Chloro-benzylamino)-pyrido[4,3-d]pyrimidin-5-yl]-piperazin-1-yl}-pentane-1,4-dione |
| Compound 124 | 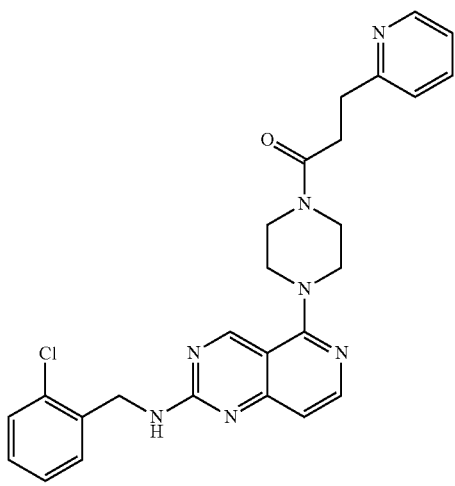 [SMILES: O=C(CCc1ccccn1)N1CCN(c2nccc3nc(NCc4ccccc4Cl)ncc23)CC1] | 1-{4-[2-(2-Chloro-benzylamino)-pyrido[4,3-d]pyrimidin-5-yl]-piperazin-1-yl}-3-pyridin-2-yl-propan-1-one |
| Compound 125 | 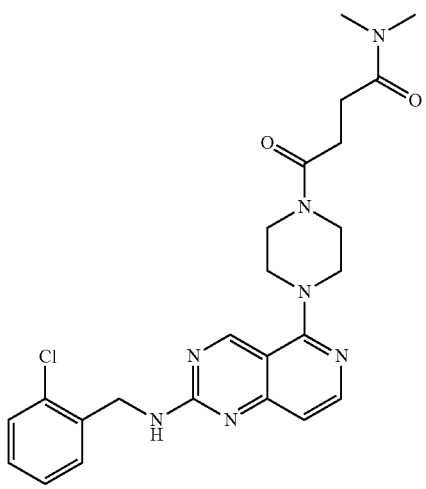 [SMILES: CN(C)C(=O)CCC(=O)N1CCN(c2nccc3nc(NCc4ccccc4Cl)ncc23)CC1] | 4-{4-[2-(2-Chloro-benzylamino)-pyrido[4,3-d]pyrimidin-5-yl]-piperazin-1-yl}-N,N-dimethyl-4-oxo-butyramide |

| Compound 126 | 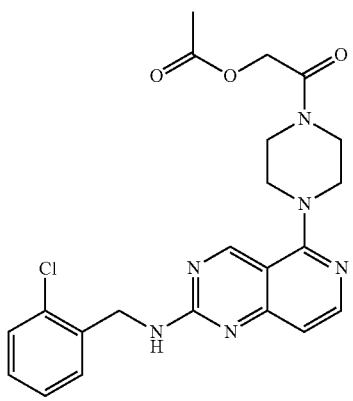 [SMILES: CC(=O)OCC(=O)N1CCN(c2nccc3nc(NCc4ccccc4Cl)ncc23)CC1] | Acetic acid 2-{4-[2-(2-chloro-benzylamino)-pyrido[4,3-d]pyrimidin-5-yl]-piperazin-1-yl}-2-oxo-ethyl ester |
| --- | --- | --- |
| Compound 128 | 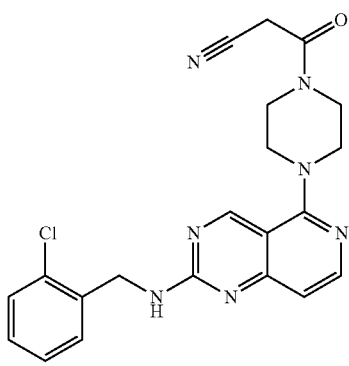 [SMILES: N#CCC(=O)N1CCN(c2nccc3nc(NCc4ccccc4Cl)ncc23)CC1] | 3-{4-[2-(2-Chloro-benzylamino)-pyrido[4,3-d]pyrimidin-5-yl]-piperazin-1-yl}-3-oxo-propionitrile |
| Compound 129 | 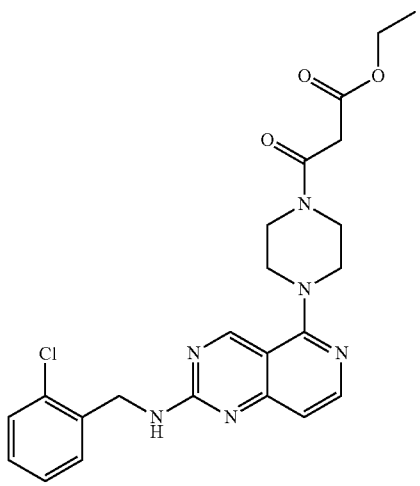 [SMILES: CCOC(=O)CC(=O)N1CCN(c2nccc3nc(NCc4ccccc4Cl)ncc23)CC1] | 3-{4-[2-(2-Chloro-benzylamino)-pyrido[4,3-d]pyrimidin-5-yl]-piperazin-1-yl}-3-oxo-propionic acid ethyl ester |
| Compound 130 | 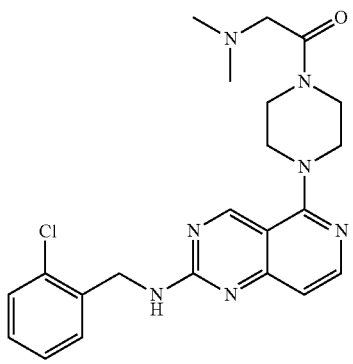 [SMILES: CN(C)CC(=O)N1CCN(c2nccc3nc(NCc4ccccc4Cl)ncc23)CC1] | 1-{4-[2-(2-Chloro-benzylamino)-pyrido[4,3-d]pyrimidin-5-yl]-piperazin-1-yl}-2-dimethylamino-ethanone |

| | | |
|---|---|---|
| Compound 131 | 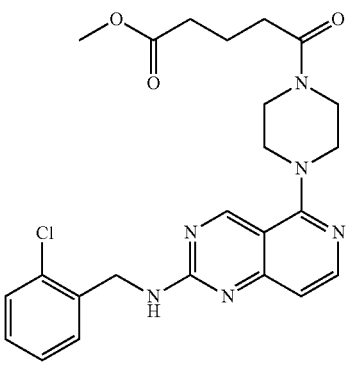 [SMILES: COC(=O)CCCC(=O)N1CCN(c2nccc3nc(NCc4ccccc4Cl)ncc23)CC1] | 5-{4-[2-(2-Chloro-benzylamino)-pyrido[4,3-d]pyrimidin-5-yl]-piperazin-1-yl}-5-oxo-pentanoic acid methyl ester |
| Compound 132 | 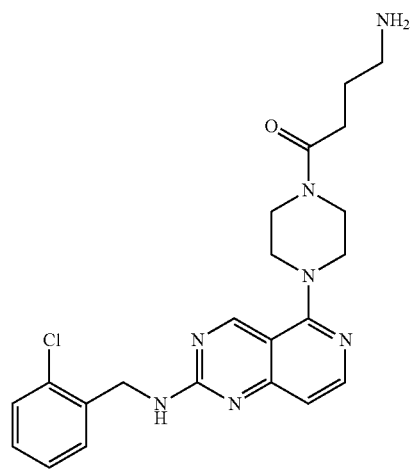 [SMILES: NCCCC(=O)N1CCN(c2nccc3nc(NCc4ccccc4Cl)ncc23)CC1] | 4-Amino-1-{4-[2-(2-chloro-benzylamino)-pyrido[4,3-d]pyrimidin-5-yl]-piperazin-1-yl}-butan-1-one |
| Compound 133 | 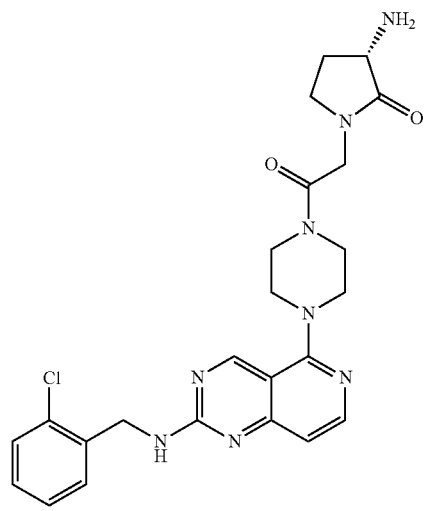 [SMILES: N[C@H]1CCN(CC(=O)N2CCN(c3nccc4nc(NCc5ccccc5Cl)ncc34)CC2)C1=O] | (S)-3-Amino-1-(2-{4-[2-(2-chloro-benzylamino)-pyrido[4,3-d]pyrimidin-5-yl]-piperazin-1-yl}-2-oxo-ethyl)-pyrrolidin-2-one |
| Compound 134 | 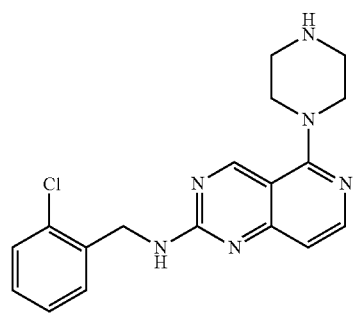 [SMILES: Clc1ccccc1CNc1ncc2c(N3CCNCC3)nccc2n1] | (2-Chloro-benzyl)-(5-piperazin-1-yl-pyrido[4,3-d]pyrimidin-2-yl)-amine |

-continued
Compound 135
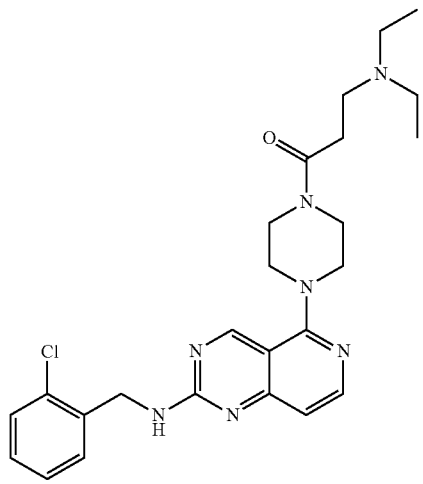 [SMILES: CCN(CC)CCC(=O)N1CCN(c2nccc3nc(NCc4ccccc4Cl)ncc23)CC1]
1-{4-[2-(2-Chloro-benzylamino)-pyrido[4,3-d]pyrimidin-5-yl]-piperazin-1-yl}-3-diethylamino-propan-1-one
Compound 136
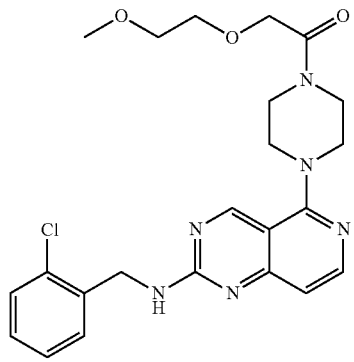 [SMILES: COCCOCC(=O)N1CCN(c2nccc3nc(NCc4ccccc4Cl)ncc23)CC1]
1-{4-[2-(2-Chloro-benzylamino)-pyrido[4,3-d]pyrimidin-5-yl]-piperazin-1-yl}-2-(2-methoxy-ethoxy)-ethanone
Compound 137
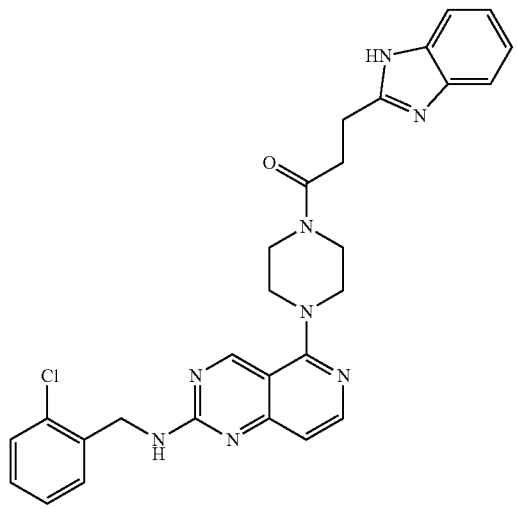 [SMILES: O=C(CCc1nc2ccccc2[nH]1)N1CCN(c2nccc3nc(NCc4ccccc4Cl)ncc23)CC1]
3-(1H-Benzoimidazol-2-yl)-1-{4-[2-(2-chloro-benzylamino)-pyrido[4,3-d]pyrimidin-5-yl]-piperazin-1-yl}-propan-1-one -continued

| Compound 138 | 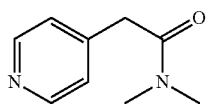 | 1-{4-[2-(2-Chloro-benzylamino)-pyrido[4,3-d]pyrimidin-5-yl]-piperazin-1-yl}-2-pyridin-4-yl-ethanone |
| Compound 139 | 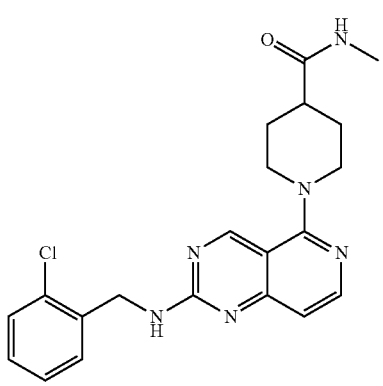 [SMILES: CNC(=O)C1CCN(c2nccc3nc(NCc4ccccc4Cl)ncc23)CC1] | 1-[2-(2-Chloro-benzylamino)-pyrido[4,3-d]pyrimidin-5-yl]-piperidine-4-carboxylic acid methylamide |
| Compound 140 | 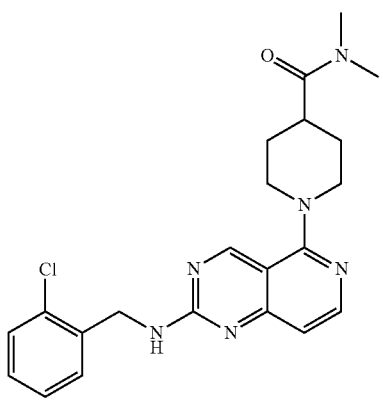 [SMILES: CN(C)C(=O)C1CCN(c2nccc3nc(NCc4ccccc4Cl)ncc23)CC1] | 1-[2-(2-Chloro-benzylamino)-pyrido[4,3-d]pyrimidin-5-yl]-piperidine-4-carboxylic acid dimethylamide |
| Compound 141 | 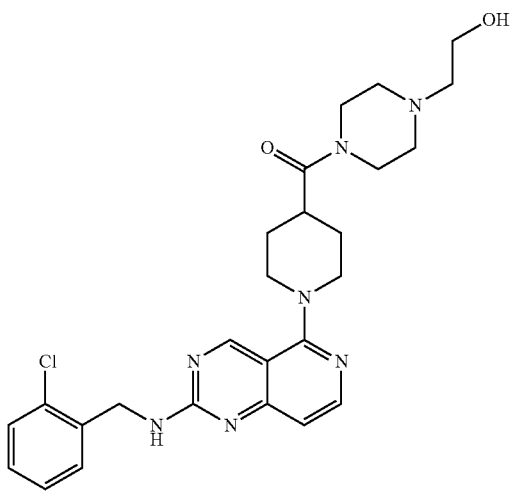 [SMILES: O=C(C1CCN(c2nccc3nc(NCc4ccccc4Cl)ncc23)CC1)N1CCN(CCO)CC1] | {1-[2-(2-Chloro-benzylamino)-pyrido[4,3-d]pyrimidin-5-yl]-piperidin-4-yl}-[4-(2-hydroxy-ethyl)-piperazin-1-yl]-methanone |

-continued
| | | |
|---|---|---|
| Compound 142 | 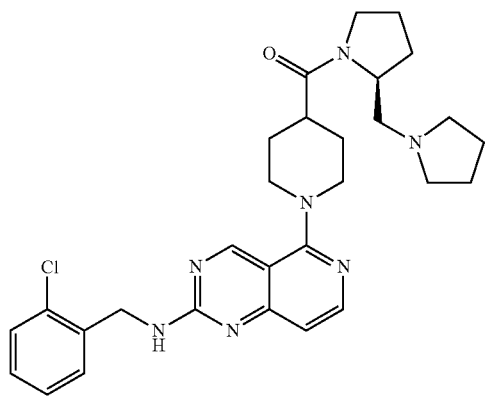 [SMILES: O=C(C1CCN(c2nccc3nc(NCc4ccccc4Cl)ncc23)CC1)N1CCC[C@H]1CN1CCCC1] | {1-[2-(2-Chloro-benzylamino)-pyrido[4,3-d]pyrimidin-5-yl]-piperidin-4-yl}-((S)-2-pyrrolidin-1-ylmethyl-pyrrolidin-1-yl)-methanone |
| Compound 143 | 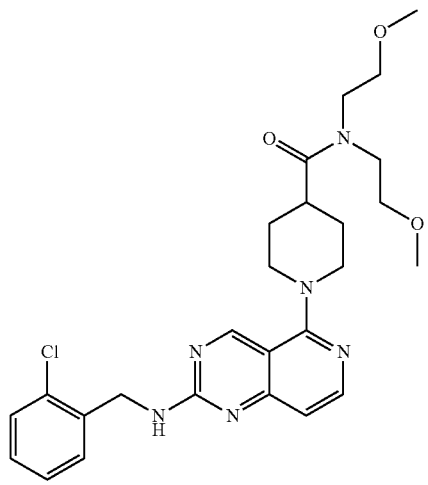 [SMILES: COCCN(CCOC)C(=O)C1CCN(c2nccc3nc(NCc4ccccc4Cl)ncc23)CC1] | 1-[2-(2-Chloro-benzylamino)-pyrido[4,3-d]pyrimidin-5-yl]-piperidine-4-carboxylic acid bis-(2-methoxy-ethyl)-amide |
| Compound 144 | 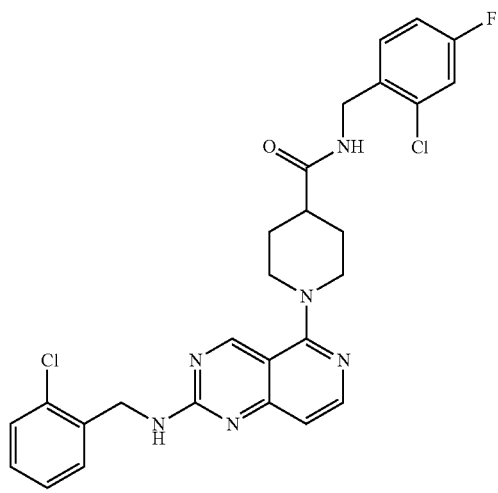 [SMILES: O=C(NCc1ccc(F)cc1Cl)C1CCN(c2nccc3nc(NCc4ccccc4Cl)ncc23)CC1] | 1-[2-(2-Chloro-benzylamino)-pyrido[4,3-d]pyrimidin-5-yl]-piperidine-4-carboxylic acid 2-chloro-4-fluoro-benzylamide |

-continued
| Compound 145 | 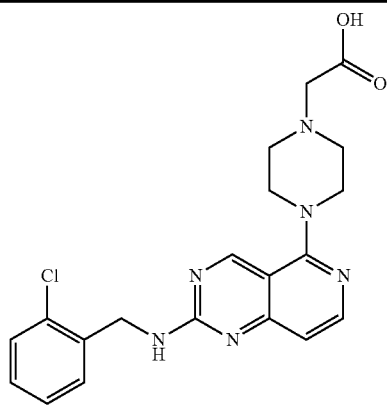 | {4-[2-(2-Chloro-benzylamino)-pyrido[4,3-d]pyrimidin-5-yl]-piperazin-1-yl}-acetic acid |
| Compound 146 | 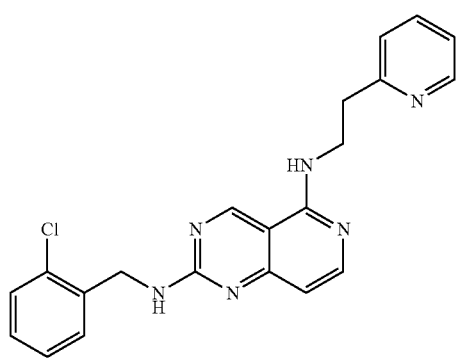 [SMILES: Clc1ccccc1CNc1ncc2c(NCCc3ccccn3)nccc2n1] | N2-(2-Chloro-benzyl)-N5-(2-pyridin-2-yl-ethyl)-pyrido[4,3-d]pyrimidine-2,5-diamine |
| Compound 147 | 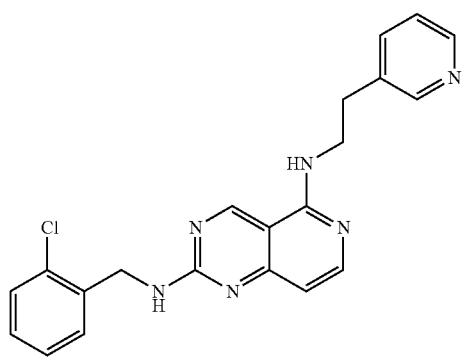 [SMILES: Clc1ccccc1CNc1ncc2c(NCCc3cccnc3)nccc2n1] | N2-(2-Chloro-benzyl)-N5-(2-pyridin-3-yl-ethyl)-pyrido[4,3-d]pyrimidine-2,5-diamine |
| Compound 148 | 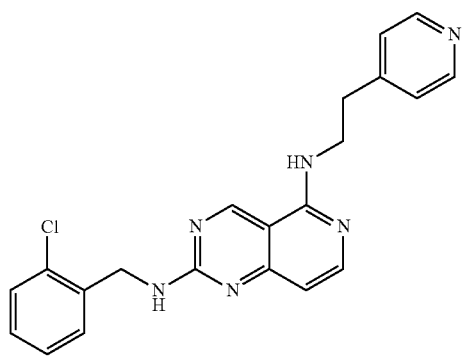 [SMILES: Clc1ccccc1CNc1ncc2c(NCCc3ccncc3)nccc2n1] | N2-(2-Chloro-benzyl)-N5-(2-pyridin-4-yl-ethyl)-pyrido[4,3-d]pyrimidine-2,5-diamine |

-continued
| | | |
|---|---|---|
| Compound 149 | 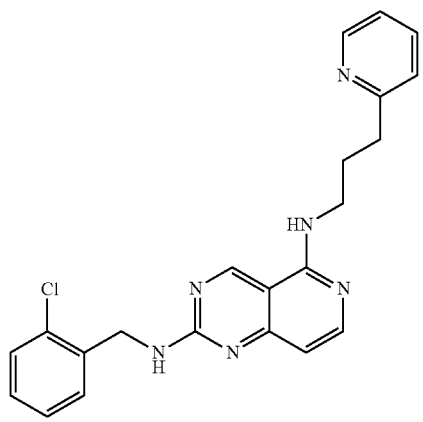 [SMILES: Clc1ccccc1CNc1ncc2c(NCCCc3ccccn3)nccc2n1] | N2-(2-Chloro-benzyl)-N5-(3-pyridin-2-yl-propyl)-pyrido[4,3-d]pyrimidine-2,5-diamine |
| Compound 150 | 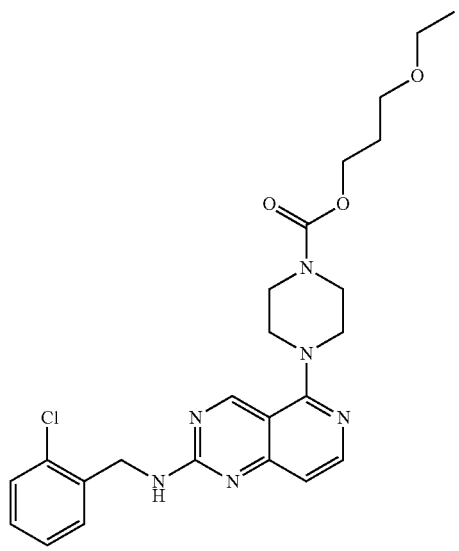 [SMILES: CCOCCCOC(=O)N1CCN(c2nccc3nc(NCc4ccccc4Cl)ncc23)CC1] | 4-[2-(2-Chloro-benzylamino)-pyrido[4,3-d]pyrimidin-5-yl]-piperazine-1-carboxylic acid 3-ethoxy-propyl ester |
| Compound 151 | 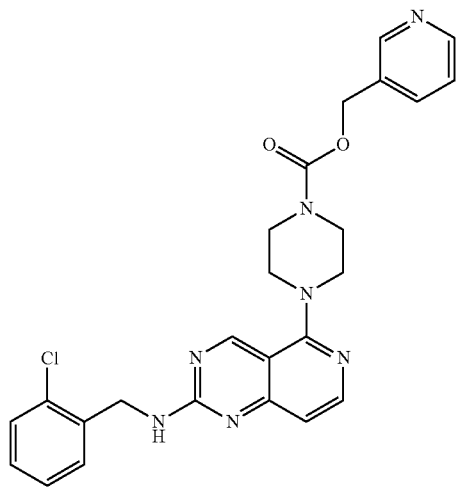 [SMILES: O=C(OCc1cccnc1)N1CCN(c2nccc3nc(NCc4ccccc4Cl)ncc23)CC1] | 4-[2-(2-Chloro-benzylamino)-pyrido[4,3-d]pyrimidin-5-yl]-piperazine-1-carboxylic acid pyridin-3-ylmethyl ester |

-continued
| Compound 152 | 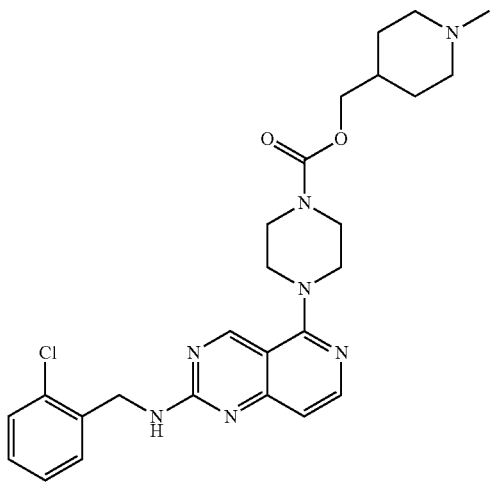 [SMILES: CN1CCC(COC(=O)N2CCN(c3nccc4nc(NCc5ccccc5Cl)ncc34)CC2)CC1] | 4-[2-(2-Chloro-benzylamino)-pyrido[4,3-d]pyrimidin-5-yl]-piperazine-1-carboxylic acid 1-methyl-piperidin-4-ylmethyl ester |
| Compound 153 | 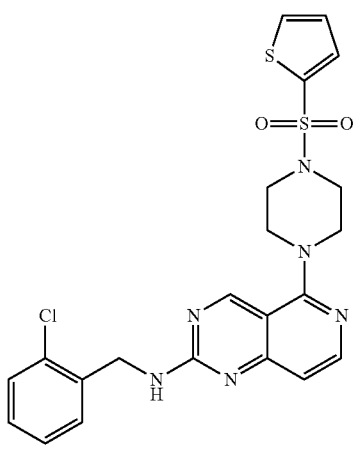 [SMILES: O=S(=O)(c1cccs1)N1CCN(c2nccc3nc(NCc4ccccc4Cl)ncc23)CC1] | (2-Chloro-benzyl)-{5-[4-(thiophene-2-sulfonyl)-piperazin-1-yl]-pyrido[4,3-d]pyrimidin-2-yl}-amine |
| Compound 154 | 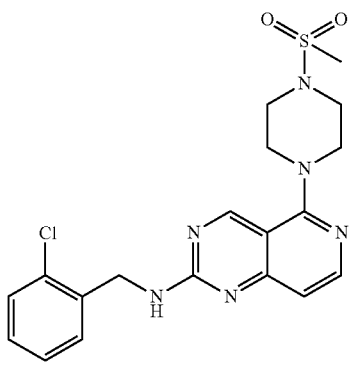 [SMILES: CS(=O)(=O)N1CCN(c2nccc3nc(NCc4ccccc4Cl)ncc23)CC1] | (2-Chloro-benzyl)-[5-(4-methanesulfonyl-piperazin-1-yl)-pyrido[4,3-d]pyrimidin-2-yl]-amine |

-continued
| Compound 155 | 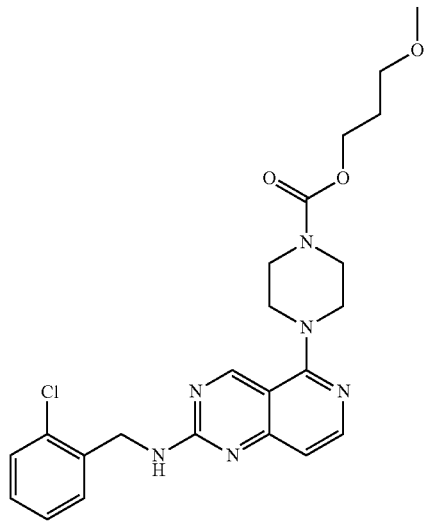 [SMILES: COCCCOC(=O)N1CCN(c2nccc3nc(NCc4ccccc4Cl)ncc23)CC1] | 4-[2-(2-Chloro-benzylamino)-pyrido[4,3-d]pyrimidin-5-yl]-piperazine-1-carboxylic acid 3-methoxy-propyl ester |
| Compound 156 | 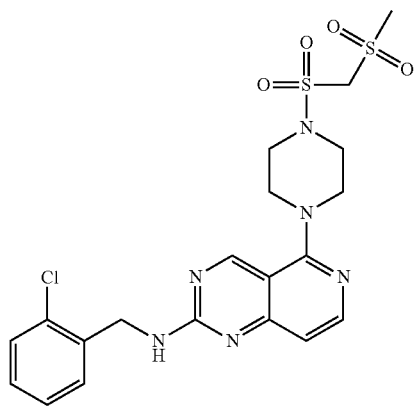 [SMILES: CS(=O)(=O)CS(=O)(=O)N1CCN(c2nccc3nc(NCc4ccccc4Cl)ncc23)CC1] | (2-Chloro-benzyl)-[5-(4-methanesulfonylmeth-anesulfonyl-piperazin-1-yl)-pyrido[4,3-d]pyrimidin-2-yl]-amine |
| Compound 157 | 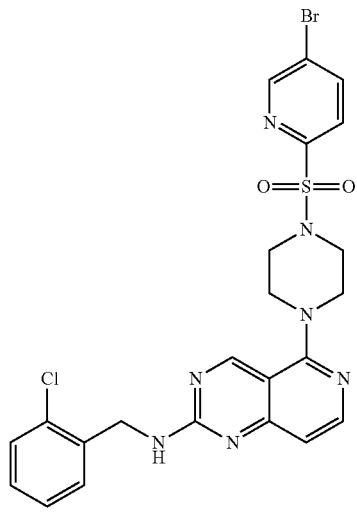 [SMILES: O=S(=O)(c1ccc(Br)cn1)N1CCN(c2nccc3nc(NCc4ccccc4Cl)ncc23)CC1] | {5-[4-(5-Bromo-pyridine-2-sulfonyl)-piperazin-1-yl]-pyrido[4,3-d]pyrimidin-2-yl}-(2-chloro-benzyl)-amine | and the physiologically acceptable salts, prodrugs, solvates and stereoisomers thereof, including mixtures thereof in all ratios.

4. A process for the preparation of a pyridopyrimidine compound as claimed in claim 1, comprising:
(a) reacting a compound of formula (IV) wherein Ar, R3, R4, R5, R6, n are as defined in claim 1

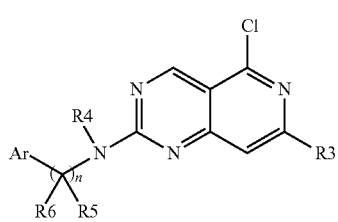

with a compound of formula (V)

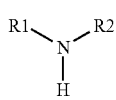

wherein R1, R2 are as defined claim 1,
to obtain a compound of formula (I).

5. A pharmaceutical composition comprising at least one pyridopyrimidine compound as claimed in claim 1, and least one additional compound selected from physiologically acceptable excipients, auxiliaries, adjuvants, diluents, carriers and/or additional pharmaceutically active substance other than said at least one pyridopyrimidine compound.

6. The composition as claimed in claim 5, wherein in said composition further comprises at least one additional pharmacologically active substance.

7. A kit comprising a therapeutically effective amount of at least one pyridopyrimidine compound as claimed in claim 1 and a therapeutically effective amount of at least one further pharmacologically active substance other than the pyridopyrimidine compound.

8. A kit comprising at least one pharmaceutical composition according to claim 5 comprising a therapeutically effective amount of at least one pyridopyrimidine compound as claimed in claim 1 and a therapeutically effective amount of at least one further pharmacologically active substance other than the pyridopyrimidine compound.

9. A pyridopyrimidine compound according to claim 1, wherein R4 is independently selected from hydrogen, methyl, —X291 —NHX292, and —X293—NX294 —X295.

10. A pyridopyrimidine compound according to claim 1, wherein R5, R6 are independently from each other selected from hydrogen and methyl.

11. A pyridopyrimidine compound according to claim 1, wherein Ar is phenyl which is unsubstituted or substituted with one or more identical or different substituents selected from —F, —Cl, methyl, and methoxy.

12. A pyridopyrimidine compound according to claim 1, wherein:
R3 is H;
R4 is H;
R5, R6 are independently from each other selected from hydrogen and methyl; and
Ar is phenyl which is unsubstituted or substituted with one or more identical or different substituents selected from —F, —Cl, methyl, and methoxy.

13. A pyridopyrimidine compound according to claim 2, wherein R1, R2 are independently from each other selected from hydrogen, propyl, isobutyl, phenyl, benzyl, benzo[1,3]dioxolyl, pyridinylmethyl, piperidinylethyl, piperidinylpropyl, pyrrolidinylpropyl, and 2,3-dihydro-benzo[1,4]dioxinyl, which in each case is unsubstituted or substituted with one or more identical or different substituents selected from —F, —Cl, —CN, methyl,methoxy,ethoxy,methylcarbonyl,methylcarboxyate-yl (carboxoic acid methyl ester), and isopropoxy.

14. A pyridopyrimidine compound according to claim 13, wherein:
R3 is H;
R4 is H;
R5, R6 are independently from each other selected from hydrogen and methyl; and
Ar is phenyl which is unsubstituted or substituted with one or more identical or different substituents selected from —F, —Cl, methyl, and methoxy.

15. A pyridopyrimidine compound according to claim 2, wherein R1, R2, together with the nitrogen atom to which they are attached, form "heterocyclyl" selected from pyrrolidinyl, piperidinyl, and piperazinyl,
which in each case is unsubstituted or substituted with one or more identical or different substituents Z,
wherein Z is selected from hydrogen —COOH, fluorophenyl, thiazolyl, pyridinyl, pyrimidinyl, methyl-piperidinyl-methyl, N,N-dimethyl-oxo-butyramide, amino-butanone-yl, carboxy-methyl, pyridinyl-ethyl-amino-yl, pyridinyl-propyl-amino-yl, methyl-carbonyl, cyano-methyl-carbonyl, butanonyl-carbonyl, methoxy-ethoxy-methyl-carbonyl, dimethyl-amino-methyl-carbonyl, diethyl-amino-ethyl-carbonyl, furanyl-carbonyl, morpholinyl-carbonyl, pyridinyl-methyl-carbonyl, pyridinyl-ethyl-carbonyl, methyl-pyrazolyl-ethyl-carbonyl, imidazolyl-ethyl-carbonyl, pyrrolidinyl-carbonyl,methyl-piperazinyl-carbonyl, ethyl-piperazinyl-carbonyl, propyl-piperazinyl-carbonyl, pyridinyl-piperazinyl-carbonyl, amino-pyrrolidone-methyl-carbonyl, benzoimidazolyl-ethyl-carbonyl, hydroxyl-ethyl-piperazinyl-carbonyl, pyrrolidinyl-methyl-pyrrolidinyl-carbonylpyridinyl-acetamide-yl, methyl-carboxylic acid amide-yl, carboxylic acid methylamide-yl, carboxylic acid dimethylamide-yl, carboxylic acid diethylamide-yl, carboxylic acid hydroxy-ethylamide-yl, carboxylic acid propylamide-yl, carboxylic acid isopropylamide-yl, carboxylic acid cyclopropylamide-yl, carboxylic acid allylamide-yl, carboxylic acid (furanyl-methyl)-amide-yl, carboxylic acid pyridinyl-amide-yl, carboxylic acid (pyridinylmethyl)-amide-yl, carboxylic acid (dimethylaminoethyl)-amide-yl, carboxylic acid (diethylaminoethyl)-amide-yl, carboxylic acid (diethylamino-propyl)-amide-yl, carboxylic acid (methoxy-ethyl)-amide-yl, carboxylic acid (methoxy-propyl)-amide-yl, carboxylic acid (ethoxy-propyl)-amide-yl, carboxylic acid (methyl-isoxazolyl)-amide-yl, carboxylic acid bis(methoxy-ethyl)amide-yl, carboxylic acid (chloro)(fluoro)benzylamide-yl, carboxylic acid ethyl ester, carboxylic acid methoxy-propyl-ester, carboxylic acid ethoxy-propyl-ester, carboxylic acid pyridinylmethyl-ester, carboxylic acid methyl-piperidinyl-methyl-ester, acetic acid-oxo-ethyl ester,oxo-proprionic acid ethyl ester, oxo-pentanoic acid methyl ester, carbonyl-amino-propionic acid ethyl ester, methyl-sulfonyl, methyl-sulfonyl-methyl-sulfonyl, thiophenyl-sulfonyl, and bromo-pyridinyl- sulfonyl;

with the proviso that if R1, R2, together with the nitrogen atom to which they are attached, form "heterocyclyl", which is unsubstituted or substituted with one or more identical or different substituents Z, "heterocyclyl" is not 4-piperidine-1-yl-carboxylic acid (4-carboxy-piperidine-1-yl), 3-piperidine-1-yl-carboxylic acid (3-carboxy-piperidine-1-yl), 4-piperidine-1-yl-carboxylic acid ethyl ester (4-ethylcarboxyate-piperidine-1-yl), or 3-piperidine-1-yl-carboxylic acid ethyl ester (3-ethylcarboxyate-piperidine-1-yl).

16. A pyridopyrimidine compound according to claim 15, wherein:
R3 is H;
R4 is H;
R5, R6 are independently from each other selected from hydrogen and methyl; and
Ar is phenyl which is unsubstituted or substituted with one or more identical or different substituents selected from —F, —Cl, methyl, and methoxy.

17. A pyridopyrimidine compound according to claim 1, wherein
Ar is phenyl which is unsubstituted or substituted with one or more identical or different substituents selected from —F, —Cl, methyl, and methoxy;
R4 is independently selected hydrogen, methyl,— $NHX_{292}$, and —$X_{293}$-$NX_{294}X_{295}$, wherein $X_{292}$, —$X_{293}$, $X_{294}$, and $X_{295}$ are independently from each other alkyl; and
R5, R6 are each independently from each other selected from hydrogen and methyl.

* * * * *

UNITED STATES PATENT AND TRADEMARK OFFICE
CERTIFICATE OF CORRECTION

PATENT NO. : 8,530,650 B2  
APPLICATION NO. : 13/132181  
DATED : September 10, 2013  
INVENTOR(S) : Schiemann et al.

Page 1 of 1

It is certified that error appears in the above-identified patent and that said Letters Patent is hereby corrected as shown below:

In The Claims

Column 238, line 27 reads "wherein Z is selected from hydrogen - COOH, fluoro-" should read -- wherein Z is COOH, fluoro- --

Column 238, line 43 reads "pyrrolidinyl-carbonylpyridinyl-acetamide-yl, methyl" should read -- pyrrolidinyl-carbonyl, pyridinyl-acetamide-yl, methyl- --

Signed and Sealed this
Twenty-fourth Day of March, 2015

Michelle K. Lee
*Director of the United States Patent and Trademark Office*